(12) United States Patent
Anderson et al.

(10) Patent No.: US 9,074,204 B2
(45) Date of Patent: Jul. 7, 2015

(54) NUCLEIC ACID ENCODING REACTIONS

(75) Inventors: Megan Anderson, Washington, DC (US); Peilin Chen, Richmond, CA (US); Brian Fowler, San Mateo, CA (US); Robert C. Jones, Los Altos, CA (US); Fiona Kaper, Solano Beach, CA (US); Ronald Lebofsky, Etobicoke (CA); Andrew May, San Francisco, CA (US)

(73) Assignee: Fluidigm Corporation, South San Francisco, CA (US)

( * ) Notice: Subject to any disclaimer, the term of this patent is extended or adjusted under 35 U.S.C. 154(b) by 0 days.

(21) Appl. No.: 13/476,911

(22) Filed: May 21, 2012

(65) Prior Publication Data

US 2013/0005585 A1    Jan. 3, 2013

Related U.S. Application Data

(60) Provisional application No. 61/519,348, filed on May 20, 2011.

(51) Int. Cl.
*C12Q 1/68* (2006.01)
*C12N 15/10* (2006.01)
*C12N 15/65* (2006.01)
*C12N 15/66* (2006.01)

(52) U.S. Cl.
CPC ............... *C12N 15/10* (2013.01); *C12N 15/65* (2013.01); *C12N 15/66* (2013.01)

(58) Field of Classification Search
CPC ................................................... C12Q 1/6869
See application file for complete search history.

(56) References Cited

U.S. PATENT DOCUMENTS

| | | | |
|---|---|---|---|
| 4,683,202 A | 7/1987 | Mullis | |
| 5,066,584 A | 11/1991 | Gyllensten et al. | |
| 6,605,451 B1 | 8/2003 | Marmaro et al. | |
| 6,824,981 B2 | 11/2004 | Chait et al. | |
| 7,153,658 B2 | 12/2006 | Andersen et al. | |
| 7,312,034 B2 | 12/2007 | Virgos et al. | |
| 8,318,434 B2 | 11/2012 | Cuppens | |
| 8,450,063 B2 | 5/2013 | Dube et al. | |
| 8,628,923 B2 | 1/2014 | Hamilton et al. | |
| 8,691,509 B2 | 4/2014 | May et al. | |
| 8,697,363 B2 | 4/2014 | Mir et al. | |
| 2003/0119004 A1 | 6/2003 | Wenz et al. | |
| 2004/0081993 A1 | 4/2004 | Cantor et al. | |
| 2004/0086892 A1 | 5/2004 | Crothers et al. | |
| 2004/0091879 A1 | 5/2004 | Nolan et al. | |
| 2004/0110191 A1 | 6/2004 | Winkler et al. | |
| 2004/0209299 A1 | 10/2004 | Pinter et al. | |
| 2004/0229349 A1 | 11/2004 | Daridon | |
| 2005/0064488 A1 | 3/2005 | Huh et al. | |
| 2005/0095634 A1 | 5/2005 | Baker et al. | |
| 2005/0252773 A1 | 11/2005 | McBride et al. | |
| 2005/0260640 A1 | 11/2005 | Andersen et al. | |
| 2006/0053503 A1 | 3/2006 | Culiat et al. | |
| 2007/0020640 A1 | 1/2007 | McCloskey et al. | |
| 2007/0219364 A1 | 9/2007 | Andersen et al. | |
| 2008/0108063 A1 | 5/2008 | Lucero et al. | |
| 2008/0223721 A1 | 9/2008 | Cohen et al. | |
| 2009/0053719 A1 | 2/2009 | Lo et al. | |
| 2009/0163366 A1 | 6/2009 | Nickerson et al. | |
| 2009/0233802 A1* | 9/2009 | Bignell et al. | 506/2 |
| 2009/0239308 A1 | 9/2009 | Dube et al. | |
| 2009/0317798 A1 | 12/2009 | Heid et al. | |
| 2010/0120038 A1 | 5/2010 | Mir et al. | |
| 2010/0178655 A1 | 7/2010 | Hamilton et al. | |
| 2010/0203538 A1 | 8/2010 | Dube et al. | |
| 2010/0273219 A1* | 10/2010 | May et al. | 435/91.5 |
| 2010/0285537 A1 | 11/2010 | Zimmermann | |
| 2011/0053806 A1 | 3/2011 | Amin | |
| 2011/0129841 A1 | 6/2011 | Heid et al. | |
| 2011/0143949 A1 | 6/2011 | Heid et al. | |
| 2011/0207134 A1* | 8/2011 | Faham et al. | 435/6.11 |
| 2013/0323732 A1 | 12/2013 | Anderson et al. | |

(Continued)

FOREIGN PATENT DOCUMENTS

| | | |
|---|---|---|
| CN | 101067156 A | 11/2007 |
| EP | 0197196 A1 | 10/1986 |

(Continued)

OTHER PUBLICATIONS

Gill et al. (Nucleic Acid Isothermal Amplification Technologies—A Review, Nucleosides, Nucleotides, and Nucleic Acids, 27:224-243, Nov. 2008).*
Life Technologies (Ion Torrent Amplicon Sequencing, attached, Feb. 10, 2011).*
Kaper et al. (Parallel preparation of targeted resequencing libraries from 480 genomic regions using multiplex PCR on the Access Array system, AACR 2010 Abstract & presentation, Apr. 19, 2010).*
Gillevet et al. (Quantitative Assessment of the Human Gut Microbiome using Multitag Pyrosequencing, Chem Biodivers. May 2010 ; 7(5): 1065-1075).*
Hayden et al. (Multiplex-Ready PCR: A new method for multiplexed SSR and SNP genotyping, BMC Genomics 2008, 9:80).*

(Continued)

*Primary Examiner* — Christopher M Babic
*Assistant Examiner* — Aaron Priest
(74) *Attorney, Agent, or Firm* — Weaver Austin Villeneuve & Sampson LLP

(57) ABSTRACT

Described herein are methods useful for incorporating one or more adaptors and/or nucleotide tag(s) and/or barcode nucleotide sequence(s) one, or typically more, target nucleotide sequences. In particular embodiments, nucleic acid fragments having adaptors, e.g., suitable for use in high-throughput DNA sequencing are generated. In other embodiments, information about a reaction mixture is encoded into a reaction product. Also described herein are methods and kits useful for amplifying one or more target nucleic acids in preparation for applications such as bidirectional nucleic acid sequencing. In particular embodiments, methods of the invention entail additionally carrying out bidirectional DNA sequencing. Also described herein are methods for encoding and detecting and/or quantifying alleles by primer extension.

35 Claims, 43 Drawing Sheets

(56) References Cited

U.S. PATENT DOCUMENTS

| | | |
|---|---|---|
| 2014/0087973 A1 | 3/2014 | Amin |
| 2014/0154679 A1 | 6/2014 | Dube et al. |
| 2014/0186827 A1 | 7/2014 | Jones et al. |
| 2014/0193812 A1 | 7/2014 | Hamilton et al. |
| 2014/0227691 A1 | 8/2014 | May et al. |
| 2014/0272952 A1 | 9/2014 | May et al. |
| 2014/0296090 A1 | 10/2014 | Mir et al. |

FOREIGN PATENT DOCUMENTS

| | | |
|---|---|---|
| EP | 2201143 B1 | 11/2012 |
| WO | WO/01/59161 | 8/2001 |
| WO | WO02/081729 | 10/2002 |
| WO | WO2004/040001 | 5/2004 |
| WO | WO/2004/051218 | 6/2004 |
| WO | WO/2005/064020 | 7/2005 |
| WO | WO/2005/107938 | 11/2005 |
| WO | WO/2006/023919 | 3/2006 |
| WO | WO/2006/128010 | 11/2006 |
| WO | WO/2007/024798 | 3/2007 |
| WO | WO2007/033385 | 3/2007 |
| WO | WO/2007/044091 | 4/2007 |
| WO | WO/2010/027870 | 3/2010 |
| WO | WO/2010/115154 | 10/2010 |
| WO | WO/2011/142836 | 11/2011 |
| WO | WO/2011/143659 | 11/2011 |
| WO | WO/2012/162267 | 11/2012 |

OTHER PUBLICATIONS

Brownie et al. (The elimination of primer-dimer accumulation in PCR, Nucleic Acids Research, 1997, vol. 25, No. 16).*
U.S. Appl. No. 61/605,016, filed Feb. 29, 2012, Fowler et al.
International Search Report and Written Opinion dated May 10, 2010 issued in PCT/US2009/055083 (WO/2010/027870).
International Preliminary Examination Report dated Mar. 10, 2011 issued in PCT/US2009/055083 (WO/2010/027870).
International Search Report and Written Opinion dated Aug. 30, 2010 issued in PCT/US2010/029854 (WO/2010/115154).
International Preliminary Examination Report dated Oct. 13, 2011 issued in PCT/US2010/029854 (WO/2010/115154).
International Search Report and Written Opinion dated Dec. 7, 2012 issued in PCT/US2012/038894 (WO/2012/162267).
CN Office Action dated Nov. 1, 2012 issued in CN200980142505.9.
CN Office Action dated Mar. 4, 2013 issued in CN201080021508.X.
EP Extended Search Report dated Oct. 15, 2012 issued in EP09812052.0.
EP Extended Search Report dated Jul. 19, 2012 issued in EP10759511.8.
EP Office Action dated Mar. 15, 2013 issued in EP10759511.8.
US Office Action dated May 3, 2012 issued in U.S. Appl. No. 12/548,132.
US Final Office Action dated Feb. 12, 2013 issued in U.S. Appl. No. 12/548,132.
US Office Action dated Jun. 28, 2012 issued in U.S. Appl. No. 12/753,703.
US Final Office Action dated Mar. 25, 2013 issued in U.S. Appl. No. 12/753,703.
US Office Action dated Jul. 10, 2013 issued in U.S. Appl. No. 12/753,703.
Binladen et al. (2007) "The use of coded PCR Primers enables High-Throughput Sequencing of multiple homolog amplification products by 454 parallel sequencing" *PLOS One* 2(e197): 1-9.
Brownie et al. (1997) "The elimination of primer-dimer accumulation in PCR" *Nucleic Acids Research* 25(16): 3235-3241.
Guo et al. (2003) "Methodology for using a universal primer to label amplified DNA segments for molecular analysis" *Biotechnology Letters* 25:2079-2083.
Hayden et al. (2008) "Multiplex-Ready PCR: A new method for multiplexed SSR and SNP genotyping" *BMC Genomics* 9(1): 80(1-12).
Kita-Matsuo et al. (2005) "Adaptor-tagged competitive polymerase chain reaction: amplification bias and quantified gene expression levels" *Analytical Biochemistry* 339(1): 15-28.
Makrigiorgos et al. (2002) "A PCR-based amplification method retaining the quantitative difference between two complex genomes" *Nature Biotechnology* 20: 936-39 (Published online: Aug. 5, 2002, doi:1 0.1 038/nbt724).
Neilan et al. (1997) "A universal procedure for primer labelling of amplicons" *Nucleic Acids Research* 25(14): 2938-2939.
Sawasaki et al. (2002) "A cell-free protein synthesis system for high-throughput proteomics" *PNAS* 99(23):14652-14657.
Sellner et al. (2004) "MLPA and MAPH: New Techniques for Detection of Gene Deletion" *Human Mutation* 23(5): 413-419.
Stürzenbaum (1999) "Transfer RNA Reduces the Formation of Primer Artifacts During Quantitative PCR" *BioTechniques* 27:50-52.
Teo et al. (2002) "Reliable and reproducible LightCycler qPCR for HIV-1 DNA 2-LTR circles" *Journal of Immunological Methods* 270: 109-118.
Uematsu et al. (2001) "Multiplex polymerase chain reaction (PCR) with color-tagged module-shuffling primers for comparing gene expression levels in various cells" *Nucleic Acids Research, Oxford University Press, GB* 29(16):E84(1-6).
U.S. Appl. No. 14/184,499, filed Feb. 19, 2014, Mir et al.
U.S. Appl. No. 14/180,262, filed Feb. 13, 2014, May et al.
International Preliminary Report on Patentability dated Apr. 8, 2014 issued in PCT/US2012/038894 (WO/2012/162267).
AU Office Action dated May 23, 2014 issued in AU2010232439.
CN Second Office Action dated Sep. 17, 2013 issued in CN200980142505.9.
CN Third Office Action dated Apr. 9, 2014 issued in CN200980142505.9.
CN Office Action dated Jan. 13, 2014 issued in CN201080021508.X.
EA Office Action dated Nov. 27, 2013 issued in EA201171206.
EA Office Action dated Jul. 18, 2014 issued in EA201171206.
Singapore Written Opinion dated Oct. 31, 2013 issued in SG201107142-0.
US Notice of Allowance dated Nov. 18, 2013 issued in U.S. Appl. No. 12/548,132.
US Notice of Allowance dated Nov. 14, 2013 issued in U.S. Appl. No. 12/753,703.
CN Decision of Rejection dated Oct. 21, 2014 issued in CN200980142505.9.
EP Extended Search Report dated Sep. 16, 2014 issued in EP14158911.9.
IL Office Action dated Mar. 3, 2014 issued in IL215462 (translation only).
Japanese Office Action dated Aug. 25, 2014 issued in JP2012-503757.

* cited by examiner

Degenerate-tailed hairpin sequencing linkers

A- Sequencer specific tag1
B- Sequencer specific tag2
Rest. Site: Optional restriction site/specific enzyme cutting site
        (dUTP, phosphothiorate possible)
NNNNNNNNN- Degenerate primer region-10mer, 20mer, 3' end protected Fragment DNA (general nuclease)

Digest 5' ends (T4 polymerase, Exo III)

Degenerate-tailed sequencing linker

A - Sequencer specific tag1
B - Sequencer specific tag2
Rest. Site: restriction site/specific enzyme cutting site (dUTP possible)
NNNNNNNN- Degenerate primer region-10mer, 20mer Fragment DNA (general nuclease)

Digest 5' ends (T4 polymerase, Exo III)

Measured:

Theoretical:

Brightfield　　　　Syto10 DNA stain　　　　Cy5 antibody

PRE

POST

Syto10 DNA stain

Cell ghost

Cycle 1 Wild type detection by priming on WT tag and extending all bases

Cycle 2 Mutant detection by priming on Mutant tag and extending all bases

Mutant – Few of these

SEQUENCE LISTING

```
<160> NUMBER OF SEQ ID NOS: 809

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
agatgtgtat aagagacag                                               19

<210> SEQ ID NO 2
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(14)
<223> OTHER INFORMATION: a, c, t, g, unknown or other

<400> SEQUENCE: 2
```
tgcatagcaa tgnnctaggt gactggagtt cagacgtgtg ctcttccgat ct        52

<210> SEQ ID NO 3
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (39)..(40)
<223> OTHER INFORMATION: a, c, t, g, unknown or other

<400> SEQUENCE: 3
agatcggaag agcacacgtc tgaactccag tcacctagnn cattgctatg ca        52

<210> SEQ ID NO 4
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (29)..(30)
<223> OTHER INFORMATION: a, c, t, g, unknown or other
<220> FEATURE:
<221> NAME/KEY: modified_base
<222> LOCATION: (31)..(31)
<223> OTHER INFORMATION: LNA

<400> SEQUENCE: 4
caagcagaag acggcatacg agatagctnn ctaggtgact ggagttcaga cgtgtgctct    60
tccgatct                                                              68

<210> SEQ ID NO 5
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (39)..(40)
<223> OTHER INFORMATION: a, c, t, g, unknown or other

<400> SEQUENCE: 5
agatcggaag agcacacgtc tgaactccag tcacctagnn agctatctcg tatgccgtct    60
tctgcttg                                                              68

<210> SEQ ID NO 6
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (29)..(30)
<223> OTHER INFORMATION: a, c, t, g, unknown or other

<400> SEQUENCE: 6
caagcagaag acggcatacg agatagctnn ctaggtgact ggagttcaga cgtgtgctct    60

```
tccgatct                                                             68

<210> SEQ ID NO 7
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (39)..(40)
<223> OTHER INFORMATION: a, c, t, g, unknown or other

<400> SEQUENCE: 7
agatcggaag agcacacgtc tgaactccag tcacctagnn agctatctcg tatgccgtct    60
tctgcttg                                                             68

<210> SEQ ID NO 8
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(6)
<223> OTHER INFORMATION: a, c, t, g, unknown or other

<400> SEQUENCE: 8 ctagnnagct                                                           10

<210> SEQ ID NO 9
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
aatgatacgg cgaccaccga gatctacact gacgacatgg ttctaca                  47

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tacggtagca gagacttggt ct                                             22

<210> SEQ ID NO 11
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
aatgatacgg cgaccaccga gatcttacgg tagcagagac ttggtct                  47

<210> SEQ ID NO 12
```

```
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
acactgacga catggttcta ca                                              22

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
acactgacga catggttcta ca                                              22

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
tacggtagca gagacttggt ct                                              22

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
tgtagaacca tgtcgtcagt gt                                              22

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
agaccaagtc tctgctaccg ta                                              22

<210> SEQ ID NO 17
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
acactgacga catggttcta caccttatag gtccaagggt agc                       43

<210> SEQ ID NO 18
<211> LENGTH: 46
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
tacggtagca gagacttggt ctaaagtcac agtcttgata ccttca              46

<210> SEQ ID NO 19
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
acactgacga catggttcta cagttgaggc actgaagatg g                   41

<210> SEQ ID NO 20
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
tacggtagca gagacttggt cttttaagta aagtgtctta cctcaagttt          50

<210> SEQ ID NO 21
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
acactgacga catggttcta cagcatactt aaatgtcaag aaatacagaa tca      53

<210> SEQ ID NO 22
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
tacggtagca gagacttggt cttaaaatct acctttaaga cgctctaata aat      53

<210> SEQ ID NO 23
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
acactgacga catggttcta cagtacttaa caactacaa ggaagtattg a         51

<210> SEQ ID NO 24
<211> LENGTH: 43
<212> TYPE: DNA
```

<213> ORGANISM: Artificial Sequence
<220> FEATURE:
<223> OTHER INFORMATION: Description of Artificial Sequence: Synthetic primer

<400> SEQUENCE: 24
tacggtagca gagacttggt ctaccaacac ccaaatcgag aga        43

<210> SEQ ID NO 25
<211> LENGTH: 51
<212> TYPE: DNA
<213> ORGANISM: Artificial Sequence
<220> FEATURE:
<223> OTHER INFORMATION: Description of Artificial Sequence: Synthetic primer

<400> SEQUENCE: 25
acactgacga catggttcta catcagtcat gtatatttgt ggttaaaatg t        51

<210> SEQ ID NO 26
<211> LENGTH: 42
<212> TYPE: DNA
<213> ORGANISM: Artificial Sequence
<220> FEATURE:
<223> OTHER INFORMATION: Description of Artificial Sequence: Synthetic primer

<400> SEQUENCE: 26
tacggtagca gagacttggt ctccttcccg gcttccataa ga        42

<210> SEQ ID NO 27
<211> LENGTH: 42
<212> TYPE: DNA
<213> ORGANISM: Artificial Sequence
<220> FEATURE:
<223> OTHER INFORMATION: Description of Artificial Sequence: Synthetic primer

<400> SEQUENCE: 27
acactgacga catggttcta cagcggtcaa aaatgtccct cc        42

<210> SEQ ID NO 28
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 28
tacggtagca gagacttggt ctactggagt acacaaggca atgtt        45

<210> SEQ ID NO 29
<211> LENGTH: 48
<212> TYPE: DNA
<213> ORGANISM: Artificial Sequence
<220> FEATURE:
<223> OTHER INFORMATION: Description of Artificial Sequence: Synthetic primer

<400> SEQUENCE: 29
acactgacga catggttcta catcttctgc agtctttatt agcattgt        48

<210> SEQ ID NO 30
<211> LENGTH: 48
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 30
tacggtagca gagacttggt ctagtttcaa ataagttgta ctgccaag                 48

<210> SEQ ID NO 31
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
acactgacga catggttcta catgcttttt tgcttttact gattaacg                 48

<210> SEQ ID NO 32
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
tacggtagca gagacttggt ctcctgtgct cgttttcca tatcc                     45

<210> SEQ ID NO 33
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
acactgacga catggttcta cattacaaac agatatgacc agaaggc                  47

<210> SEQ ID NO 34
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
tacggtagca gagacttggt cttaacagag ctgtaattca ttttattcct               50

<210> SEQ ID NO 35
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
acactgacga catggttcta caccctgagc ttttaagtgg tagc                     44

<210> SEQ ID NO 36
<211> LENGTH: 43
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 36
tacggtagca gagacttggt ctacccacaa acaagaaagg caa          43

<210> SEQ ID NO 37
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
acactgacga catggttcta catgggctaa gaaagcctac acc          43

<210> SEQ ID NO 38
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
tacggtagca gagacttggt ctacctgacc attaccagaa gttgc        45

<210> SEQ ID NO 39
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
acactgacga catggttcta cacttcattt ggagtacctt aaca         44

<210> SEQ ID NO 40
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
tacggtagca gagacttggt ctaccttggt tcccagatga ct           42

<210> SEQ ID NO 41
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
acactgacga catggttcta catctataat gtgcttaatt tttagggttc a  51

<210> SEQ ID NO 42
<211> LENGTH: 48
<212> TYPE: DNA
<213> ORGANISM: Artificial Sequence
<220> FEATURE:
<223> OTHER INFORMATION: Description of Artificial Sequence: Synthetic primer

<400> SEQUENCE: 42
tacggtagca gagacttggt ctagaatgtc ttagcaaagt agtcatgg                48

<210> SEQ ID NO 43
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
acactgacga catggttcta catcacttaa ttggtttttg gcttttgga               49

<210> SEQ ID NO 44
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
tacggtagca gagacttggt ctccagactg tcgcatggat                         40

<210> SEQ ID NO 45
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
acactgacga catggttcta catgttgtca atgcttggta ctcat                   45

<210> SEQ ID NO 46
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
tacggtagca gagacttggt ctggcccgag cctctttact g                       41

<210> SEQ ID NO 47
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
acactgacga catggttcta cacctcatcc agcttttaca tggc                    44

<210> SEQ ID NO 48
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 48
tacggtagca gagacttggt ctgccactcc caacaggttt c                41

<210> SEQ ID NO 49
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
acactgacga catggttcta catgcagcac tccacaacat ca               42

<210> SEQ ID NO 50
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
tacggtagca gagacttggt ctgctttgaa acatgcacta cga              43

<210> SEQ ID NO 51
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
acactgacga catggttcta catcattgct cttcaaataa caaagcat         48

<210> SEQ ID NO 52
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
tacggtagca gagacttggt ctaaaaatcc accagtaatt gtctatgtc        49

<210> SEQ ID NO 53
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
acactgacga catggttcta caggtaccag tttgttttat tttagatgat tgt   53

<210> SEQ ID NO 54
<211> LENGTH: 46
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 54
tacggtagca gagacttggt ctacatacct tgttggctac atctcc             46

<210> SEQ ID NO 55
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
acactgacga catggttcta cacgatatgc tggaatggct t                  41

<210> SEQ ID NO 56
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
tacggtagca gagacttggt ctcagtcatt gtttaatgag gagagtg            47

<210> SEQ ID NO 57
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
acactgacga catggttcta cagcttggct tcaagttgtc t                  41

<210> SEQ ID NO 58
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
tacggtagca gagacttggt ctaggtgaaa ttctaaatag tacctgct           48

<210> SEQ ID NO 59
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
acactgacga catggttcta cagctagcat taaaaacaaa aaagcaact          49

<210> SEQ ID NO 60
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
```
tacggtagca gagacttggt ctaaagcaca ttccatcaat gc                42

<210> SEQ ID NO 61
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
acactgacga catggttcta caattagatg acccatattc tgtttcttac        50

<210> SEQ ID NO 62
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
tacggtagca gagacttggt ctcaataatg gctaaagtgt tgtctgg           48

<210> SEQ ID NO 63
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
acactgacga catggttcta cagtgctgta gatggtgcac ttg               43

<210> SEQ ID NO 64
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
tacggtagca gagacttggt ctattaggtc tttttgagag tatgaattct g      51

<210> SEQ ID NO 65
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
acactgacga catggttcta cactgcatac acattgtgac ctt               43

<210> SEQ ID NO 66
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
tacggtagca gagacttggt ctcccccatg tcccataatg ctt                43

<210> SEQ ID NO 67
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
acactgacga catggttcta catgcatgtg gaactttgtg ga                 42

<210> SEQ ID NO 68
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
tacggtagca gagacttggt cttggcatcc ttgtacttcg c                  41

<210> SEQ ID NO 69
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
acactgacga catggttcta caatgattgc tatgggaagt gct                43

<210> SEQ ID NO 70
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
tacggtagca gagacttggt ctcgatgaga tgccttggga ct                 42

<210> SEQ ID NO 71
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
acactgacga catggttcta cacaagcaaa gtctctatgg tgat               44

<210> SEQ ID NO 72
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
tacggtagca gagacttggt ctacttctat cttttttcaga acgagaacta t      51

```
<210> SEQ ID NO 73
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
acactgacga catggttcta cagcaacatg actgtccttt cacc                    44

<210> SEQ ID NO 74
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
tacggtagca gagacttggt ctgcaaacct cgctttgaag a                       41

<210> SEQ ID NO 75
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
acactgacga catggttcta caggcaacta ccatccagca a                       41

<210> SEQ ID NO 76
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
tacggtagca gagacttggt ctgcagagct tcttctaagt gcat                    44

<210> SEQ ID NO 77
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
acactgacga catggttcta cagtcatgga agaagtgtca gc                      42

<210> SEQ ID NO 78
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
tacggtagca gagacttggt cttgtattct aatttggcat aaggcat                 47
```

```
<210> SEQ ID NO 79
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
acactgacga catggttcta cagcccatac acattcaaac acttac                    46

<210> SEQ ID NO 80
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
tacggtagca gagacttggt ctcagaatag gattcaatcg agggt                     45

<210> SEQ ID NO 81
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
acactgacga catggttcta catcaaatga tagtttaaat agtgtcagta gtag           54

<210> SEQ ID NO 82
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
tacggtagca gagacttggt ctataattta ttggtgtatc tagttctcca tc             52

<210> SEQ ID NO 83
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
acactgacga catggttcta cagccgacct agcccataaa                           40

<210> SEQ ID NO 84
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
tacggtagca gagacttggt ctccttgatt gtctttgctc actt                      44
```

```
<210> SEQ ID NO 85
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
acactgacga catggttcta caactctgga aggcaaagtc ct                           42

<210> SEQ ID NO 86
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
tacggtagca gagacttggt ctccccgtga cctgtatgga ga                           42

<210> SEQ ID NO 87
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
acactgacga catggttcta catggacagc aggaatgtgt tt                           42

<210> SEQ ID NO 88
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
tacggtagca gagacttggt ctggtctctc ttcttcttca tgct                         44

<210> SEQ ID NO 89
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
acactgacga catggttcta catgataagc ctaccaatta tagtgaacg                    49

<210> SEQ ID NO 90
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
tacggtagca gagacttggt ctgctttgtc cagatgaact cttt                         44

<210> SEQ ID NO 91
```

```
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
acactgacga catggttcta cagttttaaaa tatgccacag atattccttc a            51

<210> SEQ ID NO 92
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
tacggtagca gagacttggt ctgccttttg aggctgacca ct                      42

<210> SEQ ID NO 93
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
acactgacga catggttcta cagcagtgag aatacgtcca cac                     43

<210> SEQ ID NO 94
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
tacggtagca gagacttggt ctcagctgat gacaaagatg ataatgaa                48

<210> SEQ ID NO 95
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
acactgacga catggttcta cagccacttg caaagtttct tct                     43

<210> SEQ ID NO 96
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
tacggtagca gagacttggt ctagctgacc tagttccaat ctttt                   45

<210> SEQ ID NO 97
<211> LENGTH: 41
```

-continued

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
acactgacga catggttcta cagacgacac aggaagcaga t                    41

<210> SEQ ID NO 98
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
tacggtagca gagacttggt ctggagattt cgctcctgaa gaa                  43

<210> SEQ ID NO 99
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
acactgacga catggttcta catcctgtga gcgaagttcc a                    41

<210> SEQ ID NO 100
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
tacggtagca gagacttggt ctacatctgc taaacatgag tggg                 44

<210> SEQ ID NO 101
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
acactgacga catggttcta cacccaaaag tccacctga                       39

<210> SEQ ID NO 102
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
tacggtagca gagacttggt ctgcttggtg gcatggtttg                      40

<210> SEQ ID NO 103
<211> LENGTH: 40
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 103
acactgacga catggttcta cagccagctc cgttcagagt                           40

<210> SEQ ID NO 104
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 104
tacggtagca gagacttggt ctgcagcttg cttaggtcca c                         41

<210> SEQ ID NO 105
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 105
acactgacga catggttcta cagcacctac tgctgaaaag agag                      44

<210> SEQ ID NO 106
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 106
tacggtagca gagacttggt ctccacatct ttctgtataa atggctca                  48

<210> SEQ ID NO 107
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 107
acactgacga catggttcta caccacggaa agtactccag atg                       43

<210> SEQ ID NO 108
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 108
tacggtagca gagacttggt ctgcctcttt ctcttggttt tca                       43

<210> SEQ ID NO 109
<211> LENGTH: 46
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 109
acactgacga catggttcta caccagttca ggaaaatgac aatggg            46

<210> SEQ ID NO 110
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110
tacggtagca gagacttggt ctgggctggc tttttttgctt                  40

<210> SEQ ID NO 111
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 111
acactgacga catggttcta catctgccat gccaacaaag tc                42

<210> SEQ ID NO 112
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112
tacggtagca gagacttggt ctgtcccttc aacacaatac accc              44

<210> SEQ ID NO 113
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113
acactgacga catggttcta catctaccat cacaaaacag gttgc             45

<210> SEQ ID NO 114
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 114
tacggtagca gagacttggt ctgactgtgc ccctcctcta                   40

<210> SEQ ID NO 115
<211> LENGTH: 44
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 115
acactgacga catggttcta caacttttcc acagctacat ctct                           44

<210> SEQ ID NO 116
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 116
tacggtagca gagacttggt cttgtcatcc aattcaggta tggt                           44

<210> SEQ ID NO 117
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 117
acactgacga catggttcta caccattcct acagaaggca gaa                            43

<210> SEQ ID NO 118
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 118
tacggtagca gagacttggt ctaagaagac gcagatgctt gc                             42

<210> SEQ ID NO 119
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 119
acactgacga catggttcta cagcattaat tctgctatgc ccaaa                          45

<210> SEQ ID NO 120
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 120
tacggtagca gagacttggt cttttttgagt ctgcattttt tcttacac                      48

<210> SEQ ID NO 121
<211> LENGTH: 45
<212> TYPE: DNA
<213> ORGANISM: Artificial Sequence
<220> FEATURE:
<223> OTHER INFORMATION: Description of Artificial Sequence: Synthetic

```
primer

<400> SEQUENCE: 121
acactgacga catggttcta catgcaccca acaaaaatca gttag                      45

<210> SEQ ID NO 122
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 122
tacggtagca gagacttggt ctagcttatc attgaagacc ttggaa                     46

<210> SEQ ID NO 123
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 123
acactgacga catggttcta cagagtcaga ggaagttttg cttttg                     46

<210> SEQ ID NO 124
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 124
tacggtagca gagacttggt ctggttagtt ctgtgtggct ggt                        43

<210> SEQ ID NO 125
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 125
acactgacga catggttcta cattccaggg aaaaggctga atta                       44

<210> SEQ ID NO 126
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 126
tacggtagca gagacttggt ctggtatgtc tttggatgac tggg                       44

<210> SEQ ID NO 127
<211> LENGTH: 46
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 127
acactgacga catggttcta cacccatact tcagaaacaa tccact            46

<210> SEQ ID NO 128
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 128
tacggtagca gagacttggt ctgggctcag tctctttgat aggt               44

<210> SEQ ID NO 129
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 129
acactgacga catggttcta catctctcag tgacattgac caagaa            46

<210> SEQ ID NO 130
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 130
tacggtagca gagacttggt ctgcaacagg tcatcttcag agt                43

<210> SEQ ID NO 131
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 131
acactgacga catggttcta catctcaaga aacagttctc tcagtt            46

<210> SEQ ID NO 132
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 132
tacggtagca gagacttggt ctgttctgaa tctggtctct gtatatct          48

<210> SEQ ID NO 133
<211> LENGTH: 48
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 133
acactgacga catggttcta cagggtgata atgaaaaaca tagtccca                    48

<210> SEQ ID NO 134
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 134
tacggtagca gagacttggt ctgcagcagc agcttgatgt aa                          42

<210> SEQ ID NO 135
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 135
acactgacga catggttcta cagctattca ggaaggtgca aa                          42

<210> SEQ ID NO 136
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 136
tacggtagca gagacttggt ctccctggtt ttagaattcg tggg                        44

<210> SEQ ID NO 137
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 137
acactgacga catggttcta catgattcag attccatcct ttccct                      46

<210> SEQ ID NO 138
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 138
tacggtagca gagacttggt ctactttcag attctatctt tttagtttcc aa               52

<210> SEQ ID NO 139
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 139
```

-continued acactgacga catggttcta caggcccacg aattctaaaa cca                    43

<210> SEQ ID NO 140
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 140
acactgacga catggttcta catgaaagta aaggaatcaa aggagga                47

<210> SEQ ID NO 141
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 141
tacggtagca gagacttggt ctacaggact tgtacttgag gagc                   44

<210> SEQ ID NO 142
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 142
acactgacga catggttcta caggagttcg aaatagctcc tcaag                  45

<210> SEQ ID NO 143
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 143
tacggtagca gagacttggt ctagaaggtg ctttacttga ccca                   44

<210> SEQ ID NO 144
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 144
acactgacga catggttcta catcctagag gagccaagcc at                     42

<210> SEQ ID NO 145
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 145

```
tacggtagca gagacttggt ctaggactta ttccatttct accaggg                47
```

<210> SEQ ID NO 146
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 146

```
acactgacga catggttcta catctagaga ttcgacccct tca                   43
```

<210> SEQ ID NO 147
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 147

```
tacggtagca gagacttggt ctcatctgtc tacctggaga tgtatatg               48
```

<210> SEQ ID NO 148
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 148

```
acactgacga catggttcta catcaacttc caaggacatc atccc                  45
```

<210> SEQ ID NO 149
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 149

```
tacggtagca gagacttggt ctggctccat taccattatt catctg                 46
```

<210> SEQ ID NO 150
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 150

```
acactgacga catggttcta cagccaacag aaccttacca aaca                   44
```

<210> SEQ ID NO 151
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 151

```
tacggtagca gagacttggt ctgactggcg tactaataca ggt                   43
```

<210> SEQ ID NO 152
<211> LENGTH: 50
<212> TYPE: DNA
<213> ORGANISM: Artificial Sequence
<220> FEATURE:
<223> OTHER INFORMATION: Description of Artificial Sequence: Synthetic primer

<400> SEQUENCE: 152
acactgacga catggttcta catcaactaa atcaagtgga agtgaatctg          50

<210> SEQ ID NO 153
<211> LENGTH: 42
<212> TYPE: DNA
<213> ORGANISM: Artificial Sequence
<220> FEATURE:
<223> OTHER INFORMATION: Description of Artificial Sequence: Synthetic primer

<400> SEQUENCE: 153
tacggtagca gagacttggt ctaactggag tttgtgcctg gg          42

<210> SEQ ID NO 154
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 154
acactgacga catggttcta caagaagaaa attggaggaa tctgc          45

<210> SEQ ID NO 155
<211> LENGTH: 49
<212> TYPE: DNA
<213> ORGANISM: Artificial Sequence
<220> FEATURE:
<223> OTHER INFORMATION: Description of Artificial Sequence: Synthetic primer

<400> SEQUENCE: 155
tacggtagca gagacttggt ctccatcatt atactctata gtgggactg          49

<210> SEQ ID NO 156
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 156
acactgacga catggttcta cagtccttcc cttcctgata tgtctc          46

<210> SEQ ID NO 157
<211> LENGTH: 41
<212> TYPE: DNA
<213> ORGANISM: Artificial Sequence
<220> FEATURE:
<223> OTHER INFORMATION: Description of Artificial Sequence: Synthetic primer

<400> SEQUENCE: 157
tacggtagca gagacttggt ctgtgctcac gtttccaggt t          41

<210> SEQ ID NO 158
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 158
acactgacga catggttcta caccagcaaa gcgccatgat a                        41

<210> SEQ ID NO 159
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 159
tacggtagca gagacttggt ctcactttt gcttttcac tggatt                    46

<210> SEQ ID NO 160
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 160
acactgacga catggttcta cattcatcat cccttcctcg                          40

<210> SEQ ID NO 161
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 161
tacggtagca gagacttggt ctccatgttc cttttgcgga t                        41

<210> SEQ ID NO 162
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 162
acactgacga catggttcta caggaaccaa acaaagtaaa gaaaacca                 48

<210> SEQ ID NO 163
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 163
tacggtagca gagacttggt ctggacagtc ctcaattctc accc                     44

-continued

<210> SEQ ID NO 164
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 164
acactgacga catggttcta caccgtttcc tcaggtgcta caa             43

<210> SEQ ID NO 165
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 165
tacggtagca gagacttggt ctgaatcttt aatgtttgga tttgcctt        48

<210> SEQ ID NO 166
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 166
acactgacga catggttcta cacggtgatt gacagtgttt cag             43

<210> SEQ ID NO 167
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 167
tacggtagca gagacttggt ctctgataca gggacaggat ta              42

<210> SEQ ID NO 168
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 168
acactgacga catggttcta catggatgcc cctgaccaaa aa              42

<210> SEQ ID NO 169
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 169
tacggtagca gagacttggt ctgcttttcc tagggcttgg gt              42

<210> SEQ ID NO 170

```
<210> SEQ ID NO 170
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 170
acactgacga catggttcta catctagcag ctcaagcaaa cac           43

<210> SEQ ID NO 171
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 171
tacggtagca gagacttggt ctccactgga ttctgtgctg tc            42

<210> SEQ ID NO 172
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 172
acactgacga catggttcta cacgcagata gcacttcagc tc            42

<210> SEQ ID NO 173
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 173
tacggtagca gagacttggt ctagaatttt cttagtttca ttcttcctct c  51

<210> SEQ ID NO 174
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 174
acactgacga catggttcta cagcagcttc tgccatctct ct            42

<210> SEQ ID NO 175
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 175
tacggtagca gagacttggt ctccgtctac tcccacgttc t             41

<210> SEQ ID NO 176
<211> LENGTH: 52
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 176
acactgacga catggttcta catgctgcat atttcagata tttctttcct ta            52

<210> SEQ ID NO 177
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 177
tacggtagca gagacttggt ctatgaaaac acaacatgaa tataaacatc aat           53

<210> SEQ ID NO 178
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 178
acactgacga catggttcta caatctgtct tttggttttt cttgatagt                49

<210> SEQ ID NO 179
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 179
tacggtagca gagacttggt ctaatagttg ttttagaaga tatttgcaag c             51

<210> SEQ ID NO 180
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 180
acactgacga catggttcta catatatcac ttttaaactt ttcttttagt tgtgc         55

<210> SEQ ID NO 181
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 181
tacggtagca gagacttggt ctcgataatc tggatgactc attattgtt                49

<210> SEQ ID NO 182
<211> LENGTH: 51
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 182
acactgacga catggttcta cattcttatt ctgaggttat cttttacca c            51

<210> SEQ ID NO 183
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 183
tacggtagca gagacttggt ctcattacac cagttcgtcc ct                     42

<210> SEQ ID NO 184
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 184
acactgacga catggttcta catgaccaat ggctaagtga agatga                 46

<210> SEQ ID NO 185
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 185
tacggtagca gagacttggt ctccaggaag aggaaggaa aaaca                   45

<210> SEQ ID NO 186
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 186
acactgacga catggttcta catcttaaat ggctacgacc cag                    43

<210> SEQ ID NO 187
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 187
tacggtagca gagacttggt ctccagatga ttctttaaca ggtagc                 46

<210> SEQ ID NO 188
<211> LENGTH: 40
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 188
acactgacga catggttcta cagtcagagg cgctatgtgt                          40

<210> SEQ ID NO 189
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 189
tacggtagca gagacttggt ctagatatgg ttaagaaaac tgttcca                  47

<210> SEQ ID NO 190
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 190
acactgacga catggttcta catgacagtt tgacagttaa aggcat                   46

<210> SEQ ID NO 191
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 191
tacggtagca gagacttggt ctcacacaca ggtaacggct ga                       42

<210> SEQ ID NO 192
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 192
acactgacga catggttcta catgtggtct gccagctaaa gg                       42

<210> SEQ ID NO 193
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 193
tacggtagca gagacttggt ctcccaatga aagtaaagta caaacc                   46

<210> SEQ ID NO 194
<211> LENGTH: 44
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 194
acactgacga catggttcta catccacaaa cagaacaaga tgct                           44

<210> SEQ ID NO 195
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 195
tacggtagca gagacttggt ctggccttttt ccttcaaaca ggatt                         45

<210> SEQ ID NO 196
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 196
acactgacga catggttcta cagcaacaga taactcagat tgcctt                         46

<210> SEQ ID NO 197
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 197
tacggtagca gagacttggt ctgtttcctc tggtcctggt atga                           44

<210> SEQ ID NO 198
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 198
acactgacga catggttcta caggacaaaa tgtttcactt ttgggtaa                       48

<210> SEQ ID NO 199
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 199
tacggtagca gagacttggt ctactagata ttccttgtca ttatctgcac                     50

<210> SEQ ID NO 200
<211> LENGTH: 49
<212> TYPE: DNA
<213> ORGANISM: Artificial Sequence
<220> FEATURE:
<223> OTHER INFORMATION: Description of Artificial Sequence: Synthetic -continued

```
      primer

<400> SEQUENCE: 200
acactgacga catggttcta cacctcagaa aaagtagaaa atggaagtc                    49

<210> SEQ ID NO 201
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 201
tacggtagca gagacttggt ctacaagtca acaaccccca ca                          42

<210> SEQ ID NO 202
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 202
acactgacga catggttcta cagatgagtc atatttgtgg gttttca                     47

<210> SEQ ID NO 203
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 203
tacggtagca gagacttggt ctggatcaga gtcagtggt                              39

<210> SEQ ID NO 204
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 204
acactgacga catggttcta cagtagagga gccgtcaaat cca                         43

<210> SEQ ID NO 205
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 205
tacggtagca gagacttggt cttcatggtg ttttatccct cttga                       45

<210> SEQ ID NO 206
<211> LENGTH: 43
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 206
acactgacga catggttcta caggtttctg ctttgggaca acc　　　　　　　　　　　43

<210> SEQ ID NO 207
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 207
tacggtagca gagacttggt ctcctcacgg aggcattcta aag　　　　　　　　　　　43

<210> SEQ ID NO 208
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 208
acactgacga catggttcta cagtagaatg tttactacca aatggaatg　　　　　　　　49

<210> SEQ ID NO 209
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 209
tacggtagca gagacttggt ctcacaaagt cgtcttgttt catca　　　　　　　　　　45

<210> SEQ ID NO 210
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 210
acactgacga catggttcta cagcaagaaa atacccccctc ca　　　　　　　　　　　42

<210> SEQ ID NO 211
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 211
tacggtagca gagacttggt ctgatctttt cttcacggtt gcc　　　　　　　　　　　43

<210> SEQ ID NO 212
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 212
acactgacga catggttcta cagacgactt tgtgaccttc gg                42

<210> SEQ ID NO 213
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 213
tacggtagca gagacttggt cttttagaaa gggacaacag ttaagc           46

<210> SEQ ID NO 214
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 214
acactgacga catggttcta catgttcatg ctgtgtatgt aatagaa          47

<210> SEQ ID NO 215
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 215
tacggtagca gagacttggt ctacatacat tgctctacta tgaggtga         48

<210> SEQ ID NO 216
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 216
acactgacga catggttcta cattctgaac gtttgtaaag aagctgt          47

<210> SEQ ID NO 217
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 217
tacggtagca gagacttggt ctgattagag tagattagtc attttcttac ctt   53

<210> SEQ ID NO 218
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 218
acactgacga catggttcta caccagaatt gccaaagcac a                41

<210> SEQ ID NO 219
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 219
tacggtagca gagacttggt ctatttagca ctcaactata tcttgtcag               49

<210> SEQ ID NO 220
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 220
acactgacga catggttcta caccccttgaa aaatgaaaga gagatggt               48

<210> SEQ ID NO 221
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 221
tacggtagca gagacttggt ctcagaggat agcaacatac ttcgag                  46

<210> SEQ ID NO 222
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 222
acactgacga catggttcta caccatgact gtgtaccaga ac                      42

<210> SEQ ID NO 223
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 223
tacggtagca gagacttggt ctaacttgtt actcaccta tactgact                 48

<210> SEQ ID NO 224
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 224
acactgacga catggttcta catgaaaaac cttacaggaa atggc    45

<210> SEQ ID NO 225
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 225
tacggtagca gagacttggt ctgtggaaat gcgtctggaa taaga    45

<210> SEQ ID NO 226
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 226
acactgacga catggttcta cagcctttat tctcaactgc caa    43

<210> SEQ ID NO 227
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 227
tacggtagca gagacttggt ctagcatcag catttgactt tacct    45

<210> SEQ ID NO 228
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 228
acactgacga catggttcta catctacaaa atccctttgg gt    42

<210> SEQ ID NO 229
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 229
tacggtagca gagacttggt ctgaaaacat actacaggtc aacaga    46

<210> SEQ ID NO 230
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 230
acactgacga catggttcta catcgagtgt gtgcatatgt gt    42

<210> SEQ ID NO 231
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 231
tacggtagca gagacttggt ctactgctaa acactaatat aacctttgga          50

<210> SEQ ID NO 232
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 232
acactgacga catggttcta caattttaca taggtggaat gaatggctga          50

<210> SEQ ID NO 233
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 233
tacggtagca gagacttggt ctatcagcgg tataatcagg agtttttaaa gg        52

<210> SEQ ID NO 234
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 234
acactgacga catggttcta cagggaagaa aagtgttttg aaatgtgt            48

<210> SEQ ID NO 235
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 235
tacggtagca gagacttggt ctacaccaat agggttcagc aaa                 43

<210> SEQ ID NO 236
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 236
acactgacga catggttcta catctttggc cagtacctca tgg                 43

<210> SEQ ID NO 237
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 237
tacggtagca gagacttggt ctcacactgc tgaaccagtc aa                           42

<210> SEQ ID NO 238
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 238
acactgacga catggttcta catggcagtc aaaccttctc tctt                         44

<210> SEQ ID NO 239
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 239
tacggtagca gagacttggt ctaccagtcc tgcgtgggaa                              40

<210> SEQ ID NO 240
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 240
acactgacga catggttcta cagactggtt cagcagtgtg gt                           42

<210> SEQ ID NO 241
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 241
tacggtagca gagacttggt ctgccagtaa aatatatgga tccttttcca                   50

<210> SEQ ID NO 242
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 242
acactgacga catggttcta catgcttttt ctgtaaatca tctgtgaa                     48

```
<210> SEQ ID NO 243
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 243
tacggtagca gagacttggt ctgtagaaat tgctttgagc tgttctt                47

<210> SEQ ID NO 244
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 244
acactgacga catggttcta catcaacctt ttgaacagca tgcaa                  45

<210> SEQ ID NO 245
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 245
tacggtagca gagacttggt ctgagagaaa acaatttaag tgacatacca             50

<210> SEQ ID NO 246
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 246
acactgacga catggttcta caggcagtgt tttagatggc tca                    43

<210> SEQ ID NO 247
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 247
tacggtagca gagacttggt ctccaagcac cgaacagcaa aa                     42

<210> SEQ ID NO 248
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 248
acactgacga catggttcta cattctcata cacagatgta ttgcttgg               48

<210> SEQ ID NO 249
```

<210> SEQ ID NO 249
<211> LENGTH: 53
<212> TYPE: DNA
<213> ORGANISM: Artificial Sequence
<220> FEATURE:
<223> OTHER INFORMATION: Description of Artificial Sequence: Synthetic primer

<400> SEQUENCE: 249
tacggtagca gagacttggt ctacctgtac tagctgaatt aaatactgag aaa    53

<210> SEQ ID NO 250
<211> LENGTH: 41
<212> TYPE: DNA
<213> ORGANISM: Artificial Sequence
<220> FEATURE:
<223> OTHER INFORMATION: Description of Artificial Sequence: Synthetic primer

<400> SEQUENCE: 250
acactgacga catggttcta catcggccat gcagaaactg a    41

<210> SEQ ID NO 251
<211> LENGTH: 56
<212> TYPE: DNA
<213> ORGANISM: Artificial Sequence
<220> FEATURE:
<223> OTHER INFORMATION: Description of Artificial Sequence: Synthetic primer

<400> SEQUENCE: 251
tacggtagca gagacttggt ctaccttaag aatttaatgg gaaataatt agactt    56

<210> SEQ ID NO 252
<211> LENGTH: 52
<212> TYPE: DNA
<213> ORGANISM: Artificial Sequence
<220> FEATURE:
<223> OTHER INFORMATION: Description of Artificial Sequence: Synthetic primer

<400> SEQUENCE: 252
acactgacga catggttcta caatgagtgt ttaaattgtt tagcaaagat ta    52

<210> SEQ ID NO 253
<211> LENGTH: 41
<212> TYPE: DNA
<213> ORGANISM: Artificial Sequence
<220> FEATURE:
<223> OTHER INFORMATION: Description of Artificial Sequence: Synthetic primer

<400> SEQUENCE: 253
tacggtagca gagacttggt ctgcctcgac ttgcctattc a    41

<210> SEQ ID NO 254
<211> LENGTH: 41
<212> TYPE: DNA
<213> ORGANISM: Artificial Sequence
<220> FEATURE:
<223> OTHER INFORMATION: Description of Artificial Sequence: Synthetic primer

<400> SEQUENCE: 254
acactgacga catggttcta caccagaggt ttggcctgct t    41

<210> SEQ ID NO 255
<211> LENGTH: 52

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 255
tacggtagca gagacttggt ctgaaaagag tctcaaacac aaactagagt ca           52

<210> SEQ ID NO 256
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 256
acactgacga catggttcta catgtgagaa agagattagc agttagtt               48

<210> SEQ ID NO 257
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 257
tacggtagca gagacttggt ctcaatgaaa cccccaagaa agt                    43

<210> SEQ ID NO 258
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 258
acactgacga catggttcta catcagggta aaataataat aaagcaaagg t           51

<210> SEQ ID NO 259
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 259
tacggtagca gagacttggt ctactcttcc ttaccatccc cat                    43

<210> SEQ ID NO 260
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 260
acactgacga catggttcta caggccactg tggttgaatt gg                     42

<210> SEQ ID NO 261
<211> LENGTH: 47
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 261
tacggtagca gagacttggt ctggctttca gtagttttca tggttca                    47

<210> SEQ ID NO 262
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 262
acactgacga catggttcta catgatggcg tgatccccaa at                         42

<210> SEQ ID NO 263
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 263
tacggtagca gagacttggt ctactttcaa catacaggtt gcctt                      45

<210> SEQ ID NO 264
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 264
acactgacga catggttcta cactaataaa atactcatgt tttagcctgt t               51

<210> SEQ ID NO 265
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 265
tacggtagca gagacttggt ctttcaagcc gcctttgc                              38

<210> SEQ ID NO 266
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 266
acactgacga catggttcta catgtgggac ttattgaggt ggtg                       44

<210> SEQ ID NO 267
<211> LENGTH: 43
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 267
tacggtagca gagacttggt ctacacaaac accgacagac tca                        43

<210> SEQ ID NO 268
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 268
acactgacga catggttcta catctcaagt tggcctgaat cact                       44

<210> SEQ ID NO 269
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 269
tacggtagca gagacttggt ctccaaaaca ttttaaacag agaaaacca                  49

<210> SEQ ID NO 270
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 270
acactgacga catggttcta catgctccaa actgaccaaa ctg                        43

<210> SEQ ID NO 271
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 271
tacggtagca gagacttggt ctgctagggt ctttcgaatg tatgc                      45

<210> SEQ ID NO 272
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 272
acactgacga catggttcta cagccaacgc cacaaccac                             39

<210> SEQ ID NO 273
<211> LENGTH: 40
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 273
tacggtagca gagacttggt ctggcgagac acgcccttac                              40

<210> SEQ ID NO 274
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 274
acactgacga catggttcta cacctggacc ttgagggatt g                            41

<210> SEQ ID NO 275
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 275
tacggtagca gagacttggt cttcccaagg accacctcac a                            41

<210> SEQ ID NO 276
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 276
acactgacga catggttcta cacgcagttg ggcacttttg                              40

<210> SEQ ID NO 277
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 277
tacggtagca gagacttggt ctcccaggcc tttctccact ta                           42

<210> SEQ ID NO 278
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 278
acactgacga catggttcta caggctccct ggacccattt ta                           42

<210> SEQ ID NO 279
<211> LENGTH: 46
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 279
tacggtagca gagacttggt ctactgctaa ggcataggaa ttttcg    46

<210> SEQ ID NO 280
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 280
acactgacga catggttcta cacagtggag cgaattcctt t    41

<210> SEQ ID NO 281
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 281
tacggtagca gagacttggt ctgggagcca tcggaactg    39

<210> SEQ ID NO 282
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 282
acactgacga catggttcta catgctcacc gcagttccat tc    42

<210> SEQ ID NO 283
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 283
tacggtagca gagacttggt ctcccccata ggagctggag    40

<210> SEQ ID NO 284
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 284
acactgacga catggttcta cagggaaagg gcgtcatcag tt    42

<210> SEQ ID NO 285
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 285
tacggtagca gagacttggt ctagcaagtg aaggaagaga ggg                          43

<210> SEQ ID NO 286
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 286
acactgacga catggttcta catgatccta ccctcactct tca                          43

<210> SEQ ID NO 287
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 287
tacggtagca gagacttggt ctccagggag gctgct                                  36

<210> SEQ ID NO 288
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 288
acactgacga catggttcta cagtgtggcg ctgagtgtac tt                           42

<210> SEQ ID NO 289
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 289
tacggtagca gagacttggt ctaggtggca ccaaagctgt at                           42

<210> SEQ ID NO 290
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 290
acactgacga catggttcta caccataggt ctgccgcaaa ttc                          43

<210> SEQ ID NO 291
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 291
tacggtagca gagacttggt ctgacagagc gggacaagga tg                          42

<210> SEQ ID NO 292
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 292
acactgacga catggttcta cacctggtgc caccgtcatc                             40

<210> SEQ ID NO 293
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 293
tacggtagca gagacttggt ctcagcagcc gagaacaag                              39

<210> SEQ ID NO 294
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 294
acactgacga catggttcta cagtggatcc ctagctattc ttaatcca                    48

<210> SEQ ID NO 295
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 295
tacggtagca gagacttggt ctaacctgtg actcaccccc ta                          42

<210> SEQ ID NO 296
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 296
acactgacga catggttcta cactcactct ccataaatgc tacga                       45

<210> SEQ ID NO 297
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 297
```
tacggtagca gagacttggt ctgtgtgaag gagtcactga aaca                          44

<210> SEQ ID NO 298
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 298
acactgacga catggttcta catgcttgta taaagaaaaa caaaatctgc                    50

<210> SEQ ID NO 299
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 299
tacggtagca gagacttggt ctctctctaa aacactgatt tccca                         45

<210> SEQ ID NO 300
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 300
acactgacga catggttcta cagtccctga gagtctagag taatgt                        46

<210> SEQ ID NO 301
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 301
tacggtagca gagacttggt ctaccaggct ttggctgtg                                39

<210> SEQ ID NO 302
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 302
acactgacga catggttcta caaagttttc agggatacat tgtttttat                     49

<210> SEQ ID NO 303
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 303
tacggtagca gagacttggt ctacagtttt ttccagttta ttgtatttgc            50

<210> SEQ ID NO 304
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 304
acactgacga catggttcta catccttggg attacgctcc ct                    42

<210> SEQ ID NO 305
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 305
tacggtagca gagacttggt ctggacccat tagaaccaac tcca                  44

<210> SEQ ID NO 306
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 306
acactgacga catggttcta catctcctcc ggcccctc                         38

<210> SEQ ID NO 307
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 307
tacggtagca gagacttggt ctaacctcct acccctccag aa                    42

<210> SEQ ID NO 308
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 308
acactgacga catggttcta catctcttgc cggaatgtca gc                    42

<210> SEQ ID NO 309
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 309
tacggtagca gagacttggt ctcccccacag aaaaccca                        38

<210> SEQ ID NO 310
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 310
acactgacga catggttcta cattgaagag gtgatttgtg ttcctg        46

<210> SEQ ID NO 311
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 311
tacggtagca gagacttggt ctgacgtgga tagcagcaag gg            42

<210> SEQ ID NO 312
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 312
acactgacga catggttcta cacttccatt ttgaaagaga aaagaaagag    50

<210> SEQ ID NO 313
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 313
tacggtagca gagacttggt ctggcgtctg cgtacttcca              40

<210> SEQ ID NO 314
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 314
acactgacga catggttcta cattgacggc ccccac                  36

<210> SEQ ID NO 315
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 315
tacggtagca gagacttggt cttgccggaa aacttgggag a            41

<210> SEQ ID NO 316
<211> LENGTH: 52
<212> TYPE: DNA
<213> ORGANISM: Artificial Sequence
<220> FEATURE:
<223> OTHER INFORMATION: Description of Artificial Sequence: Synthetic primer

<400> SEQUENCE: 316
acactgacga catggttcta caaaaatgtt agtggtcatt tttctaatgt ct        52

<210> SEQ ID NO 317
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 317
tacggtagca gagacttggt ctagtgtcag gactttattt gaagca              46

<210> SEQ ID NO 318
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 318
acactgacga catggttcta catgtacttg tccatctttc tccag               45

<210> SEQ ID NO 319
<211> LENGTH: 42
<212> TYPE: DNA
<213> ORGANISM: Artificial Sequence
<220> FEATURE:
<223> OTHER INFORMATION: Description of Artificial Sequence: Synthetic primer

<400> SEQUENCE: 319
tacggtagca gagacttggt ctcccaaccc agctgaaact ct                  42

<210> SEQ ID NO 320
<211> LENGTH: 42
<212> TYPE: DNA
<213> ORGANISM: Artificial Sequence
<220> FEATURE:
<223> OTHER INFORMATION: Description of Artificial Sequence: Synthetic primer

<400> SEQUENCE: 320
acactgacga catggttcta cataatgatg gcagcgtgtc cc                  42

<210> SEQ ID NO 321
<211> LENGTH: 42
<212> TYPE: DNA
<213> ORGANISM: Artificial Sequence
<220> FEATURE:
<223> OTHER INFORMATION: Description of Artificial Sequence: Synthetic primer

<400> SEQUENCE: 321
tacggtagca gagacttggt ctgggaacag acacgtgaag gc                  42

```
<210> SEQ ID NO 322
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 322
acactgacga catggttcta catgccaaag aagtagaatg agaaaaatg              49

<210> SEQ ID NO 323
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 323
tacggtagca gagacttggt ctaggacagt cagaaatgca gga                    43

<210> SEQ ID NO 324
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 324
acactgacga catggttcta caggaaaagt gtgcctggta ggg                    43

<210> SEQ ID NO 325
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 325
tacggtagca gagacttggt ctggaggaac aaggaagggt g                      41

<210> SEQ ID NO 326
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 326
acactgacga catggttcta cagctacata gtgtctcact ttccaa                 46

<210> SEQ ID NO 327
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 327
tacggtagca gagacttggt ctgatcccca gggccacca                         39

<210> SEQ ID NO 328
```

-continued

```
<210> SEQ ID NO 328
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 328
acactgacga catggttcta cagccctcct cttgctgct                               39

<210> SEQ ID NO 329
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 329
tacggtagca gagacttggt ctgtatctaa catacacaac tgctaatgg                    49

<210> SEQ ID NO 330
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 330
acactgacga catggttcta catggtgagg gctgaggtg                               39

<210> SEQ ID NO 331
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 331
tacggtagca gagacttggt ctcctgtgcc agggacctta c                            41

<210> SEQ ID NO 332
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 332
acactgacga catggttcta catcacaatt gccagttaac gtct                         44

<210> SEQ ID NO 333
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 333
tacggtagca gagacttggt ctccacacag caaagcagaa ac                           42

<210> SEQ ID NO 334
<211> LENGTH: 41
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 334
acactgacga catggttcta cagcgtcttc acctggaagg g                           41

<210> SEQ ID NO 335
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 335
tacggtagca gagacttggt ctccggacat agtccaggag g                           41

<210> SEQ ID NO 336
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 336
acactgacga catggttcta cagcgtggac aaccccac                               39

<210> SEQ ID NO 337
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 337
tacggtagca gagacttggt ctggctcctt atctcccctc c                           41

<210> SEQ ID NO 338
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 338
acactgacga catggttcta caggatgcag agcttcttcc ca                          42

<210> SEQ ID NO 339
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 339
tacggtagca gagacttggt ctttctcttc cgcacccag                              39

<210> SEQ ID NO 340
<211> LENGTH: 44
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 340
acactgacga catggttcta caggtcttct ctgtttcagg gcat                    44

<210> SEQ ID NO 341
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 341
tacggtagca gagacttggt ctgctgacct aaagccacct cc                      42

<210> SEQ ID NO 342
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 342
acactgacga catggttcta cagtgtcact cgtaattagg tcca                    44

<210> SEQ ID NO 343
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 343
tacggtagca gagacttggt ctggcctcag tacaaactca ttagc                   45

<210> SEQ ID NO 344
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 344
acactgacga catggttcta catgttcatt catgatccca ctgc                    44

<210> SEQ ID NO 345
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 345
tacggtagca gagacttggt ctccaccagt cactcacact tg                      42

<210> SEQ ID NO 346
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 346
acactgacga catggttcta catccctgcc agcgagat                                    38

<210> SEQ ID NO 347
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 347
tacggtagca gagacttggt ctagggatgc aaaggcctca                                  40

<210> SEQ ID NO 348
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 348
acactgacga catggttcta cagccttctt taagcaatgc catctttat                        49

<210> SEQ ID NO 349
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 349
tacggtagca gagacttggt ctcaatggaa gcacagactg caa                              43

<210> SEQ ID NO 350
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 350
acactgacga catggttcta cacccctgct cctatagcca a                                41

<210> SEQ ID NO 351
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 351
tacggtagca gagacttggt ctatgaggta ctcgtcggca tc                               42

<210> SEQ ID NO 352
<211> LENGTH: 40
<212> TYPE: DNA
<213> ORGANISM: Artificial Sequence
<220> FEATURE:

<223> OTHER INFORMATION: Description of Artificial Sequence: Synthetic
       primer

<400> SEQUENCE: 352
acactgacga catggttcta caacttctac cgtgccctga                               40

<210> SEQ ID NO 353
<211> LENGTH: 45
<212> TYPE: DNA
<213> ORGANISM: Artificial Sequence
<220> FEATURE:
<223> OTHER INFORMATION: Description of Artificial Sequence: Synthetic
       primer

<400> SEQUENCE: 353
tacggtagca gagacttggt ctgttcaaat gagtagacac agctt                         45

<210> SEQ ID NO 354
<211> LENGTH: 41
<212> TYPE: DNA
<213> ORGANISM: Artificial Sequence
<220> FEATURE:
<223> OTHER INFORMATION: Description of Artificial Sequence: Synthetic
       primer

<400> SEQUENCE: 354
acactgacga catggttcta catacccctcc atgaggcaca c                            41

<210> SEQ ID NO 355
<211> LENGTH: 44
<212> TYPE: DNA
<213> ORGANISM: Artificial Sequence
<220> FEATURE:
<223> OTHER INFORMATION: Description of Artificial Sequence: Synthetic
       primer

<400> SEQUENCE: 355
tacggtagca gagacttggt ctggagagct gtaaattctg gctt                          44

<210> SEQ ID NO 356
<211> LENGTH: 42
<212> TYPE: DNA
<213> ORGANISM: Artificial Sequence
<220> FEATURE:
<223> OTHER INFORMATION: Description of Artificial Sequence: Synthetic
       primer

<400> SEQUENCE: 356
acactgacga catggttcta caccctgacc ggagtaacct tc                            42

<210> SEQ ID NO 357
<211> LENGTH: 42
<212> TYPE: DNA
<213> ORGANISM: Artificial Sequence
<220> FEATURE:
<223> OTHER INFORMATION: Description of Artificial Sequence: Synthetic
       primer

<400> SEQUENCE: 357
tacggtagca gagacttggt ctaggagcag gactgtttcc ag                            42

<210> SEQ ID NO 358
<211> LENGTH: 42
<212> TYPE: DNA
<213> ORGANISM: Artificial Sequence
<220> FEATURE:
<223> OTHER INFORMATION: Description of Artificial Sequence: Synthetic

```
primer

<400> SEQUENCE: 358
acactgacga catggttcta cagacgacac cttcctccca gt                           42

<210> SEQ ID NO 359
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 359
tacggtagca gagacttggt ctgcaggctc ggtcatgtgt tta                          43

<210> SEQ ID NO 360
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 360
acactgacga catggttcta catgttgagg acattcacag ggt                          43

<210> SEQ ID NO 361
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 361
tacggtagca gagacttggt ctggtcctgg tagtgtgggt ct                           42

<210> SEQ ID NO 362
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 362
acactgacga catggttcta cagctctgtg cagaatcctg tct                          43

<210> SEQ ID NO 363
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 363
tacggtagca gagacttggt ctttggtggc tgcctttctg g                            41

<210> SEQ ID NO 364
<211> LENGTH: 43
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 364
acactgacga catggttcta cagcaacccc gagtatctca aca         43

<210> SEQ ID NO 365
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 365
tacggtagca gagacttggt ctgcgcgacc cttaggtatt ct          42

<210> SEQ ID NO 366
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 366
acactgacga catggttcta catgtcaaca gcacattcga cag         43

<210> SEQ ID NO 367
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 367
tacggtagca gagacttggt ctggtcctgg gtatcgaaag agt         43

<210> SEQ ID NO 368
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 368
acactgacga catggttcta cagacccaaa acccaaaatg gc          42

<210> SEQ ID NO 369
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 369
tacggtagca gagacttggt ctccctgctt ctgtctccta c           41

<210> SEQ ID NO 370
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 370
acactgacga catggttcta caggaatcct atggctttcc aacc          44

<210> SEQ ID NO 371
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 371
tacggtagca gagacttggt ctcccctcc tctgttgctg                40

<210> SEQ ID NO 372
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 372
acactgacga catggttcta catctgtatc aggcaaagtc atagaa        46

<210> SEQ ID NO 373
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 373
tacggtagca gagacttggt ctgcctcaaa gacaatggct cc            42

<210> SEQ ID NO 374
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 374
acactgacga catggttcta cagaaaacgg cattttgagt gt            42

<210> SEQ ID NO 375
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 375
tacggtagca gagacttggt ctaagggtgc agttatgcct ca            42

<210> SEQ ID NO 376
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 376
acactgacga catggttcta cactggtgtt gttgggcagt                       40

<210> SEQ ID NO 377
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 377
tacggtagca gagacttggt ctatctccgc aagaaagggg ag                    42

<210> SEQ ID NO 378
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 378
acactgacga catggttcta catgtcctgc ttgcttacct cg                    42

<210> SEQ ID NO 379
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 379
tacggtagca gagacttggt ctgcctcttg cttctctttt cct                   43

<210> SEQ ID NO 380
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 380
acactgacga catggttcta caggggtcag aggcaagcag                       40

<210> SEQ ID NO 381
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 381
tacggtagca gagacttggt cttgggcctg tgttatctcc                       40

<210> SEQ ID NO 382
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 382
acactgacga catggttcta cagagaaagc cccctactg c            41

<210> SEQ ID NO 383
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 383
tacggtagca gagacttggt ctagcatctt atccgagtgg aagg           44

<210> SEQ ID NO 384
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 384
acactgacga catggttcta catccaaata ctccacacgc aaa            43

<210> SEQ ID NO 385
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 385
tacggtagca gagacttggt ctgctgcccc caccatgag               39

<210> SEQ ID NO 386
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 386
acactgacga catggttcta cagctgctca ccatcgcta               39

<210> SEQ ID NO 387
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 387
tacggtagca gagacttggt ctccaactgg ccaagacct               39

<210> SEQ ID NO 388
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 388
acactgacga catggttcta catgtgctgt gactgcttgt ag            42

<210> SEQ ID NO 389
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 389
tacggtagca gagacttggt ctgccctgac tttcaactct gt                           42

<210> SEQ ID NO 390
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 390
acactgacga catggttcta catacggcca ggcattgaag t                            41

<210> SEQ ID NO 391
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 391
tacggtagca gagacttggt ctcctcctgg ccctgtc                                 38

<210> SEQ ID NO 392
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 392
acactgacga catggttcta caggaaaccg tagctgccct g                            41

<210> SEQ ID NO 393
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 393
tacggtagca gagacttggt ctaagaccca ggtccagatg aa                           42

<210> SEQ ID NO 394
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 394
acactgacga catggttcta catttcgctt cccacaggtc tc                           42

<210> SEQ ID NO 395
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 395
tacggtagca gagacttggt ctcagccaga ctgccttccg                          40

<210> SEQ ID NO 396
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 396
acactgacga catggttcta caatatttag tagccaggac agtagaag                 48

<210> SEQ ID NO 397
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 397
tacggtagca gagacttggt ctctctacca gtgccaggag c                        41

<210> SEQ ID NO 398
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 398
acactgacga catggttcta caatctgggg tatcaggtag gtgtc                    45

<210> SEQ ID NO 399
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 399
tacggtagca gagacttggt ctcctggagt cgattgatta gagcc                    45

<210> SEQ ID NO 400
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 400
acactgacga catggttcta caaaggaccc catatagcac aggta                    45

```
<210> SEQ ID NO 401
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 401
tacggtagca gagacttggt ctacactttg aatgctcttt ccttcc            46

<210> SEQ ID NO 402
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 402
acactgacga catggttcta caggtgccag tcttgctcac ag                42

<210> SEQ ID NO 403
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 403
tacggtagca gagacttggt ctgtagaggg cctgggttaa gtatg             45

<210> SEQ ID NO 404
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 404
acactgacga catggttcta catcaacttg agggagggag cttta             45

<210> SEQ ID NO 405
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 405
tacggtagca gagacttggt ctatatgacg tgtctgctcc acttc             45

<210> SEQ ID NO 406
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 406
acactgacga catggttcta cagaaagtgg tgcattgatg gaagg             45

<210> SEQ ID NO 407
```

-continued

```
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 407
tacggtagca gagacttggt ctaagagcac gttcttctgc tgtat            45

<210> SEQ ID NO 408
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 408
acactgacga catggttcta catgcaattc tgaggtgtta aaggga           46

<210> SEQ ID NO 409
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 409
tacggtagca gagacttggt ctggacagca cttcctgatt ttgtt            45

<210> SEQ ID NO 410
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 410
acactgacga catggttcta cacgcctcat gtggttttat gcag             44

<210> SEQ ID NO 411
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 411
tacggtagca gagacttggt ctactagtat tctgagctgt gtgc             44

<210> SEQ ID NO 412
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 412
acactgacga catggttcta catacctaca taaaactctt tccagaatgt       50

<210> SEQ ID NO 413
<211> LENGTH: 45
```

<212> TYPE: DNA
<213> ORGANISM: Artificial Sequence
<220> FEATURE:
<223> OTHER INFORMATION: Description of Artificial Sequence: Synthetic
      primer

<400> SEQUENCE: 413
tacggtagca gagacttggt ctgcaatgga agaaagtgtg agcag                45

<210> SEQ ID NO 414
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 414
acactgacga catggttcta catgttaagt cttagtcatt agggagatac a          51

<210> SEQ ID NO 415
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 415
tacggtagca gagacttggt ctagagtcca gctgctgctc ata                  43

<210> SEQ ID NO 416
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 416
acactgacga catggttcta caaagctgtc aattctggct tctcc                45

<210> SEQ ID NO 417
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 417
tacggtagca gagacttggt ctcaacctct gcattgaaag ttccc                45

<210> SEQ ID NO 418
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 418
acactgacga catggttcta catgcattat acccagcagt atcag                45

<210> SEQ ID NO 419
<211> LENGTH: 44
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 419
tacggtagca gagacttggt ctaaccccctt acctggaatc tgga                    44

<210> SEQ ID NO 420
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 420
acactgacga catggttcta catcaatgca gaggttgaag atggt                    45

<210> SEQ ID NO 421
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 421
tacggtagca gagacttggt ctactttgta attcaacatt catcgttgtg               50

<210> SEQ ID NO 422
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 422
acactgacga catggttcta catgtaggat tcagagtaaa atcaaagtgt               50

<210> SEQ ID NO 423
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 423
tacggtagca gagacttggt cttgctctgg gagtcttcag aataga                   46

<210> SEQ ID NO 424
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 424
acactgacga catggttcta cagtgtttgt tccaatacag cagatga                  47

<210> SEQ ID NO 425
<211> LENGTH: 43
<212> TYPE: DNA
<213> ORGANISM: Artificial Sequence
```

<220> FEATURE:
<223> OTHER INFORMATION: Description of Artificial Sequence: Synthetic
      primer

<400> SEQUENCE: 425
tacggtagca gagacttggt cttacatgca cagttgctct ggg            43

<210> SEQ ID NO 426
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 426
acactgacga catggttcta catcctcttg agatgggtag tttctat        47

<210> SEQ ID NO 427
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 427
tacggtagca gagacttggt ctctgcccag caagtatgat ttgtc          45

<210> SEQ ID NO 428
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 428
acactgacga catggttcta catgtgcatg taccacctat catctaa        47

<210> SEQ ID NO 429
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 429
tacggtagca gagacttggt ctgggctctt ttttgccagt cattt          45

<210> SEQ ID NO 430
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 430
acactgacga catggttcta cagatgtcag ataccacagc atctt          45

<210> SEQ ID NO 431
<211> LENGTH: 49
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 431
tacggtagca gagacttggt cttgttttct cattccattt aaagcagta                    49

<210> SEQ ID NO 432
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 432
acactgacga catggttcta cagccagaac caccatcttt cagta                        45

<210> SEQ ID NO 433
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 433
tacggtagca gagacttggt cttttttgaa cagtacccgt tccct                        45

<210> SEQ ID NO 434
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 434
acactgacga catggttcta cagggaagga aagaattttg cttaagat                     48

<210> SEQ ID NO 435
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 435
tacggtagca gagacttggt ctgataaagc tccagcagga aatgg                        45

<210> SEQ ID NO 436
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 436
acactgacga catggttcta cagttagaag gctggctccc                              40

<210> SEQ ID NO 437
<211> LENGTH: 50
<212> TYPE: DNA
<213> ORGANISM: Artificial Sequence
<220> FEATURE:
<223> OTHER INFORMATION: Description of Artificial Sequence: Synthetic
```

```
primer

<400> SEQUENCE: 437
tacggtagca gagacttggt cttggaaagc ttctcaaagt atttcatttt            50

<210> SEQ ID NO 438
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 438
acactgacga catggttcta catactgaat gcaaaggaca ccaca                 45

<210> SEQ ID NO 439
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 439
tacggtagca gagacttggt ctcagcaagt tgcagcgttt atagt                 45

<210> SEQ ID NO 440
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 440
acactgacga catggttcta cagtaaaatg tgctccccaa aagca                 45

<210> SEQ ID NO 441
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 441
tacggtagca gagacttggt ctgtctgaaa gccagggagt tgg                   43

<210> SEQ ID NO 442
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 442
acactgacga catggttcta caagtttgaa tccatgcttt gctct                 45

<210> SEQ ID NO 443
<211> LENGTH: 45
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 443
tacggtagca gagacttggt ctcacagtgc agtgaattgg aagac        45

<210> SEQ ID NO 444
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 444
acactgacga catggttcta caggatcctg ggtgtttgta tttgc        45

<210> SEQ ID NO 445
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 445
tacggtagca gagacttggt cttgtctaag aacacagagg agaattta     48

<210> SEQ ID NO 446
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 446
acactgacga catggttcta cagcagaaca ttttgtttcc tcact        45

<210> SEQ ID NO 447
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 447
tacggtagca gagacttggt cttccctgct tccaacactt gttat        45

<210> SEQ ID NO 448
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 448
acactgacga catggttcta catcaatgat aataaattct cctctgtgtt ct    52

<210> SEQ ID NO 449
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 449
tacggtagca gagacttggt ctctagtgag gatgaagagc ttccc        45

<210> SEQ ID NO 450
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 450
acactgacga catggttcta caaccaaata acaagtgttg gaagca       46

<210> SEQ ID NO 451
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 451
tacggtagca gagacttggt ctagtcctag ccctttcacc cata         44

<210> SEQ ID NO 452
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 452
acactgacga catggttcta caacaagtgt tggaagcagg g            41

<210> SEQ ID NO 453
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 453
tacggtagca gagacttggt ctcaggagtc ctagcccttt ca           42

<210> SEQ ID NO 454
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 454
acactgacga catggttcta caagggaagc tcttcatcct cacta        45

<210> SEQ ID NO 455
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 455
tacggtagca gagacttggt cttggtgaaa taaaggaaga tactagtttt g        51

<210> SEQ ID NO 456
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 456
acactgacga catggttcta cactcctttc tggacgcttt tgcta              45

<210> SEQ ID NO 457
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 457
tacggtagca gagacttggt cttcagactg ttaatacaga tttctctcca          50

<210> SEQ ID NO 458
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 458
acactgacga catggttcta cagtctcaga acaaacctga gatgc              45

<210> SEQ ID NO 459
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 459
tacggtagca gagacttggt ctagattagg ggttttgcaa cctga              45

<210> SEQ ID NO 460
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 460
acactgacga catggttcta catcttgctt ttttatttca ggatgctt            48

<210> SEQ ID NO 461
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 461
tacggtagca gagacttggt ctccagtact aatgaagtgg gctcc                45

<210> SEQ ID NO 462
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 462
acactgacga catggttcta catctaagca tagcattcaa ttttggc              47

<210> SEQ ID NO 463
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 463
tacggtagca gagacttggt ctgtgagcac aattagccgt aataaca             47

<210> SEQ ID NO 464
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 464
acactgacga catggttcta cagcattcaa ttttggccct ctgtt                45

<210> SEQ ID NO 465
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 465
tacggtagca gagacttggt cttgggaaat gagaacattc caagtaca             48

<210> SEQ ID NO 466
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 466
acactgacga catggttcta cagttttcat cactggaacc tatttca              47

<210> SEQ ID NO 467
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 467
tacggtagca gagacttggt cttgctagag gaaaactttg aggaaca              47

<210> SEQ ID NO 468
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 468
acactgacga catggttcta caatattgct tgagctggct tcttt                45

<210> SEQ ID NO 469
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 469
tacggtagca gagacttggt cttcgtatac caccactttt tccca                45

<210> SEQ ID NO 470
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 470
acactgacga catggttcta catgtgctca ctgtacttgg aatgt                45

<210> SEQ ID NO 471
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 471
tacggtagca gagacttggt cttctcagtt cagaggcaac gaaac                45

<210> SEQ ID NO 472
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 472
acactgacga catggttcta caagtggtgg tatacgatat gggtt                45

<210> SEQ ID NO 473
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 473
tacggtagca gagacttggt ctagacagtt aatatcactg caggctt               47

<210> SEQ ID NO 474
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 474
acactgacga catggttcta caacaaaacc tagagcctcc tttga          45

<210> SEQ ID NO 475
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 475
tacggtagca gagacttggt ctctgcccac tctgggtcct ta             42

<210> SEQ ID NO 476
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 476
acactgacga catggttcta caactcattc tttccttgat tttcttcct      49

<210> SEQ ID NO 477
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 477
tacggtagca gagacttggt ctagtgaact tgatgctcag tatttgc        47

<210> SEQ ID NO 478
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 478
acactgacga catggttcta catcctcttc tgcatttcct ggatt          45

<210> SEQ ID NO 479
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 479
tacggtagca gagacttggt ctaagtatcc attgggacat gaagtta        47

```
<210> SEQ ID NO 480
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 480
acactgacga catggttcta cacctggatt tgaaaacgga gcaaa            45

<210> SEQ ID NO 481
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 481
tacggtagca gagacttggt ctaaccccaa gggactaatt catgg            45

<210> SEQ ID NO 482
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 482
acactgacga catggttcta catctatgct tgtttcccga ctgtg            45

<210> SEQ ID NO 483
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 483
tacggtagca gagacttggt ctggcactca ggaaagtatc tcgtt            45

<210> SEQ ID NO 484
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 484
acactgacga catggttcta cactgcacac tgactcacac attta            45

<210> SEQ ID NO 485
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 485
tacggtagca gagacttggt ctgctgaaga ccccaaagat ctcat            45

<210> SEQ ID NO 486
```

```
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 486
acactgacga catggttcta cacctgagtg ccataatcag tacca              45

<210> SEQ ID NO 487
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 487
tacggtagca gagacttggt ctcaaatacc agtgaactta agaatttgt c         51

<210> SEQ ID NO 488
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 488
acactgacga catggttcta cattcttctc ttggaaggct aggat              45

<210> SEQ ID NO 489
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 489
tacggtagca gagacttggt cttggaaggt aaagaacctg caact              45

<210> SEQ ID NO 490
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 490
acactgacga catggttcta caaggtgcat ttgttaactt cagctc             46

<210> SEQ ID NO 491
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 491
tacggtagca gagacttggt ctcaaattga tagttgttct agcagtga           48

<210> SEQ ID NO 492
<211> LENGTH: 44
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 492
acactgacga catggttcta catactcttc ttggctccag ttgc            44

<210> SEQ ID NO 493
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 493
tacggtagca gagacttggt ctggaggaag tcttctacca ggcat           45

<210> SEQ ID NO 494
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 494
acactgacga catggttcta caccatgagt tgtaggtttc tgctg           45

<210> SEQ ID NO 495
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 495
tacggtagca gagacttggt ctggaggaag tcttctacca ggcat           45

<210> SEQ ID NO 496
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 496
acactgacga catggttcta caacaactat caatttgcaa ttcagtacaa tta  53

<210> SEQ ID NO 497
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 497
tacggtagca gagacttggt ctagcagcag tataagcaat atgga           45

<210> SEQ ID NO 498
<211> LENGTH: 46
<212> TYPE: DNA
```

<213> ORGANISM: Artificial Sequence
<220> FEATURE:
<223> OTHER INFORMATION: Description of Artificial Sequence: Synthetic primer

<400> SEQUENCE: 498
acactgacga catggttcta catgcaattc agtacaatta ggtggg        46

<210> SEQ ID NO 499
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 499
tacggtagca gagacttggt ctgctttcaa aacgaaagct gaacc        45

<210> SEQ ID NO 500
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 500
acactgacga catggttcta cattttaggt gcttttgaat tgtgga        46

<210> SEQ ID NO 501
<211> LENGTH: 44
<212> TYPE: DNA
<213> ORGANISM: Artificial Sequence
<220> FEATURE:
<223> OTHER INFORMATION: Description of Artificial Sequence: Synthetic primer

<400> SEQUENCE: 501
tacggtagca gagacttggt ctcggagcag aatggtcaag tgat        44

<210> SEQ ID NO 502
<211> LENGTH: 47
<212> TYPE: DNA
<213> ORGANISM: Artificial Sequence
<220> FEATURE:
<223> OTHER INFORMATION: Description of Artificial Sequence: Synthetic primer

<400> SEQUENCE: 502
acactgacga catggttcta catccatatt gcttatactg ctgctta        47

<210> SEQ ID NO 503
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 503
tacggtagca gagacttggt ctagcagaat ggtcaagtga tgaat        45

<210> SEQ ID NO 504
<211> LENGTH: 47
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 504
acactgacga catggttcta cacgagtgat tctattgggt taggatt                47

<210> SEQ ID NO 505
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 505
tacggtagca gagacttggt ctgagaccta catcaggcct tcatc                  45

<210> SEQ ID NO 506
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 506
acactgacga catggttcta caccaaatct gctttcttga taaaatcctc             50

<210> SEQ ID NO 507
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 507
tacggtagca gagacttggt ctccccaact taagccatgt aactga                 46

<210> SEQ ID NO 508
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 508
acactgacga catggttcta caggggacgc tcttgtatta tctgt                  45

<210> SEQ ID NO 509
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 509
tacggtagca gagacttggt ctgtgaaaga gttcactcca aatcagt                47

<210> SEQ ID NO 510
<211> LENGTH: 45
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 510
acactgacga catggttcta caccttcttc cgataggttt tccca                    45

<210> SEQ ID NO 511
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 511
tacggtagca gagacttggt cttgatgggg agtctgaatc aaatg                    45

<210> SEQ ID NO 512
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 512
acactgacga catggttcta catggccagt aagtctattt tctctgaag                49

<210> SEQ ID NO 513
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 513
tacggtagca gagacttggt ctagagatac tgaagatgtt ccttggat                 48

<210> SEQ ID NO 514
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 514
acactgacga catggttcta caccatcatg tgagtcatca gaacct                   46

<210> SEQ ID NO 515
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 515
tacggtagca gagacttggt ctctgatccc ctgtgtgaga gaaaa                    45

<210> SEQ ID NO 516
<211> LENGTH: 48
<212> TYPE: DNA
<213> ORGANISM: Artificial Sequence
<220> FEATURE:
<223> OTHER INFORMATION: Description of Artificial Sequence: Synthetic

```
primer

<400> SEQUENCE: 516
acactgacga catggttcta catgagtcat cagaacctaa cagttcat                        48

<210> SEQ ID NO 517
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 517
tacggtagca gagacttggt ctctgatccc ctgtgtgaga gaaaa                           45

<210> SEQ ID NO 518
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 518
acactgacga catggttcta caccaaggaa catcttcagt atctctagg                       49

<210> SEQ ID NO 519
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 519
tacggtagca gagacttggt ctcagatggg ctggaagtaa ggaaa                           45

<210> SEQ ID NO 520
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 520
acactgacga catggttcta caccattctt ttctctcaca caggg                           45

<210> SEQ ID NO 521
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 521
tacggtagca gagacttggt ctcagcatga gaacagcagt ttatt                           45

<210> SEQ ID NO 522
<211> LENGTH: 46
<212> TYPE: DNA
<213> ORGANISM: Artificial Sequence
<220> FEATURE:
<223> OTHER INFORMATION: Description of Artificial Sequence: Synthetic
      primer
```

-continued

<400> SEQUENCE: 522
acactgacga catggttcta caagccaggc tgtttgcttt tattac                46

<210> SEQ ID NO 523
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 523
tacggtagca gagacttggt cttgatttga acaccactga gaagc                 45

<210> SEQ ID NO 524
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 524
acactgacga catggttcta cacacatggc tccacatgca agttt                 45

<210> SEQ ID NO 525
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 525
tacggtagca gagacttggt cttgacaatt cagtttttga gtaccttgtt            50

<210> SEQ ID NO 526
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 526
acactgacga catggttcta catctaccca ctctctttttc agtgc                45

<210> SEQ ID NO 527
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 527
tacggtagca gagacttggt cttcttggtc atttgacagt tctgc                 45

<210> SEQ ID NO 528
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 528
acactgacga catggttcta caaatattaa ctaaatagga aataccagc ttca            54

<210> SEQ ID NO 529
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 529
tacggtagca gagacttggt cttttatttt ttgggggaa attttttagg atct             54

<210> SEQ ID NO 530
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 530
acactgacga catggttcta caagttgcct tattaacggt atcttca                   47

<210> SEQ ID NO 531
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 531
tacggtagca gagacttggt ctaccacttc tctgtattac atactagctt a              51

<210> SEQ ID NO 532
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 532
acactgacga catggttcta cacaaaacta taagataagg aatccagcaa                50

<210> SEQ ID NO 533
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 533
tacggtagca gagacttggt cttctttacc atactgttta gcaggaaa                  48

<210> SEQ ID NO 534
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 534
```
acactgacga catggttcta cagttgtatc cgctgctttg tcc 43

<210> SEQ ID NO 535
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 535
tacggtagca gagacttggt ctacatgtta gctgactgat gatggt 46

<210> SEQ ID NO 536
<211> LENGTH: 47
<212> TYPE: DNA
<213> ORGANISM: Artificial Sequence
<220> FEATURE:
<223> OTHER INFORMATION: Description of Artificial Sequence: Synthetic primer

<400> SEQUENCE: 536
acactgacga catggttcta caacaaatgg ttttaccaag gaaggat 47

<210> SEQ ID NO 537
<211> LENGTH: 49
<212> TYPE: DNA
<213> ORGANISM: Artificial Sequence
<220> FEATURE:
<223> OTHER INFORMATION: Description of Artificial Sequence: Synthetic primer

<400> SEQUENCE: 537
tacggtagca gagacttggt cttcatacat ttttctctaa ctgcaaaca 49

<210> SEQ ID NO 538
<211> LENGTH: 43
<212> TYPE: DNA
<213> ORGANISM: Artificial Sequence
<220> FEATURE:
<223> OTHER INFORMATION: Description of Artificial Sequence: Synthetic primer

<400> SEQUENCE: 538
acactgacga catggttcta cagcacggtt tctgtagccc ata 43

<210> SEQ ID NO 539
<211> LENGTH: 47
<212> TYPE: DNA
<213> ORGANISM: Artificial Sequence
<220> FEATURE:
<223> OTHER INFORMATION: Description of Artificial Sequence: Synthetic primer

<400> SEQUENCE: 539
tacggtagca gagacttggt ctacacaaca aagagcatac atagggt 47

<210> SEQ ID NO 540
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 540
acactgacga catggttcta cattcctgag ttttcatgga cagca    45

<210> SEQ ID NO 541
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 541
tacggtagca gagacttggt cttcacttgc tgagtgtgtt tctca    45

<210> SEQ ID NO 542
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 542
acactgacga catggttcta catttcctac tgtggttgct tccaa    45

<210> SEQ ID NO 543
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 543
tacggtagca gagacttggt ctttcatggc tatttgcctt ttgag    45

<210> SEQ ID NO 544
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 544
acactgacga catggttcta catggagcca cataacacat tcaaa    45

<210> SEQ ID NO 545
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 545
tacggtagca gagacttggt ctactcagtc ataacagctc aaagt    45

<210> SEQ ID NO 546
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 546
acactgacga catggttcta caacatgtct tttcttccct agtatgt    47

<210> SEQ ID NO 547
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 547
tacggtagca gagacttggt ctatgtgtta aagttcattg gaacagaa                48

<210> SEQ ID NO 548
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 548
acactgacga catggttcta catttccagc gcttctgagt tttac                   45

<210> SEQ ID NO 549
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 549
tacggtagca gagacttggt cttgtcaata cctgctttgt tgcag                   45

<210> SEQ ID NO 550
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 550
acactgacga catggttcta caagcattgg aggaatatcg taggtaa                 47

<210> SEQ ID NO 551
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 551
tacggtagca gagacttggt ctacactgtg acgtactggg tttttt                  45

<210> SEQ ID NO 552
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 552
acactgacga catggttcta cagcattgga ggaatatcgt aggt                    44

<210> SEQ ID NO 553
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 553
tacggtagca gagacttggt cttttttaga aaacactttc tcggtgt                    47

<210> SEQ ID NO 554
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 554
acactgacga catggttcta cagtcactgg ttaaaactaa ggtggg                     46

<210> SEQ ID NO 555
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 555
tacggtagca gagacttggt ctttggagtt gaagccagct gatta                      45

<210> SEQ ID NO 556
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 556
acactgacga catggttcta cactttcttc agaagctcca cccta                      45

<210> SEQ ID NO 557
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 557
tacggtagca gagacttggt ctgagattgg tacagcggca gag                        43

<210> SEQ ID NO 558
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 558
acactgacga catggttcta caaacctatt taaaactcca caaggaaac c                51

```
<210> SEQ ID NO 559
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 559
tacggtagca gagacttggt ctatctaatt cttttacagg agattggtac a            51

<210> SEQ ID NO 560
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 560
acactgacga catggttcta catgtttcag gaaggaatgt tccca                  45

<210> SEQ ID NO 561
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 561
tacggtagca gagacttggt ctagcttcat cataccttc actaaga                 47

<210> SEQ ID NO 562
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 562
acactgacga catggttcta caaaaataac ctaagggatt tgctttgt               48

<210> SEQ ID NO 563
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 563
tacggtagca gagacttggt cttgaaacaa actcccacat accact                 46

<210> SEQ ID NO 564
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 564
acactgacga catggttcta catgttaata aaaataaaac ttaacaattt tccccctt    57

<210> SEQ ID NO 565
```

```
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 565
tacggtagca gagacttggt ctattactaa gtcataaaaa taaaccaggt agaata         56

<210> SEQ ID NO 566
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 566
acactgacga catggttcta catccttaat gatcagggca tttct                      45

<210> SEQ ID NO 567
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 567
tacggtagca gagacttggt cttgctcttt cttgtaaata cacatttgct                 50

<210> SEQ ID NO 568
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 568
acactgacga catggttcta catccttaat gatcagggca tttct                      45

<210> SEQ ID NO 569
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 569
tacggtagca gagacttggt ctaccaagac atatcaggat ccacc                      45

<210> SEQ ID NO 570
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 570
acactgacga catggttcta caacatattt ctgaaagtct aggagctga                  49

<210> SEQ ID NO 571
<211> LENGTH: 50
```

<212> TYPE: DNA
<213> ORGANISM: Artificial Sequence
<220> FEATURE:
<223> OTHER INFORMATION: Description of Artificial Sequence: Synthetic
      primer

<400> SEQUENCE: 571
tacggtagca gagacttggt cttgctctttt cttgtaaata cacatttgct            50

<210> SEQ ID NO 572
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 572
acactgacga catggttcta catgtgtcat gtaatcaaat agtagatgtg            50

<210> SEQ ID NO 573
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 573
tacggtagca gagacttggt ctagcaattt caacagtcta atcaatgtc             49

<210> SEQ ID NO 574
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 574
acactgacga catggttcta cactactact atatgtgcat tgagagtttt t          51

<210> SEQ ID NO 575
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 575
tacggtagca gagacttggt ctacagagga cttaccatga cttgc                 45

<210> SEQ ID NO 576
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 576
acactgacga catggttcta catgtgcatt gagagttttt atactagtga ttt        53

<210> SEQ ID NO 577
<211> LENGTH: 46
<212> TYPE: DNA

<213> ORGANISM: Artificial Sequence
<220> FEATURE:
<223> OTHER INFORMATION: Description of Artificial Sequence: Synthetic
      primer

<400> SEQUENCE: 577
tacggtagca gagacttggt cttgatttgt gttttcactg tctgtc                    46

<210> SEQ ID NO 578
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 578
acactgacga catggttcta catcatgatg aaagtctgaa gaaaaatga                 49

<210> SEQ ID NO 579
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 579
tacggtagca gagacttggt ctcagaggac ttaccatgac ttgc                      44

<210> SEQ ID NO 580
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 580
acactgacga catggttcta catggcttat aaaatattaa tgtgcttctg t              51

<210> SEQ ID NO 581
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 581
tacggtagca gagacttggt ctacaactgt ttcatatact tcatcttcta gg             52

<210> SEQ ID NO 582
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 582
acactgacga catggttcta catggcttat aaaatattaa tgtgcttctg t              51

<210> SEQ ID NO 583
<211> LENGTH: 48
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 583
tacggtagca gagacttggt cttcttcaga ggtatctaca actgtttc                    48

<210> SEQ ID NO 584
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 584
acactgacga catggttcta caacaggatt tggaaaaaca tcaggg                      46

<210> SEQ ID NO 585
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 585
tacggtagca gagacttggt ctttcctagt cttgctagtt cttacttt                    48

<210> SEQ ID NO 586
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 586
acactgacga catggttcta catggaaagt caatgccaaa tgtcc                       45

<210> SEQ ID NO 587
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 587
tacggtagca gagacttggt cttcacattc atcagcgttt gcttc                       45

<210> SEQ ID NO 588
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 588
acactgacga catggttcta catgtagata cctctgaaga agatagtttt t                51

<210> SEQ ID NO 589
<211> LENGTH: 47
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 589
tacggtagca gagacttggt cttggatcag tatcatttgg ttccact                        47

<210> SEQ ID NO 590
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 590
acactgacga catggttcta caaaatctcc aaggaagttg taccg                         45

<210> SEQ ID NO 591
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 591
tacggtagca gagacttggt ctggctagaa atacgtggca aagaa                         45

<210> SEQ ID NO 592
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 592
acactgacga catggttcta caacccctat tgcatatttc ttcatgtg                      48

<210> SEQ ID NO 593
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 593
tacggtagca gagacttggt cttctgtatg agattcaaga tgctgct                       47

<210> SEQ ID NO 594
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 594
acactgacga catggttcta cagcctacca aaatcagaga agccat                        46

<210> SEQ ID NO 595
<211> LENGTH: 47
<212> TYPE: DNA
<213> ORGANISM: Artificial Sequence
<220> FEATURE:
<223> OTHER INFORMATION: Description of Artificial Sequence: Synthetic -continued primer

<400> SEQUENCE: 595
tacggtagca gagacttggt cttgcattga aagtctcttt aggtgat                47

<210> SEQ ID NO 596
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 596
acactgacga catggttcta cagcagtaaa gcaggcaata tctgg                  45

<210> SEQ ID NO 597
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 597
tacggtagca gagacttggt ctgagtcctc cttctgtgag caaac                  45

<210> SEQ ID NO 598
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 598
acactgacga catggttcta cacctctgaa agtggactgg aaa                    43

<210> SEQ ID NO 599
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 599
tacggtagca gagacttggt ctaacttatt tgttttcttt ttcaaagtgg at          52

<210> SEQ ID NO 600
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 600
acactgacga catggttcta catctgtagc tttgaagaat gcaggt                 46

<210> SEQ ID NO 601
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 601
tacggtagca gagacttggt ctttgcaaat gtaagtggtg cttc                44

<210> SEQ ID NO 602
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 602
acactgacga catggttcta cagttcagcc cagtttgaag ca                  42

<210> SEQ ID NO 603
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 603
tacggtagca gagacttggt ctaaacacag aaggaatcgt catct               45

<210> SEQ ID NO 604
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 604
acactgacga catggttcta caaatattta gtgaatgtga ttgatggtac ttta     54

<210> SEQ ID NO 605
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 605
tacggtagca gagacttggt ctagaacatt tcctcagaat tgtcccaaa           49

<210> SEQ ID NO 606
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 606
acactgacga catggttcta caaccaactt tgtccttaac tagctct             47

<210> SEQ ID NO 607
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 607
tacggtagca gagacttggt ctggatcatt ttcacactgt ccttcc                    46

<210> SEQ ID NO 608
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 608
acactgacga catggttcta caactacagt tatttattac cccagaagc                 49

<210> SEQ ID NO 609
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 609
tacggtagca gagacttggt ctagtcagta tcactgtatt ccacttt                   47

<210> SEQ ID NO 610
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 610
acactgacga catggttcta catcagatat aaaagaagag gtcttggc                  48

<210> SEQ ID NO 611
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 611
tacggtagca gagacttggt cttgcctcta gaaatcatga ctaggtttg                 49

<210> SEQ ID NO 612
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 612
acactgacga catggttcta catgccagca ctcttatttt aactcct                   47

<210> SEQ ID NO 613
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 613
```
tacggtagca gagacttggt ctacagctca acgtttttat aattttcatt t       51

<210> SEQ ID NO 614
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 614
acactgacga catggttcta cactgatgtt gaattaacca aaaatattcc c       51

<210> SEQ ID NO 615
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 615
tacggtagca gagacttggt cttggattac tcttagattt gtgttttgg          49

<210> SEQ ID NO 616
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 616
acactgacga catggttcta cagttgagct gttgccacct gaaaa              45

<210> SEQ ID NO 617
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 617
tacggtagca gagacttggt cttcttcaga gtctggattg acagttat           48

<210> SEQ ID NO 618
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 618
acactgacga catggttcta cattcaacca aaacacaaat ctaagagtaa         50

<210> SEQ ID NO 619
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 619
tacggtagca gagacttggt cttcgtttac acaagtcaag tctgtt        46

<210> SEQ ID NO 620
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 620
acactgacga catggttcta caaataattt tgtcttccaa gtagctaatg a        51

<210> SEQ ID NO 621
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 621
tacggtagca gagacttggt ctattgacac ttgggttgct tgttt        45

<210> SEQ ID NO 622
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 622
acactgacga catggttcta catcttgctt taggaaatac taaggaact        49

<210> SEQ ID NO 623
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 623
tacggtagca gagacttggt ctacctagag tcatttttat atgctgcttt        50

<210> SEQ ID NO 624
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 624
acactgacga catggttcta cataaacaag caacccaagt gtcaa        45

<210> SEQ ID NO 625
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 625
tacggtagca gagacttggt ctcctgccca tttgttcatg taatc        45

<210> SEQ ID NO 626
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 626
acactgacga catggttcta caaaatagtg taaagcagca tataaaaatg ac            52

<210> SEQ ID NO 627
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 627
tacggtagca gagacttggt cttgttcaga gagcttgatt tcctta                  46

<210> SEQ ID NO 628
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 628
acactgacga catggttcta caaacaaatg ggcaggactc ttagg                   45

<210> SEQ ID NO 629
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 629
tacggtagca gagacttggt ctttcaacac aagctaaact agtagga                 47

<210> SEQ ID NO 630
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 630
acactgacga catggttcta caaaggaaat caagctctct gaaca                   45

<210> SEQ ID NO 631
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 631
tacggtagca gagacttggt ctacaatcag aaacaactac actactct                48

<210> SEQ ID NO 632
<211> LENGTH: 49
<212> TYPE: DNA
<213> ORGANISM: Artificial Sequence
<220> FEATURE:
<223> OTHER INFORMATION: Description of Artificial Sequence: Synthetic primer

<400> SEQUENCE: 632
acactgacga catggttcta cacttgtgtt gaaattgtaa ataccttgg             49

<210> SEQ ID NO 633
<211> LENGTH: 41
<212> TYPE: DNA
<213> ORGANISM: Artificial Sequence
<220> FEATURE:
<223> OTHER INFORMATION: Description of Artificial Sequence: Synthetic primer

<400> SEQUENCE: 633
tacggtagca gagacttggt cttctgcctt ttggctaggt g                     41

<210> SEQ ID NO 634
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 634
acactgacga catggttcta caccctcaga tgttattttc caagca                46

<210> SEQ ID NO 635
<211> LENGTH: 51
<212> TYPE: DNA
<213> ORGANISM: Artificial Sequence
<220> FEATURE:
<223> OTHER INFORMATION: Description of Artificial Sequence: Synthetic primer

<400> SEQUENCE: 635
tacggtagca gagacttggt ctgcacttca aatgtactct tctgcaatat g          51

<210> SEQ ID NO 636
<211> LENGTH: 49
<212> TYPE: DNA
<213> ORGANISM: Artificial Sequence
<220> FEATURE:
<223> OTHER INFORMATION: Description of Artificial Sequence: Synthetic primer

<400> SEQUENCE: 636
acactgacga catggttcta caacagttga aattaaacgg aagtttgct             49

<210> SEQ ID NO 637
<211> LENGTH: 49
<212> TYPE: DNA
<213> ORGANISM: Artificial Sequence
<220> FEATURE:
<223> OTHER INFORMATION: Description of Artificial Sequence: Synthetic primer

<400> SEQUENCE: 637
tacggtagca gagacttggt ctgcagaagt ttcctcacta atattctca             49

```
<210> SEQ ID NO 638
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 638
acactgacga catggttcta catactgaag ctctgcaaaa agctg            45

<210> SEQ ID NO 639
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 639
tacggtagca gagacttggt cttgaaacaa cagaatcatg acatttactt       50

<210> SEQ ID NO 640
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 640
acactgacga catggttcta catgtcatga ttctgttgtt tcaatgt          47

<210> SEQ ID NO 641
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 641
tacggtagca gagacttggt cttctactgg cagcagtata tttgtt           46

<210> SEQ ID NO 642
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 642
acactgacga catggttcta cagaaaatta caagagaaat actgaaaatg aagat  55

<210> SEQ ID NO 643
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 643
tacggtagca gagacttggt cttcagtaaa tagcaagtcc gtttca            46

<210> SEQ ID NO 644
```

```
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 644
acactgacga catggttcta cagcagcaag caatttgaag gtaca            45

<210> SEQ ID NO 645
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 645
tacggtagca gagacttggt ctcagctttt tgcagagctt cagta            45

<210> SEQ ID NO 646
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 646
acactgacga catggttcta cactgcagag gtacatccaa taagt            45

<210> SEQ ID NO 647
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 647
tacggtagca gagacttggt ctagtatttc tcttgtaatt ttcagtaatt tcttc   55

<210> SEQ ID NO 648
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 648
acactgacga catggttcta cattgatggc agtgattcaa gtaaaaa          47

<210> SEQ ID NO 649
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 649
tacggtagca gagacttggt ctatgacatg cttcttgagc tttcg            45

<210> SEQ ID NO 650
<211> LENGTH: 43
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 650
acactgacga catggttcta catggccagt ttatgaagga ggg                 43

<210> SEQ ID NO 651
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 651
tacggtagca gagacttggt ctgcgacact aatattttc ccacttg              47

<210> SEQ ID NO 652
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 652
acactgacga catggttcta catgtaaatt tctttgatca gaaaccagaa g        51

<210> SEQ ID NO 653
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 653
tacggtagca gagacttggt ctccctggaa ggtcactagt tgatt               45

<210> SEQ ID NO 654
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 654
acactgacga catggttcta cacccagttg gtactggaaa tcaac               45

<210> SEQ ID NO 655
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 655
tacggtagca gagacttggt cttcactagt accttgctct ttttcat             47

<210> SEQ ID NO 656
<211> LENGTH: 49
<212> TYPE: DNA
```

<213> ORGANISM: Artificial Sequence
<220> FEATURE:
<223> OTHER INFORMATION: Description of Artificial Sequence: Synthetic primer

<400> SEQUENCE: 656
acactgacga catggttcta catgaaaaag agcaaggtac tagtgaaat          49

<210> SEQ ID NO 657
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 657
tacggtagca gagacttggt ctttaggtgg caccacagtc tcaat              45

<210> SEQ ID NO 658
<211> LENGTH: 44
<212> TYPE: DNA
<213> ORGANISM: Artificial Sequence
<220> FEATURE:
<223> OTHER INFORMATION: Description of Artificial Sequence: Synthetic primer

<400> SEQUENCE: 658
acactgacga catggttcta caagctgccc caaagtgtaa agaa               44

<210> SEQ ID NO 659
<211> LENGTH: 49
<212> TYPE: DNA
<213> ORGANISM: Artificial Sequence
<220> FEATURE:
<223> OTHER INFORMATION: Description of Artificial Sequence: Synthetic primer

<400> SEQUENCE: 659
tacggtagca gagacttggt cttgatgttt tgagattttc agtttgtct          49

<210> SEQ ID NO 660
<211> LENGTH: 43
<212> TYPE: DNA
<213> ORGANISM: Artificial Sequence
<220> FEATURE:
<223> OTHER INFORMATION: Description of Artificial Sequence: Synthetic primer

<400> SEQUENCE: 660
acactgacga catggttcta cactgtggtg ccacctaagc tct                43

<210> SEQ ID NO 661
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 661
tacggtagca gagacttggt ctacaagttg caggactttt tgctg              45

<210> SEQ ID NO 662
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 662
acactgacga catggttcta catgaaagtt aaagtacatg aaaatgtaga aaaa            54

<210> SEQ ID NO 663
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 663
tacggtagca gagacttggt cttggttgac catcaaatat tccttctc                  48

<210> SEQ ID NO 664
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 664
acactgacga catggttcta caaatcagtc cccttattca gtcatt                    46

<210> SEQ ID NO 665
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 665
tacggtagca gagacttggt cttcagctat agtactgttt gaattatttt cat            53

<210> SEQ ID NO 666
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 666
acactgacga catggttcta catcagcctt agcttttac acaagt                     46

<210> SEQ ID NO 667
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 667
tacggtagca gagacttggt cttcagctat agtactgttt gaattatttt cat            53

<210> SEQ ID NO 668
<211> LENGTH: 49
<212> TYPE: DNA
<213> ORGANISM: Artificial Sequence
<220> FEATURE:

<223> OTHER INFORMATION: Description of Artificial Sequence: Synthetic
primer

<400> SEQUENCE: 668
acactgacga catggttcta caatttgatg gtcaaccaga aagaataaa       49

<210> SEQ ID NO 669
<211> LENGTH: 47
<212> TYPE: DNA
<213> ORGANISM: Artificial Sequence
<220> FEATURE:
<223> OTHER INFORMATION: Description of Artificial Sequence: Synthetic
primer

<400> SEQUENCE: 669
tacggtagca gagacttggt ctacctcatc agaatggtag gaatagc       47

<210> SEQ ID NO 670
<211> LENGTH: 50
<212> TYPE: DNA
<213> ORGANISM: Artificial Sequence
<220> FEATURE:
<223> OTHER INFORMATION: Description of Artificial Sequence: Synthetic
primer

<400> SEQUENCE: 670
acactgacga catggttcta cagacaaaaa tcatctctcc gaaaaacaag       50

<210> SEQ ID NO 671
<211> LENGTH: 53
<212> TYPE: DNA
<213> ORGANISM: Artificial Sequence
<220> FEATURE:
<223> OTHER INFORMATION: Description of Artificial Sequence: Synthetic
primer

<400> SEQUENCE: 671
tacggtagca gagacttggt cttgcatctt ttacattgga tattactttg gaa       53

<210> SEQ ID NO 672
<211> LENGTH: 48
<212> TYPE: DNA
<213> ORGANISM: Artificial Sequence
<220> FEATURE:
<223> OTHER INFORMATION: Description of Artificial Sequence: Synthetic
primer

<400> SEQUENCE: 672
acactgacga catggttcta catgattctg gtattgagcc agtattga       48

<210> SEQ ID NO 673
<211> LENGTH: 46
<212> TYPE: DNA
<213> ORGANISM: Artificial Sequence
<220> FEATURE:
<223> OTHER INFORMATION: Description of Artificial Sequence: Synthetic
primer

<400> SEQUENCE: 673
tacggtagca gagacttggt ctttattttt gcagggtgaa gagcta       46

<210> SEQ ID NO 674
<211> LENGTH: 51
<212> TYPE: DNA
<213> ORGANISM: Artificial Sequence
<220> FEATURE:
<223> OTHER INFORMATION: Description of Artificial Sequence: Synthetic primer

<400> SEQUENCE: 674
acactgacga catggttcta catccaaagt aatatccaat gtaaaagatg c    51

<210> SEQ ID NO 675
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 675
tacggtagca gagacttggt ctcaggtggc cctacctcaa aatta    45

<210> SEQ ID NO 676
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 676
acactgacga catggttcta caactagctc ttcaccctgc aaaaa    45

<210> SEQ ID NO 677
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 677
tacggtagca gagacttggt cttgaaactg tctgtaaata tgtctttcac t    51

<210> SEQ ID NO 678
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 678
acactgacga catggttcta caggtagggc cacctgcatt tag    43

<210> SEQ ID NO 679
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 679
tacggtagca gagacttggt cttgaagaat atcctctgaa tcatccaat    49

<210> SEQ ID NO 680
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 680
acactgacga catggttcta cagccaaacg aaaattatgg caggt                    45

<210> SEQ ID NO 681
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 681
tacggtagca gagacttggt cttgttgtaa aatttcttca ctctgaatgt c             51

<210> SEQ ID NO 682
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 682
acactgacga catggttcta catgaatgta gcacgcattc acataa                   46

<210> SEQ ID NO 683
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 683
tacggtagca gagacttggt cttgcagatg agactgactt atgaagc                  47

<210> SEQ ID NO 684
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 684
acactgacga catggttcta caaccaaaat atgtctggat tggagaa                  47

<210> SEQ ID NO 685
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 685
tacggtagca gagacttggt ctacagattt tccacttgct gtgct                    45

<210> SEQ ID NO 686
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 686
acactgacga catggttcta catcaccttg tgatgttagt ttgga                45

<210> SEQ ID NO 687
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 687
tacggtagca gagacttggt ctgcatctga tacctggaca gattttt                46

<210> SEQ ID NO 688
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 688
acactgacga catggttcta caagtgtttt ctgaaataga agatagtacc aa            52

<210> SEQ ID NO 689
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 689
tacggtagca gagacttggt ctagccttt tgggatatta aatgttctgg              50

<210> SEQ ID NO 690
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 690
acactgacga catggttcta catcagtctc atctgcaaat acttgtg               47

<210> SEQ ID NO 691
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 691
tacggtagca gagacttggt cttcttgtga gctggtctga atgtt                45

<210> SEQ ID NO 692
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 692
acactgacga catggttcta caaggtatca gatgcttcat tacaaaacg         49

<210> SEQ ID NO 693
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 693
tacggtagca gagacttggt cttgttctgg agtacgtata gcagtattt          49

<210> SEQ ID NO 694
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 694
acactgacga catggttcta caaccagctc acaagagaag aaaa               44

<210> SEQ ID NO 695
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 695
tacggtagca gagacttggt ctacttgctt tccacttgct gt                 42

<210> SEQ ID NO 696
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 696
acactgacga catggttcta catggtaaat tcatctgctt tctctgga           48

<210> SEQ ID NO 697
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 697
tacggtagca gagacttggt ctcacagtgc tctgggtttc tctta              45

<210> SEQ ID NO 698
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 698
acactgacga catggttcta cacccagagc actgtgtaaa ctcagaa    47

<210> SEQ ID NO 699
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 699
tacggtagca gagacttggt ctagtgacac tttggttcct aatacca    47

<210> SEQ ID NO 700
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 700
acactgacga catggttcta catctccata tctctctcaa tttcaaca    48

<210> SEQ ID NO 701
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 701
tacggtagca gagacttggt ctagaaaaag tttcagtttt accaatttcc a    51

<210> SEQ ID NO 702
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 702
acactgacga catggttcta cagggaaaag aacaggcttc accta    45

<210> SEQ ID NO 703
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 703
tacggtagca gagacttggt cttggcatga cttggcagtt tagaa    45

<210> SEQ ID NO 704
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 704
acactgacga catggttcta caactttgaa acagaagcag tagaaattg    49

```
<210> SEQ ID NO 705
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 705
tacggtagca gagacttggt ctggcaacac gaaaggtaaa aatgaac                47

<210> SEQ ID NO 706
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 706
acactgacga catggttcta cattacatgt cccgaaaatg aggaa                  45

<210> SEQ ID NO 707
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 707
tacggtagca gagacttggt ctactgacta cacaaaaatg gctga                  45

<210> SEQ ID NO 708
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 708
acactgacga catggttcta caaggtcact atttgttgta agtattttg tt           52

<210> SEQ ID NO 709
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 709
tacggtagca gagacttggt ctaggatttt tcttgatttt ctattatcct gtc         53

<210> SEQ ID NO 710
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 710
acactgacga catggttcta cacttttttag gagaaccctc aatcaaaaga a          51
```

<210> SEQ ID NO 711
<211> LENGTH: 55
<212> TYPE: DNA
<213> ORGANISM: Artificial Sequence
<220> FEATURE:
<223> OTHER INFORMATION: Description of Artificial Sequence: Synthetic primer

<400> SEQUENCE: 711
tacggtagca gagacttggt ctcagaatat tatataccat acctatagag ggaga    55

<210> SEQ ID NO 712
<211> LENGTH: 49
<212> TYPE: DNA
<213> ORGANISM: Artificial Sequence
<220> FEATURE:
<223> OTHER INFORMATION: Description of Artificial Sequence: Synthetic primer

<400> SEQUENCE: 712
acactgacga catggttcta caagcatctg ttacattcac tgaaaattg    49

<210> SEQ ID NO 713
<211> LENGTH: 47
<212> TYPE: DNA
<213> ORGANISM: Artificial Sequence
<220> FEATURE:
<223> OTHER INFORMATION: Description of Artificial Sequence: Synthetic primer

<400> SEQUENCE: 713
tacggtagca gagacttggt ctggtaatcg gctctaaaga aacatga    47

<210> SEQ ID NO 714
<211> LENGTH: 56
<212> TYPE: DNA
<213> ORGANISM: Artificial Sequence
<220> FEATURE:
<223> OTHER INFORMATION: Description of Artificial Sequence: Synthetic primer

<400> SEQUENCE: 714
acactgacga catggttcta cagtatttac agtaacatgg atattctctt agattt    56

<210> SEQ ID NO 715
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 715
tacggtagca gagacttggt ctacatgtct taccgaaagg gtaca    45

<210> SEQ ID NO 716
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 716
acactgacga catggttcta caatgtagca aatgagggtc tgcaa    45

```
<210> SEQ ID NO 717
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 717
tacggtagca gagacttggt ctccaaagtc agatgttcat acaaatgaga            50

<210> SEQ ID NO 718
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 718
acactgacga catggttcta caagggtctg caacaaaggc ata                   43

<210> SEQ ID NO 719
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 719
tacggtagca gagacttggt cttcctgaaa ctgctaaatt gcttg                 45

<210> SEQ ID NO 720
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 720
acactgacga catggttcta caccattgca gcacaactaa ggaac                 45

<210> SEQ ID NO 721
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 721
tacggtagca gagacttggt ctaaaatgga tgtcctgaaa ctgct                 45

<210> SEQ ID NO 722
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 722
acactgacga catggttcta cattgtatga acatctgact ttggaaaaa             49

<210> SEQ ID NO 723
```

```
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 723
tacggtagca gagacttggt ctctgttcaa ctctgtgaaa atgtga            46

<210> SEQ ID NO 724
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 724
acactgacga catggttcta catcaagcaa tttagcagtt tcagg             45

<210> SEQ ID NO 725
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 725
tacggtagca gagacttggt ctttgctttt gtctgttttc ctcca             45

<210> SEQ ID NO 726
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 726
acactgacga catggttcta caacagagtt gaacagtgtg ttagga            46

<210> SEQ ID NO 727
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 727
tacggtagca gagacttggt ctagttacag ctactgcttg attgga            46

<210> SEQ ID NO 728
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 728
acactgacga catggttcta catgacaatg agattcatca gtttaacaa         49

<210> SEQ ID NO 729
<211> LENGTH: 46
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 729
tacggtagca gagacttggt ctagggcttt aaaattacca ccacca              46

<210> SEQ ID NO 730
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 730
acactgacga catggttcta caggccaggg gttgtgcttt tt                  42

<210> SEQ ID NO 731
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 731
tacggtagca gagacttggt ctcgcgttgc ctttgtttct tctta               45

<210> SEQ ID NO 732
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 732
acactgacga catggttcta caacaagtct tcagaatgcc agagat              46

<210> SEQ ID NO 733
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 733
tacggtagca gagacttggt ctttatgaga acacgcagag ggaac               45

<210> SEQ ID NO 734
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 734
acactgacga catggttcta caatcttgca aaaacatcca ctctg               45

<210> SEQ ID NO 735
<211> LENGTH: 45
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 735
tacggtagca gagacttggt cttttcattc atccattcct gcact                      45

<210> SEQ ID NO 736
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 736
acactgacga catggttcta cattgttttt attgtgtgat acatgtttac ttt             53

<210> SEQ ID NO 737
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 737
tacggtagca gagacttggt ctagccaact gtattccttt tccagt                     46

<210> SEQ ID NO 738
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 738
acactgacga catggttcta caattgcata aaaattaaca gcaaaatgc                  50

<210> SEQ ID NO 739
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 739
tacggtagca gagacttggt cttgagggaa catataaaag ttaacacaca                 50

<210> SEQ ID NO 740
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 740
acactgacga catggttcta caagtttttg tacagagaat agttgtagtt g               51

<210> SEQ ID NO 741
<211> LENGTH: 45
<212> TYPE: DNA
<213> ORGANISM: Artificial Sequence
```

<220> FEATURE:
<223> OTHER INFORMATION: Description of Artificial Sequence: Synthetic
      primer

<400> SEQUENCE: 741
tacggtagca gagacttggt ctcacattcc atagctgcca gtttc                45

<210> SEQ ID NO 742
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 742
acactgacga catggttcta catatttgtt cagggctctg tgtga                45

<210> SEQ ID NO 743
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 743
tacggtagca gagacttggt ctagttgaag aagcaccctt tctgg                45

<210> SEQ ID NO 744
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 744
acactgacga catggttcta cagataaatt cagttttat tctcagttat tcagt       55

<210> SEQ ID NO 745
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 745
tacggtagca gagacttggt ctgaacaagt gttttgcag ctgtg                 45

<210> SEQ ID NO 746
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 746
acactgacga catggttcta catcggctat aaaaaagata atggaaagg            49

<210> SEQ ID NO 747
<211> LENGTH: 47
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 747
tacggtagca gagacttggt ctacccatct gtaagttcaa taatggc              47

<210> SEQ ID NO 748
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 748
acactgacga catggttcta caagcaataa aactagtagt gcagataccc           50

<210> SEQ ID NO 749
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 749
tacggtagca gagacttggt ctcaactgtc agtctgccat tcttt                45

<210> SEQ ID NO 750
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 750
acactgacga catggttcta caatcctccc ctcttagctg tctta                45

<210> SEQ ID NO 751
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 751
tacggtagca gagacttggt ctttaacata agagattctg gggctt               46

<210> SEQ ID NO 752
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 752
acactgacga catggttcta cattcttcat ggagcagaac tggtg                45

<210> SEQ ID NO 753
<211> LENGTH: 49
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 753
tacggtagca gagacttggt cttcagtaca tctaagaaat tgagcatcc                49

<210> SEQ ID NO 754
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 754
acactgacga catggttcta catgatgcct gtacacctct tga                      43

<210> SEQ ID NO 755
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 755
tacggtagca gagacttggt ctgcacaaaa actttaactg tctgaagaat a             51

<210> SEQ ID NO 756
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 756
acactgacga catggttcta cacttttttaa agtgaatatt tttaaggcag ttcta        55

<210> SEQ ID NO 757
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 757
tacggtagca gagacttggt ctaggaaaag gtctagggtc aggaa                    45

<210> SEQ ID NO 758
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 758
acactgacga catggttcta cactaacagt actcggcctg ctc                      43

<210> SEQ ID NO 759
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 759
tacggtagca gagacttggt ctacctgtat agggtatgct ctttga                    46

<210> SEQ ID NO 760
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 760
acactgacga catggttcta cagaccttt cctctgccct tatca                     45

<210> SEQ ID NO 761
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 761
tacggtagca gagacttggt ctagaaagaa atatatggta agtttcaaga ataca          55

<210> SEQ ID NO 762
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 762
acactgacga catggttcta caatgtgact tttttggtgt gtgtaa                    46

<210> SEQ ID NO 763
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 763
acactgacga catggttcta caagaggaag aaaaggaagc agcaa                     45

<210> SEQ ID NO 764
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 764
tacggtagca gagacttggt cttcatatta gaaataacaa tgtgtaccat ataact         56

<210> SEQ ID NO 765
<211> LENGTH: 51
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 765
acactgacga catggttcta cattagttgc ttttgaattt acagtttagt g         51

<210> SEQ ID NO 766
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 766
tacggtagca gagacttggt ctagcctcat tatatgtcct cttactctct            50

<210> SEQ ID NO 767
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 767
acactgacga catggttcta catggaactt ttttgttctg attgct                46

<210> SEQ ID NO 768
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 768
tacggtagca gagacttggt ctcacggttg tgacatccct tgata                 45

<210> SEQ ID NO 769
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 769
acactgacga catggttcta caatcacagg caaatgttga atgataa               47

<210> SEQ ID NO 770
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 770
tacggtagca gagacttggt ctaagttaat aaaactgata aaaacaaagc atttac     56

<210> SEQ ID NO 771
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 771
acactgacga catggttcta caactactaa tgcccacaaa gagataa                           47

<210> SEQ ID NO 772
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 772
tacggtagca gagacttggt cttttgaag ttgcaagatg ataaattctg                          50

<210> SEQ ID NO 773
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 773
acactgacga catggttcta catggcgtcc atcatcagat ttatattc                           48

<210> SEQ ID NO 774
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 774
tacggtagca gagacttggt ctactaacaa gcacttatca aaactgaaa                          49

<210> SEQ ID NO 775
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 775
acactgacga catggttcta caaccggtac aaacctttca ttgt                               44

<210> SEQ ID NO 776
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 776
tacggtagca gagacttggt ctgctgaaag tctggatcta aaaatttgct                         50

<210> SEQ ID NO 777
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 777
acactgacga catggttcta caacgggagc cccttcactt    40

<210> SEQ ID NO 778
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 778
tacggtagca gagacttggt ctgccaactg gtagctccaa ctaat    45

<210> SEQ ID NO 779
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 779
acactgacga catggttcta caaggcatat tagagtttcc tttcttgc    48

<210> SEQ ID NO 780
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 780
tacggtagca gagacttggt cttgcagcaa ttaacatatg aggctt    46

<210> SEQ ID NO 781
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 781
acactgacga catggttcta caacttgccc ctttcgtcta tttgt    45

<210> SEQ ID NO 782
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 782
tacggtagca gagacttggt ctgccctctt ttggactagc agaa    44

<210> SEQ ID NO 783
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 783
acactgacga catggttcta caccagtggc gaccagaatc c    41

<210> SEQ ID NO 784
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 784
tacggtagca gagacttggt ctttccttga tactggactg tcaaaa                46

<210> SEQ ID NO 785
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 785
acactgacga catggttcta caacatttag ggttttttcat tcttttttgg t         51

<210> SEQ ID NO 786
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 786
tacggtagca gagacttggt ctggaccact tgggatcatt tgcat                 45

<210> SEQ ID NO 787
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 787
acactgacga catggttcta caaagcagct tttccactta ttttctt               47

<210> SEQ ID NO 788
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 788
tacggtagca gagacttggt ctataatatt ccttgagttt acattaactt acca       54

<210> SEQ ID NO 789
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 789
acactgacga catggttcta catgtgaact gaaatcacct aacctat               47

<210> SEQ ID NO 790
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 790
tacggtagca gagacttggt cttgataaag gactttgata atatatctca caattag          57

<210> SEQ ID NO 791
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 791
acactgacga catggttcta caactgtgtg taatatttgc gtgctt                      46

<210> SEQ ID NO 792
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 792
tacggtagca gagacttggt ctgtggaaac agacttcctt ttggc                       45

<210> SEQ ID NO 793
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 793
acactgacga catggttcta cactcctaat tgtgagatat attatcaaag tcc              53

<210> SEQ ID NO 794
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 794
tacggtagca gagacttggt ctagaaatcc aaggctcttc tctttt                      46

<210> SEQ ID NO 795
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 795
acactgacga catggttcta caagagattg atgaccaaaa gaactgc                     47

```
<210> SEQ ID NO 796
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 796
tacggtagca gagacttggt cttttaaatg gagtcatctg aggagaa          47

<210> SEQ ID NO 797
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 797
acactgacga catggttcta caagctgacg aagaacttgc attga            45

<210> SEQ ID NO 798
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 798
tacggtagca gagacttggt ctcctgggaa ctctcctgtt ctttg            45

<210> SEQ ID NO 799
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 799
acactgacga catggttcta cagaaaaaca atttatatct gtcagtgaat cc    52

<210> SEQ ID NO 800
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 800
tacggtagca gagacttggt cttgtgtcct gcttattttt ctcaca           46

<210> SEQ ID NO 801
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 801
acactgacga catggttcta catctgatca aagaacagga gagttc           46

<210> SEQ ID NO 802
```

```
<211> LENGTH: 58
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 802
tacggtagca gagacttggt cttaagtact aatgtgtggt ttgaaattat attccagt        58

<210> SEQ ID NO 803
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 803
caagcagaag acggcatacg agat                                             24

<210> SEQ ID NO 804
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (2)..(2)
<223> OTHER INFORMATION: LNA
<220> FEATURE:
<221> NAME/KEY: modified_base
<222> LOCATION: (4)..(4)
<223> OTHER INFORMATION: LNA
<220> FEATURE:
<221> NAME/KEY: modified_base
<222> LOCATION: (7)..(7)
<223> OTHER INFORMATION: LNA

<400> SEQUENCE: 804
acactgacga catggttcta ca                                               22

<210> SEQ ID NO 805
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (2)..(2)
<223> OTHER INFORMATION: LNA
<220> FEATURE:
<221> NAME/KEY: modified_base
<222> LOCATION: (4)..(4)
<223> OTHER INFORMATION: LNA
<220> FEATURE:
<221> NAME/KEY: modified_base
<222> LOCATION: (7)..(7)
<223> OTHER INFORMATION: LNA

<400> SEQUENCE: 805
tacggtagca gagacttggt ct                                               22

<210> SEQ ID NO 806
<211> LENGTH: 22
<212> TYPE: DNA
<213> ORGANISM: Artificial Sequence
```

```
<220> FEATURE:
<223> OTHER INFORMATION: Description of Artificial Sequence: Synthetic
      primer
<220> FEATURE:
<221> NAME/KEY: modified_base
<222> LOCATION: (2)..(2)
<223> OTHER INFORMATION: LNA
<220> FEATURE:
<221> NAME/KEY: modified_base
<222> LOCATION: (4)..(4)
<223> OTHER INFORMATION: LNA
<220> FEATURE:
<221> NAME/KEY: modified_base
<222> LOCATION: (6)..(6)
<223> OTHER INFORMATION: LNA

<400> SEQUENCE: 806
tgtagaacca tgtcgtcagt gt                                                    22

<210> SEQ ID NO 807
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (2)..(2)
<223> OTHER INFORMATION: LNA
<220> FEATURE:
<221> NAME/KEY: modified_base
<222> LOCATION: (5)..(5)
<223> OTHER INFORMATION: LNA
<220> FEATURE:
<221> NAME/KEY: modified_base
<222> LOCATION: (7)..(7)
<223> OTHER INFORMATION: LNA

<400> SEQUENCE: 807
agaccaagtc tctgctaccg ta                                                    22

<210> SEQ ID NO 808
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 808
tacggtagca gagacttggt ctgtcctgcc tcgagagatt g                               41

<210> SEQ ID NO 809
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 809
tacggtagca gagacttggt ctaccttcat gttcttcaaa ttcctcct                        48
```

NUCLEIC ACID ENCODING REACTIONS

CROSS-REFERENCE TO RELATED APPLICATIONS

This application claims the benefit of U.S. provisional application No. 61/519,348, filed May 20, 2011, which is hereby incorporated by reference in its entirety.

SEQUENCE LISTING

The instant application contains a Sequence Listing which has been submitted in ASCII format via EFS-Web and is hereby incorporated by reference in its entirety. Said ASCII copy, created on Jul. 19, 2012, is named FLUDP013.txt and is 186,379 bytes in size.

FIELD OF THE INVENTION

The present invention relates generally to the incorporation of nucleic acid sequences into target nucleic acids, e.g., the addition of one or more adaptors and/or nucleotide tag(s) and/or barcode nucleotide sequence(s) to target nucleotide sequences. The methods described herein are useful, e.g., in the areas of high-throughput assays for detection and/or sequencing of particular target nucleic acids.

BACKGROUND OF THE INVENTION

The ability to detect specific nucleic acid sequences in a sample has resulted in new approaches in diagnostic and predictive medicine, environmental, food and agricultural monitoring, molecular biology research, and many other fields. For many applications, it is desirable to detect and/or analyze many target nucleic acids in multiple samples, e.g., multiple individual cells within a population, simultaneously.

SUMMARY OF THE INVENTION

In certain embodiments, the invention provides a method of adding adaptor molecules to each end of a plurality of target nucleic acids that include sticky ends. The method entails annealing adaptor molecules to the sticky ends of double-stranded target nucleic acid molecules to produce annealed adaptor-target nucleic acid molecules, wherein the adaptor molecules are:
  (i) hairpin structures each including:
  an adaptor nucleotide sequence, which is linked to
  a nucleotide linker, which is linked to
  a nucleotide sequence that is capable of annealing to the adaptor nucleotide sequence and is linked to
  a degenerate tail sequence; or
  (ii) double-stranded or single-stranded molecules each including:
  a first adaptor nucleotide sequence, which is linked to
  a nucleotide linker, which is linked to
  a second adaptor nucleotide sequence; and
  a degenerate tail sequence on each strand, wherein double-stranded molecules each include two degenerate tail sequences as sticky end(s). After annealing, the method entails filling any gaps in the resulting annealed adaptor-target nucleic acid molecules, and ligating any adjacent nucleotide sequences in the annealed adaptor-target nucleic acid molecules to produce adaptor-modified target nucleic acid molecules. In related embodiments, the invention provides a plurality of adaptor molecules, wherein the adaptor molecules are the hairpin structures of (i) above or the double-stranded or single-stranded molecules of (ii) above. Also contemplated is a kit, which, in various embodiments, can include the plurality of adaptor molecules in combination with a DNAse enzyme, an exonuclease, an endonuclease, a polymerase, a ligase, or any combination thereof.

In other embodiments, the invention provides a method for tagging a plurality of target nucleic acids with nucleotide sequences. The method entails preparing a first reaction mixture for each target nucleic acid, the first reaction mixture including a pair of inner primers and a pair of outer primers, wherein:
  (i) the inner primers include:
  a forward, inner primer including a first nucleotide tag, a first barcode nucleotide sequence, and a target-specific portion; and
  a reverse, inner primer including a target-specific portion, a first barcode nucleotide sequence, and a second nucleotide tag; and
  (ii) the outer primers include:
  a forward, outer primer including a second barcode nucleotide sequence and a first nucleotide tag-specific portion; and
  a reverse, outer primer including a second nucleotide tag-specific portion and a second barcode nucleotide sequence, wherein the outer primers are in excess of the inner primers. Each first reaction mixture is subjected to a reaction to produce a plurality of tagged target nucleotide sequences, each including 5'-second barcode nucleotide sequence-first nucleotide tag sequence-first barcode nucleotide sequence-target nucleotide sequence-first barcode nucleotide sequence-second nucleotide tag sequence-second barcode nucleotide sequence-3'. In related embodiments, the invention provides a kit that includes a polymerase in combination with the inner primers of (i) above and the outer primers of (ii) above, wherein the outer primers are in excess of the inner primers.

In certain embodiments, the invention provides a method for tagging a plurality of target nucleic acids with nucleotide sequences. The method entails preparing a first reaction mixture for each target nucleic acid, the first reaction mixture including a pair of inner primers, a pair of stuffer primers, and a pair of outer primers, wherein:
  (i) the inner primers include:
  a forward, inner primer including a first nucleotide tag and a target-specific portion; and
  a reverse, inner primer including a target-specific portion and a second nucleotide tag;
  (ii) the stuffer primers include:
  a forward, stuffer primer including a third nucleotide tag, a first barcode nucleotide sequence, and a first nucleotide tag-specific portion; and
  a reverse, stuffer primer including a second nucleotide tag-specific portion, a first barcode nucleotide sequence, a fourth nucleotide tag; and
  (iii) the outer primers include:
  a forward, outer primer including a second barcode nucleotide sequence and a third nucleotide tag-specific portion; and
  a reverse, outer primer including a fourth nucleotide tag-specific portion and a second barcode nucleotide sequence, wherein the outer primers are in excess of the stuffer primers, which are in excess of the inner primers. Each first reaction mixture is subjected to a reaction to produce a plurality of tagged target nucleotide sequences, each including 5'-second barcode nucleotide sequence-third nucleotide tag sequence-first barcode nucleotide sequence-first nucleotide tag sequence-target nucleotide sequence-second nucleotide tag sequence-first barcode nucleotide sequence-fourth nucleotide tag sequence-second barcode nucleotide sequence-3'. In related embodiments, the invention provides a kit that includes a polymerase in combination with the inner primers of (i) above, the suffer primers of (ii) above, and the outer primers of (iii) above, wherein the outer primers are in excess of the stuffer primers, which are in excess of the inner primers.

In particular embodiments, the invention provides a method for combinatorial tagging of a plurality of target nucleotide sequences. The method employs a plurality of tagged target nucleotide sequences derived from target nucleic acids, each tagged target nucleotide sequence including an endonuclease site and a first barcode nucleotide sequence, wherein tagged target nucleotide sequences in the plurality include the same endonuclease site, but N different first barcode nucleotide sequences, wherein N is an integer greater than 1. The method entails cutting the plurality of tagged target nucleotide sequences with an endonuclease specific for the endonuclease site to produce a plurality of sticky-ended, tagged target nucleotide sequences. The method further entails ligating a plurality of adaptors including a second barcode nucleotide sequence and complementary sticky ends to the plurality of sticky-ended, tagged target nucleotide sequences in a first reaction mixture, wherein the plurality of adaptors include M different second barcode nucleotide sequences, wherein M is an integer greater than 1. This ligation produces a plurality of combinatorially tagged target nucleotide sequences, each including first and second barcode nucleotide sequences, wherein the plurality includes N×M different first and second barcode combinations. In related embodiments, the invention provides a plurality of adaptors including:

a plurality of first adaptors, each including the same endonuclease site, N different barcode nucleotide sequences, wherein N is an integer greater than 1, a first primer binding site and a sticky end;

a second adaptor including a second primer binding site and a sticky end; and a plurality of third adaptors including a second barcode nucleotide sequence and sticky ends complementary to those produced upon cutting the first adaptors at the endonuclease site, wherein the plurality of third adaptors include M different second barcode nucleotide sequences, wherein M is an integer greater than 1. Also contemplated is a kit including the plurality of first adaptors, the second adaptor, and the plurality of third adaptors, in combination with an endonuclease specific for the endonuclease site in the first adaptors and/or a ligase.

In other embodiments, the invention provides a method for combinatorial tagging of a plurality of target nucleotide sequences, wherein the method entails annealing a plurality of barcode primers to a plurality of tagged target nucleotide sequences derived from target nucleic acids. Each tagged target nucleotide sequence includes a nucleotide tag at one end and a first barcode nucleotide sequence, wherein tagged target nucleotide sequences in the plurality include the same nucleotide tag, but N different first barcode nucleotide sequences, wherein N is an integer greater than one. Each barcode primer includes:

a first tag-specific portion linked to;

a second barcode nucleotide sequence linked to;

a second tag-specific portion, wherein the barcode primers in the plurality each include the same first and second tag-specific portions, but M different second barcode nucleotide sequences, wherein M is an integer greater than one. The method further entails amplifying the tagged target nucleotide sequences in a first reaction mixture to produce a plurality of combinatorially tagged target nucleotide sequences, each including first and second barcode nucleotide sequences, wherein the plurality includes N×M different first and second barcode combinations. In related embodiments, the invention provides a kit including one or more nucleotide tags(s), which can be used for producing tagged target nucleotide sequences, together with the plurality of barcode primers above.

In certain embodiments, the invention provides an assay method for detecting a plurality of target nucleic acids that entails preparing M first reaction mixtures that will be pooled prior to assay, wherein M is an integer greater than 1. Each first reaction mixture includes:

sample nucleic acid(s);

a first, forward primer including a target-specific portion;

a first, reverse primer including a target-specific portion, wherein the first, forward primer or the first, reverse primer additionally includes a barcode nucleotide sequence, and wherein each barcode nucleotide sequence in each of the M reaction mixtures is different. Each first reaction mixture is subjected to a first reaction to produce a plurality of barcoded target nucleotide sequences, each including a target nucleotide sequence linked to a barcode nucleotide sequence. The method further entails, for each of the M first reaction mixtures, pooling the barcoded target nucleotide sequences to form an assay pool. The assay pool, or one or more aliquots thereof, is subjected to a second reaction using unique pairs of second primers, wherein each second primer pair includes:

a second, forward or a reverse primer that anneals to a target nucleotide sequence; and a second, reverse or a forward primer, respectively, that anneals to a barcode nucleotide sequence. The method then entails determining, for each unique, second primer pair, whether a reaction product is present in the assay pool, or aliquot thereof, whereby the presence of a reaction product indicates the presence of a particular target nucleic acid in a particular first reaction mixture.

A variation of this assay method for detecting a plurality of target nucleic acids entails, in particular embodiments, preparing M first reaction mixtures that will be pooled prior to assay, wherein M is an integer greater than 1, and each first reaction mixture includes:

sample nucleic acid(s)

a first, forward primer including a target-specific portion;

a first, reverse primer including a target-specific portion, wherein the first, forward primer or the first, reverse primer additionally includes a nucleotide tag; and at least one barcode primer including a barcode nucleotide sequence and a nucleotide tag-specific portion, wherein the barcode primer is in excess of the first, forward and/or first, reverse primer(s), and wherein each barcode nucleotide sequence in each of the M reaction mixtures is different. Each first reaction mixture is subjected to a first reaction to produce a plurality of barcoded target nucleotide sequences, each including a target nucleotide sequence linked to a nucleotide tag, which is linked to a barcode nucleotide sequence. The method further entails, for each of the M first reaction mixtures, pooling the barcoded target nucleotide sequences to form an assay pool. The assay pool, or one or more aliquots thereof, is subjected to a second reaction using unique pairs of second primers, wherein each second primer pair includes:

a second, forward or a reverse primer that anneals to a target nucleotide sequence; and a second, reverse or a forward primer, respectively, that anneals to a barcode nucleotide sequence. The method then entails determining, for each unique, second primer pair, whether a reaction product is present in the assay pool, or aliquot thereof, whereby the presence of a reaction product indicates the presence of a particular target nucleic acid in a particular first reaction mixture.

In certain embodiments, the invention provides methods and kits useful for amplifying one or more target nucleic acids in preparation for applications such as bidirectional nucleic acid sequencing. In some embodiments, methods of the invention entail additionally carrying out bidirectional DNA sequencing.

In particular bidirectional embodiments, these methods entail amplifying, tagging, and barcoding a plurality of target nucleic acids in a plurality of samples. Nucleotide tag sequences can include primer binding sites that can be used to facilitate amplification and/or DNA sequencing. Barcode nucleotide sequences can encode information about amplification products, such as the identity of the sample from which the amplification product was derived.

In certain bidirectional embodiments, a method for amplifying a target nucleic acid entails amplifying a target nucleic acid using:
a set of inner primers, wherein the set includes:
an inner, forward primer including a target-specific portion and a first primer binding site;
an inner, reverse primer including a target-specific portion and a second primer binding site, wherein the first and second primer binding sites are different;
a first set of outer primers, wherein the set includes:
a first outer, forward primer including a portion specific for the first primer binding site; and
a first outer, reverse primer including a barcode nucleotide sequence and a portion specific for the second primer binding site;
a second set of outer primers, wherein the set includes:
a second outer, forward primer including a barcode nucleotide sequence and a portion specific for the first primer binding site; and
a second outer, reverse primer including a portion specific for the second primer binding site. This amplification produces two target amplicons, wherein:
a first target amplicon includes 5'-first primer binding site-target nucleotide sequence-second primer binding site-barcode nucleotide sequence-3'; and
a second target amplicon includes 5'-barcode nucleotide sequence-first primer binding site-target nucleotide sequence-second primer binding site-3'. In variations of these embodiments, the barcode nucleotide sequence in each target amplicon is the same, and each target amplicon includes only one barcode nucleotide sequence.

In some bidirectional embodiments, the first and second primer binding sites are binding sites for DNA sequencing primers. The outer primers can, optionally, each additionally include an additional nucleotide sequence, wherein:
the first outer, forward primer includes a first additional nucleotide sequence, and the first outer, reverse primer includes a second additional nucleotide sequence; and
the second outer, forward primer includes the second additional nucleotide sequence, and the second outer, reverse primer includes the first additional nucleotide sequence; and the first and second additional nucleotide sequences are different. In such embodiments, the amplification produces two target amplicons, wherein:
a first target amplicon includes: 5'-first additional nucleotide sequence-first primer binding site-target nucleotide sequence-second primer binding site-barcode nucleotide sequence-second additional nucleotide sequence-3'; and
a second target amplicon includes: 5'-second additional nucleotide sequence-barcode nucleotide sequence-first primer binding site-target nucleotide sequence-second primer binding site-first additional nucleotide sequence 3'. In particular embodiments, the first and/or second additional nucleotide sequence includes a primer binding site. In an illustrative embodiment, the first set of outer primers includes PE1-CS1 and PE2-BC-CS2, and the second set of outer primers includes PE1-CS2 and PE2-BC-CS1 (Table 1, Example 9).

In certain bidirectional embodiments, the amplification is carried out in a single amplification reaction. In other embodiments, the amplification includes employing the inner primers in a first amplification reaction and employing the outer primers in a second amplification reaction, wherein the second amplification reaction is separate from the first. In a variation of this, latter embodiment, the second amplification reaction includes two separate amplification reactions, wherein one employs the first set of outer primers and the other employs the second set of outer primers. The target amplicons produced in the two separate second amplification reactions can, optionally, be pooled.

In any of the above-described bidirectional embodiments, the method can include amplifying a plurality of target nucleic acids. The plurality of target nucleic acids can be, for example, genomic DNA, cDNA, fragmented DNA, DNA reverse-transcribed from RNA, a DNA library, or nucleic acids is extracted or amplified from a cell, a bodily fluid or a tissue sample. In specific embodiments, the plurality of target nucleic acids is amplified from a formalin-fixed, paraffin-embedded tissue sample.

Any of the above-described bidirectional methods can additionally include sequencing the target amplicons. For example, when the target amplicons produced as described above include additional nucleotide sequences, the method can include an additional amplification using primers that bind to the first and second additional nucleotide sequences to produce templates for DNA sequencing. In specific embodiments, one or both of the primers that bind to the first and second additional nucleotide sequences are immobilized on a substrate. In particular embodiments, the amplification to produce DNA sequencing templates can be carried out by isothermal nucleic acid amplification. In certain embodiments, the method includes performing DNA sequencing using the templates and primers that bind to the first and second primer binding sites and prime sequencing of the target nucleotide sequence(s); these primers are preferably present in substantially equal amounts. In some embodiments, the method includes performing DNA sequencing using the templates and primers that bind to the first and second primer binding sites and prime sequencing of the barcode nucleotide sequences(s); these primers are preferably present in substantially equal amounts. In specific embodiments, the method includes performing DNA sequencing using the templates and primers that bind to the first and second primer binding sites and prime sequencing of the barcode nucleotide sequences(s), wherein the primers are reverse complements of the primers that prime sequencing of the target nucleotide sequences. In illustrative embodiments, the primers employed to prime sequencing of the target nucleotide sequence(s) and barcode nucleotide sequence(s) include CS1, CS2, CS1rc, and CS2rc (Table 2, Example 9).

In any of the above-described bidirectional embodiments, the barcode nucleotide sequence can be selected so as to avoid substantial annealing to the target nucleic acids. In certain embodiments, the barcode nucleotide sequence identifies a particular sample.

When bidirectional DNA sequencing is carried out according to the above-described methods, in some embodiments, at least 50 percent of the sequences determined from DNA sequencing are present at greater than 50 percent of the average number of copies of sequences and less than 2-fold the average number of copies of sequences. In certain embodiments, at least 70 percent of the sequences determined from DNA sequencing are present at greater than 50 percent of the average number of copies of sequences and less than 2-fold the average number of copies of sequences. In specific embodiments, at least 90 percent of the sequences determined from DNA sequencing are present at greater than 50 percent of the average number of copies of sequences and less than 2-fold the average number of copies of sequences.

In any of the above-described bidirectional embodiments, the average length of the target amplicons is less than 200 bases. In various embodiments, the first amplification (i.e., the amplification to produce target amplicons) is carried out in a volume in the range of about 1 picoliter to about 50 nanoliters or about 5 picoliters to about 25 nanoliters. In particular embodiments, the first amplification (i.e., the amplification to produce target amplicons) reaction(s) is/are formed in, or distributed into, separate compartments of a microfluidic device prior to amplification. The microfluidic device can be, for example, one that is fabricated, at least in part, from an elastomeric material. In certain embodiments, the first amplification (i.e., the amplification to produce target amplicons) reaction(s) is/are carried out in (a) fluid droplet(s).

Another aspect of the invention includes a kit useful for carrying out the bidirectional embodiments discussed above. In certain embodiments, the kit includes:
a first set of outer primers, wherein the set includes:
a first outer, forward primer including a portion specific for a first primer binding site; and
a first outer, reverse primer including a barcode nucleotide sequence and a portion specific for a second primer binding site, wherein the first and second primer binding sites are different;
a second set of outer primers, wherein the set includes:
a second outer, forward primer including a barcode nucleotide sequence and a portion specific for the first primer binding site; and
a second outer, reverse primer including a portion specific for the second primer binding site. In particular embodiments, the first and second primer binding sites are binding sites for DNA sequencing primers. In specific embodiments, the outer primers each additionally include an additional nucleotide sequence, wherein:
the first outer, forward primer includes a first additional nucleotide sequence, and the first outer, reverse primer includes a second additional nucleotide sequence; and
the second outer, forward primer includes the second additional nucleotide sequence, and the second outer, reverse primer includes the first additional nucleotide sequence, and the first and second additional nucleotide sequences are different. In an illustrative embodiment, the first set of outer primers includes PE1-CS1 and PE2-BC-CS2, and the second set of outer primers includes PE1-CS2 and PE2-BC-CS1 (Table 1, Example 9). In certain embodiments, the kit additionally includes a set of inner primers, wherein the set includes:
an inner, forward primer including a target-specific portion and the first primer binding site; and an inner, reverse primer including a target-specific portion and the second primer binding site. In some embodiments, the kit includes a plurality of sets of inner primers, each specific for a different target nucleic acid.

Any of the above described kits useful for carrying out DNA bidirectional embodiments can additionally include DNA sequencing primers that bind to the first and second primer binding sites and prime sequencing of the target nucleotide sequence(s) and/or additionally include DNA sequencing primers that bind to the first and second primer binding sites and prime sequencing of the barcode nucleotide sequence(s). In specific embodiments, the primers that bind to the first and second primer binding sites and prime sequencing of the barcode nucleotide sequences(s) are reverse complements of the primers that prime sequencing of the target nucleotide sequences. For example, the primers employed to prime sequencing of the target nucleotide sequence(s) and barcode nucleotide sequence(s) include CS1, CS2, CS1rc, and CS2rc (Table 2, Example 9).

The invention further provides, in some embodiments, a method for detecting, and/or quantifying the relative amounts of, at least two different target nucleic acids in a nucleic acid sample. The method entails, producing first and second tagged target nucleotide sequences from first and second target nucleic acids in the sample,
the first tagged target nucleotide sequence including a first nucleotide tag; and
the second tagged target nucleotide sequence including a second nucleotide tag, wherein the first and second nucleotide tags are different. The tagged target nucleotide sequences are subjected to a first primer extension reaction using a first primer that anneals to the first nucleotide tag, and a second primer extension reaction using a second primer that anneals to the second nucleotide tag. The method further entails detecting and/or quantifying a signal that indicates extension of the first primer, and a signal that indicates extension of the second primer, wherein the a signal for a given primer indicates the presence, and/or relative amount of, the corresponding target nucleic acid.

DETAILED DESCRIPTION

Figure 1A:
FIG. 1A-1D: Illustration of hairpin adaptor molecules to produce adaptor-modified target nucleic acid molecules, e.g. a library suitable for use in high-throughput DNA sequencing. (A) Hairpin adaptor molecules each including: an adaptor nucleotide sequence, which is linked to a nucleotide linker, which is linked to a nucleotide sequence that is capable of annealing to the adaptor nucleotide sequence and is linked to a degenerate tail sequence; N=an nucleotide; an optional specific enzyme cutting site can be included in the nucleotide linker (B) Target nucleic acid molecule preparation can include fragmentation and digestion of 5' ends to produce 3' sticky ends. (C) Annealing, gap-filling, and ligation is carried out. (D) The resultant DNA is conveniently linearized using an enzyme that cuts within the linker.
Figure 1A:
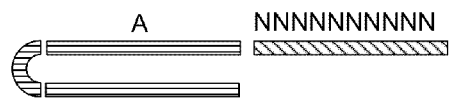
Figure 1B:
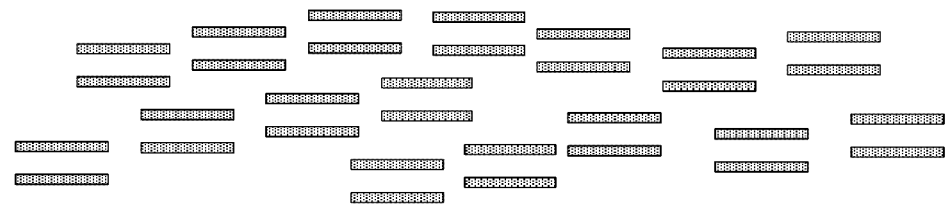
Figure 1B:
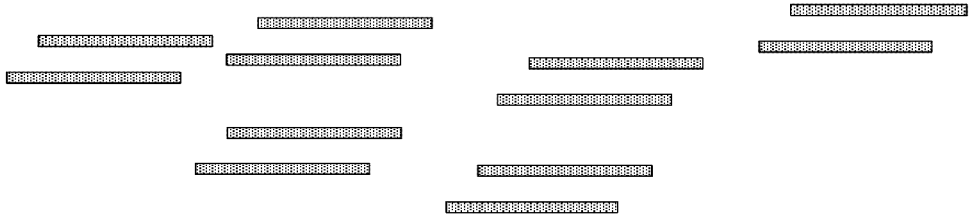
Figure 1C:
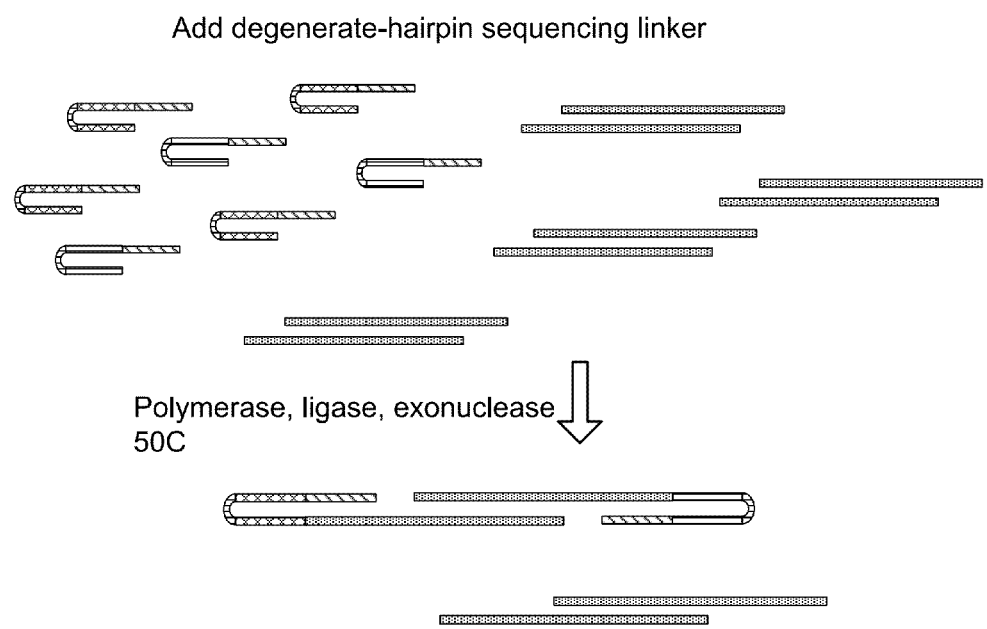

For a variety of applications, it is necessary or desirable to incorporate nucleic acid sequences into target nucleic acids derived, e.g., from a sample, such as a biological sample. The sequences incorporated can, in certain embodiments, facilitate further analysis of the target nucleic acids. Accordingly, described herein are methods useful for incorporating one or more adaptors and/or nucleotide tag(s) and/or barcode nucleotide sequence(s) one, or typically more, target nucleotide sequences. In particular embodiments, nucleic acid fragments having adaptors, e.g., suitable for use in high-throughput DNA sequencing are generated. In other embodiments, information about a reaction mixture is encoded into a reaction product. For example, if a nucleic acid amplification is carried out in the separate reaction volumes, it may be desirable to recover the contents for subsequent analysis, e.g., by PCR and/or nucleic acid sequencing. The contents of the separate reaction volumes may be analyzed separately and the results associated with the original reaction volumes. Alternatively, the particle/reaction volume identity can be encoded in the reaction product, e.g., as discussed below with respect to multi-primer nucleic acid amplification methods. Furthermore, these two strategies can be combined so that sets of separate reaction volumes are encoded, such that each reaction volume within the set is uniquely identifiable, and then pooled, with each pool then being analyzed separately.

In certain embodiments, the present invention provides amplification methods in which a barcode nucleotide sequence and additional nucleotide sequences that facilitate DNA sequencing are added to target nucleotide sequences. The barcode nucleotide sequence can encode information, such as, e.g., sample origin, about the target nucleotide sequence to which it is attached. The added sequences can, for example, serve as binding sites for DNA sequencing primers. Barcoding target nucleotide sequences can increase the number of samples that can be analyzed for one or multiple targets in a single assay, while minimizing increases in assay cost. The methods are particularly well-suited for increasing the efficiency of assays performed on microfluidic devices.

DEFINITIONS

Terms used in the claims and specification are defined as set forth below unless otherwise specified. These terms are defined specifically for clarity, but all of the definitions are consistent with how a skilled artisan would understand these terms.

The term "adjacent," when used herein to refer two nucleotide sequences in a nucleic acid, can refer to nucleotide sequences separated by 0 to about 20 nucleotides, more specifically, in a range of about 1 to about 10 nucleotides, or to sequences that directly abut one another. As those of skill in the art appreciate, two nucleotide sequences that that are to ligated together will generally directly abut one another.

The term "nucleic acid" refers to a nucleotide polymer, and unless otherwise limited, includes known analogs of natural nucleotides that can function in a similar manner (e.g., hybridize) to naturally occurring nucleotides.

The term nucleic acid includes any form of DNA or RNA, including, for example, genomic DNA; complementary DNA (cDNA), which is a DNA representation of mRNA, usually obtained by reverse transcription of messenger RNA (mRNA) or by amplification; DNA molecules produced synthetically or by amplification; and mRNA.

The term nucleic acid encompasses double- or triple-stranded nucleic acids, as well as single-stranded molecules. In double- or triple-stranded nucleic acids, the nucleic acid strands need not be coextensive (i.e, a double-stranded nucleic acid need not be double-stranded along the entire length of both strands).

A double-stranded nucleic acid that is not double-stranded along the entire length of both strands has a 5' or 3' extension that is referred to herein as a "sticky end" or as a "tail sequence." The term "sticky end" is often used to refer to a relatively short 5' or 3' extension, such as that produced by a restriction enzyme, whereas the term "tail sequence" is often used to refer to longer 5' or 3' extensions.

The term "degenerate sequence," as used herein denotes a sequence in a plurality of molecules, wherein a plurality of different nucleotide sequences are present. For example, all possible sequences for the degenerate sequence may be present.

The term "degenerate tail sequence" is used to describe a tail sequence in a plurality of molecules, wherein the tail sequences have a plurality of different nucleotide sequences; e.g., all possible different nucleotide sequences (1 per tail) may be present in the plurality of molecules.

The term nucleic acid also encompasses any chemical modification thereof, such as by methylation and/or by capping. Nucleic acid modifications can include addition of chemical groups that incorporate additional charge, polarizability, hydrogen bonding, electrostatic interaction, and functionality to the individual nucleic acid bases or to the nucleic acid as a whole. Such modifications may include base modifications such as 2'-position sugar modifications, 5-position pyrimidine modifications, 8-position purine modifications, modifications at cytosine exocyclic amines, substitutions of 5-bromo-uracil, backbone modifications, unusual base pairing combinations such as the isobases isocytidine and isoguanidine, and the like.

More particularly, in certain embodiments, nucleic acids, can include polydeoxyribonucleotides (containing 2-deoxy-D-ribose), polyribonucleotides (containing D-ribose), and any other type of nucleic acid that is an N- or C-glycoside of a purine or pyrimidine base, as well as other polymers containing nonnucleotidic backbones, for example, polyamide (e.g., peptide nucleic acids (PNAs)) and polymorpholino (commercially available from the Anti-Virals, Inc., Corvallis, Oreg., as Neugene) polymers, and other synthetic sequence-specific nucleic acid polymers providing that the polymers contain nucleobases in a configuration which allows for base pairing and base stacking, such as is found in DNA and RNA. The term nucleic acid also encompasses linked nucleic acids (LNAs), which are described in U.S. Pat. Nos. 6,794,499, 6,670,461, 6,262,490, and 6,770,748, which are incorporated herein by reference in their entirety for their disclosure of LNAs.

The nucleic acid(s) can be derived from a completely chemical synthesis process, such as a solid phase-mediated chemical synthesis, from a biological source, such as through isolation from any species that produces nucleic acid, or from processes that involve the manipulation of nucleic acids by molecular biology tools, such as DNA replication, PCR amplification, reverse transcription, or from a combination of those processes.

The order of elements within a nucleic acid molecule is typically described herein from 5' to 3'. In the case of a double-stranded molecule, the "top" strand is typically shown from 5' to 3', according to convention, and the order of elements is described herein with reference to the top strand.

The term "target nucleic acids" is used herein to refer to particular nucleic acids to be detected in the methods of the invention.

As used herein the term "target nucleotide sequence" refers to a molecule that includes the nucleotide sequence of a target nucleic acid, such as, for example, the amplification product obtained by amplifying a target nucleic acid or the cDNA produced upon reverse transcription of an RNA target nucleic acid.

As used herein, the term "complementary" refers to the capacity for precise pairing between two nucleotides. I.e., if a nucleotide at a given position of a nucleic acid is capable of hydrogen bonding with a nucleotide of another nucleic acid, then the two nucleic acids are considered to be complementary to one another at that position. Complementarity between two single-stranded nucleic acid molecules may be "partial," in which only some of the nucleotides bind, or it may be complete when total complementarity exists between the single-stranded molecules. The degree of complementarity between nucleic acid strands has significant effects on the efficiency and strength of hybridization between nucleic acid strands. A first nucleotide sequence is said to be the "complement" of a second sequence if the first nucleotide sequence is complementary to the second nucleotide sequence. A first nucleotide sequence is said to be the "reverse complement" of a second sequence, if the first nucleotide sequence is complementary to a sequence that is the reverse (i.e., the order of the nucleotides is reversed) of the second sequence.

"Specific hybridization" refers to the binding of a nucleic acid to a target nucleotide sequence in the absence of substantial binding to other nucleotide sequences present in the hybridization mixture under defined stringency conditions. Those of skill in the art recognize that relaxing the stringency of the hybridization conditions allows sequence mismatches to be tolerated.

In particular embodiments, hybridizations are carried out under stringent hybridization conditions. The phrase "stringent hybridization conditions" generally refers to a temperature in a range from about 5° C. to about 20° C. or 25° C. below than the melting temperature ($T_m$) for a specific sequence at a defined ionic strength and pH. As used herein, the $T_m$ is the temperature at which a population of double-stranded nucleic acid molecules becomes half-dissociated into single strands. Methods for calculating the $T_m$ of nucleic acids are well known in the art (see, e.g., Berger and Kimmel (1987) METHODS IN ENZYMOLOGY, VOL. 152: GUIDE TO MOLECULAR CLONING TECHNIQUES, San Diego: Academic Press, Inc. and Sambrook et al. (1989) MOLECULAR CLONING: A LABORATORY MANUAL, 2ND ED., VOLS. 1-3, Cold Spring Harbor Laboratory), both incorporated herein by reference). As indicated by standard references, a simple estimate of the $T_m$ value may be calculated by the equation: $T_m=81.5+0.41(\% \text{ G+C})$, when a nucleic acid is in aqueous solution at 1 M NaCl (see, e.g., Anderson and Young, Quantitative Filter Hybridization in NUCLEIC ACID HYBRIDIZATION (1985)). The melting temperature of a hybrid (and thus the conditions for stringent hybridization) is affected by various factors such as the length and nature (DNA, RNA, base composition) of the primer or probe and nature of the target nucleic acid (DNA, RNA, base composition, present in solution or immobilized, and the like), as well as the concentration of salts and other components (e.g., the presence or absence of formamide, dextran sulfate, polyethylene glycol). The effects of these factors are well known and are discussed in standard references in the art. Illustrative stringent conditions suitable for achieving specific hybridization of most sequences are: a temperature of at least about 60° C. and a salt concentration of about 0.2 molar at pH7.

The term "oligonucleotide" is used to refer to a nucleic acid that is relatively short, generally shorter than 200 nucleotides, more particularly, shorter than 100 nucleotides, most particularly, shorter than 50 nucleotides. Typically, oligonucleotides are single-stranded DNA molecules.

The term "adaptor" is used to refer to a nucleic acid that, in use, becomes appended to one or both ends of a nucleic acid. An adaptor may be single-stranded, double-stranded, or may include single- and double-stranded portions.

The term "primer" refers to an oligonucleotide that is capable of hybridizing (also termed "annealing") with a nucleic acid and serving as an initiation site for nucleotide (RNA or DNA) polymerization under appropriate conditions (i.e., in the presence of four different nucleoside triphosphates and an agent for polymerization, such as DNA or RNA polymerase or reverse transcriptase) in an appropriate buffer and at a suitable temperature. The appropriate length of a primer depends on the intended use of the primer, but primers are typically at least 7 nucleotides long and, more typically range from 10 to 30 nucleotides, or even more typically from 15 to 30 nucleotides, in length. Other primers can be somewhat longer, e.g., 30 to 50 nucleotides long. In this context, "primer length" refers to the portion of an oligonucleotide or nucleic acid that hybridizes to a complementary "target" sequence and primes nucleotide synthesis. Short primer molecules generally require cooler temperatures to form sufficiently stable hybrid complexes with the template. A primer need not reflect the exact sequence of the template but must be sufficiently complementary to hybridize with a template. The term "primer site" or "primer binding site" refers to the segment of the target nucleic acid to which a primer hybridizes.

A primer is said to anneal to another nucleic acid if the primer, or a portion thereof, hybridizes to a nucleotide sequence within the nucleic acid. The statement that a primer hybridizes to a particular nucleotide sequence is not intended to imply that the primer hybridizes either completely or exclusively to that nucleotide sequence. For example, in certain embodiments, amplification primers used herein are said to "anneal to a nucleotide tag." This description encompasses primers that anneal wholly to the nucleotide tag, as well as primers that anneal partially to the nucleotide tag and partially to an adjacent nucleotide sequence, e.g., a target nucleotide sequence. Such hybrid primers can increase the specificity of the amplification reaction.

As used herein, the selection of primers "so as to avoid substantial annealing to the target nucleic acids" means that primers are selected so that the majority of the amplicons detected after amplification are "full-length" in the sense that they result from priming at the expected sites at each end of the target nucleic acid, as opposed to amplicons resulting from priming within the target nucleic acid, which produces shorter-than-expected amplicons. In various embodiments, primers are selected to that at least 55%, at least 60%, at least 65%, at least 70%, at least 75%, at least 80%, at least 85%, at least 90%, at least 95%, at least 96%, at least 97%, at least 98%, or at least 99% are full-length.

The term "primer pair" refers to a set of primers including a 5' "upstream primer" or "forward primer" that hybridizes with the complement of the 5' end of the DNA sequence to be amplified and a 3' "downstream primer" or "reverse primer" that hybridizes with the 3' end of the sequence to be amplified. As will be recognized by those of skill in the art, the terms "upstream" and "downstream" or "forward" and "reverse" are not intended to be limiting, but rather provide illustrative orientation in particular embodiments.

In embodiments in which two primer pairs are used, e.g., in an amplification reaction, the primer pairs may be denoted "inner" and "outer" primer pairs to indicate their relative position; i.e., "inner" primers are incorporated into the reaction product (e.g., an amplicon) at positions in between the positions at which the outer primers are incorporated.

In embodiments in which three primer pairs are used, e.g., in an amplification reaction, the term "stuffer primer" can be used to refer to a primer that has a position in between inner and outer primers; i.e., the "stuffer" primer is incorporated into the reaction product (e.g., an amplicon) at positions intermediate between the inner and outer primers.

A primer pair is said to be "unique" if it can be employed to specifically produce (e.g., amplify) a particular reaction product (e.g., amplicon) in a given reaction (e.g., amplification) mixture.

A "probe" is a nucleic acid capable of binding to a target nucleic acid of complementary sequence through one or more types of chemical bonds, generally through complementary base pairing, usually through hydrogen bond formation, thus forming a duplex structure. The probe binds or hybridizes to a "probe binding site." The probe can be labeled with a detectable label to permit facile detection of the probe, particularly once the probe has hybridized to its complementary target. Alternatively, however, the probe may be unlabeled, but may be detectable by specific binding with a ligand that is labeled, either directly or indirectly. Probes can vary significantly in size. Generally, probes are at least 7 to 15 nucleotides in length. Other probes are at least 20, 30, or 40 nucleotides long. Still other probes are somewhat longer, being at least 50, 60, 70, 80, or 90 nucleotides long. Yet other probes are longer still, and are at least 100, 150, 200 or more nucleotides long. Probes can also be of any length that is within any range bounded by any of the above values (e.g., 15-20 nucleotides in length).

The primer or probe can be perfectly complementary to the target nucleic acid sequence or can be less than perfectly complementary. In certain embodiments, the primer has at least 65% identity to the complement of the target nucleic acid sequence over a sequence of at least 7 nucleotides, more typically over a sequence in the range of 10-30 nucleotides, and often over a sequence of at least 14-25 nucleotides, and more often has at least 75% identity, at least 85% identity, at least 90% identity, or at least 95%, 96%, 97%. 98%, or 99% identity. It will be understood that certain bases (e.g., the 3' base of a primer) are generally desirably perfectly complementary to corresponding bases of the target nucleic acid sequence. Primer and probes typically anneal to the target sequence under stringent hybridization conditions.

The term "nucleotide tag" is used herein to refer to a predetermined nucleotide sequence that is added to a target nucleotide sequence. The nucleotide tag can encode an item of information about the target nucleotide sequence, such the identity of the target nucleotide sequence or the identity of the sample from which the target nucleotide sequence was derived. In certain embodiments, such information may be encoded in one or more nucleotide tags, e.g., a combination of two nucleotide tags, one on either end of a target nucleotide sequence, can encode the identity of the target nucleotide sequence.

The term "affinity tag" is used herein to refer to a portion of a molecule that is specifically bound by a binding partner. This portion can, but need not be, a nucleotide sequence. The specific binding can be used to facilitate affinity purification of affinity tagged molecules.

The term "transposon end" refers to an oligonucleotide that is capable of being appended to a nucleic acid by a transposase enzyme.

As used herein the term "barcode primer" refers to a primer that includes a specific barcode nucleotide sequence that encodes information about the amplicon produced when the barcode primer is employed in an amplification reaction. For example, a different barcode primer can be employed to amplify one or more target sequences from each of a number of different samples, such that the barcode nucleotide sequence indicates the sample origin of the resulting amplicons.

As used herein, the term "encoding reaction" refers to reaction in which at least one nucleotide tag is added to a target nucleotide sequence. Nucleotide tags can be added, for example, by an "encoding PCR" in which the at least one primer comprises a target-specific portion and a nucleotide tag located on the 5' end of the target-specific portion, and a second primer that comprises only a target-specific portion or a target-specific portion and a nucleotide tag located on the 5' end of the target-specific portion. For illustrative examples of PCR protocols applicable to encoding PCR, see pending WO Application US03/37808 as well as U.S. Pat. No. 6,605,451. Nucleotide tags can also be added by an "encoding ligation" reaction that can comprise a ligation reaction in which at least one primer comprises a target-specific portion and nucleotide tag located on the 5' end of the target-specific portion, and a second primer that comprises a target-specific portion only or a target-specific portion and a nucleotide tag located on the 5' end of the target specific portion. Illustrative encoding ligation reactions are described, for example, in U.S. Patent Publication No. 2005/0260640, which is hereby incorporated by reference in its entirety, and in particular for ligation reactions.

As used herein an "encoding reaction" can produce a "tagged target nucleotide sequence," which includes a nucleotide tag linked to a target nucleotide sequence.

As used herein with reference to a portion of a primer, the term "target-specific" nucleotide sequence refers to a sequence that can specifically anneal to a target nucleic acid or a target nucleotide sequence under suitable annealing conditions.

As used herein with reference to a portion of a primer, the term "nucleotide tag-specific nucleotide sequence" refers to a sequence that can specifically anneal to a nucleotide tag under suitable annealing conditions.

Amplification according to the present teachings encompasses any means by which at least a part of at least one target nucleic acid is reproduced, typically in a template-dependent manner, including without limitation, a broad range of techniques for amplifying nucleic acid sequences, either linearly or exponentially. Illustrative means for performing an amplifying step include ligase chain reaction (LCR), ligase detection reaction (LDR), ligation followed by Q-replicase amplification, PCR, primer extension, strand displacement amplification (SDA), hyperbranched strand displacement amplification, multiple displacement amplification (MDA), nucleic acid strand-based amplification (NASBA), two-step multiplexed amplifications, rolling circle amplification (RCA), and the like, including multiplex versions and combinations thereof, for example but not limited to, OLA/PCR, PCR/OLA, LDR/PCR, PCR/PCR/LDR, PCR/LDR, LCR/PCR, PCR/LCR (also known as combined chain reaction—CCR), and the like. Descriptions of such techniques can be found in, among other sources, Ausbel et al.; PCR Primer: A Laboratory Manual, Diffenbach, Ed., Cold Spring Harbor Press (1995); The Electronic Protocol Book, Chang Bioscience (2002); Msuih et al., J. Clin. Micro. 34:501-07 (1996); The Nucleic Acid Protocols Handbook, R. Rapley, ed., Humana Press, Totowa, N.J. (2002); Abramson et al., Curr Opin Biotechnol. 1993 February; 4(1):41-7, U.S. Pat. No. 6,027,998; U.S. Pat. No. 6,605,451, Barany et al., PCT Publication No. WO 97/31256; Wenz et al., PCT Publication No. WO 01/92579; Day et al., Genomics, 29(1): 152-162 (1995), Ehrlich et al., Science 252:1643-50 (1991); Innis et al., PCR Protocols: A Guide to Methods and Applications, Academic Press (1990); Favis et al., Nature Biotechnology 18:561-64 (2000); and Rabenau et al., Infection 28:97-102 (2000); LCR Kit Instruction Manual, Cat. #200520, Rev. #050002, Stratagene, 2002; Barany, Proc. Natl. Acad. Sci. USA 88:188-93 (1991); Bi and Sambrook, Nucl. Acids Res. 25:2924-2951 (1997); Zirvi et al., Nucl. Acid Res. 27:e40i-viii (1999); Dean et al., Proc Natl Acad Sci USA 99:5261-66 (2002); Barany and Gelfand, Gene 109:1-11 (1991); Walker et al., Nucl. Acid Res. 20:1691-96 (1992); Polstra et al., BMC Inf. Dis. 2:18-(2002); Lage et al., Genome Res. 2003 February; 13(2):294-307, and Landegren et al., Science 241:1077-80 (1988), Demidov, V., Expert Rev Mol Diagn. 2002 November; 2(6):542-8., Cook et al., J Microbiol Methods. 2003 May; 53(2):165-74, Schweitzer et al., Curr Opin Biotechnol. 2001 February; 12(1):21-7, U.S. Pat. No. 5,830,711, U.S. Pat. No. 6,027,889, U.S. Pat. No. 5,686,243, PCT Publication No. WO0056927A3, and PCT Publication No. WO9803673A1.

In some embodiments, amplification comprises at least one cycle of the sequential procedures of: annealing at least one primer with complementary or substantially complementary sequences in at least one target nucleic acid; synthesizing at least one strand of nucleotides in a template-dependent manner using a polymerase; and denaturing the newly-formed nucleic acid duplex to separate the strands. The cycle may or may not be repeated. Amplification can comprise thermocycling or can be performed isothermally.

The term "qPCR" is used herein to refer to quantitative real-time polymerase chain reaction (PCR), which is also known as "real-time PCR" or "kinetic polymerase chain reaction."

The term "substantially" as used herein with reference to a parameter means that the parameter is sufficient to provide a useful result. Thus, "substantially complementary," as applied to nucleic acid sequences generally means sufficiently complementary to work in the described context. Typically, substantially complementary means sufficiently complementary to hybridize under the conditions employed. In some embodiments described herein, reaction products must be differentiated from unreacted primers. In this context, the statement that the "reaction products are substantially double-stranded," taken with the statement that the "primers are substantially single-stranded," means that there is a sufficient difference between the amount of double-stranded reaction products and the single-stranded primer, that the presence and/or amount of the reaction products can be determined.

A "reagent" refers broadly to any agent used in a reaction, other than the analyte (e.g., nucleic acid being analyzed). Illustrative reagents for a nucleic acid amplification reaction include, but are not limited to, buffer, metal ions, polymerase, reverse transcriptase, primers, template nucleic acid, nucleotides, labels, dyes, nucleases, and the like. Reagents for enzyme reactions include, for example, substrates, cofactors, buffer, metal ions, inhibitors, and activators.

The term "universal detection probe" is used herein to refer to any probe that identifies the presence of an amplification product, regardless of the identity of the target nucleotide sequence present in the product.

The term "universal qPCR probe" is used herein to refer to any such probe that identifies the presence of an amplification product during qPCR. In particular embodiments, nucleotide tags according to the invention can comprise a nucleotide sequence to which a detection probe, such as a universal qPCR probe binds. Where a tag is added to both ends of a target nucleotide sequence, each tag can, if desired, include a sequence recognized by a detection probe. The combination of such sequences can encode information about the identity or sample source of the tagged target nucleotide sequence. In other embodiments, one or more amplification primers can comprise a nucleotide sequence to which a detection probe, such as a universal qPCR probe binds. In this manner, one, two, or more probe binding sites can be added to an amplification product during the amplification step of the methods of the invention. Those of skill in the art recognize that the possibility of introducing multiple probe binding sites during preamplification (if carried out) and amplification facilitates multiplex detection, wherein two or more different amplification products can be detected in a given amplification mixture or aliquot thereof.

The term "universal detection probe" is also intended to encompass primers labeled with a detectable label (e.g., a fluorescent label), as well as non-sequence-specific probes, such as DNA binding dyes, including double-stranded DNA (dsDNA) dyes, such as SYBR Green.

The term "label," as used herein, refers to any atom or molecule that can be used to provide a detectable and/or quantifiable signal. In particular, the label can be attached, directly or indirectly, to a nucleic acid or protein. Suitable labels that can be attached to probes include, but are not limited to, radioisotopes, fluorophores, chromophores, mass labels, electron dense particles, magnetic particles, spin labels, molecules that emit chemiluminescence, electrochemically active molecules, enzymes, cofactors, and enzyme substrates.

The term "stain", as used herein, generally refers to any organic or inorganic molecule that binds to a component of a reaction or assay mixture to facilitate detection of that component.

The term "dye," as used herein, generally refers to any organic or inorganic molecule that absorbs electromagnetic radiation at a wavelength greater than or equal 340 nm.

The term "fluorescent dye," as used herein, generally refers to any dye that emits electromagnetic radiation of longer wavelength by a fluorescent mechanism upon irradiation by a source of electromagnetic radiation, such as a lamp, a photodiode, or a laser.

The term "elastomer" has the general meaning used in the art. Thus, for example, Allcock et al. (Contemporary Polymer Chemistry, 2nd Ed.) describes elastomers in general as polymers existing at a temperature between their glass transition temperature and liquefaction temperature. Elastomeric materials exhibit elastic properties because the polymer chains readily undergo torsional motion to permit uncoiling of the backbone chains in response to a force, with the backbone chains recoiling to assume the prior shape in the absence of the force. In general, elastomers deform when force is applied, but then return to their original shape when the force is removed.

As use herein, the term "variation" is used to refer to any difference. A variation can refer to a difference between individuals or populations. A variation encompasses a difference from a common or normal situation. Thus, a "copy number variation" or "mutation" can refer to a difference from a common or normal copy number or nucleotide sequence. An "expression level variation" or "splice variant" can refer to an expression level or RNA or protein that differs from the common or normal expression level or RNA or protein for a particular, cell or tissue, developmental stage, condition, etc.

A "polymorphic marker" or "polymorphic site" is a locus at which nucleotide sequence divergence occurs. Illustrative markers have at least two alleles, each occurring at frequency of greater than 1%, and more typically greater than 10% or 20% of a selected population. A polymorphic site may be as small as one base pair. Polymorphic markers include restriction fragment length polymorphism (RFLPs), variable number of tandem repeats (VNTR's), hypervariable regions, minisatellites, dinucleotide repeats, trinucleotide repeats, tetranucleotide repeats, simple sequence repeats, deletions, and insertion elements such as Alu. The first identified allelic form is arbitrarily designated as the reference form and other allelic forms are designated as alternative or variant alleles. The allelic form occurring most frequently in a selected population is sometimes referred to as the wildtype form. Diploid organisms may be homozygous or heterozygous for allelic forms. A diallelic polymorphism has two forms. A triallelic polymorphism has three forms.

A "single nucleotide polymorphism" (SNP) occurs at a polymorphic site occupied by a single nucleotide, which is the site of variation between allelic sequences. The site is usually preceded by and followed by highly conserved sequences of the allele (e.g., sequences that vary in less than $\frac{1}{100}$ or $\frac{1}{1000}$ members of the populations). A SNP usually arises due to substitution of one nucleotide for another at the polymorphic site. A transition is the replacement of one purine by another purine or one pyrimidine by another pyrimidine. A transversion is the replacement of a purine by a pyrimidine or vice versa. SNPs can also arise from a deletion of a nucleotide or an insertion of a nucleotide relative to a reference allele.

As used herein with respect to reactions, reaction mixtures, reaction volumes, etc., the term "separate" refers to reactions, reaction mixtures, reaction volumes, etc., where reactions are carried out in isolation from other reactions. Separate reactions, reaction mixtures, reaction volumes, etc. include those carried out in droplets (See, e.g., U.S. Pat. No. 7,294,503, issued Nov. 13, 2007 to Quake et al., entitled "Microfabricated crossflow devices and methods," which is incorporated herein by reference in its entirety and specifically for its description of devices and methods for forming and analyzing droplets; U.S. Patent Publication No. 20100022414, published Jan. 28, 2010, by Link et al., entitled "Droplet libraries," which is incorporated herein by reference in its entirety and specifically for its description of devices and methods for forming and analyzing droplets; and U.S. Patent Publication No. 20110000560, published Jan. 6, 2011, by Miller et al., entitled "Manipulation of Microfluidic Droplets," which is incorporated herein by reference in its entirety and specifically for its description of devices and methods for forming and analyzing droplets.), which may, but need not, be in an emulsion, as well as those wherein reactions, reaction mixtures, reaction volumes, etc. are separated by mechanical barriers, e.g., separate vessels, separate wells of a microtiter plate, or separate compartments of a matrix-type microfluidic device.

Production of Adaptor-Modified Target Nucleic Acid Molecules

In certain embodiments, the invention relates to a method of adding adaptor molecules to each end of a plurality of target nucleic acids that include sticky ends. These embodiments are useful, for example, in fragment generation for high-throughput DNA sequencing. The adaptors can be selected to facilitate sequencing using the DNA sequencing platform of choice.

In particular embodiments, such a method entails annealing adaptor molecules to the sticky ends of double-stranded target nucleic acid molecules to produce annealed adaptor-target nucleic acid molecules. The target nucleic acid molecules that include sticky ends can be produced by any convenient method. In certain embodiments, DNA molecules are fragmented, e.g., by any of enzymatic digestion, nebulization, sonication, and the like. For example, DNA molecules can be fragmented by digestion with a DNAse enzyme, such as DNAse I, terminated by heat treatment. Fragmentation that does not produce sticky ends can be followed by digesting the fragmented DNA molecules with an enzyme to produce sticky ends. In particular embodiments, the sticky ends of double-stranded target nucleic acid molecules are 3' extensions. A strand-specific endonuclease that does not have polymerase activity under the conditions employed in the digestion can be used to produce sticky ends. In an illustrative embodiment, sticky ends are produced by digesting 5' ends with Exonuclease III in the absence of dNTPs.

In a first embodiment, the adaptor molecules are hairpin structures each including: an adaptor nucleotide sequence, which is linked to a nucleotide linker, which is linked to a nucleotide sequence that is capable of annealing to the adaptor nucleotide sequence and is linked to a degenerate tail sequence. See FIG. 1A. This embodiment employs two types of adaptor molecules, wherein the each type includes an adaptor nucleotide sequence that is different from the other type (i.e., a first adaptor nucleotide sequence and a second adaptor nucleotide sequence).

Figure 2A:
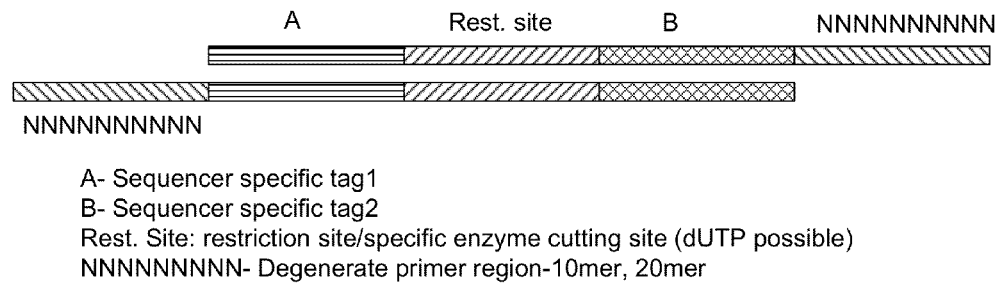
FIG. 2A-2D: Illustration of double-stranded adaptor molecules to produce adaptor-modified target nucleic acid molecules, e.g. a library suitable for use in high-throughput DNA sequencing. (A) Double-stranded adaptor molecules each including: a first adaptor nucleotide sequence, which is linked to a nucleotide linker, which is linked to a second adaptor nucleotide sequence; and a degenerate tail sequence on each strand, wherein double-stranded molecules each include two degenerate tail sequences as sticky end(s); N=an nucleotide; an optional specific enzyme cutting site can be included in the nucleotide linker. (B) Target nucleic acid molecule preparation can include fragmentation and digestion of 5' ends to produce 3' sticky ends. (C) Annealing, gap-filling, and ligation is carried out. (D) The resultant circular DNA is conveniently linearized using an enzyme that cuts within the linker.
Figure 2B:
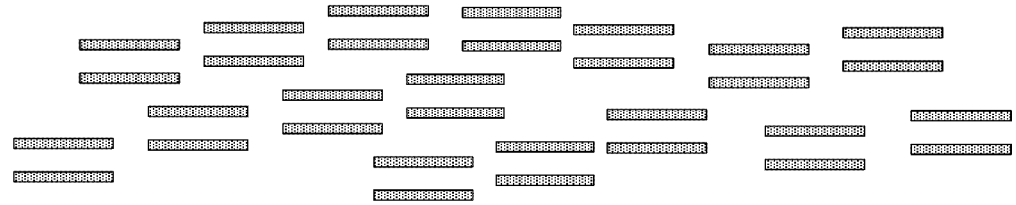
Figure 2B:
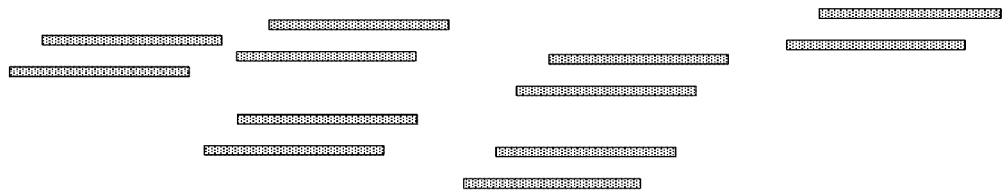
Figure 2C:
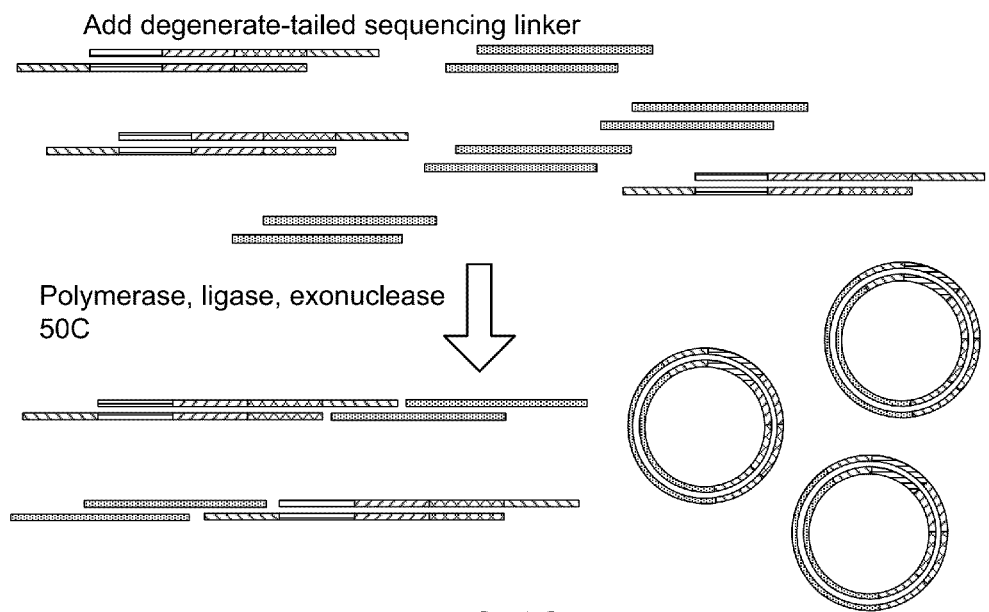

In a second embodiment, the adaptor molecules are double-stranded or single-stranded molecules each including: a first adaptor nucleotide sequence, which is linked to a nucleotide linker, which is linked to a second adaptor nucleotide sequence; and a degenerate tail sequence on each strand, wherein double-stranded molecules each include two degenerate tail sequences as sticky end(s). See FIG. 2A.

In certain embodiments, for example, those in which target nucleic acid molecules are being prepared for high-throughput DNA sequencing, the first and second adaptor sequences can include primer binding sites that are capable of being specifically bound by DNA sequencing primers, i.e., sequencer-specific tag 1 and sequencer specific tag 2. See FIGS. 1A and 2A.

In all cases, the degenerate tail sequence(s) can be at the 3' ends of the adaptor molecules. The degenerate tail sequences of the adaptor molecules are essentially complementary to at least a portion of the sticky ends on target nucleic acid molecules; i.e., the adaptor molecules are capable of annealing to the target nucleic acid molecules under the conditions employed. The length of the degenerate tail sequences will typically be sufficient to facilitate this annealing, e.g., about 10 to about 20 nucleotides. In certain embodiments, the degenerate tail sequences are protected at their 3' ends, e.g., with phosphothionate or dUTP to protect against exonuclease digestion.

The adaptor molecules can, optionally, include one or more additional nucleotide sequences. In certain embodiments, the nucleotide linker portion of the adaptor molecules can include an endonuclease site, a barcode nucleotide sequence, an affinity tag, and any combination thereof. For example, the nucleotide linker can include a restriction enzyme site and, optionally, at least one barcode nucleotide sequence.

In both the first and second embodiments, after annealing to target nucleic acids molecules, the method entails filling any gaps in the annealed adaptor-target nucleic acid molecules (e.g. using a DNA polymerase), and ligating any adjacent nucleotide sequences in the annealed adaptor-target nucleic acid molecules to produce adaptor-modified target nucleic acid molecules. In some embodiments, sticky end generation and ligation can be carried out in the same reaction mixture. For example an exonuclease can be used in concert with a ligase (e.g., a thermostable ligase) and a polymerase (e.g., PHUSION®) in a single reaction mixture.

Figure 1D:
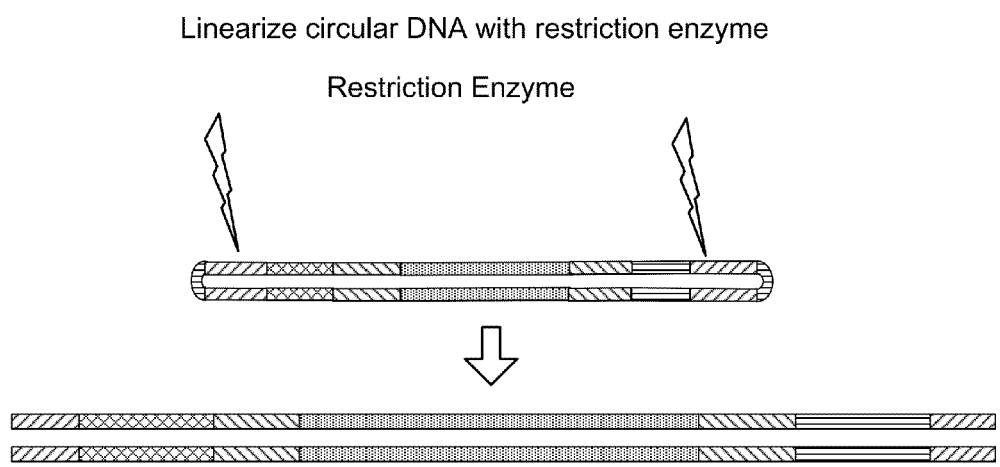
Figure 2D:
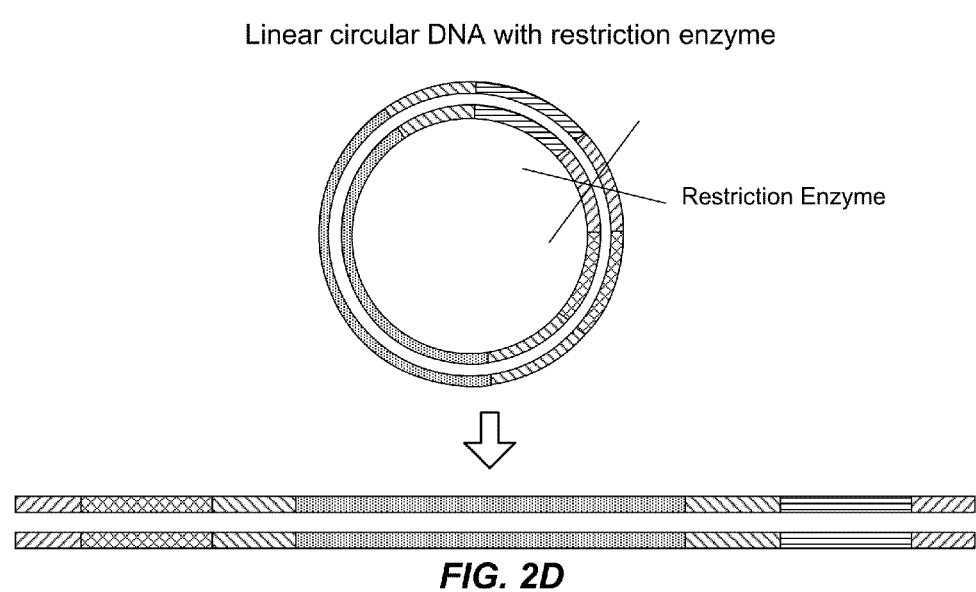

When the adaptor molecules are hairpin structures, ligation of adaptors to target nucleic acids converts the annealed adaptor-target nucleic acid molecules to single-stranded circular DNA molecules that can form a double-stranded structure as shown in FIG. 1D. When the adaptor molecules are single-stranded or double-stranded molecules, ligation of adaptors to target nucleic acids converts the annealed adaptor-target nucleic acid molecules to double-stranded circular DNA molecules. When the nucleotide linker includes an endonuclease site, the method can additionally include digesting the single-stranded or double-stranded circular DNA molecules to produce linear DNA molecules. See FIGS. 1D and 2D. In particular, double-stranded circular DNA molecules can be digested with a restriction enzyme that cuts at a site in the nucleotide linker to produce linear DNA molecules. In particular embodiments, the linear DNA molecules include 5'-a first portion of a nucleotide linker-second adaptor nucleotide sequence-a first degenerate tail sequence-target nucleic acid molecule-a second degenerate tail sequence-first adaptor nucleotide sequence-a second portion of a nucleotide linker-3'.

In an illustrative embodiment, the method described above can be carried out by:
  producing the plurality of target nucleic acid molecules that include sticky ends by:
    digesting DNA molecules with DNAse I to produce fragmented DNA molecules, and then heat inactivating the DNAse I;
    digesting the fragmented DNA molecules with an nuclease having 5' to 3' exonuclease activity (such as Exonuclease III) in the absence of deoxynucleotides to produce a plurality sticky-ended target nucleic acid molecules;
  annealing the adaptors to the sticky ends of the plurality of target nucleic acid molecules, wherein the nucleotide linker of the adaptors includes an endonuclease site;
  filling any gaps and ligating any adjacent nucleotide sequences in the annealed adaptor-target nucleic acid molecules in a single reaction including a polymerase and a ligase to produce circular DNA molecules; and
  digesting the circular DNA molecules with an endonuclease that cuts at the endonuclease site to produce linear DNA molecules.

In particular embodiments, methods of adding adaptor molecules to each end of a plurality of target nucleic acids can include sequencing the adaptor-modified target nucleic acid molecules by any available method, such as any available high-throughput DNA sequencing technique.

Incorporation of Nucleic Acid Sequences into Target Nucleic Acids

Reactions to incorporate one or more nucleotide sequences into target nucleic acids can be carried out using two or more primers that contain one or more nucleic acid sequences in addition to portions that anneal to the target nucleic acids. One or more of these portions may contain random sequences to incorporate nucleic acid sequences into essentially all nucleic acids in the sample. Alternatively, or in addition, one or more of these portions may be specific for one or more sequences common to a plurality of, or all, nucleic acids present. In other embodiments, the primers include portions specific for one or more particular target nucleic acids. Nucleic acid sequences can be incorporated using as few as two primers. However, various embodiments employ three, four, five, or six or more primers, as discussed in more detail below. Such reactions are discussed below in terms of nucleic acid amplification; however, those of skill in the art will readily appreciate that the strategies discussed below can be employed in other types of reactions, e.g., polymerase extension and ligation.

Three-Primer Methods

In particular embodiments, the invention provides an amplification method for incorporating a plurality (e.g., at least three) of selected nucleotide sequences into one or more target nucleic acid(s). The method entails amplifying a plurality of target nucleic acids, in some embodiments, in a plurality of samples. In illustrative embodiments, the same set of target nucleic acids can be amplified in each of two or more different samples. The samples can differ from one another in any way, e.g., the samples can be from different tissues, subjects, environmental sources, etc. At least three primers can be used to amplify each target nucleic acid, namely: forward and reverse amplification primers, each primer including a target-specific portion and one or both primers including a nucleotide tag (e.g., first and second nucleotide tags). The target-specific portions can specifically anneal to a target under suitable annealing conditions. The nucleotide tag for the forward primer can have a sequence that is the same as, or different from, a nucleotide tag for the reverse primer. Generally, the nucleotide tags are 5' of the target-specific portions. The third primer is a barcode primer comprising a barcode nucleotide sequence and a first and/or second nucleotide tag-specific portion. The barcode nucleotide sequence is a sequence selected to encode information about the amplicon produced when the barcode primer is employed in an amplification reaction. The tag-specific portion can specifically anneal to the one or both nucleotide tags in the forward and reverse primers. The barcode primer is generally 5' of the tag-specific portion.

The barcode primer is typically present in the amplification mixture in excess of the forward and/or reverse or (inner) primer(s). More specifically, if the barcode primer anneals to the nucleotide tag in the forward primer, the barcode primer is generally present in excess of the forward primer. If the barcode primer anneals to the nucleotide tag in the reverse primer, the barcode primer is generally present in excess of the reverse primer. In each instance the third primer in the amplification mixture, i.e., the reverse primer or the forward primer, respectively, can be present, in illustrative embodiments, at a concentration approximately similar to that of the barcode primer. Generally the barcode primer is present in substantial excess. For example, the concentration of the barcode primer in the amplification mixtures can be at least 2-fold, at least 4-fold, at least 5-fold, at least 10-fold, at least 15-fold, at least 20-fold, at least 25-fold, at least 30-fold, at least 35-fold, at least 40-fold, at least 45-fold, at least 50-fold, at least 100-fold, at least 500-fold, at least $10^3$-fold, at least $5 \times 10^3$-fold, at least $10^4$-fold, at least $5 \times 10^4$-fold, at least $10^5$-fold, at least $5 \times 10^5$-fold, at least $10^6$-fold, or higher, relative to the concentration of the forward and/or reverse primer(s). In addition, the concentration excess of the barcode primer can fall within any range having any of the above values as endpoints (e.g., 2-fold to $10^5$-fold). In illustrative embodiments, where the barcode primer has a tag-specific portion that is specific for the nucleotide tag on the forward primer, the forward primer can be present in picomolar to nanomolar concentrations, e.g., about 5 pM to 500 nM, about 5 pM to 100 nM, about 5 pM to 50 nM, about 5 pM to 10 nM, about 5 pM to 5 nM, about 10 pM to 1 nM, about 50 pM to about 500 pM, about 100 pM or any other range having any of these values as endpoints (e.g., 10 pM to 50 pM). Suitable, illustrative concentrations of barcode primer that could be used on combination with any of these concentrations of forward primer include about 10 nM to about 10 μM, about 25 nM to about 7.5 μM, about 50 nM to about 5 μM, about 75 nM to about 2.5 μM, about 100 nM to about 1 μM, about 250 nM to about 750 nM, about 500 nM or any other range having any of these values as endpoints (e.g., 100 nM to 500 nM). In amplification reactions using such concentrations of forward and barcode primers, the reverse primer have a concentration on the same order as the barcode primer (e.g. within about 10-fold, within about 5-fold, or equal).

Each amplification mixture can be subjected to amplification to produce target amplicons comprising tagged target nucleotide sequences, each comprising first and second nucleotide tags flanking the target nucleotide sequence, and at least one barcode nucleotide sequence at the 5' or 3' end of the target amplicon (relative to one strand of the target amplicon).

In certain embodiments, the first and second nucleotide tags and/or the barcode nucleotide sequence are selected so as to avoid substantial annealing to the target nucleic acids. In such embodiments, the tagged target nucleotide sequences can include molecules having the following elements: 5'-(barcode nucleotide sequence)-(first nucleotide tag from the forward primer)-(target nucleotide sequence)-(second nucleotide tag sequence from the reverse primer)-3' or 5'-(first nucleotide tag from the forward primer)-(target nucleotide sequence)-(second nucleotide tag sequence from the reverse primer)-(barcode nucleotide sequence)-3'.

Four-Primer Methods

In some embodiments, more than three primers can be employed to add desired elements to a target nucleotide sequence. For example, four primers can be employed to produce molecules having the same elements discussed above, plus an optional additional barcode e.g., 5'-(barcode nucleotide sequence)-(first nucleotide tag from the forward primer)-(target nucleotide sequence)-(second nucleotide tag from the reverse primer)-(additional barcode nucleotide sequence)-3'. In an illustrative four-primer embodiment, the forward primer includes a target-specific portion and first nucleotide tag, and the reverse primer includes a target-specific portion and a second nucleotide tag. Together, these two primers constitute the "inner primers." The remaining two primers are the "outer primers," which anneal to the first and second nucleotide tags present in the inner primers. One outer primer is a barcode primer, as described above. The second outer primer can include a second tag-specific portion and an additional barcode nucleotide sequence, i.e., it can be a second barcode primer.

Amplification to incorporate elements from more than three primers can be carried out in one or multiple amplification reactions. For example, a four-primer amplification can be carried out in one amplification reaction, in which all four primers are present. Alternatively, a four-primer amplification can be carried out, e.g., in two amplification reactions: one to incorporate the inner primers and a separate amplification reaction to incorporate the outer primers. Where all four primers are present in one amplification reaction, the outer primers are generally present in the reaction mixture in excess. The relative concentration values give above for the barcode primer relative to the forward and/or reverse primers also applies to the concentrations of the outer primers relative to inner primers in a one-step, four-primer amplification reaction.

Combinatorial Methods

In an illustrative embodiment of the four-primer amplification reaction, each of the outer primers contains a unique barcode. For example, one barcode primer would be constructed of the elements 5'-(first barcode nucleotide sequence)-(first nucleotide tag)-3', and the second barcode primer would be constructed of the elements 5'-(second barcode nucleotide sequence)-(second nucleotide tag)-3'. In this embodiment, a number (J) of first barcode primers can be combined with a number (K) of second barcode primers to create J×K unique amplification products.

In a further illustrative embodiment of the invention, more than four primers can be combined in a single reaction to append different combinations of barcode nucleotide sequences and nucleotide tags. For example, outer barcode primers containing the following elements: 5'-(first barcode nucleotide sequence)-(first nucleotide tag)-3',5'-(first barcode nucleotide sequence)-(second nucleotide tag)-3',5'-(second barcode nucleotide sequence)-(first nucleotide tag)-3',5'-(second barcode nucleotide sequence)-(second nucleotide tag)-3', can be combined with inner target-specific primers as described above to produce amplification product pools containing all combinations of the barcode primers with the desired amplicon sequence.

In other illustrative embodiments of the invention, outer barcode primers in any of the combinations described above, or other combinations that would be obvious to one of skill in the art, can be combined with more than one pair of target primer sequences bearing the same first and second nucleotide tag sequences. For example, inner primers containing up to ten different target-specific forward primer sequences combined with the same first nucleotide tag and up to ten different target-specific reverse primer sequences combined with the same second nucleotide tag can be combined with the up to 2 or up to 4 outer barcode primers to generate multiple amplification products as described above. In various embodiments, at least 10, at least 20, at least 50, at least 100, at least 200, at least 500, at least 1000, at least 2000, at least 5000 or at least 10000 different target-specific primer pairs bearing the same first nucleotide tag and second nucleotide tag would be combined with the up to 2 or up to 4 outer barcode primers to generate multiple amplification products.

Bidirectional Combinatorial Methods

In an illustrative embodiment of the four-primer amplification reaction, inner and outer primers can each include a unique barcode, such that amplification produces a barcode combination at each end of the resultant amplicons. This approach is useful when the amplicons are to be sequenced because the barcode combination can be read from either end of the sequence. For example, four primers can be employed to produce molecules having the following elements: 5'-second barcode nucleotide sequence-first nucleotide tag sequence-first barcode nucleotide sequence-target nucleotide sequence-first barcode nucleotide sequence-second nucleotide tag sequence-second barcode nucleotide sequence-3'. In an illustrative four-primer embodiment, two inner primers can include:

a forward, inner primer including a first nucleotide tag, a first barcode nucleotide sequence, and a target-specific portion; and a reverse, inner primer including a target-specific portion, a first barcode nucleotide sequence, and a second nucleotide tag. Two outer primers can include:

a forward, outer primer including a second barcode nucleotide sequence and a first nucleotide tag-specific portion; and a reverse, outer primer including a second nucleotide tag-specific portion and a second barcode nucleotide sequence. As discussed above, if the inner and outer primers are included in the same reaction mixture, the outer primers are preferably present in excess.

A similar combination of elements may be produced in a six-primer amplification method that employs "stuffer" primers, in addition to inner and outer primers. Thus, for example, two inner primers can include:

a forward, inner primer including a first nucleotide tag and a target-specific portion; and a reverse, inner primer including a target-specific portion and a second nucleotide tag. Two stuffer primers can include:

a forward, stuffer primer including a third nucleotide tag, a first barcode nucleotide sequence, and a first nucleotide tag-specific portion; and a reverse, stuffer primer including a second nucleotide tag-specific portion, a first barcode nucleotide sequence, a fourth nucleotide tag. Two outer primers can include:

a forward, outer primer including a second barcode nucleotide sequence and a third nucleotide tag-specific portion; and a reverse, outer primer including a fourth nucleotide tag-specific portion and a second barcode nucleotide sequence. Nucleic acid amplification produces an amplicon including the following elements: 5'-second barcode nucleotide sequence-third nucleotide tag sequence-first barcode nucleotide sequence-first nucleotide tag sequence-target nucleotide sequence-second nucleotide tag sequence-first barcode nucleotide sequence-fourth nucleotide tag sequence-second barcode nucleotide sequence-3'. Amplification can be carried out in one, two, three amplification reactions. For example, all three primer pairs can be included in one reaction. Alternatively, two reactions can be carried out, e.g., a first reaction including the inner and stuffer primers, and a second reaction including only the outer primers; or a first reaction including only the inner primers, followed by a second reaction including the stuffer and outer primers. Where more than one primer pair is present, the primer pair that is the "outer" pair, relative to the other pair is preferably present in excess, as discussed above. Thus, if the inner and stuffer primers are included in a reaction mixture, the stuffer primers are preferably present in excess, and if the stuffer and outer primers are included in a reaction mixture, the outer primers are preferably present in excess. When all three primer pairs are included in a single reaction, the stuffer primers can be present at a concentration intermediate between that of the inner primers and the outer primers.

In certain embodiments of the above-described four-primer and six-primer amplification methods, e.g., where the molecules produced in the reaction will be subjected to DNA sequencing, the outer primers can additionally include first and second primer binding sites that are capable of being bound by DNA sequencing primers. For example, a four-primer reaction can produce tagged target nucleotide sequences including 5'-first primer binding site-second barcode nucleotide sequence-first nucleotide tag sequence-first barcode nucleotide sequence-target nucleotide sequence-first barcode nucleotide sequence-second nucleotide tag sequence-second barcode nucleotide sequence-second primer binding site-3'. This embodiment offers the advantage that the barcode combination can be determined in a sequencing read from either end of the molecule. Similarly, a six-primer reaction can produce tagged target nucleotide sequences comprising 5'-first primer binding site-second barcode nucleotide sequence-third nucleotide tag sequence-first barcode nucleotide sequence-first nucleotide tag sequence-target nucleotide sequence-second nucleotide tag sequence-first barcode nucleotide sequence-fourth nucleotide tag sequence-second barcode nucleotide sequence-second primer binding site-3'.

Combinatorial Ligation-Based Tagging

In certain embodiments, the invention includes a ligation-based method for combinatorial tagging (e.g., barcoding) of a plurality of target nucleotide sequences. The method employs a plurality of tagged target nucleotide sequences derived from target nucleic acids. Each tagged target nucleotide sequences includes an endonuclease site and a first barcode nucleotide sequence. Tagged target nucleotide sequences in the plurality include the same endonuclease site, but N different first barcode nucleotide sequences, wherein N is an integer greater than 1.

The tagged target nucleotide sequences are cut with an endonuclease specific for the endonuclease site to produce a plurality of sticky-ended, tagged target nucleotide sequences. A plurality of adaptors is then ligated, in a first reaction mixture, to the tagged target nucleotide sequences. The plurality of adaptors includes a second barcode nucleotide sequence and complementary sticky ends to the plurality of sticky-ended, tagged target nucleotide sequences. Furthermore, the plurality of adaptors includes M different second barcode nucleotide sequences, wherein M is an integer greater than 1. The ligation produces a plurality of combinatorially tagged target nucleotide sequences, each including first and second barcode nucleotide sequences, wherein the plurality includes N×M different first and second barcode combinations.

In certain embodiments, the endonuclease site is adjacent to the first barcode nucleotide sequence in the tagged target nucleotide sequences. In variations of such embodiments, second barcode nucleotide sequence is adjacent to the complementary sticky end in the adaptors. In specific embodiments, the combinatorially tagged target nucleotide sequences, for example, include the first and second barcode nucleotide sequences separated by fewer than 5 nucleotides.

In particular embodiments, e.g., when the combinatorially tagged target nucleic nucleotide sequences are intended for sequencing, the tagged target nucleotide sequences can include first and second primer binding site, which can have either of the following arrangements: 5'-endonuclease site-first barcode nucleotide sequence-first primer binding site-target nucleotide sequence-second primer binding site; and 5'-first primer binding site-target nucleotide sequence-second primer binding site-first barcode nucleotide sequence-endonuclease site-3'. To facilitate sequencing, the first and second primer binding sites can be binding sites for DNA sequencing primers. In variations of such embodiments, the combinatorially tagged nucleic can include the second barcode nucleotide sequence in one of the following arrangements: 5'-second barcode nucleotide sequence-first barcode nucleotide sequence-first primer binding site-target nucleotide sequence-second primer binding site; or 5'-first primer binding site-target nucleotide sequence-second primer binding site-first barcode nucleotide sequence-second barcode nucleotide sequence-3'.

Tagged target nucleotide sequences useful in this method can be prepared by any convenient means, such as, for example, by ligating adaptors onto a plurality of target nucleic acids, wherein the adaptors include: a first adaptor including the endonuclease site, the first barcode nucleotide sequence, the first primer binding site, and a sticky end; and a second adaptor including a second primer binding site and a sticky end.

Figure 5A:
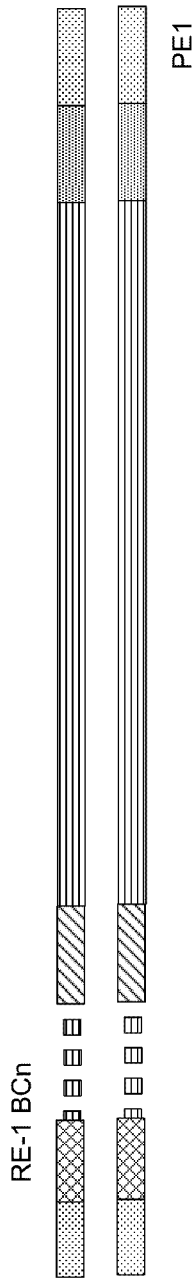
FIG. 5A-5B: A combinatorial ligation-based tagging method employing tagged target nucleotide sequences (A) to produce combinatorially tagged target nucleotide sequences. PE1, PE1=Illumina sequencing flowcell binding sequences; Seq1, Seq2=sequencing priming sites; BC1, BC2=barcode sequences. See Example 2.
Figure 5B:
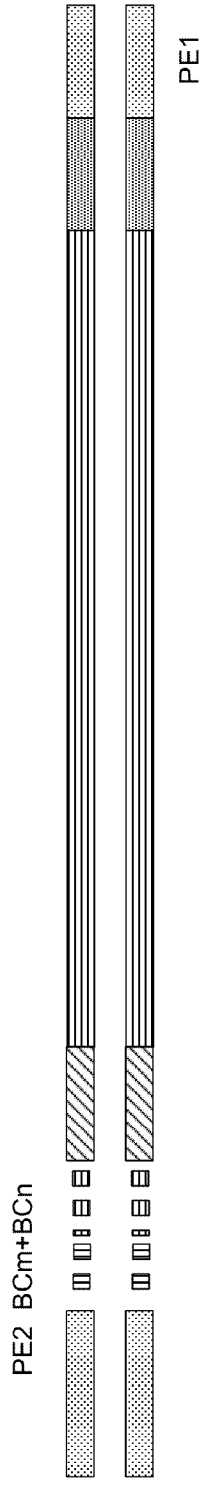

In some embodiments, it is advantageous to include one or more additional nucleotide sequences in the tagged target nucleotide sequences, e.g., to facilitate handling and/or identification. Thus, the tagged target nucleotide sequences can include a first additional nucleotide sequence having an arrangement selected from: 5'-endonuclease site-first barcode nucleotide sequence-first primer binding site-target nucleotide sequence-second primer binding site-first additional nucleotide sequence; and/or 5'-first additional nucleotide sequence-first primer binding site-target nucleotide sequence-second primer binding site-first barcode nucleotide sequence-endonuclease site-3'. For example, in Illumina sequencing, flow cell binding sequences (e.g., PE1 and PE2) are incorporated at either end of a DNA template to be sequenced. In the present method, the tagged target nucleotide sequences can include one flow cell binding sequence as the first additional nucleotide sequence, and the other flow cell binding sequence can be introduced via an adaptor. See, e.g., FIG. 5A-B. Thus, the present method can employ adaptors that include a second additional nucleotide sequence and have the arrangement: 5'-second additional nucleotide sequence-second barcode nucleotide sequence-complementary sticky end-3'. In this case, ligation of the adaptors to the above-described tagged target nucleotide sequences containing a first additional nucleotide sequence produces combinatorially tagged target nucleotide sequences including: 5'-second additional nucleotide sequence-second barcode nucleotide sequence-first barcode nucleotide sequence-first primer binding site-target nucleotide sequence-second primer binding site-first additional nucleotide sequence; and/or 5'-second additional nucleotide sequence-first primer binding site-target nucleotide sequence-second primer binding site-first barcode nucleotide sequence-second barcode nucleotide sequence-first additional nucleotide sequence -3'. In variations of this embodiment, the first and/or second additional nucleotide sequences include a primer binding site.

Tagged target nucleotide sequences that contain a first additional nucleotide sequence can be prepared by any convenient means, such as, for example, by ligating adaptors onto a plurality of target nucleic acids, wherein the adaptors include: a first adaptor including the endonuclease site, the first barcode nucleotide sequence, the first primer binding site, and a sticky end; and a second adaptor including a first additional nucleotide sequence, a second primer binding site and a sticky end.

Combinatorial Insertional Mutagenesis-Based Tagging

Combinatorial tagging can also be carried out using insertional mutagenesis. In certain embodiments, combinatorial tagging of a plurality of target nucleotide sequences is carried out by annealing a plurality of barcode primers to a plurality of tagged target nucleotide sequences derived from target nucleic acids, and then amplifying the tagged target nucleotide sequences in a first reaction mixture to produce a plurality of combinatorially tagged target nucleotide sequences, each including first and second barcode nucleotide sequences, wherein the plurality includes N×M different first and second barcode combinations.

In particular embodiments, each tagged target nucleotide sequence includes a nucleotide tag at one end and a first barcode nucleotide sequence, wherein tagged target nucleotide sequences in the plurality include the same nucleotide tag, but N different first barcode nucleotide sequences, wherein N is an integer greater than one. In variations of such embodiments, the first barcode nucleotide sequence is separated from the nucleotide tag by the target nucleotide sequence. Each barcode primer includes: a first tag-specific portion linked to a second barcode nucleotide sequence, which is itself linked to a second tag-specific portion, wherein the barcode primers in the plurality each include the same first and second tag-specific portions, but M different second barcode nucleotide sequences, wherein M is an integer greater than one. The first tag-specific portion of the barcode primer anneals to a 5' portion of the nucleotide tag, and the second tag-specific portion of the barcode primer anneals to an adjacent 3' portion of the nucleotide tag, and the second barcode nucleotide sequence does not anneal to the nucleotide tag, forming a loop between the annealed first and second tag-specific portions.

In particular embodiments, useful e.g. in DNA sequencing, the tagged nucleotide sequences additionally include a primer binding site between the target nucleotide sequence and the first barcode nucleotide sequence. In variations of such embodiments, the first and second tag-specific portions of the barcode primer are sufficiently long to serve as primer binding sites. To facilitate sequencing one or more, or preferably all, of these binding sites are binding sites for DNA sequencing primers. In such embodiments, the combinatorially tagged target nucleotide sequences can include 5'-first tag-specific portion-second barcode nucleotide sequence-second tag-specific portion-target nucleotide sequence-primer binding site-first barcode nucleotide sequence-3'.

Figure 6:
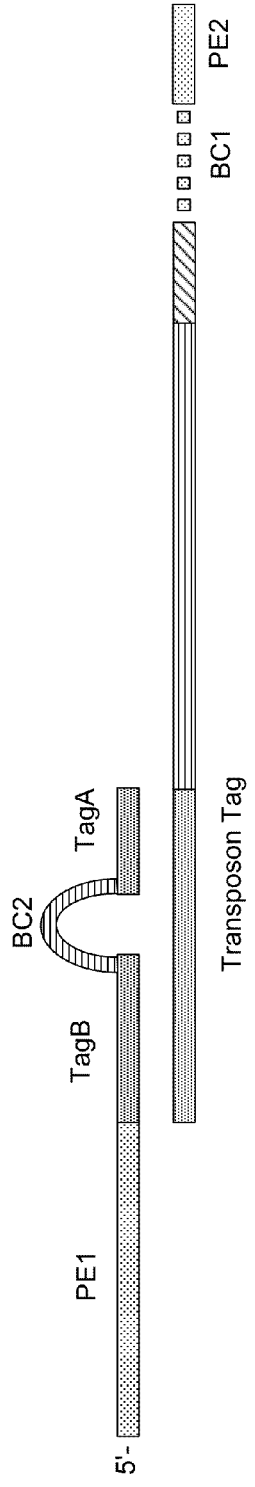
FIG. 6: Combinatorial insertional mutagenesis-based tagging for sequencing (e.g., Illumina sequencing). A barcode is inserted into Transposon tag sequence. TagA and TagB need to be long enough to prime sequencing. BC2 should contain a 4-base barcode plus 3 degenerate primers at 5' end (e.g. NNNAGTC). Transposon end sequence=5'-AGATGTG-TATAAGAGACAG-3' (SEQ ID NO:1). PE1, PE1=Illumina sequencing flowcell binding sequences; BC1, BC2=barcode sequences.

In some embodiments, it is advantageous to include one or more additional nucleotide sequences in the tagged target nucleotide sequences, e.g., to facilitate handling and/or identification. Thus, the tagged target nucleotide sequences can include a first additional nucleotide sequence having the arrangement: 5'-nucleotide tag-target nucleotide sequence-primer binding site-first barcode nucleotide sequence-first additional nucleotide sequence-3'. For example, in Illumina sequencing, flow cell binding sequences (e.g., PE1 and PE2) are incorporated at either end of a DNA template to be sequenced. In the present method, the tagged target nucleotide sequences can include one flow cell binding sequence as the first additional nucleotide sequence, and the other flow cell binding sequence can be introduced via the barcode primers. See, e.g., FIG. 6. Thus, the present method can employ bar code primers that include a second additional nucleotide sequence and have the arrangement: 5'-second additional nucleotide sequence-first tag-specific portion-second barcode nucleotide sequence-second tag-specific portion-3'. In this case, amplification produces combinatorially tagged target nucleotide sequences that include 5'-second additional nucleotide sequence-first tag-specific portion-second barcode nucleotide sequence-second tag-specific portion-target nucleotide sequence-primer binding site-first barcode nucleotide sequence-first additional nucleotide sequence-3'. In variations of this embodiment, the first and/or second additional nucleotide sequences include a primer binding site.

The target nucleotide sequences can be tagged by any convenient means, including the primer-based methods described herein. In certain embodiments, the nucleotide tag includes a transposon end, which is incorporated into the tagged target nucleotide sequences using a transposase.

Reactions to Incorporate Nucleic Acid Sequences

Any method can be employed to incorporate nucleic acids sequences into target nucleic acids. In illustrative embodiments, PCR is employed. When using three or more primers, the amplification is generally carried out for at least three cycles to incorporate the first and second nucleotide tags and the barcode nucleotide sequence. In various embodiments, amplification is carried out for 5, 10, 15, 20, 25, 30, 35, 40, 45, or 50 cycles, or for any number of cycles falling within a range having any of these values as endpoints (e.g. 5-10 cycles). In particular embodiments, amplification is carried out for a sufficient number of cycles to normalize target amplicon copy number across targets and across samples (e.g., 15, 20, 25, 30, 35, 40, 45, or 50 cycles, or for any number of cycles falling within a range having any of these values as endpoints).

Particular embodiments of the above-described method provide substantially uniform amplification, yielding a plurality of target amplicons wherein the majority of amplicons are present at a level relatively close to the average copy number calculated for the plurality of target amplicons. Thus, in various embodiments, at least 50, at least 55, at least 60, at least 65, at least 70, at least 75, at least 80, at least 85, at least 90, at least 91, at least 92, at least 93, at least 94, at least 95, at least 96, at least 97, at least 98, or at least 99 percent of the target amplicons are present at greater than 50 percent of the average number of copies of target amplicons and less than 2-fold the average number of copies of target amplicons.

Applications

In illustrative embodiments, the barcode nucleotide sequence identifies a particular sample. Thus, for example, a set of T target nucleic acids can be amplified in each of S samples, where S and T are integers, typically greater than one. In such embodiments, amplification can be performed separately for each sample, wherein the same set of forward and reverse primers is used for each sample and the set of forward and reverse primers has at least one nucleotide tag that is common to all primers in the set. A different barcode primer can be used for each sample, wherein the bar code primers have different barcode nucleotide sequences, but the same tag-specific portion that can anneal to the common nucleotide tag. This embodiment has the advantage of reducing the number of different primers that would need to be synthesized to encode sample origin in amplicons produced for a plurality of target sequences. Alternatively, different sets of forward and reverse primers can be employed for each sample, wherein each set has a nucleotide tag that is different from the primers in the other set, and different barcode primers are used for each sample, wherein the barcode primers have different barcode nucleotide sequences and different tag-specific portions. In either case, the amplification produces a set of T amplicons from each sample that bear sample-specific barcodes.

In embodiments wherein the same set of forward and reverse primers is used for each sample, the forward and reverse primers for each target can be initially combined separately from the sample, and each barcode primer can be initially combined with its corresponding sample. Aliquots of the initially combined forward and reverse primers can then be added to aliquots of the initially combined sample and barcode primer to produce S×T amplification mixtures. These amplification mixtures can be formed in any article that can be subjected to conditions suitable for amplification. For example, the amplification mixtures can be formed in, or distributed into, separate compartments of a microfluidic device prior to amplification. Suitable microfluidic devices include, in illustrative embodiments, matrix-type microfluidic devices, such as those described below.

In certain embodiments, target amplicons produced in any of the methods described herein can be recovered from the amplification mixtures. For example, a matrix-type microfluidic device that is adapted to permit recovery of the contents of each reaction compartment (see below) can be employed for the amplification to generate the target amplicons. In variations of these embodiments, the target amplicons can be subjected to further amplification and/or analysis. In certain embodiments, the amount of target amplicons produced in the amplification mixtures can be quantified during amplification, e.g., by quantitative real-time PCR, or after.

In embodiments that are useful in single-particle analysis, combinatorial barcoding can be used to encode the identity of a reaction volume, and thus particle, that was the source of an amplification product. In specific embodiments, nucleic acid amplification is carried out using at least two barcode sequences, and the combination of barcode sequences encodes the identity of the reaction volume that was the source of the reaction product (termed "combinatorial barcoding"). These embodiments are conveniently employed when the separate reaction volumes are in separate compartments of a matrix-type microfluidic device, e.g., like those available from Fluidigm Corp. (South San Francisco, Calif.) and described below (see "Microfluidic Devices"). Each separate compartment can contain a combination of barcode nucleotide sequences that identifies the row and column of the compartment in which the encoding reaction was carried out.

If the reaction volumes are recovered and subjected to further analysis that includes detection of the barcode combination (e.g., by DNA sequencing), the results can be associated with a particular compartment and, thereby, with a particular particle in the compartment. Such embodiments are particularly useful when separate reaction volumes are combined during or after the recovery process, such that reaction products from a plurality of separate reaction volumes are combined ("pooled"). In a matrix-type microfluidic device, for example, reaction products from all compartments in a row, all compartments in a column, or all compartments in the device could be pooled. If all compartments in a row are pooled, each column within a row preferably has a unique barcode combination. If all compartments in a column are pooled, each row within a column has a unique barcode combination. If all compartments with a device are pooled, every compartment within the device has a unique barcode combination.

Barcoding and Pooling of Reaction Mixtures for Subsequent Analysis

In other embodiments, a barcoding and pooling strategy is used to detect a plurality of target nucleic acids in individual reaction mixtures, which can, for example, contain individual particles, such as cells. This strategy is described for single-cell analysis of gene expression in Example 7, below.

In one embodiment, the method entails preparing M first reaction mixtures that will be pooled prior to assay, wherein M is an integer greater than 1. Each reaction mixture includes sample nucleic acid(s); a first, forward primer comprising a target-specific portion; and a first, reverse primer comprising a target-specific portion. The first, forward primer or the first, reverse primer can additionally include a barcode nucleotide sequence, wherein each barcode nucleotide sequence in each of the M reaction mixtures is different. Alternatively, the first, forward primer or the first, reverse primer additionally includes a nucleotide tag, and each reaction mixture additionally includes at least one barcode primer including a barcode nucleotide sequence and a nucleotide tag-specific portion, wherein each barcode nucleotide sequence in each of the M reaction mixtures is different. In this embodiment, the barcode primer is generally in excess of the first, forward and/or first, reverse primer(s). Each first reaction mixture is subjected to a first reaction to produce a plurality of barcoded target nucleotide sequences, each comprising a target nucleotide sequence linked to a barcode nucleotide sequence. The barcoded target nucleotide sequences for each of the M first reaction mixtures are pooled to form an assay pool. Within this assay pool, a particular target nucleotide sequence from a particular reaction mixture is uniquely identified by a particular barcode nucleotide sequence. The assay pool, or one or more aliquots thereof, is subjected to a second reaction using unique pairs of second primers, wherein each second primer pair includes a second, forward or a reverse primer that anneals to a target nucleotide sequence; and a second, reverse or a forward primer, respectively, that anneals to a barcode nucleotide sequence. The method includes determining whether a reaction product is present in the assay pool, or aliquot thereof for each unique, second primer pair. For each unique, second primer pair, the presence of a reaction product indicates the presence of a particular target nucleic acid in a particular first reaction mixture.

In certain embodiments, the method entails preparing M×N first reaction mixtures, wherein N is an integer greater than 1, and each first reaction mixture includes a pair of first, forward and reverse primers that is specific for a different target nucleic acid. After the first reaction, N assay pools are prepared, each including M first reaction mixtures, wherein each barcoded target nucleotide sequence in an assay pool includes a different barcode nucleotide sequence. The second reaction is carried out in each of the N assay pools, with each assay pool being separate from every other assay pool.

For the first reaction, any reaction capable of producing target nucleotide sequences linked to a barcode nucleotide sequences can be carried out. Convenient first reactions include amplification and ligation.

The second reaction can be any reaction that relies on primer-based detection of barcoded target nucleotide sequences. Methods that include amplification and/or ligation steps, including any of those described herein and/or known in the art can be used. For example, the presence of reaction products can be detected using polymerase chain reaction (PCR) or ligase chain reaction (LCR). In some embodiments, real-time detection is employed.

Figure 8A:
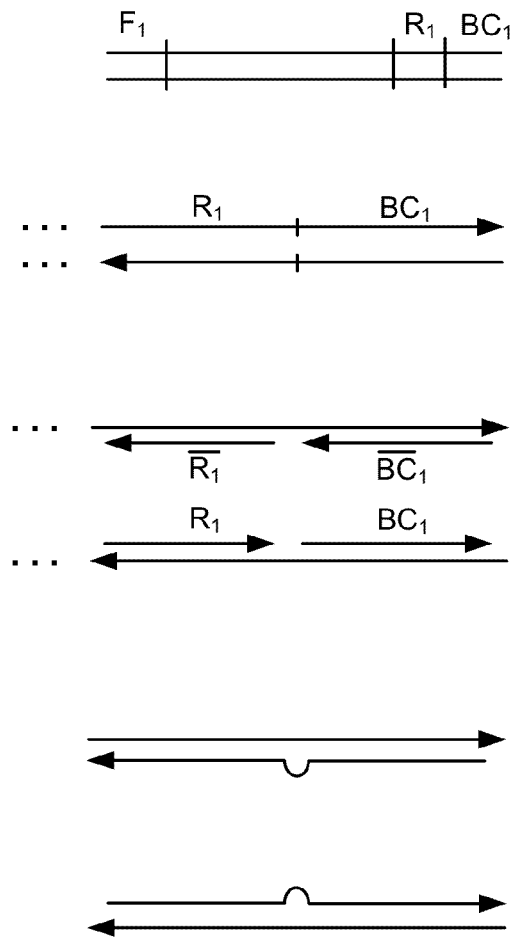
FIG. 8A-C: Barcoding and pooling of reaction mixtures for subsequent analysis: exemplary strategies for amplification/detection of barcoded target nucleotide sequences. (A) An illustrative embodiment employs LCR to detect barcoded target nucleotide sequences having the structure: 5'-forward primer sequence-target nucleotide sequence-reverse primer sequence-barcode nucleotide sequence-3'. In this case, one primer can anneal to the reverse primer sequence, and the other primer can anneal to the adjacent barcode nucleotide sequence, which is followed by ligation and repeated cycles of annealing and ligation. (B) Detection can be carried out in real time using a flap endonuclease-ligase chain reaction. This reaction employs a labeled probe and an unlabeled probe, wherein the simultaneous hybridization of the probes to a reaction product results in the formation of a flap at the 5' end of the labeled probe, and cleavage of the flap produces a signal. As shown, cleavage of the flap can separate a fluorophore from a quencher to generate a signal. (C) An alternative real time detection method that is useful, e.g., for detecting amplicons produced by LCR from barcoded target nucleotide sequences having the structure: 5'-forward primer sequence-target nucleotide sequence-reverse primer sequence-barcode nucleotide sequence-3'. This method relies on using a double-stranded DNA-binding dye to detect melting temperature differences between the reactions products and the primers employed for the LCR. The melting temperature analysis includes detection at a temperature at which reaction products are substantially double-stranded and capable of producing signal in the presence of a double-stranded DNA-binding dye, but primers are substantially single-stranded and incapable of producing signal ("Temp High"). For example, to detect barcoded target nucleotide sequences having the structure: 5'-forward primer sequence-target nucleotide sequence-reverse primer sequence-barcode nucleotide sequence-3', one primer can anneal to the reverse primer sequence, and the other primer can anneal to the adjacent barcode nucleotide sequence, which is followed by ligation and repeated cycles of annealing and ligation. See FIG. 8C.

An illustrative second reaction can employ LCR to detect barcoded target nucleotide sequences having the structure: 5'-forward primer sequence-target nucleotide sequence-reverse primer sequence-barcode nucleotide sequence-3'. In this case, one primer can anneal to the reverse primer sequence, and the other primer can anneal to the adjacent barcode nucleotide sequence, which is followed by ligation and repeated cycles of annealing and ligation. The reverse primer sequence provides target information, and the barcode nucleotide sequence identifies the pool (which could, for example, represent a pool of all target amplified in a particular sample). See FIG. 8A.

An illustrative second reaction can include real time detection, e.g., using a flap endonuclease-ligase chain reaction. This reaction employs a labeled probe and an unlabeled probe, wherein the simultaneous hybridization of the probes to a reaction product results in the formation of a flap at the 5' end of the labeled probe, and cleavage of the flap produces a signal. For example, cleavage of the flap can separate a fluorophore from a quencher to generate a signal. An illustrative embodiment can be employed the detect reaction products having the structure: 5'-forward primer sequence-target nucleotide sequence-reverse primer sequence-barcode nucleotide sequence-3'. In this case, the reaction can employ an unlabeled probe that anneals to the reverse primer sequence and a labeled probe that anneals to the adjacent barcode nucleotide sequence. Annealing of the 3' end of the unlabeled probe prevents annealing of the 5' end of the labeled probe, forming a flap. This 5' flap portion can be labeled with a fluorophore, and the portion that anneals to the barcode nucleotide sequence can bear a quencher, so that cleavage of the flap by an enzyme such as 5' flap endonuclease releases the flap, whereby the quencher can no longer quench the fluorophore. See FIG. 8B.

An alternative real time detection method that is useful, e.g., for detecting amplicons produced by LCR, relies on using a double-stranded DNA-binding dye to detect melting temperature differences between the reactions products and the primers employed for the LCR. The melting temperature analysis includes detection at a temperature at which reaction products are substantially double-stranded and capable of producing signal in the presence of a double-stranded DNA-binding dye, but primers are substantially single-stranded and incapable of producing signal. For example, to detect barcoded target nucleotide sequences having the structure: 5'-forward primer sequence-target nucleotide sequence-reverse primer sequence-barcode nucleotide sequence-3', one primer can anneal to the reverse primer sequence, and the other primer can anneal to the adjacent barcode nucleotide sequence, which is followed by ligation and repeated cycles of annealing and ligation. See FIG. 8C. The length of the ligated primer sequences, e.g., $R_1$ plus $BC_1$ and its complement, is sufficiently longer than the length of $R_1$ or $BC_1$ and their complements so that at high temperature, the ligated primer sequences are substantially double-stranded (i.e. producing a signal), whereas the unligated primer sequences are substantially single-stranded (i.e, no producing a signal). In various embodiments, at least about 10, 20, 30, 40, 50, 60, 70, 80, or 90 percent of the unligated primers are single-stranded. In each of these embodiments, the percentage of ligated primers that are double-stranded can be at least about 10, 20, 30, 40, 50, 60, 70, 80, or 90 percent.

In certain embodiments, the first reaction mixtures are prepared in separate compartments of a microfluidic device, the separate compartments being arranged as an array defined by rows and columns, e.g., like those available from Fluidigm Corp. (South San Francisco, Calif.) and described below (see "Microfluidic Devices"). For example, a matrix-type microfluidic device that is adapted to permit recovery of the contents of reaction compartments (see below) can be employed for the first reaction. This approach is particularly convenient for preparing N assay pools, each including M first reaction mixtures. More specifically, the first reactions are carried out in separate compartments of a microfluidic device, wherein the separate compartments are arranged as an array defined by rows and columns. Each of the N assay pools is obtained by pooling the first reaction mixtures in a row or a column of the device. The barcode nucleotide sequence in each barcoded target nucleotide sequence, taken with the identity of the assay pool, identifies the row and column of the compartment that was the source of the barcoded target nucleotide sequence. In particular embodiments, the second reaction mixtures are prepared in separate compartments of a microfluidic device, having separate compartments arranged as an array defined by rows and columns. For example, the first reaction mixtures can be prepared in separate compartments of a first microfluidic device to incorporate the barcode nucleotide sequences (e.g., Fluidigm Corporation's ACCESS ARRAY™ IFC (Integrated Fluidic Circuit) or MA006 IFC), and the second reaction mixtures can prepared in separate compartments of a second, different microfluidic device, e.g., to facilitate detection (e.g., one of Fluidigm Corporation's DYNAMIC ARRAY™ IFCs, using PCR or RT-PCR, with a double-stranded DNA binding dye, such as EvaGreen for detection).

In particular embodiments, at least one of the first and/or second reactions is performed individual particles, such as cells. Particle capture and assay can be carried out as described below or as known in the art. Fluidigm Corporation's MA006 IFC is well-suited for this purpose. The particles may be substantially intact when subjected to the first and/or second reactions, provided the necessary reagents will come into contact with the target nucleic acids of interest. Alternatively, the particles may be disrupted prior the first or second reaction to facilitate barcoding and/or subsequent analysis. In some embodiments, the particles are treated with an agent that elicits biological response prior to performing the plurality of first reactions.

Subsequent Analysis

Any of the above-described methods of incorporating nucleic acid sequences into target nucleic acids (including the barcoding and pooling method described above) can be include any of a number of analytical steps, such as determining the amount of at least one target nucleic acid in the first reaction mixtures or determining the copy number(s) of one or more DNA molecule(s) in the first reaction mixtures. In certain embodiments in which tagged or barcoded target nucleotide sequences are produced by PCR, e.g., those in which copy number determinations are being made, it is advantageous to conduct fewer than 20 cycles of PCR to preserve the relative copy numbers of different target nucleotide sequences.

Any of the above-described methods can include determining the genotype(s) at one or more loci in the first reaction mixtures and/or determining a haplotype for a plurality of loci in the first reaction mixtures. Haplotype determinations can, for example, be carried out by condensing chromosomes and distributing chromosomes into first reaction mixtures to produce a plurality of first reaction mixtures that include a single chromosome. This distribution can be carried out, e.g., as described below with respect to single particle analysis (in this case, the "particle" under analysis is a chromosome). A plurality of loci in the first reaction mixtures, and therefore necessarily on the same chromosome, can be sequenced to provide a haplotype for those loci.

In any of the above-described methods, e.g., where RT-PCR is carried out, the expression of levels of one or more RNA molecule(s) in the first reaction mixtures can be determined. As for DNA copy number determinations, it is advantageous to conduct fewer than 20 cycles of PCR to preserve the relative copy numbers of differences.

Regardless of whether the target nucleic acids in the first reaction mixtures are DNA or RNA, subsequent analysis can include determining the sequence of the target nucleotide sequences generated therefrom.

In some embodiments, the methods described herein include performing a plurality of reactions in each first reaction mixture, wherein one of the plurality of reactions includes amplification to produce a tagged or barcoded target nucleotide sequence, analyzing the results of the plurality of reactions, and associating the results of the analysis with each first reaction mixture. This association can be facilitated by the tagging or barcoding of target nucleotide sequences as alluded to above. For example, combinatorial barcoding can be used to encode information about the source reaction mixture. Alternatively, a combination of primer sequence and barcode can encode this information as discussed above with respect the barcoding and pooling method.

Bidirectional Nucleic Acid Sequencing

In particular embodiments, the invention provides methods for preparing nucleic acids for bidirectional DNA sequencing, which facilitates the sequencing of both ends of amplification products in a single read sequencing run. Such methods are illustrated in Example 9.

The DNA to be sequenced can be any type of DNA. In particular embodiments, the DNA is genomic DNA or cDNA from an organism. In some embodiments, the DNA can be fragmented DNA. The DNA to be sequenced can be a representation of the RNA in a sample, where the DNA is obtained, e.g., by reverse transcription or amplification of RNA. In certain embodiments, the DNA can be a DNA library.

To prepare nucleic acids for bidirectional DNA sequencing according to the methods described herein, each target nucleic acid to be sequenced is amplified using a set of inner primers, wherein the set includes:

an inner, forward primer including a target-specific portion and a first primer binding site;

an inner, reverse primer including a target-specific portion and a second primer binding site, wherein the first and second primer binding sites are different. These first and second primer binding sites serve the dual function of acting as nucleotide tags that facilitate the addition of further nucleotide sequences (as described below) and, in certain embodiments, as primer binding sites to which DNA sequencing primers can anneal. In the specific embodiment of Example 9, the first and second primer binding sites are designated as "CS1" and "CS2" for "Common Sequence tag 1" and "Common Sequence tag 2." In this embodiment, the target-specific portions of the inner primers are designated "TS-F" for "Target-Specific Forward" and "TS-R" for "Target-Specific Reverse."

Upon amplification, the target nucleotide sequences become tagged with first and second primer binding sites. These tagged target nucleotide sequences are annealed to two sets of outer primers that anneal to the first and second primer binding sites. The two sets of outer primers include:
a first set of outer primers, wherein the set includes:
    a first outer, forward primer including a portion specific for the first primer binding site; and
    a first outer, reverse primer including a barcode nucleotide sequence and a portion specific for the second primer binding site;
a second set of outer primers, wherein the set includes:
    a second outer, forward primer including a barcode nucleotide sequence and a portion specific for the first primer binding site; and
    a second outer, reverse primer including a portion specific for the second primer binding site. Amplification then produces two target amplicons, namely:
a first target amplicon that includes 5'-first primer binding site-target nucleotide sequence-second primer binding site-barcode nucleotide sequence-3'; and
a second target amplicon that includes 5'-barcode nucleotide sequence-first primer binding site-target nucleotide sequence-second primer binding site-3'. In particular embodiments, the barcode nucleotide sequence in each of the two target amplicons is the same, and each target amplicon includes only one barcode nucleotide sequence. In some embodiments, where more than one target nucleic acid is amplified, each pair of target amplicons produced can have the same barcode sequence, but different pairs can have different barcode sequences. In this case, the barcode sequences would differ between different target amplicons produced from different target nucleic acids. As discussed above, sets of different target nucleic acids, e.g., from a particular biological sample can be barcoded with the same set-specific sequence (i.e., one that differs between sets). In a specific embodiment, the set-specific barcode can be a sample-specific barcode, i.e., one that identifies the sample from which the target amplicons were derived.

In certain embodiments, the outer primers each additionally include an additional nucleotide sequence, wherein:
the first outer, forward primer includes a first additional nucleotide sequence, and the first outer, reverse primer includes a second additional nucleotide sequence; and
the second outer, forward primer includes the second additional nucleotide sequence, and the second outer, reverse primer includes the first additional nucleotide sequence, and the first and second additional nucleotide sequences are different. In such embodiments, the outer primer amplification produces two target amplicons, namely:
a first target amplicon that includes 5'-first additional nucleotide sequence-first primer binding site-target nucleotide sequence-second primer binding site-barcode nucleotide sequence-second additional nucleotide sequence-3'; and
a second target amplicon that includes 5'-second additional nucleotide sequence-barcode nucleotide sequence-first primer binding site-target nucleotide sequence-second primer binding site-first additional nucleotide sequence 3'. (Those of skill in the art understand that amplicons described in this manner herein are described in terms of one strand and that the complementary strand will have the 5' to 3' order of these nucleotide sequences reversed.)

The first and/or second additional nucleotide sequences can also include a primer binding site. An illustrative primer configuration of this type described in Example 9, wherein the additional nucleotide sequences are designated "PE-1" and "PE-2." These sequences are adaptor sequences used by the Genome Analyzer (commercially available from Illumina, Inc., San Diego, Calif.). The barcode nucleotide sequence is designated "BC." Outer primer amplification using these primers produces two target amplicons, namely:
a first target amplicon that includes 5'-PE1-CS1-target nucleotide sequence-CS2-BC-PE2-3'; and
a second target amplicon that includes 5'-PE2-BC-CS1-target nucleotide sequence-CS2-PE1-3'. In a specific, illustrative embodiment, the first set of outer primers, PE1-CS1 and PE2-BC-CS2, and the second set of outer primers, PE1-CS2 and PE2-BC-CS1, have the nucleotide sequences shown in Table 1 in Example 9.

The inner and outer primer amplifications can be carried out in a single amplification reaction. Alternatively, the inner primer amplification can be carried out in a first amplification reaction, and the outer primer amplification can be carried out in a second, amplification reaction that is separate from the first. In certain embodiments, the second amplification reaction can be carried out in two separate second amplification reactions: one that employs the first set of outer primers and another employs the second set of outer primers. See Example 9, FIG. 2. In such embodiments, the target amplicons produced in each separate second amplification reaction can be pooled for further analysis, such as DNA sequencing.

In many embodiments, the methods described above will be carried out on a plurality of target nucleic acids, such as, e.g., a DNA library. In this case, the methods can be used to produce a pool of target amplicons that includes two types of amplicons (described above and illustrated in Example 9, FIG. 2, as "A" and "B") for each target nucleic acid. One type of target amplicon ("A") facilitates sequencing of the 5' end of the target nucleic acid, and the other type of target amplicon ("B") facilitates sequencing of the 3' end of the target nucleic acid. In addition, each target amplicon includes a barcode sequence, which, in certain embodiments, is the same in each of the two types of target amplicons. The barcode nucleotide sequence can encode information about the target nucleotide sequence, such as the identity of the reaction that produced it and/or the identity of the sample from which the target nucleic acid was derived. As described in more detail below, the target nucleotide sequence and the barcode nucleotide sequence in each target amplicon can readily be determined using any suitable available DNA sequencing method. In particular embodiments, the DNA sequencing method is a high-throughput sequencing method, such as the bridge amplification (cluster generation) and sequencing method commercialized by Illumina, Inc., San Diego, Calif. In certain embodiments, e.g., those employing bridge amplification and sequencing, the average length of the target amplicons is less than 200 bases, less than 150 bases, or less than 100 bases.

In bridge amplification and sequencing, target amplicons, e.g., produced as described herein are hybridized to a lawn of immobilized primer pairs via the first and second additional nucleotide sequences (e.g., PE1 and PE2). One immobilized primer in each primer pair is cleavable. First strand synthesis is carried out to produce double-stranded molecules. These are denatured, and the original hybridized target amplicon strand that served as the template for first strand synthesis is washed away, leaving immobilized first strands. These can flip over and hybridize to a suitable adjacent primer, forming a bridge. Second strand synthesis is carried out to produce double-stranded bridges. These are denatured, and each bridge yields two immobilized single-stranded molecules that can once again hybridize to suitable immobilized primers. Isothermal bride amplification is carried out to produce multiple double-stranded bridges. Double-stranded bridges are denatured, and "reverse" strands are cleaved and washed away, leaving clusters of immobilized "forward" strands available as a template for DNA sequencing.

Figure 3:
FIG. 3: A four-primer, combinatorial barcoding method can be employed to put a combination of two barcodes on either end of each amplicon. Inner primers include target-specific portions ("TS-F" in the forward primer and "TS-R" in the reverse primer), a barcode nucleotide sequence ("bc2"), and different nucleotide tags. Outer primers include tag-specific portions ("CS1" and "CS2"), a different barcode nucleotide sequence ("bc1"), primer binding sites for sequencing primers ("A" and "B").
Figure 4:
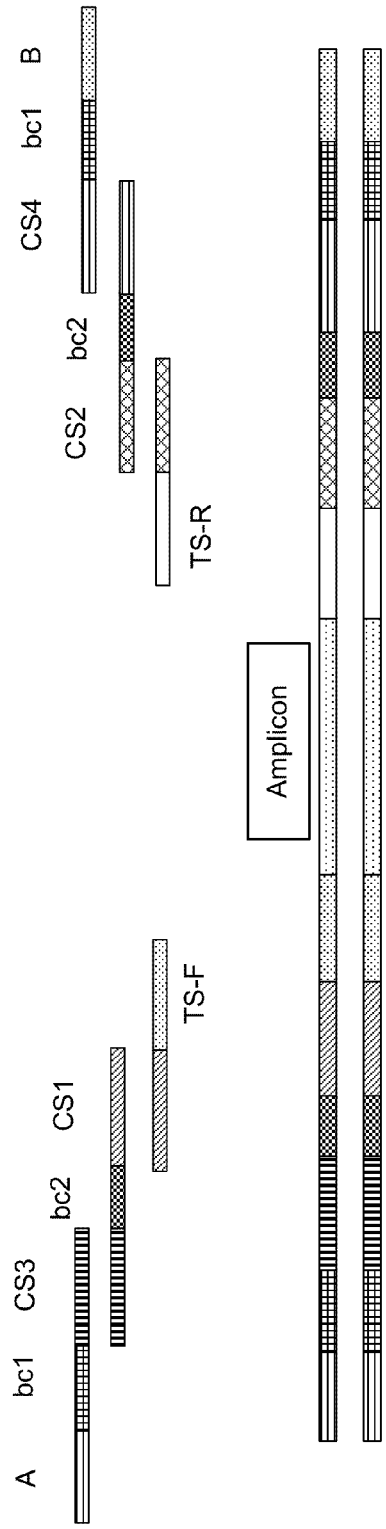
FIG. 4: A six-primer, combinatorial barcoding method can be employed to put a combination of two barcodes on either end of each amplicon Inner primers include target-specific portions ("TS-F" in the forward primer and "TS-R" in the reverse primer) and different nucleotide tags. Stuffer primers include tag-specific portions ("CS1" and "CS2"), a barcode nucleotide sequence ("bc2"), and two additional different nucleotide tags. Outer primers include portions specific for the two additional nucleotide tags ("CS3" and "CS4"), a different barcode nucleotide sequence ("bc1"), and primer binding sites for sequencing primers ("A" and "B").

When target amplicons produced as described herein are subjected to bridge amplification and sequencing, primers that anneal to the first and second primer binding sites (e.g., CS1 and CS2) can be employed to sequence either the target nucleotide sequence or the barcode nucleotide sequence, both of which are present in the immobilized template produced from the amplicon. In certain embodiments, a pair of primers suitable for sequencing the target nucleotide sequence is contacted with the immobilized templates under conditions suitable for annealing, followed by DNA sequencing. After these sequences have been read, the sequencing products can be denatured and washed away. The immobilized templates can then be contacted with a pair of primers suitable for sequencing the barcode nucleotide sequence under conditions suitable for annealing, followed by DNA sequencing. The order of these sequencing reactions is non-critical and can be reversed (i.e., the barcode nucleotide sequences can be sequenced first, followed by sequencing of the target nucleotide sequences). See Example 9, FIG. 3. In certain embodiments, primers that prime sequencing of the barcode nucleotide sequence are reverse complements of the primers that prime sequencing of the target nucleotide sequences. In a specific, illustrative embodiment, the primers employed to prime sequencing of the target nucleotide sequence(s) and barcode nucleotide sequence(s) are CS1, CS2, CS1rc, and CS2rc (Table 2, Example 9).

Conveniently, both types of target amplicons are subjected to bridge amplification and sequencing in the same reaction(s) to allow for simultaneous sequencing of the templates from each type of target amplicon. See Example 9, FIG. 3. This allows for the simultaneous sequencing of each target nucleotide sequence from the 5' end (e.g., by sequencing templates from amplicon type A in Example 9, FIG. 3) and from the 3' end (e.g., by sequencing templates from amplicon type B in Example 9, FIG. 3). In particular embodiments, the primers that bind to the first and second primer binding sites and prime sequencing of the target nucleotide sequence(s) are present in substantially equal concentrations so as to produce both 5' and 3' DNA sequence information from each target nucleotide sequence. Similarly, in certain embodiments, the primers that bind to the first and second primer binding sites and prime sequencing of the barcode nucleotide sequence(s) are present in substantially equal concentrations so as to produce barcode sequences from each template type (i.e., derived from amplicon type A or amplicon type B in Example 9, FIG. 3).

When the inner amplification is performed as a separate reaction, especially when amplifying a plurality of target nucleic acids, it may be convenient to perform individual reactions (e.g., with 1, 2, 3, 4, 5 or more target nucleic acids amplified per reaction) in separate compartments of a microfluidic device, such as any of those described herein or known in the art. As discussed below, suitable microfluidic devices can be fabricated, at least in part, from an elastomeric material.

In particular embodiments, the inner or (inner and outer) amplification(s) is/are carried out in a microfluidic device designed to facilitate recovery of amplification products after the amplification reaction has been carried out, such as the ACCESS ARRAY™ IFC described herein (See FIGS. 2-9) and available from Fluidigm, Inc., South San Francisco, Calif. In illustrative devices of this type, dilation pumping can utilized to remove substantially all of the reaction products from the microfluidic device, providing uniformity between the various reaction product pools. Thus, it is possible to produce pools of barcoded reaction products that are uniform with respect to volume and copy number. In various embodiments, the volume and/or copy number uniformity is such that the variability, with respect to volume and/or copy number, of each pool recovered from the device is less than about 100 percent, less than about 90 percent, less than about 80 percent, less than about 70 percent, less than about 60 percent, less than about 50 percent, less than about 40 percent, less than about 30 percent, less than about 20 percent, less than about 17 percent, or less than about 15, 12, 10, 9, 8, 7, 6, 5, 4.5, 4, 3.5, 3, 2.5, 2, 1.5, 1, or 0.5 percent. Those of skill in the art appreciate that the volume and/or copy number variability may fall within any range bounded by any of these values (e.g., about 2 to about 7 percent). In an illustrative embodiment, the volume samples recovered from a microfluidic device vary by no more than approximately 10%. Standard pipetting error is on the order of between 5 and 10%. Thus, the observed variability in volumes is largely attributable to pipetting error. Utilizing the systems and methods described herein, the time and labor required to prepare sequencing libraries is reduced in comparison with conventional techniques.

Those of skill in the art will be aware of other devices and strategies that can be employed to perform the inner (or inner and outer) amplification(s) described herein on a plurality of different target nucleic acids, each in separate reactions. For example, droplet-based amplification is well-suited to performing this inner amplification. See, e.g., U.S. Pat. No. 7,294,503, issued Nov. 13, 2007 to Quake et al., entitled "Microfabricated crossflow devices and methods," which is incorporated herein by reference in its entirety and specifically for its description of devices and methods for forming and analyzing droplets; U.S. Patent Publication No. 20100022414, published Jan. 28, 2010, by Link et al., entitled "Droplet libraries," which is incorporated herein by reference in its entirety and specifically for its description of devices and methods for forming and analyzing droplets; and U.S. Patent Publication No. 20110000560, published Jan. 6, 2011, by Miller et al., entitled "Manipulation of Microfluidic Droplets," which is incorporated herein by reference in its entirety and specifically for its description of devices and methods for forming and analyzing droplets. In particular embodiments, inner amplification is carried out in fluid droplets in an emulsion.

Encoding and Detecting/Quantifying Alleles by Primer Extension

Nucleic acid encoding can be employed in a method for detecting and estimating the fraction of particular target nucleic acids (e.g., rare mutations) in a nucleic acid sample. This method entails producing first and second tagged target nucleotide sequences from first and second target nucleic acids in the sample. For example, the method can be carried out by using allele-specific amplification to introduce allele-specific nucleotide tags into the resultant tagged target nucleotide sequences. The tagged target nucleotide sequences are then subjected to primer extension reactions using primers specific for each nucleotide tag. The method entails detecting and/or quantifying a signal that indicates extension of the first primer and a signal that indicates extension of the second primer. The signal for a given primer indicates the presence, and/or relative amount, of the corresponding target nucleic acid. This method can be conveniently carried out on a high-throughput (e.g., next-generation) DNA sequencing platform to detect, e.g., known mutations in a sample by detecting the presence of tags, rather than by determining the DNA sequence of each molecule. The advantages of this method are speed, sensitivity, and precision. The large number of clonal molecules examined in next-generation sequencing allows reliable detection of very rare sequences (e.g., less than 1 in $10^6$ sequences). Furthermore, the fraction of target sequence(s) (e.g., mutations) can be determined more precisely than with PCR, as next-generation sequencing platforms are available with very high numbers of reads.

To facilitate primer extension on a DNA sequencing platform, adaptors for, e.g., high-throughput DNA sequencing can be introduced into the first and second tagged target nucleotide sequences. In particular embodiments, the adaptors are introduced at each end of the tagged target nucleotide sequence molecule. These adaptors can conveniently be introduced, together with the nucleotide tags, in one reaction.

Nucleotide tags and/or DNA sequencing adaptors can be introduced into the target nucleotide sequences using any suitable method, such as, e.g., amplification or ligation. For example, first and second tagged target nucleotide sequences can be produced by amplifying first and second target nucleic acids with first and second primer pairs, respectively. At least one primer in the first primer pair comprises a first nucleotide tag and at least one primer in the second primer pair comprises a second nucleotide tag. When introducing DNA sequencing adaptors in the same reaction, one primer in each primer pair comprises 5'-(DNA sequencing adaptor)-(nucleotide tag)-(target-specific portion)-3' and the other primer in each primer pair comprises 5'-(DNA sequencing adaptor)-(target-specific portion)-3'.

Many high-throughput DNA sequencing techniques include an amplification step prior to DNA sequencing. Accordingly, in some embodiments, the tagged target nucleotide sequences are further amplified prior to primer extension on a DNA sequencing platform. For example, emulsion amplification or bridge amplification can be carried out. Emulsion PCR (emPCR) isolates individual DNA molecules along with primer-coated beads in aqueous droplets within an oil phase. PCR produces copies of the DNA molecule, which bind to primers on the bead, followed by immobilization for later sequencing. emPCR is used in the methods by Marguilis et al. (commercialized by 454 Life Sciences, Branford, Conn.), Shendure and Porreca et al. (referred to herein as "454 sequencing;" also known as "polony sequencing") and SOLiD sequencing, (Life Technologies, Foster City, Calif.). See M. Margulies, et al. (2005) "Genome sequencing in microfabricated high-density picoliter reactors" Nature 437: 376-380; J. Shendure, et al. (2005) "Accurate Multiplex Polony Sequencing of an Evolved Bacterial Genome" Science 309 (5741): 1728-1732. In vitro clonal amplification can also be carried out by "bridge PCR," where fragments are amplified upon primers attached to a solid surface. Braslaysky et al. developed a single-molecule method (commercialized by Helicos Biosciences Corp., Cambridge, Mass.) that omits this amplification step, directly fixing DNA molecules to a surface. I. Braslaysky, et al. (2003) "Sequence information can be obtained from single DNA molecules" Proceedings of the National Academy of Sciences of the United States of America 100: 3960-3964.

DNA molecules that are physically bound to a surface can be sequenced in parallel. "Sequencing by synthesis," like dye-termination electrophoretic sequencing, uses a DNA polymerase to determine the base sequence. "Pyrosequencing" uses DNA polymerization, adding one nucleotide at a time and detecting and quantifying the number of nucleotides added to a given location through the light emitted by the release of attached pyrophosphates (commercialized by 454 Life Sciences, Branford, Conn.). See M. Ronaghi, et al. (1996). "Real-time DNA sequencing using detection of pyrophosphate release" Analytical Biochemistry 242: 84-89. Reversible terminator methods (commercialized by Illumina, Inc., San Diego, Calif. and Helicos Biosciences Corp., Cambridge, Mass.) use reversible versions of dye-terminators, adding one nucleotide at a time, and detecting fluorescence at each position in real time, by repeated removal of the blocking group to allow polymerization of another nucleotide.

In one embodiment of the detection-by-primer extension method, which can conveniently be carried out on the 454 sequencing platform, the first and second primer extension reactions are carried out sequentially in at least two cycles of primer extension. In particular, a first cycle of primer extension is carried out using the first primer that anneals to the first nucleotide tag, and a second cycle of primer extension is carried out using the second primer that anneals to the second nucleotide tag. All deoxynucleoside triphosphates (dNTPs) are provided in each cycle of primer extension. The incorporation of any dNTP into a DNA molecule produces a detectable signal. The signal detected in the first cycle indicates the presence of the first target nucleic acid in the nucleic acid sample, whereas the signal detected in the second cycle indicates the presence of the second target nucleic acid in the nucleic acid sample. Thus, each target nucleic acid (e.g., mutation) can be detected with only a single cycle of the sequencing platform.

Because the signal detected is proportional to the number of copies of target nucleic acid, the signal can also be used to estimate the amount of the target nucleic acid in the sample. In particular, the signal can be used to determine the amounts of the two or more target nucleic acids relative to one another.

Figure 31A:
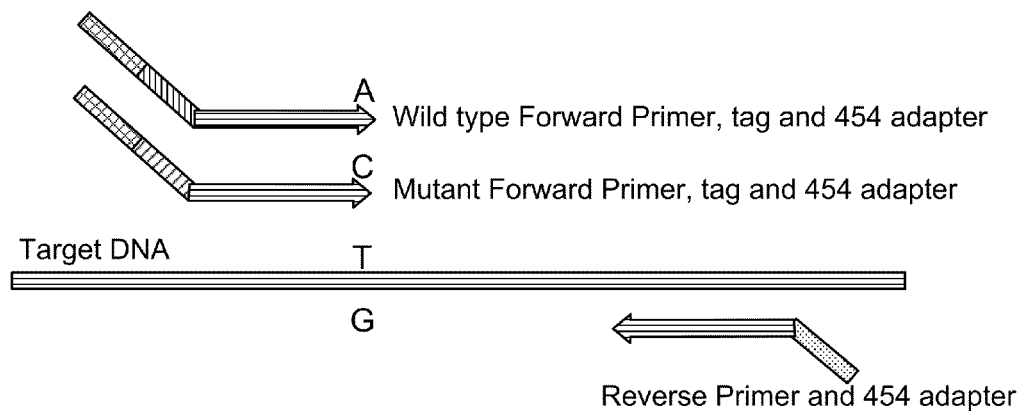
FIG. 31A-B: (A) Allele-specific PCR on target DNA is done in one reaction prior to the 454 sequencing emulsion PCR reaction. The forward primers have 454 adapters and allele-specific tags. Different tags are indicated with different shadings. This reaction produces amplicons which are ready for 454 bead emulsion PCR. (B) After emulsion PCR and loading onto the sequencer, the amplicons on individual beads in each well are either wildtype or mutant. The first 454 cycle flows a primer which binds to the wildtype tag (pink arrow), and it flows all the dNTP's. As this primer extends, multiple nucleotides are incorporated, giving a very robust signal, but only in wells with wildtype molecules. The second cycle flows in all dNTP's and a primer to the mutant tag and produces signal only in the wells with mutant molecules.
Figure 31B:
Figure 31B:

In an illustrative embodiment that uses the 454 sequencing platform to detect wild-type and mutant target nucleic acids, allele-specific PCR reactions are prepared with specific tags for wild-type and each mutant to be detected. As shown in FIG. 31, the forward primers have 454 adapters and allele-specific tags (indicated with different shadings). The adaptors are 5' of the tags, which are 5' of the allele-specific portion of the primer. The reverse primer includes a 454 adaptor 5' of the target-specific portion. As shown in FIG. 31, only one reverse primer is needed to detect a single nucleotide polymorphism. In this example, the two allele-specific PCR reactions are carried out in a single PCR reaction, although this is not a requirement of the method. The PCR reaction produces tagged target nucleotide sequences that are ready for 454 bead emulsion PCR. The emulsion PCR step can be omitted, for example, by annealing the tagged target nucleotide sequences directly to beads preloaded with allele-specific oligonucleotides (i.e., each individual bead bears only one type of oligonucleotide). In either case, an individual bead will bear only one type of tagged target nucleotide. The beads are loaded onto a 454 sequencer. The first 454 cycle flows a primer that binds, e.g., to the wild-type tag and all four dNTPs. As this primer extends, multiple nucleotides are incorporated, giving a very robust signal, but only in wells containing wild-type beads. The second 454 cycle flows a primer that binds to the mutant tag and all four dNTPs, giving a signal only in wells containing mutant beads.

In another embodiment of the detection-by-primer extension method, which can conveniently be carried out on the SOLiD sequencing platform, the first and second primer extension reactions are carried out by oligonucleotide ligation and detection. In this embodiment, the ligation of a labeled di-base oligonucleotide to the first and/or second primer(s) produces a detectable signal, and the total signal detected for a particular primer indicates the presence, and/or relative amount of, the corresponding target nucleic acid in the nucleic acid sample. In a variation of this embodiment, the ligation of a labeled di-base oligonucleotide to the first primer produces the same detectable signal as the ligation of a labeled di-base oligonucleotide to the second primer, and the first and second primer extension reactions are carried out separately, e.g., in simultaneous or sequential cycles. In another variation, the ligation of a labeled di-base oligonucleotide to the first primer produces a different detectable signal than the ligation of a labeled di-base oligonucleotide to the second primer. The use of different signals allows the first and second primer extension reactions to be carried out simultaneously, in one reaction mixture. Any type of detectable signal can be employed in the method, but a fluorescent signal is typically employed, e.g., for SOLiD sequencing.

Tagged target nucleotide sequences containing, e.g., allele-specific tags and suitable DNA sequencing adaptors are prepared for primer extension on a SOLiD sequencing platform as described above. Emulsion PCR can be carried out, although this step is not strictly necessary. As described above with respect to 454 sequencing, any method that produces clonal populations of tagged target nucleotide sequences attached to beads may be employed to produce tagged target nucleotide sequences suitable for primer extension on a SOLiD sequencing platform.

In yet another embodiment of the detection-by-primer extension method, which can conveniently be carried out on the Illumina sequencing platform, the first and second primer extension reactions include sequencing-by-synthesis. In this embodiment, each deoxynucleoside triphosphate is labeled with a distinct, base-specific label, and the incorporation of a deoxynucleoside triphosphate into a DNA molecule produces a base-specific detectable signal. The total signal detected for a particular primer indicates the presence and/or relative amount of the corresponding target nucleic acid in the nucleic acid sample. In a variation of this embodiment, the extension of the first primer produces the same detectable signal as the extension of the second primer, and the first and second primer extension reactions are carried out separately, e.g., in simultaneous or sequential cycles. In another variation, the extension of the first primer produces a different detectable signal than the extension of the second primer. The use of different signals allows the first and second primer extension reactions to be carried out simultaneously, in one reaction mixture. Any type of detectable signal can be employed in the method, but a fluorescent signal is typically employed, e.g., for Illumina sequencing. Tagged target nucleotide sequences containing allele-specific tags and suitable DNA sequencing adaptors can be prepared for primer extension on an Illumina sequencing platform as described above. For primer extension on an Illumina sequencing platform, the tagged target nucleotide sequences are typically further amplified by bridge PCR prior to DNA sequencing.

In the specific detection-by-primer extension embodiments described above, as well as in some other implementations of the method, amplification produces clonal populations of tagged target nucleotide sequences that are, or become, located at discrete reaction sites. The number of reaction sites including the first nucleotide tag relative to the number of reaction sites including the second nucleotide tag indicates the amount of the first target nucleic acid relative to the second target nucleic acid in the sample. In particular embodiments of this type, the method can entail detecting and comparing the total signal from all reaction sites including the first nucleotide tag with the total signal from all reaction sites including the second nucleotide tag. Alternatively or in addition, the method can entail detecting and comparing the number of reaction sites including the first nucleotide tag with the number of reaction sites including the second nucleotide tag. In either case, the comparison can include any conventional means of comparing two values, such as, e.g., determining a ratio.

The selection of suitable, distinguishable nucleotide tags for use in the method is within the level of skill in the art. In certain embodiments, the first nucleotide tag can include a homopolymer of a first nucleotide (e.g., poly-A), whereas the second nucleotide tag can include a homopolymer of second, different nucleotide (e.g, poly-G).

Although the detection-by-primer extension method is described above with respect to the analysis of two target nucleic acids, the method encompasses the analysis of three or more target nucleic acids, each of which is tagged with a distinct nucleotide tag. The resultant tagged target nucleotide sequences are subjected to three or more primer extension reactions, each using a primer that anneals to a distinct nucleotide tag, and a signal is detected and/or quantified for the extension of each primer. In particular embodiments, two or more tagged target nucleotide sequences include different barcodes, which as described above, can encode information, e.g., sample or reaction mixture, about the tagged target nucleotide sequence.

The above detection-by-primer extension method can, if desired, be carried out in multiplex. In certain embodiments, for example, multiple samples can be analyzed together in one or more primer extension reactions by incorporating one or more barcodes into the nucleotide tags, wherein the barcodes encode sample identity. Primers may be employed that are both allele- and barcode-specific for the primer extension reaction or, alternatively, the barcode may preferably be adjacent to the nucleotide tag to which the primer anneals, and the primer extension reaction can be a DNA sequencing reaction, which need only detect the sequence of the barcode. In the former embodiment, primer extension would indicate the presence of an allele from a particular sample, whereas in the latter embodiment, primer extension would indicate the presence of the allele, and the barcode nucleotide sequence would identify the sample.

Single-Particle Analysis Applications

Incorporation of Nucleic Acid Sequences into Single Particles

In certain embodiments, the above-described methods of incorporating nucleic acid sequences into target nucleic acids (including the barcoding and pooling method described above) are used in the context of assaying single particles in a population of particles. In general, nucleic acid sequences are introduced into target nucleic acids that are associated with, or contained in, a particle. Thus, the first reactions described above are carried out in reaction volumes that contain individual particles. The ability to associate the results of single-particle analysis with each particle assayed can be exploited where, for example, two or more parameters are associated with a phenotype. The two or more parameters measured can be different types of parameters, e.g., RNA expression level and nucleotide sequence. Further applications of the single-cell analysis methods described herein are described below.

Single-particle analysis entails capturing particles of a population in separate reaction volumes to produce a plurality of separate reaction volumes containing only one particle each. Particle-containing separate reaction volumes can be formed in droplets, in emulsions, in vessels, in wells of a microtiter plate, or in compartments of a matrix-type microfluidic device. In illustrative embodiments, the separate reaction volumes are present within individual compartments of a microfluidic device, such as, for example, any of those described herein. See also, U.S. Patent Publication No. 2004/0229349, published Nov. 18, 2004, Daridon et al., which is incorporated herein by reference in its entirety and, in particular, for its description of micro-fluidic particle analysis systems.

In certain embodiments, a parameter is assayed by performing a reaction, such as nucleic acid amplification, in each separate reaction volume to produce one or more reaction products, which is/are analyzed to obtain the results that are then associated with the particle and entered into the data set. The particles may be captured in separate reaction volumes before being contacted with one or more reagent(s) for performing one or more reactions. Alternatively, or in addition, the particles may be contacted with one or more of such reagent(s), and the reaction mixture may be distributed into separate reaction volumes. In various embodiments, at least 2, 3, 4, 5, 6, 7, 8, 9, or 10 or more reactions are performed in each separate reaction volume. The analysis of the reaction products can be carried out in the separate reaction volumes. In some embodiments, however, it is advantageous to recover the contents of the separate reaction volumes for subsequent analysis or other purposes. For example, if a nucleic acid amplification is carried out in the separate reaction volumes, it may be desirable to recover the contents for subsequent analysis, e.g., by PCR and/or nucleic acid sequencing. The contents of the separate reaction volumes may be analyzed separately and the results associated with the particles present in the original reaction volumes. Alternatively, the particle/reaction volume identity can be encoded in the reaction product, e.g., as discussed above with respect to multi-primer nucleic acid amplification methods. Furthermore, these two strategies can be combined so that sets of separate reaction volumes are encoded, such that each reaction volume within the set is uniquely identifiable, and then pooled, with each pool then being analyzed separately, as illustrated by the barcoding and pooling method described above.

Particles

The methods described herein can be used to analyze any type of particle, e.g., by carrying out any of the above-described reactions on nucleic acids from one or more individual particles. In certain embodiments, a particle generally includes any object that is small enough to be suspended in a fluid, but large enough to be distinguishable from the fluid. Particles may be microscopic or near-microscopic and may have diameters of about 0.005 to 100 µm, 0.1 to 50 µm, or about 0.5 to 30 µm. Alternatively, or in addition, particles may have masses of about $10^{-20}$ to $10^{-5}$ grams, $10^{-16}$ to $10^{-7}$ grams, or $10^{-14}$ to $10^{-8}$ grams. In certain embodiments, the particle is a particle from a biological source ("a biological particle"). Biological particles include, for example, molecules such as nucleic acids, proteins, carbohydrates, lipids, and combinations or aggregates thereof (e.g., lipoproteins), as well as larger entities, such as viruses, chromosomes, cellular vesicles and organelles, and cells. Particles that can be analyzed as described herein also include those that have an insoluble component, e.g., a bead, to which molecules to be analyzed are attached.

In illustrative embodiments, the particles are cells. Cells suitable for use as particles in the methods described herein generally include any self-replicating, membrane-bounded biological entity or any non-replicating, membrane-bounded descendant thereof. Non-replicating descendants may be senescent cells, terminally differentiated cells, cell chimeras, serum-starved cells, infected cells, non-replicating mutants, anucleate cells, etc. Cells used in the methods described herein may have any origin, genetic background, state of health, state of fixation, membrane permeability, pretreatment, and/or population purity, among other characteristics. Suitable cells may be eukaryotic, prokaryotic, archaeon, etc., and may be from animals, plants, fungi, protists, bacteria, and/or the like. In illustrative embodiments, human cells are analyzed. Cells may be from any stage of organismal development, e.g., in the case of mammalian cells (e.g., human cells), embryonic, fetal, or adult cells may be analyzed. In certain embodiments, the cells are stem cells. Cells may be wild-type; natural, chemical, or viral mutants; engineered mutants (such as transgenics); and/or the like. In addition, cells may be growing, quiescent, senescent, transformed, and/or immortalized, among other states. Furthermore, cells may be a monoculture, generally derived as a clonal population from a single cell or a small set of very similar cells; may be presorted by any suitable mechanism, such as affinity binding, FACS, drug selection, etc.; and/or may be a mixed or heterogeneous population of distinct cell types.

Particles that include membranes (e.g., cells or cellular vesicles or organelles), cell walls, or any other type of barrier separating one or more interior components from the exterior space may be intact or disrupted, partially (e.g., permeabilized) or fully (e.g., to release interior components). Where the particles are cells, fixed and/or unfixed cells may be used. Living or dead, fixed or unfixed cells may have intact membranes, and/or be permeabilized/disrupted membranes to allow uptake of ions, stains, dyes, labels, ligands, etc., and/or be lysed to allow release of cell contents.

One advantage of the methods described herein is that they can be used to analyze virtually any number of particles, including numbers well below the millions of particles required for other methods. In various embodiments, the number of particles analyzed can be about 10, about 50, about 100, about 500, about 1000, about 2000, about 3000, about 4000, about 5000, about 6000, about 7,000, about 8000, about 9,000, about 10,000, about 15,000, about 20,000, about 25,000, about 30,000, about 35,000, about 40,000, about 45,000, about 50,000, about 75,000, or about 100,000. In specific embodiments, the number of particles analyzed can fall within a range bounded by any two values listed above.

Particle Capture

Particles may be captured in separate reaction volumes by any means known in the art or described herein. In certain embodiments, a capture feature retains one or more cells at a capture site within separate reaction volume. In preferred embodiments, the capture feature preferentially retains only a single cell at the capture site. In certain preferred embodiments, each capture site is located within a separate compartment of the microfluidic device. The term "separate compartment" is used herein to refer to a compartment that is at least temporarily separate from other compartments within a microfluidic device, such that the compartments can contain separate reaction volumes. Temporary separation can be achieved, e.g., with the use of valves, as in the case of microfluidic devices available from Fluidgm, Inc. (South San Francisco, Calif.). The degree of separation must be such that assays/reactions can be carried out separately within the compartments. As used herein, the term "capture feature"

includes single or plural mechanisms, operating in series and/or in parallel. Capture features may act to overcome the positioning force exerted by fluid flow. Suitable capture features may be based on physical barriers coupled with flow (termed "mechanical capture"), chemical interactions (termed "affinity-based capture), vacuum forces, fluid flow in a loop, gravity, centrifugal forces, magnetic forces, electrical forces (e.g., electrophoretic or electroosmotic forces), and/or optically generated forces, among others.

Capture features may be selective or nonselective. Selective mechanisms may be fractionally selective, that is, retaining less than all (a subset of) inputted particles. Fractionally selective mechanisms may rely at least in part on stochastic focusing features (see below). Alternatively, or in addition, selective mechanisms may be particle-dependent, that is, retaining particles based on one or more properties of the inputted particle, such as size, surface chemistry, density, magnetic character, electrical charge, optical property (such as refractive index), and/or the like.

Mechanical Capture

Mechanical capture may be based at least partially on particle contact with any suitable physical barrier(s) disposed, e.g., in a microfluidic device. Such particle-barrier contact generally restricts longitudinal particle movement along the direction of fluid flow, producing flow-assisted retention. Flow-assisted particle-barrier contact also may restrict side-to-side/orthogonal (transverse) movement. Suitable physical barriers may be formed by protrusions that extend inward from any portion of a channel or other passage (that is, walls, roof, and/or floor). For example, the protrusions may be fixed and/or movable, including columns, posts, blocks, bumps, walls, and/or partially/completely closed valves, among others. Some physical barriers, such as valves, may be movable or regulatable. Alternatively, or in addition, a physical barrier may be defined by a recess(es) (e.g., niches), formed in a channel or other passage, or by a fluid-permeable membrane. Other physical barriers may be formed based on the cross-sectional dimensions of passages. For example, size-selective channels may retain particles that are too large to enter the channels. (Size-selective channels also may be referred to as filter channels, microchannels, or particle-restrictive or particle-selective channels.) Examples 6 and 8 provide illustrative mechanical capture embodiments.

Affinity-Based Capture

Affinity-based capture may retain particles based on one or more chemical interaction(s), i.e., wherein a binding partner binds a particle component. The chemical interactions may be covalent and/or noncovalent interactions, including ionic, electrostatic, hydrophobic, van der Waals, and/or metal coordination interactions, among others. Chemical interactions may retain particles selectively and/or non-selectively. Selective and non-selective retention may be based on specific and/or non-specific chemical interactions between particles and surfaces, e.g., in a microfluidic device.

Specific chemical mechanisms may use specific binding partners (SBPs), for example, with first and second SBPs disposed on particles and device surfaces, respectively. Exemplary SBPs may include biotin/avidin, antibody/antigen, lectin/carbohydrate, etc. SBPs may be disposed locally within microfluidic devices before, during and/or after formation of the devices. For example, surfaces of a substrate and/or a fluid layer component may be locally modified by adhesion/attachment of a SBP member before the substrate and fluid layer component are joined. Alternatively, or in addition, an SBP may be locally associated with a portion of a microfluidic device after the device has been formed, for example, by local chemical reaction of the SBP member with the device (such as one catalyzed by local illumination with light). See also Example 7, which describes an embodiment in which beads bearing an SBP member are mechanically caught at capture sites to display the SBP member for affinity-based capture of particles (i.e., cells).

Non-specific chemical mechanisms may rely on local differences in the surface chemistry of microfluidic devices. Such local differences may be created before, during and/or after microfluidic device formation, as described above. The local differences may result from localized chemical reactions, for example, to create hydrophobic or hydrophilic regions, and/or localized binding of materials. The bound materials may include poly-L-lysine, poly-D-lysine, polyethylenimine, albumin, gelatin, collagen, laminin, fibronectin, entactin, vitronectin, fibrillin, elastin, heparin, keratan sulfate, heparan sulfate, chondroitin sulfate, hyaluronic acid, and/or extracellular matrix extracts/mixtures, among others.

Other Capture Features

Other capture features may be used alternatively, or in addition to, affinity-based or mechanical capture. Some or all of these mechanisms, and/or the mechanisms described above, may rely at least partially on friction between particles and microfluidic device channels or passages to assist retention.

Capture features may be based on vacuum forces, fluid flow, and/or gravity. Vacuum-based capture features may exert forces that pull particles into tighter contact with passage surfaces, for example, using a force directed outwardly from a channel. Application of a vacuum, and/or particle retention, may be assisted by an aperture/orifice in the wall of a channel or other passage. By contrast, fluid flow-based capture features may produce fluid flow paths, such as loops, that retain particles. These fluid flow paths may be formed by a closed channel-circuit having no outlet (e.g., by valve closure and active pumping), and/or by an eddy, such as that produced by generally circular fluid-flow within a recess. Gravity-based capture features may hold particles against the bottom surfaces of passages, thus combining with friction to restrict particle movement. Gravity-based retention may be facilitated by recesses and/or reduced fluid flow rates.

Capture features may be based on centrifugal forces, magnetic forces, and/or optically generated forces. Capture features based on centrifugal force may retain particles by pushing the particle against passage surfaces, typically by exerting a force on the particles that is generally orthogonal to fluid flow. Such forces may be exerted by centrifugation of a microfluidic device and/or by particle movement within a fluid flow path. Magnetic force-based capture features may retain particles using magnetic fields, generated external and/or internal to a microfluidic device. The magnetic field may interact with ferromagnetic and/or paramagnetic portions of particles. For example, beads may be formed at least partially of ferromagnetic materials, or cells may include surface-bound or internalized ferromagnetic particles. Electrical force-based capture features may retain charged particles and/or populations using electrical fields. By contrast, capture features that operate based on optically generated forces may use light to retain particles. Such mechanisms may operate based on the principal of optical tweezers, among others.

Another form of capture feature is a blind-fill channel, where a channel has a inlet, but no outlet, either fixedly or transiently. For example, when the microfluidic device is made from a gas permeable material, such as PDMS, gas present in a dead-end channel can escape, or be forced out of the channel through the gas permeable material when urged out by the inflow of liquid through the inlet. This is a preferred example of blind-filling. Blind-filling can be used with a channel or compartment that has an inlet, and an outlet that is gated or valved by a valve. In this example, blind filling of a gas-filled channel or compartment occurs when the outlet valve is closed while filling the channel or compartment through the inlet. If the inlet also has a valve, that valve can then be closed after the blind fill is complete, and the outlet can then be opened to expose the channel or compartment contents to another channel or compartment. If a third inlet is in communication with the channel or compartment, that third inlet can introduce another fluid, gas or liquid, into the channel or compartment to expel the blind-filled liquid to be expelled from the channel or compartment in a measured amount.

Focusing Features

Particle capture can be enhanced in microfluidic devices with the use of a one or more focusing feature(s) to focus particle flow to each capture site. Focusing features may be categorized without limitation in various ways, for example, to reflect their origins and/or operational principles, including direct and/or indirect, fluid-mediated and/or non-fluid-mediated, external and/or internal, and so on. These categories are not mutually exclusive. Thus, a given focusing feature may position a particle in two or more ways; for example, electric fields may position a particle directly (e.g., via electrophoresis) and indirectly (e.g., via electroosmosis).

The focusing features may act to define particle position longitudinally and/or transversely. The term "longitudinal position" denotes position parallel to or along the long axis of a microfluidic channel and/or a fluid flow stream within the channel. In contrast, the term "transverse position" denotes position orthogonal to the long axis of a channel and/or an associated main fluid flow stream. Both longitudinal and transverse positions may be defined locally, by equating "long axis" with "tangent" in curved channels. Focusing features may act to move particles along a path at any angle, relative to the long axis of a channel and/or flow stream, between longitudinal and transverse flow.

The focusing features may be used alone and/or in combination. If used in combination, the features may be used serially (i.e., sequentially) and/or in parallel (i.e., simultaneously). For example, an indirect mechanism such as fluid flow may be used for rough positioning, and a direct mechanism such as optical tweezers may be used for final positioning.

Direct focusing features generally include any mechanism in which a force acts directly on a particle(s) to position the particle(s) within a microfluidic network. Direct focusing features may be based on any suitable mechanism, including optical, electrical, magnetic, and/or gravity-based forces, among others. Optical focusing features use light to mediate or at least facilitate positioning of particles. Suitable optical focusing features include "optical tweezers," which use an appropriately focused and movable light source to impart a positioning force on particles. Electrical focusing features use electricity to position particles. Suitable electrical mechanisms include "electrokinesis," that is, the application of voltage and/or current across some or all of a microfluidic network, which may, as mentioned above, move charged particles directly (e.g., via electrophoresis) and/or indirectly, through movement of ions in fluid (e.g., via electroosmosis). Magnetic focusing features use magnetism to position particles based on magnetic interactions. Suitable magnetic mechanisms involve applying a magnetic field in or around a fluid network, to position particles via their association with ferromagnetic and/or paramagnetic materials in, on, or about the particles. Gravity-based focusing features use the force of gravity to position particles, for example, to contact adherent cells with a substrate at positions of cell culture.

Indirect focusing features generally include any mechanism in which a force acts indirectly on a particle(s), for example, via fluid, to move the particle(s) within a microfluidic network, longitudinally and/or transversely. Longitudinal indirect focusing features generally may be created and/or regulated by fluid flow along channels and/or other passages. Accordingly, longitudinal focusing features may be facilitated and/or regulated by valves and/or pumps that regulate flow rate and/or path. In some cases, longitudinal focusing features may be facilitated and/or regulated by electroosmotic focusing features. Alternatively, or in addition, longitudinal focusing features may be input-based, that is, facilitated and/or regulated by input mechanisms, such as pressure or gravity-based mechanisms, including a pressure head created by unequal heights of fluid columns.

Transverse indirect focusing features generally may be created and/or regulated by fluid flow streams at channel junctions, laterally disposed regions of reduced fluid flow, channel bends, and/or physical barriers (i.e., baffles). Channel junctions may be unifying sites or dividing sites, based on the number of channels that carry fluid to the sites relative to the number that carry fluid away from the sites. Physical barriers may have any suitable design to direct particle flow toward capture sites. For example, a baffle may extend outward from any channel surface, e.g., at an angle to direct particle flow toward a capture site. Baffle length, angle with the channel surface, and distance from the capture site can be adjusted to enhance particle flow toward the capture site. Baffles may be formed by protrusions that extend inward from any portion of a channel or other passage (that is, walls, roof, and/or floor). For example, the protrusions may be fixed and/or movable, including columns, posts, blocks, bumps, walls, and/or partially/completely closed valves, among others. Some physical barriers, such as valves, may be movable or regulatable.

Figure 22A:
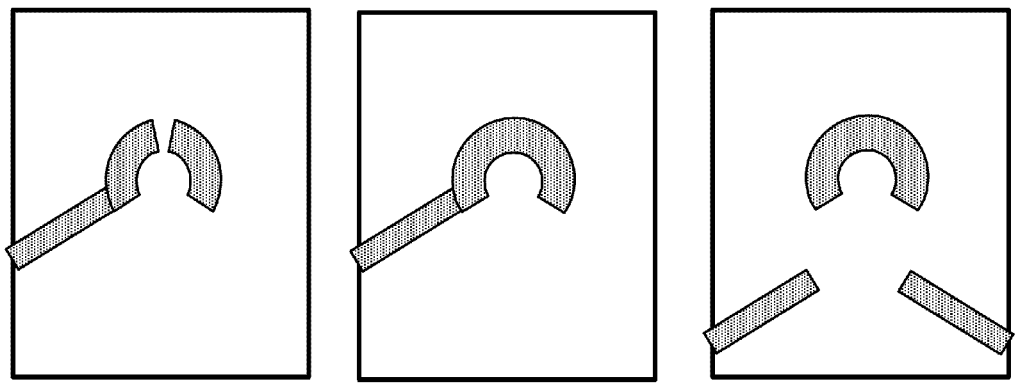
FIG. 22A-C: Capture architectures can be designed to maximize the probability that cells will come into contact with the surface markers. For example, baffles on one or more channel walls can be used to direct beads towards capture feature.
(A) Illustrative capture feature/baffle combinations. (B) Performance of the capture feature can be adjusted by adjusting one or more variables, including angle of baffles, distance of baffles from capture site, length of baffles, size and shape of capture feature, size of drain in capture feature (if present). Baffles on the channel wall are used to direct beads towards a capture feature. (C) The capture feature is coupled to a baffle on a channel wall; individual capture feature/baffle combinations can be located on alternate walls to focus flow towards the adjacent capture feature/baffle combination.

In some embodiments, multiple baffles may be employed for each capture site. For example, a baffle extending outward, at an angle, from each lateral wall of a channel can be employed to direct particle flow toward a capture site that is centrally located in the channel. See FIG. 22A-B. Where mechanical capture is employed, baffles may be spaced apart from the physical barrier(s) in the capture sites. Alternatively, or additionally, baffles may contact or be an integral part of the physical barrier(s) in the capture sites. See FIGS. 22A and 14C. For example, a baffle extending outward, at an angle, from a channel wall can contact or be an integral part of a concave capture feature (e.g., physical barrier(s)). It will be appreciated a "concave" capture feature is concave on the side of the capture feature that generally faces the direction of fluid flow. The baffle directs particle flow away from the channel wall and toward the concave capture feature, facilitating particle capture. The next capture site along the path of flow can have a similar baffle-concave capture feature configuration, with the baffle extending from the same wall of the channel. However, it is advantageous, in some embodiments, for the next baffle-concave capture feature to extend from the opposite channel wall. This alternating configuration acts to focus flow from one baffle to the next, whereby flow along each baffle enhances particle flow into each concave capture feature. See FIG. 22C.

Transverse indirect focusing features may be based on laminar flow, stochastic partitioning, and/or centrifugal force, among other mechanisms. Transverse positioning of particles and/or reagents in a microfluidic device may be mediated at least in part by a laminar flow-based mechanism. Laminar flow-based mechanisms generally include any focusing feature in which the position of an input flow stream within a channel is determined by the presence, absence, and/or relative position(s) of additional flow streams within the channel. Such laminar flow-based mechanisms may be defined by a channel junction(s) that is a unifying site, at which inlet flow streams from two, three, or more channels, flowing toward the junction, unify to form a smaller number of outlet flow streams, preferably one, flowing away from the junction. Due to the laminar flow properties of flow streams on a microfluidic scale, the unifying site may maintain the relative distribution of inlet flow streams after they unify as laminar outlet flow streams. Accordingly, particles and/or reagents may remain localized to any selected one or more of the laminar flow streams, based on which inlet channels carry particles and/or reagents, thus positioning the particles and/or reagents transversely. See, e.g., FIG. 24D.

The relative size (or flow rate) and position of each inlet flow stream may determine both position and relative width of flow streams that carry particles and/or reagents. For example, an inlet flow stream for particles/reagents that is relatively small (narrow), flanked by two larger (wider) flow streams, may occupy a narrow central position in a single outlet channel. By contrast, an inlet flow stream for particles/reagents that is relatively large (wide), flanked by a comparably sized flow stream and a smaller (narrower) flow stream, may occupy a wider position that is biased transversely toward the smaller flow stream. In either case, the laminar flow-based mechanism may be called a focusing mechanism, because the particles/reagents are "focused" to a subset of the cross-sectional area of outlet channels. Laminar flow-based mechanisms may be used to individually address particles and/or reagents to plural distinct capture sites.

A laminar flow-based mechanism may be a variable mechanism to vary the transverse position of particles/reagents. As described above, the relative contribution of each inlet flow stream may determine the transverse position of particles/reagents flow streams. Altered flow of any inlet flow stream may vary its contribution to the outlet flow stream(s), shifting particles/reagents flow streams accordingly. In an extreme case, referred to as a perfusion mechanism, a reagent (or particle) flow stream may be moved transversely, either in contact with, or spaced from, retained particles (reagents), based on presence or absence of flow from an adjacent inlet flow stream. Such a mechanism also may be used to effect variable or regulated transverse positioning of particles, for example, to direct particles to capture sites having different transverse positions.

Transverse positioning of particles and/or reagents in a microfluidic device may be mediated at least in part by a stochastic (or portioned flow) focusing feature. Stochastic transverse focusing features generally include any focusing feature in which an at least partially randomly selected subset of inputted particles or reagent is distributed laterally away from a main flow stream to a region of reduced fluid flow within a channel (or, potentially, to a distinct channel). The region of reduced flow may promote particle retention, treatment, detection, minimize particle damage, and/or promote particle contact with a substrate. Stochastic focusing features may be determined by dividing flow sites and/or locally widened channels, among others.

Dividing flow sites may effect stochastic positioning by forming regions of reduced fluid flow rate. Dividing flow sites generally include any channel junction at which inlet flow streams from one (preferably) or more inlet channels are divided into a greater number of outlet channels, including two, three, or more, channels. Such dividing sites may deliver a subset of particles, which may be selected stochastically and/or based on a property of the particles (such as mass), to a region of reduced flow rate or quasi-stagnant flow formed at or near the junction. The fraction of particles represented by the subset may be dependent upon the relative flow directions of the outlet channels relative to the inlet channels. These flow directions may be generally orthogonal to an inlet flow stream, being directed in opposite directions, to form a "T-junction." Alternatively, outlet flow directions may form angles of less than and/or greater than 90 degrees.

The dividing-flow focusing feature, with two or more outlet channels, may be used as a portioned-flow mechanism. Specifically, fluid, particles, and/or reagents carried to the channel junction may be portioned according to fluid flow through the two or more outlet channels. Accordingly, the fractional number or volume of particles or reagent that enters the two or more channels may be regulated by the relative sizes of the channels and/or the flow rate of fluid through the channels, which in turn may be regulated by valves, or other suitable flow regulatory-mechanisms. In a first set of embodiments, outlet channels may be of very unequal sizes, so that only a small fraction of particle and/or reagents are directed to the smaller channel. In a second set of embodiments, valves may be used to forms desired dilutions of reagents. In a third set of embodiments, valves may be used to selectively direct particles to one of two or more fluid paths.

Locally widened channels may promote stochastic positioning by producing regions of decreased flow rate lateral to a main flow stream. The decreased flow rate may deposit a subset of inputted particles at a region of decreased flow rate. Such widened channels may include nonlinear channels that curve or bend at an angle. Alternatively, or in addition, widened regions may be formed by recesses formed in a channel wall(s), chambers that intersect channels, and/or the like, particularly at the outer edge of a curved or bent channel.

Transverse positioning of particles and/or reagents also may be mediated at least in part by a centrifugal focusing feature. In centrifugal focusing features, particles may experience a centrifugal force determined by a change in velocity, for example, by moving through a bend in a fluid path. Size and/or density of particles may determine the rate of velocity change, distributing distinct sizes and/or densities of particle to distinct transverse positions.

Drain Features

In certain embodiments, the capture site also includes a drain feature. Where mechanical capture is employed, for example, the drain feature can include one or more interruptions in a capture feature that is/are sized to permit fluid flow, but not particle flow, through and/or around the capture feature. Thus, for example, the capture feature can include two physical barriers, separated by a space (the drain feature), wherein the space is sufficiently large to permit particle-free fluid to flow between the barriers with sufficiently low impedance to direct cells toward the barriers, thereby enhancing the probability of particle capture. The space between the physical barriers should generally be sufficiently small and/or suitably configured such that the particles to be captured at the capture site will not pass between the barriers. In a specific, illustrative embodiment, the capture feature includes two concave physical barriers, with first and second ends, wherein the barriers are arranged with a small space between first ends of the barriers, forming a drain feature, and a larger space between the second ends of the barriers. See FIG. 22B (where d3 is greater than d1, which forms a drain). In this configuration, the barriers form a "cup" suitably sized to capture a particle, with a drain at the base of the cup. By virtue of the drain, particles flow toward the cup, as long as it is unoccupied. Once a particle flows into the cup, the drain is "plugged," which tends to enhance particle flow around the cup and on to the next capture feature in the microfluidic device.

Non-Optimized Single-Particle Capture

In particular embodiments, a capture technique, such as limiting dilution is used to capture particles in separate reaction volumes. In this type of capture, there is no use of any capture feature, such as binding affinity or a mechanical feature(s), e.g., in a microfluidic device, that preferentially retains only a single cell at a capture site. For example, limiting dilution can be carried out by preparing a series of dilutions of a particle suspension, and distributing aliquots from each dilution into separate reaction volumes. The number of particles in each reaction volume is determined, and the dilution that produces the highest fraction of reaction volumes having only a single particle is then selected and used to capture particles for the parameter measurements described herein.

Optimized Single-Particle Capture

In some embodiments, the methods entail the use of an optimized capture technique to increase the expected fraction of separate reaction volumes having only one particle above that achieved using a method such as limiting dilution (i.e., above about 33 percent). In variations of these embodiments, capturing is optimized such that the expected fraction of separate reaction volumes with only one particle each is at least about 35 percent, at least about 40 percent, at least about 45 percent, at least about 50 percent, at least about 55 percent, at least about 60 percent, at least about 65 percent, at least about 70 percent, at least about 75 percent, at least about 80 percent, at least about 85 percent, at least about 90 percent, or at least about 95 percent of the total number of separate reaction volumes. In specific embodiments, the expected fraction of separate reaction volumes with only one particle each falls within a range bounded by any two percentages listed above. The expected fraction of separate reaction volume with only one particle each can be determined by empirical or statistical means, depending on the particular capture technique (e.g., limiting dilution produces reaction volumes having only one particle in a manner consistent with the Poisson distribution). As used herein, the term "optimizing" does not imply that an optimal result is achieved, but merely that some measure is taken to increase the expected fraction of separate reaction volumes with only one particle above about 33 percent. In particular embodiments, optimized single-particle capture can be achieved, for example, using a size-based mechanism that excludes retention of more than one particle at in each reaction volume (capture site).

In certain embodiments, mechanical capture is used alone or in combination with one or more other capture features to preferentially capture a single particle in each separate reaction volume (i.e., each capture site within a microfluidic device). For example, each capture site can include one or more physical barrier(s) sized to contain only one particle. The shape of the physical barrier can be designed to enhance the retention of the particle. For example, where the particles are cells, the physical barrier(s) can be sized and configured to form a concave surface suitable for retaining just one cell. In such embodiments, the physical barrier(s) can be designed so as to permit the flow of fluid through the capture site, when it is not occupied by a cell, and/or the capture site may include a drain feature that facilitates this flow. In particular embodiments, a microfluidic device contains a plurality of suitably sized/configured physical barriers, whereby a plurality of individual particles is retained within the device, one particle being retained by each physical barrier. In illustrative embodiments, the physical barriers can be located within separate compartments within a microfluidic device, one region per compartment. The compartments can be arranged to form an array, such as, for example, the microfluidic arrays available from Fluidigm Corp. (South San Francisco, Calif.) and described herein. See also FIG. 24A-G.

In certain embodiments, affinity-based capture is used alone or in combination with one or more other capture features, e.g., mechanical capture, to preferentially capture a single cell in each separate reaction volume (i.e., each capture site within a microfluidic device). For example, a discrete region of a microfluidic device surface that contains a binding partner for a particle or particle component may be sized so that only one particle can bind to the region, with the binding of subsequent particles blocked by steric hindrance. In particular embodiments, a microfluidic device contains a plurality of suitably sized regions, whereby a plurality of individual particles, one at each region, is retained within the device. In illustrative embodiments, these regions can be located within separate compartments within a microfluidic device, one region per compartment. The compartments can be arranged to form an array, such as, for example, the microfluidic arrays available from Fluidigm Corp. (South San Francisco, Calif.) and described herein.

Figure 23A:
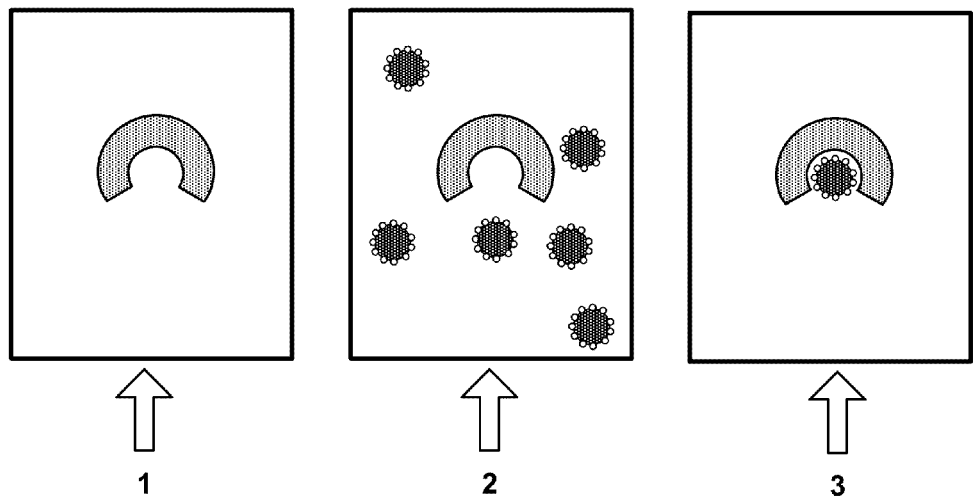
FIG. 23A-B: A strategy for using capture features to catch single, affinity-reagent-coated beads, which then display the affinity reagent (e.g., antibody) so as to capture single particles (e.g., cells). (A-1) Flow is initiated in a channel containing capture features. (A-2) Antibody-bound beads flow toward the capture features until a bead lodges in the capture feature. (A-3) The channel is then washed to remove non-captured beads. (B-1) cells bearing a cell-surface marker to which the antibody binds are flowed into the channel containing the captured beads. (B-2) Cells bearing the marker interact with and bind to antibodies displayed by the captured bead. The display area is sized so that a bound cell will inhibit other cells from interacting with the captured bead through steric occlusion, such that only one cell binds to each captured bead. (B-3) The channel is then washed to remove non-bound cells, leaving one cell immobilized at each capture site.

One approach to affinity-based, optimized single-particle capture is based on capturing a support including a binding partner that binds the particle to be assayed. In illustrative embodiments, the support can be a bead that has the binding partner distributed over its surface. See FIG. 23A. The bead can be captured by mechanical capture using a cup-shaped capture feature to produce a single immobilized support (e.g., bead) at each capture site. In addition to immobilizing the support, the capture feature can, in certain embodiments, reduce the surface area of the support (e.g., bead) that displays the binding partner. This surface can be sufficiently reduced that only one particle can bind to the area of the immobilized support (e.g., bead) that displays the binding partner. To facilitate particle-support binding, in some embodiments, the area of the immobilized support that displays the binding partners faces the flow path of the particles. In specific, illustrative embodiments, a flow channel of a microfluidic device contains a series of capture features. A suspension of beads bearing binding partners (e.g., cell-specific antibodies) is inputted into the channel to produce a series of immobilized beads at the capture sites. The channel is then washed to remove any free (i.e., non-immobilized) beads. FIG. 23A. A cell suspension is then input into the channel. An individual cell can bind to the portion of each bead that displays binding partners. Each bound cell prevents any other cells from binding to the bead through steric occlusion. Washing of the channel removes unbound cells. See FIG. 23B. Valves in between the capture sites can then be closed to create separate reaction volumes, each containing one capture site with one bound cell. One or more focusing features can be employed to direct bead, as well as, particle flow toward each capture site. Alternatively or in addition, the capture features can each include a drain feature that permits the flow of fluid through the capture site when the capture feature is not occupied by a bead.

Determination of Number and/or Characteristics of Particles Captured

In certain embodiments, it is advantageous to determine the number of particles in each separate reaction volume. This determination can be made when using limiting dilution to identify the dilution that produces the highest fraction of compartments having only a single particle. This determination can also be made after any capture technique to identify those reaction volumes that contain only one particle. For example, in some embodiments, the assay results can be sorted into multiple "bins," based on whether they come from reaction volumes containing 0, 1, 2, or more cells, permitting separate analysis of one or more of these bins. In certain embodiments, any of the methods described herein can include determining whether any compartment includes more than a single particle; and not further analyzing, or disregarding, results from, any compartment that includes more than a single particle.

In some embodiments, the number of particles in each separate reaction volume is determined by microscopy. For example, where the separate reaction volumes are in compartments of a microfluidic device that is sufficiently transparent or translucent, simple brightfield microscopy can be used to visualize and count particles, e.g., cells, per compartment. See Example 5. The microfluidic devices described below and available from Fluidigm Corp. (South San Francisco, Calif.) are suitable for use in this brightfield microscopy approach.

In certain embodiments a stain, dye, or label can be employed to detect the number of particles in each separate reaction volume. Any stain, dye, or label that can be detected in the separate reaction volumes can be used. In illustrative embodiments, a fluorescent stain, dye, or label can be used. The stain, dye, or label employed can be tailored to the particular application. Where the particles are cells, and the parameter to be measured is a feature of the cell surface, the stain, dye, or label can be a cell-surface stain, dye, or label that need not penetrate the cells. For example, a labeled antibody specific for a cell-surface marker can employed to detect the number of cells in each separate reaction volume. Where the particles are cells, and the parameter to be measure is an internal feature of the cell (e.g., nucleic acid), the stain, dye, or label can be a membrane-permeant stain, dye, or label (e.g., a double-stranded DNA binding dye).

In particular embodiments, a characteristic of a cell can be detected in each separate reaction volume, with or without a determination of the number of cells in each reaction volume. For example, a stain, dye, or label can be employed to determine whether any reaction volume (e.g., any compartment in a microfluidic device) includes a particle having the characteristic. This step can increase assay efficiency by permitting subsequent analysis of the reaction results of only those compartments that include a particle having the particular characteristic. Illustrative characteristics that can be detected in this context include, for example, a specific genomic rearrangement, copy number variation, or polymorphism; expression of a specific gene; and expression of a specific protein.

Analysis of Nucleic Acids in Single Particles

In particular embodiments, the methods described herein are used in the analysis of one or more nucleic acids. For example, the presence and/or level of a particular target nucleic acid can be determined, as can a characteristic of the target nucleic acid, e.g., the nucleotide sequence. In illustrative embodiments, a population of particles with one or more sample nucleic acids in or associated with the particle is captured in separate reaction volumes, each preferably containing only a single particle. Reactions, such ligation and/or amplification for DNA, or reverse transcription and/or amplification for RNA are carried out, which produce reaction products for any reaction volume containing one or more target nucleic acids. These reaction products can be analyzed within the reaction volumes, or the reaction volumes can be recovered, separately or in pools, for subsequent analysis, such as DNA sequencing.

In certain embodiments, the reactions incorporate one or more nucleotide sequences into the reaction products. These sequences can be incorporated by any suitable method, including ligation, transposase-mediated incorporation, or amplification using one or more primers bearing one or more nucleotide tags that include the sequence to be incorporated. These incorporated nucleotide sequence(s) can serve any function that facilitates any assay described herein. For example, one or more nucleotide sequences can be incorporated into a reaction product to encode an item of information about that reaction product, such as the identity of the reaction volume that was the source of the reaction product. In this case, the reactions are referred to herein as "encoding reactions." Multi-primer methods for adding "barcode" nucleotide sequences to target nucleic acids can be employed for this purpose and are described above. In specific embodiments, nucleic acid amplification is carried out using at least two amplification primers, wherein each amplification primer includes a barcode nucleotide sequence, and the combination of barcode nucleotide sequences encodes the identity of the reaction volume that was the source of the reaction product (termed "combinatorial barcoding"). These embodiments are conveniently employed when the separate reaction volumes are in separate compartments of a matrix-type microfluidic device, e.g., like those available from Fluidigm Corp. (South San Francisco, Calif.) and described below (see "Microfluidic Devices"). Each separate compartment can contain a combination of barcode nucleotide sequences that identifies the row and column of the compartment in which the encoding reaction was carried out. If the reaction volumes are recovered and subjected to further analysis that includes detection of the barcode combination, the results can be associated with a particular compartment and, thereby, with a particle in the compartment. This association can be carried out for all compartments that contain a single particle to permit single-particle (e.g., single-cell) analysis for a population of particles.

The following sections discuss suitable nucleic acid samples, and within these, target nucleic acids suitable for analysis in the methods described herein. Amplification primer design and illustrative amplification methods are then described. The remaining sections discuss various labeling strategies and removal of undesired reaction components. These sections are described with respect to methods that employ amplification for incorporating nucleic acid sequences into target nucleic acids and/or analyzing them. However, those of skill in the art will recognize, based on the guidance herein, that amplification is not critical to carrying out many of the methods described herein. For example, nucleic acid sequences can be incorporated by other means, such as ligation or using a transposase.

Sample Nucleic Acids

Preparations of nucleic acids ("samples") can be obtained from biological sources and prepared using conventional methods known in the art. In particular, DNA or RNA useful in the methods described herein can be extracted and/or amplified from any source, including bacteria, protozoa, fungi, viruses, organelles, as well higher organisms such as plants or animals, particularly mammals, and more particularly humans. Suitable nucleic acids can also be obtained from environmental sources (e.g., pond water), from man-made products (e.g., food), from forensic samples, and the like. Nucleic acids can be extracted or amplified from cells, bodily fluids (e.g., blood, a blood fraction, urine, etc.), or tissue samples by any of a variety of standard techniques. Illustrative samples include samples of plasma, serum, spinal fluid, lymph fluid, peritoneal fluid, pleural fluid, oral fluid, and external sections of the skin; samples from the respiratory, intestinal genital, and urinary tracts; samples of tears, saliva, blood cells, stem cells, or tumors. For example, samples of fetal DNA can be obtained from an embryo or from maternal blood. Samples can be obtained from live or dead organisms or from in vitro cultures. Illustrative samples can include single cells, formalin-fixed and/or paraffin-embedded tissue samples, and needle biopsies. Nucleic acids useful in the methods described herein can also be derived from one or more nucleic acid libraries, including cDNA, cosmid, YAC, BAC, P1, PAC libraries, and the like.

Nucleic acids of interest can be isolated using methods well known in the art, with the choice of a specific method depending on the source, the nature of nucleic acid, and similar factors. The sample nucleic acids need not be in pure form, but are typically sufficiently pure to allow the reactions of interest to be performed. Where the target nucleic acids are RNA, the RNA can be reversed transcribed into cDNA by standard methods known in the art and as described in Sambrook, J., Fritsch, E. F., and Maniatis, T., *Molecular Cloning: A Laboratory Manual*. Cold Spring Harbor Laboratory Press, NY, Vol. 1, 2, 3 (1989), for example.

Target Nucleic Acids

Target nucleic acids useful in the methods described herein can be derived from any of the sample nucleic acids described above. In typical embodiments, at least some nucleotide sequence information will be known for the target nucleic acids. For example, if PCR is employed as the encoding reaction, sufficient sequence information is generally available for each end of a given target nucleic acid to permit design of suitable amplification primers. In an alternative embodiment, target-specific sequences in primers could be replaced by random or degenerate nucleotide sequences.

The targets can include, for example, nucleic acids associated with pathogens, such as viruses, bacteria, protozoa, or fungi; RNAs, e.g., those for which over- or under-expression is indicative of disease, those that are expressed in a tissue- or developmental-specific manner; or those that are induced by particular stimuli; genomic DNA, which can be analyzed for specific polymorphisms (such as SNPs), alleles, or haplotypes, e.g., in genotyping. Of particular interest are genomic DNAs that are altered (e.g., amplified, deleted, rearranged, and/or mutated) in genetic diseases or other pathologies; sequences that are associated with desirable or undesirable traits; and/or sequences that uniquely identify an individual (e.g., in forensic or paternity determinations). When multiple target nucleic acids are employed, these can be on the same or different chromosome(s).

In various embodiments, a target nucleic acid to be amplified can be, e.g., 25 bases, 50 bases, 100 bases, 200 bases, 500 bases, or 750 bases. In certain embodiments of the methods described herein, a long-range amplification method, such as long-range PCR can be employed to produce amplicons from the amplification mixtures. Long-range PCR permits the amplification of target nucleic acids ranging from one or a few kilobases (kb) to over 50 kb. In various embodiments, the target nucleic acids that are amplified by long-range PCR are at least about 1, 2, 3, 4, 5, 6, 7, 8, 9, 10, 11, 12, 13, 14, 15, 20, 25, 30, 35, 40, 45, or 50 kb in length. Target nucleic acids can also fall within any range having any of these values as endpoints (e.g., 25 bases to 100 bases or 5-15 kb).

Primer Design

Primers suitable for nucleic acid amplification are sufficiently long to prime the synthesis of extension products in the presence of the agent for polymerization. The exact length and composition of the primer will depend on many factors, including, for example, temperature of the annealing reaction, source and composition of the primer, and where a probe is employed, proximity of the probe annealing site to the primer annealing site and ratio of primer:probe concentration. For example, depending on the complexity of the target nucleic acid sequence, an oligonucleotide primer typically contains in the range of about 15 to about 30 nucleotides, although it may contain more or fewer nucleotides. The primers should be sufficiently complementary to selectively anneal to their respective strands and form stable duplexes. One skilled in the art knows how to select appropriate primer pairs to amplify the target nucleic acid of interest.

For example, PCR primers can be designed by using any commercially available software or open source software, such as Primer3 (see, e.g., Rozen and Skaletsky (2000) *Meth. Mol. Biol.*, 132: 365-386; www.broad.mit.edu/node/1060, and the like) or by accessing the Roche UPL website. The amplicon sequences are input into the Primer3 program with the UPL probe sequences in brackets to ensure that the Primer3 program will design primers on either side of the bracketed probe sequence.

Primers may be prepared by any suitable method, including, for example, cloning and restriction of appropriate sequences or direct chemical synthesis by methods such as the phosphotriester method of Narang et al. (1979) *Meth. Enzymol.* 68: 90-99; the phosphodiester method of Brown et al. (1979) *Meth. Enzymol.* 68: 109-151; the diethylphosphoramidite method of Beaucage et al. (1981) *Tetra. Lett.*, 22: 1859-1862; the solid support method of U.S. Pat. No. 4,458,066 and the like, or can be provided from a commercial source.

Primers may be purified by using a Sephadex column (Amersham Biosciences, Inc., Piscataway, N.J.) or other methods known to those skilled in the art. Primer purification may improve the sensitivity of the methods described herein.

Amplification Methods

Nucleic acids can be amplified in accordance with the methods described herein for any useful purpose, e.g., to increase the concentration of target nucleic acids for subsequent analysis, and/or to incorporate one or more nucleotide sequences, and/or to detect and/or quantify and/or sequence one or more target nucleic acids. Amplification can be carried out in droplets, in emulsions, in vessels, in wells of a microtiter plate, in compartments of a matrix-type microfluidic device, etc.

Amplification to Increase the Concentration of Target Nucleic Acids

Amplification to increase the concentration of target nucleic acids can be aimed at amplifying all nucleic acids in a reaction mixture, all nucleic acids of a particular type (e.g., DNA or RNA), or specific target nucleic acids. In specific, illustrative embodiments, whole genome amplification can be carried out to increase the concentration of genomic DNA; RNA can be amplified, optionally preceded by a reverse transcription step; and/or general or target-specific preamplification.

Whole Genome Amplification

To analyze genomic DNA, the sample nucleic acids can be amplified using a whole genome amplification (WGA) procedure. Suitable WGA procedures include primer extension PCR (PEP) and improved PEP (I-PEP), degenerated oligonucleotide primed PCR (DOP-PCR), ligation-mediated PCR (LMP), T7-based linear amplification of DNA (TLAD), and multiple displacement amplification (MDA). These techniques are described in U.S. Patent Publication No. 20100178655, published Jul. 15, 2010 (Hamilton et al.), which is incorporated herein by reference in its entirety and specifically for its description of methods useful in single-cell nucleic acid analysis.

Kits for WGA are available commercially from, e.g., Qiagen, Inc. (Valencia, Calif. USA), Sigma-Aldrich (Rubicon Genomics; e.g., Sigma GenomePlex® Single Cell Whole Genome Amplification Kit, PN WGA4-50RXN). The WGA step of the methods described herein can be carried out using any of the available kits according to the manufacturer's instructions.

In particular embodiments, the WGA step is limited WGA, i.e., WGA is stopped before a reaction plateau is reached. Typically, WGA is performed for more than two amplification cycles. In certain embodiments, WGA is performed for fewer than about 10 amplification cycles, e.g., between four and eight cycles, inclusive. However, WGA can be performed for 3, 4, 5, 6, 7, 8, or 9 cycles or for a number of cycles falling within a range defined by any of these values.

RNA Amplification

In certain embodiments, RNA from single cell or a small population of cells can be analyzed for one or more RNA targets. Suitable RNA targets include mRNA, as well as non-coding RNA, such as small nucleolar RNA (snoRNA), microRNA (miRNA), small interfering RNA (siRNA), and Piwi-interacting RNAs (piRNA). In particular embodiments, the RNA of interest is converted to DNA, e.g., by reverse transcription or amplification.

For example, to analyze mRNA of a single cell or a small population of cells, the mRNA is generally converted to a DNA representation of the mRNA population. In certain embodiments, the method(s) employed preferably yield(s) a population of cDNAs, wherein the relative amounts of each cDNA is approximately the same as the relative amounts of the corresponding mRNAs in the sample population.

In particular embodiments, reverse transcription can be employed to produce cDNA from the mRNA template, utilizing reverse transcriptase according to standard techniques. Reverse transcription of a cell's mRNA population can be primed, e.g., with the use of specific primers, oligo-dT, or random primers. To synthesize a cDNA library representative of cellular mRNA, a first strand of cDNA complementary to the sample cellular RNA can be synthesized using reverse transcriptase. This can be done using the commercially available BRL Superscript II kit (BRL, Gaithersburg, Md.) or any other commercially available kit. Reverse transcriptase preferentially utilizes RNA as a template, but can also utilize single-stranded DNA templates. Accordingly, second strand cDNA synthesis can be carried out using reverse transcriptase and suitable primers (e.g., poly-A, random primers, etc.). Second strand synthesis can also be carried out using *E. coli* DNA polymerase I. The RNA can be removed at the same time the second cDNA strand is synthesized or afterwards. This is done by, for example, treating the mixture to an RNase such as *E. coli* RNase H, that degrades the RNA.

In other embodiments, an amplification method is employed to produce cDNA from the mRNA template. In such embodiments, an amplification method that produces a population of cDNA that is representative of the mRNA population is typically employed.

The analysis of non-coding RNA from a single cell or a small population of cells also typically begins with the conversion of the RNA of interest to DNA. This conversion can be carried out by reverse transcription or amplification. In certain embodiments, the method(s) employed preferably yield(s) a population of DNAs, wherein the relative amounts of each DNA is approximately the same as the relative amounts of the corresponding mRNAs in the sample population. The target RNAs can be selectively reverse-transcribed or amplified using primers that anneal preferentially to the RNAs of interest. Suitable primers are commercially available or can be designed by those of skill in the art. For example, Life Technologies sells MegaPlex™ Pools of primers for microRNA (miRNA) targets. These primers can be used for both reverse transcription (RT) and specific target amplification (STA). See, e.g., Example 6B.

Preamplification

Preamplification can be carried to increase the concentration of nucleic acid sequences in a reaction mixture, generally, e.g., using a set of random primers, primers that are specific for one or more sequences common to a plurality of, or all, nucleic acids present (e.g., poly-dT to prime poly-A tails), or a combination of a set of random primers and a specific primer. Alternatively, preamplification can be carried out using one or more primer pairs specific for the one or more target nucleic acids of interest. In specific, illustrative embodiments, an amplified genome produced by WGA or the DNA produced from RNA (e.g., cDNA) can preamplified to produce a preamplification reaction mixture that includes one or more amplicons specific for one or more target nucleic acids of interest. Preamplification is typically carried out using preamplification primers, a suitable buffer system, nucleotides, and DNA polymerase enzyme (e.g., a polymerase enzyme modified for "hot start" conditions).

In particular embodiments, the preamplification primers are the same sequence as those to be used in an amplification assay for which the sample is being prepared although generally in reduced concentration. The primer concentration can, e.g, be about 10 to about 250 times less than the primer concentrations used in the amplification assay. Embodiments include the use of primers that are about 10, 20, 35, 50, 65, 75, 100, 125, 150, 175, and 200 times less than that of the primer concentration in the amplification assay.

In specific embodiments, preamplification is carried out for at least two cycles. In certain embodiments, preamplification is carried out for fewer than about 20 cycles, e.g., between 8 and 18 cycles, inclusive. However, preamplification can be performed for 3, 4, 5, 6, 7, 8, 9, 10, 11, 12, 13, 14, 15, 16, 17, 18, 19, 20, 21, 22, 23, or 24 cycles or for a number of cycles falling within a range defined by any of these values. In an exemplary embodiment, preamplification is carried out for about 14 cycles in order to increase the amplicons to be detected by about 16,000 fold.

Amplification for Detection and/or Quantification of Target Nucleic Acids

Any method of detection and/or quantification of nucleic acids can be used in the methods described herein to detect amplification products. In one embodiment, PCR (polymerase chain reaction) is used to amplify and/or quantify target nucleic acids. In other embodiments, other amplification systems or detection systems are used, including, e.g., systems described in U.S. Pat. No. 7,118,910 (which is incorporated herein by reference in its entirety for its description of amplification/detection systems). In particular embodiments, real-time quantification methods are used. For example, "quantitative real-time PCR" methods can be used to determine the quantity of a target nucleic acid present in a sample by measuring the amount of amplification product formed during the amplification process itself.

Fluorogenic nuclease assays are one specific example of a real-time quantification method that can be used successfully in the methods described herein. This method of monitoring the formation of amplification product involves the continuous measurement of PCR product accumulation using a dual-labeled fluorogenic oligonucleotide probe—an approach frequently referred to in the literature as the "TaqMan® method." See U.S. Pat. No. 5,723,591; Heid et al., 1996, Real-time quantitative PCR Genome Res. 6:986-94, each incorporated herein by reference in their entireties for their descriptions of fluorogenic nuclease assays. It will be appreciated that while "TaqMan® probes" are the most widely used for qPCR, the methods described herein are not limited to use of these probes; any suitable probe can be used.

Other detection/quantification methods that can be employed in the present invention include FRET and template extension reactions, molecular beacon detection, Scorpion detection, Invader detection, and padlock probe detection.

FRET and template extension reactions utilize a primer labeled with one member of a donor/acceptor pair and a nucleotide labeled with the other member of the donor/acceptor pair. Prior to incorporation of the labeled nucleotide into the primer during a template-dependent extension reaction, the donor and acceptor are spaced far enough apart that energy transfer cannot occur. However, if the labeled nucleotide is incorporated into the primer and the spacing is sufficiently close, then energy transfer occurs and can be detected. These methods are particularly useful in conducting single base pair extension reactions in the detection of single nucleotide polymorphisms and are described in U.S. Pat. No. 5,945,283 and PCT Publication WO 97/22719.

With molecular beacons, a change in conformation of the probe as it hybridizes to a complementary region of the amplified product results in the formation of a detectable signal. The probe itself includes two sections: one section at the 5' end and the other section at the 3' end. These sections flank the section of the probe that anneals to the probe binding site and are complementary to one another. One end section is typically attached to a reporter dye and the other end section is usually attached to a quencher dye. In solution, the two end sections can hybridize with each other to form a hairpin loop. In this conformation, the reporter and quencher dye are in sufficiently close proximity that fluorescence from the reporter dye is effectively quenched by the quencher dye. Hybridized probe, in contrast, results in a linearized conformation in which the extent of quenching is decreased. Thus, by monitoring emission changes for the two dyes, it is possible to indirectly monitor the formation of amplification product. Probes of this type and methods of their use are described further, for example, by Piatek et al., 1998, Nat. Biotechnol. 16:359-63; Tyagi, and Kramer, 1996, Nat. Biotechnology 14:303-308; and Tyagi, et al., 1998, Nat. Biotechnol. 16:49-53 (1998).

The Scorpion detection method is described, for example, by Thelwell et al. 2000, Nucleic Acids Research, 28:3752-3761 and Solinas et al., 2001, "Duplex Scorpion primers in SNP analysis and FRET applications" Nucleic Acids Research 29:20. Scorpion primers are fluorogenic PCR primers with a probe element attached at the 5'-end via a PCR stopper. They are used in real-time amplicon-specific detection of PCR products in homogeneous solution. Two different formats are possible, the "stem-loop" format and the "duplex" format. In both cases the probing mechanism is intramolecular. The basic elements of Scorpions in all formats are: (i) a PCR primer; (ii) a PCR stopper to prevent PCR read-through of the probe element; (iii) a specific probe sequence; and (iv) a fluorescence detection system containing at least one fluorophore and quencher. After PCR extension of the Scorpion primer, the resultant amplicon contains a sequence that is complementary to the probe, which is rendered single-stranded during the denaturation stage of each PCR cycle. On cooling, the probe is free to bind to this complementary sequence, producing an increase in fluorescence, as the quencher is no longer in the vicinity of the fluorophore. The PCR stopper prevents undesirable read-through of the probe by Taq DNA polymerase.

Invader assays (Third Wave Technologies, Madison, Wis.) are used particularly for SNP genotyping and utilize an oligonucleotide, designated the signal probe, that is complementary to the target nucleic acid (DNA or RNA) or polymorphism site. A second oligonucleotide, designated the Invader Oligo, contains the same 5' nucleotide sequence, but the 3' nucleotide sequence contains a nucleotide polymorphism. The Invader Oligo interferes with the binding of the signal probe to the target nucleic acid such that the 5' end of the signal probe forms a "flap" at the nucleotide containing the polymorphism. This complex is recognized by a structure specific endonuclease, called the Cleavase enzyme. Cleavase cleaves the 5' flap of the nucleotides. The released flap binds with a third probe bearing FRET labels, thereby forming another duplex structure recognized by the Cleavase enzyme. This time, the Cleavase enzyme cleaves a fluorophore away from a quencher and produces a fluorescent signal. For SNP genotyping, the signal probe will be designed to hybridize with either the reference (wild type) allele or the variant (mutant) allele. Unlike PCR, there is a linear amplification of signal with no amplification of the nucleic acid. Further details sufficient to guide one of ordinary skill in the art are provided by, for example, Neri, B. P., et al., *Advances in Nucleic Acid and Protein Analysis* 3826:117-125, 2000) and U.S. Pat. No. 6,706,471.

Padlock probes (PLPs) are long (e.g., about 100 bases) linear oligonucleotides. The sequences at the 3' and 5' ends of the probe are complementary to adjacent sequences in the target nucleic acid. In the central, noncomplementary region of the PLP there is a "tag" sequence that can be used to identify the specific PLP. The tag sequence is flanked by universal priming sites, which allow PCR amplification of the tag. Upon hybridization to the target, the two ends of the PLP oligonucleotide are brought into close proximity and can be joined by enzymatic ligation. The resulting product is a circular probe molecule catenated to the target DNA strand. Any unligated probes (i.e., probes that did not hybridize to a target) are removed by the action of an exonuclease. Hybridization and ligation of a PLP requires that both end segments recognize the target sequence. In this manner, PLPs provide extremely specific target recognition.

The tag regions of circularized PLPs can then be amplified and resulting amplicons detected. For example, TaqMan® real-time PCR can be carried out to detect and quantify the amplicon. The presence and amount of amplicon can be correlated with the presence and quantity of target sequence in the sample. For descriptions of PLPs see, e.g., Landegren et al., 2003, Padlock and proximity probes for in situ and array-based analyses: tools for the post-genomic era, *Comparative and Functional Genomics* 4:525-30; Nilsson et al., 2006, Analyzing genes using closing and replicating circles *Trends Biotechnol.* 24:83-8; Nilsson et al., 1994, Padlock probes: circularizing oligonucleotides for localized DNA detection, *Science* 265:2085-8.

In particular embodiments, fluorophores that can be used as detectable labels for probes include, but are not limited to, rhodamine, cyanine 3 (Cy 3), cyanine 5 (Cy 5), fluorescein, Vic™, Liz™., Tamra™, 5-Fam™, 6-Fam™, and Texas Red (Molecular Probes). (Vic™, Liz™, Tamra™, 5-Fam™, 6-Fam™ are all available from Life Technologies, Foster City, Calif.).

In some embodiments, one can simply monitor the amount of amplification product after a predetermined number of cycles sufficient to indicate the presence of the target nucleic acid sequence in the sample. One skilled in the art can easily determine, for any given sample type, primer sequence, and reaction condition, how many cycles are sufficient to determine the presence of a given target nucleic acid. In other embodiments, detection is carried out at the end of exponential amplification, i.e., during the "plateau" phase, or endpoint PCR is carried out. In various embodiments, amplification can be carried out for about: 2, 4, 10, 15, 20, 25, 30, 35, or 40 cycles or for a number of cycles falling within any range bounded by any of these values.

By acquiring fluorescence over different temperatures, it is possible to follow the extent of hybridization. Moreover, the temperature-dependence of PCR product hybridization can be used for the identification and/or quantification of PCR products. Accordingly, the methods described herein encompass the use of melting curve analysis in detecting and/or quantifying amplicons. Melting curve analysis is well known and is described, for example, in U.S. Pat. Nos. 6,174,670; 6,472,156; and 6,569,627, each of which is hereby incorporated by reference in its entirety, and specifically for its description of the use of melting curve analysis to detect and/or quantify amplification products. In illustrative embodiments, melting curve analysis is carried out using a double-stranded DNA dye, such as SYBR Green, Pico Green (Molecular Probes, Inc., Eugene, Oreg.), EVA Green (Biotinum), ethidium bromide, and the like (see Zhu et al., 1994, Anal. Chem. 66:1941-48).

In certain embodiments, multiplex detection is carried out in individual amplification mixture, e.g., in individual reaction compartments of a microfluidic device, which can be used to further increase the number of samples and/or targets that can be analyzed in a single assay or to carry out comparative methods, such as comparative genomic hybridization (CGH). In various embodiments, up to 2, 3, 4, 5, 6, 7, 8, 9, 10, 50, 100, 500, 1000, 5000, 10000 or more amplification reactions are carried out in each individual reaction compartment.

According to certain embodiments, one can employ an internal standard to quantify the amplification product indicated by the fluorescent signal. See, e.g., U.S. Pat. No. 5,736,333.

Devices have been developed that can perform a thermal cycling reaction with compositions containing a fluorescent dye, emit a light beam of a specified wavelength, read the intensity of the fluorescent dye, and display the intensity of fluorescence after each cycle. Devices comprising a thermal cycler, light beam emitter, and a fluorescent signal detector, have been described, e.g., in U.S. Pat. Nos. 5,928,907; 6,015,674; and 6,174,670.

In some embodiments, each of these functions can be performed by separate devices. For example, if one employs a Q-beta replicase reaction for amplification, the reaction may not take place in a thermal cycler, but could include a light beam emitted at a specific wavelength, detection of the fluorescent signal, and calculation and display of the amount of amplification product.

In particular embodiments, combined thermal cycling and fluorescence detecting devices can be used for precise quantification of target nucleic acids. In some embodiments, fluorescent signals can be detected and displayed during and/or after one or more thermal cycles, thus permitting monitoring of amplification products as the reactions occur in real-time. In certain embodiments, one can use the amount of amplification product and number of amplification cycles to calculate how much of the target nucleic acid sequence was in the sample prior to amplification.

Amplification for DNA Sequencing

In certain embodiments, amplification methods are employed to produce amplicons suitable for automated DNA sequencing. Many current DNA sequencing techniques rely on "sequencing by synthesis." These techniques entail library creation, massively parallel PCR amplification of library molecules, and sequencing. Library creation starts with conversion of sample nucleic acids to appropriately sized fragments, ligation of adaptor sequences onto the ends of the fragments, and selection for molecules properly appended with adaptors. The presence of the adaptor sequences on the ends of the library molecules enables amplification of random-sequence inserts. The above-described methods for tagging nucleotide sequences can be substituted for ligation, to incorporate adaptor sequences, as described in greater detail below.

In addition, the ability of the above-described methods to provide substantially uniform amplification of target nucleotide sequences is helpful in preparing DNA sequencing libraries having good coverage. In the context of automated DNA sequencing, the term "coverage" refers to the number of times the sequence is measured upon sequencing. A DNA sequencing library that has substantially uniform coverage can yield sequence data where the coverage is also substantially uniform. Thus, in various embodiments, upon performing automated sequencing of a plurality of target amplicons prepared as described herein, the sequences of at least 50 percent of the target amplicons are present at greater than 50 percent of the average number of copies of target amplicon sequences and less than 2-fold the average number of copies of target amplicon sequences. In various embodiments of this method at least 55, at least 60, at least 65, at least 70, at least 75, at least 80, at least 85, at least 90, at least 91, at least 92, at least 93, at least 94, at least 95, at least 96, at least 97, at least 98, or at least 99 percent of the target amplicon sequences are present at greater than 50 percent of the average number of copies of target amplicon sequences and less than 2-fold the average number of copies of target amplicon sequences.

In certain embodiments, at least three primers can be employed to produce amplicons suitable for DNA sequencing: forward, reverse, and barcode primers. However, one or more of the forward primer, reverse primer, and barcode primer can includes at least one additional primer binding site. In specific embodiments, the barcode primer includes at least a first additional primer binding site upstream of the barcode nucleotide sequence, which is upstream of the first nucleotide tag-specific portion. In certain embodiments, two of the forward primer, reverse primer, and barcode primer include at least one additional primer binding site (i.e, such that the amplicon produced upon amplification includes the nucleotide tag sequences, the barcode nucleotide sequence, and the two additional binding sites). For example, if the barcode primer includes a first additional primer binding site upstream of the barcode nucleotide sequence, in specific embodiments, the reverse primer can include at least a second additional primer binding site downstream of the second nucleotide tag. Amplification then yields a molecule having the following elements: 5'-first additional primer binding site-barcode nucleotide sequence-first nucleotide tag from the forward primer-target nucleotide sequence-second nucleotide tag from the reverse primer-second additional primer binding site-3'. In specific embodiments, the first and second additional primer binding sites are capable of being bound by DNA sequencing primers, to facilitate sequencing of the entire amplicon, including the barcode, which, as discussed above, can indicate sample origin.

In other embodiments, at least four primers are employed to produce amplicons suitable for DNA. For example, inner primers can be used with outer primers that additionally include first and second primer binding sites that are capable of being bound by DNA sequencing primers. Amplification yields a molecule having the following elements: 5'-first primer binding site-second barcode nucleotide sequence-first nucleotide tag sequence-first barcode nucleotide sequence-target nucleotide sequence-first barcode nucleotide sequence-second nucleotide tag sequence-second barcode nucleotide sequence-second primer binding site-3'. Because this molecule contains the barcode combination at either end, sequence can be obtained from either end of the molecule to identify the barcode combination.

In a similar manner, six primers can be employed to prepare DNA for sequencing. More specifically, inner and stuffer primers, as discussed above, can be used with outer primers that additionally include first and second primer binding sites that are capable of being bound by DNA sequencing primers. Amplification yields a molecule having the following elements: 5'-first primer binding site-second barcode nucleotide sequence-third nucleotide tag sequence-first barcode nucleotide sequence-first nucleotide tag sequence-target nucleotide sequence-second nucleotide tag sequence-first barcode nucleotide sequence-fourth nucleotide tag sequence-second barcode nucleotide sequence-second primer binding site-3'. Because this molecule contains the barcode combination at either end, sequence can be obtained from either end of the molecule to identify the barcode combination.

The methods described herein can include subjecting at least one target amplicon to DNA sequencing using any available DNA sequencing method. In particular embodiments, a plurality of target amplicons is sequenced using a high throughput sequencing method. Such methods typically use an in vitro cloning step to amplify individual DNA molecules. As discussed above, emulsion PCR (emPCR) isolates individual DNA molecules along with primer-coated beads in aqueous droplets within an oil phase. PCR produces copies of the DNA molecule, which bind to primers on the bead, followed by immobilization for later sequencing. In vitro clonal amplification can also be carried out by "bridge PCR," where fragments are amplified upon primers attached to a solid surface. DNA molecules that are physically bound to a surface can be sequenced in parallel, for example, by a pyrosequencing or sequencing-by-synthesis method, as discussed above.

Labeling Strategies

Any suitable labeling strategy can be employed in the methods described herein. Where the assay mixture is aliquoted, and each aliquot is analyzed for presence of a single amplification product, a universal detection probe can be employed in the amplification mixture. In particular embodiments, real-time PCR detection can be carried out using a universal qPCR probe. Suitable universal qPCR probes include double-stranded DNA dyes, such as SYBR Green, Pico Green (Molecular Probes, Inc., Eugene, Oreg.), EVA Green (Biotinum), ethidium bromide, and the like (see Zhu et al., 1994, Anal. Chem. 66:1941-48). Suitable universal qPCR probes also include sequence-specific probes that bind to a nucleotide sequence present in all amplification products. Binding sites for such probes can be conveniently incorporated into the tagged target nucleotide sequences during amplification.

Alternatively, one or more target-specific qPCR probes (i.e., specific for a target nucleotide sequence to be detected) is employed in the amplification mixtures to detect amplification products. Target-specific probes could be useful, e.g., when only a few target nucleic acids are to be detected in a large number of samples. For example, if only three targets were to be detected, a target-specific probe with a different fluorescent label for each target could be employed. By judicious choice of labels, analyses can be conducted in which the different labels are excited and/or detected at different wavelengths in a single reaction. See, e.g., Fluorescence Spectroscopy (Pesce et al., Eds.) Marcel Dekker, New York, (1971); White et al., Fluorescence Analysis: A Practical Approach, Marcel Dekker, New York, (1970); Berlman, Handbook of Fluorescence Spectra of Aromatic Molecules, 2nd ed., Academic Press, New York, (1971); Griffiths, Colour and Constitution of Organic Molecules, Academic Press, New York, (1976); Indicators (Bishop, Ed.). Pergamon Press, Oxford, 19723; and Haugland, Handbook of Fluorescent Probes and Research Chemicals, Molecular Probes, Eugene (1992).

Removal of Undesired Reaction Components

It will be appreciated that reactions involving complex mixtures of nucleic acids in which a number of reactive steps are employed can result in a variety of unincorporated reaction components, and that removal of such unincorporated reaction components, or reduction of their concentration, by any of a variety of clean-up procedures can improve the efficiency and specificity of subsequently occurring reactions. For example, it may be desirable, in some embodiments, to remove, or reduce the concentration of preamplification primers prior to carrying out the amplification steps described herein.

In certain embodiments, the concentration of undesired components can be reduced by simple dilution. For example, preamplified samples can be diluted about 2-, 5-, 10-, 50-, 100-, 500-, 1000-fold prior to amplification to improve the specificity of the subsequent amplification step.

In some embodiments, undesired components can be removed by a variety of enzymatic means. Alternatively, or in addition to the above-described methods, undesired components can be removed by purification. For example, a purification tag can be incorporated into any of the above-described primers (e.g., into the barcode nucleotide sequence) to facilitate purification of the tagged target nucleotides.

In particular embodiments, clean-up includes selective immobilization of the desired nucleic acids. For example, desired nucleic acids can be preferentially immobilized on a solid support. In an illustrative embodiment, an affinity moiety, such as biotin (e.g., photo-biotin), is attached to desired nucleic acid, and the resulting biotin-labeled nucleic acids immobilized on a solid support comprising an affinity moiety-binder such as streptavidin. Immobilized nucleic acids can be queried with probes, and non-hybridized and/or non-ligated probes removed by washing (See, e.g., Published P.C.T. Application WO 03/006677 and U.S. Ser. No. 09/931, 285.) Alternatively, immobilized nucleic acids can be washed to remove other components and then released from the solid support for further analysis. This approach can be used, for example, in recovering target amplicons from amplification mixtures after the addition of primer binding sites for DNA sequencing. In particular embodiments, an affinity moiety, such as biotin, can be attached to an amplification primer such that amplification produces an affinity moiety-labeled (e.g., biotin-labeled) amplicon. Thus, for example, where three primers are employed to add barcode and nucleotide tag elements to a target nucleotide sequence, as described above, at least one of the barcode or reverse primers can include an affinity moiety. Where four primers (two inner primers and two outer primers) are employed to add desired element to a target nucleotide sequence, at least one of the outer primers can include an affinity moiety.

Microfluidic Devices

In certain embodiments, methods described herein can be carried out using a microfluidic device. In illustrative embodiments, the device is a matrix-type microfluidic device that allows the simultaneous combination of a plurality of substrate solutions with reagent solutions in separate isolated reaction compartments. It will be recognized, that a substrate solution can include one or a plurality of substrates (e.g., target nucleic acids) and a reagent solution can include one or a plurality of reagents. For example, the microfluidic device can allow the simultaneous pair-wise combination of a plurality of different amplification primers and samples. In certain embodiments, the device is configured to contain a different combination of primers and samples in each of the different compartments. In various embodiments, the number of separate reaction compartments can be greater than 50, usually greater than 100, more often greater than 500, even more often greater than 1000, and sometimes greater than 5000, or greater than 10,000.

In particular embodiments, the matrix-type microfluidic device is a DYNAMIC ARRAY™ IFC ("DA") microfluidic device. A DA microfluidic device is a matrix-type microfluidic device designed to isolate pair-wise combinations of samples and reagents (e.g., amplification primers, detection probes, etc.) and suited for carrying out qualitative and quantitative PCR reactions including real-time quantitative PCR analysis. In some embodiments, the DA microfluidic device is fabricated, at least in part, from an elastomer. DA microfluidic devices are described in PCT Publication No. WO05107938A2 (Thermal Reaction Device and Method For Using The Same) and U.S. Patent Publication No. US20050252773A1, both incorporated herein by reference in their entireties for their descriptions of DA microfluidic devices. DA microfluidic devices may incorporate high-density matrix designs that utilize fluid communication vias between layers of the microfluidic device to weave control lines and fluid lines through the device and between layers. By virtue of fluid lines in multiple layers of an elastomeric block, high density reaction cell arrangements are possible. Alternatively DA microfluidic devices may be designed so that all of the reagent and sample channels are in the same elastomeric layer, with control channels in a different layer. In certain embodiments, DA microfluidic devices may be used for reacting M number of different samples with N number of different reagents.

Although the DA microfluidic devices described in WO05107938 are well suited for conducting the methods described herein, the invention is not limited to any particular device or design. Any device that partitions a sample and/or allows independent pair-wise combinations of reagents and sample may be used. U.S. Patent Publication No. 20080108063 (which is hereby incorporated by reference it its entirety) includes a diagram illustrating the 48.48 DYNAMIC ARRAY™ IFC, a commercially available device available from Fluidigm Corp. (South San Francisco Calif.). It will be understood that other configurations are possible and contemplated such as, for example, 48×96; 96×96; 30×120; etc.

In specific embodiments, the microfluidic device can be a DIGITAL ARRAY™ IFC microfluidic device, which is adapted to perform digital amplification. Such devices can have integrated channels and valves that partition mixtures of sample and reagents into nanoliter volume reaction compartments. In some embodiments, the DIGITAL ARRAY™ IFC microfluidic device is fabricated, at least in part, from an elastomer. Illustrative DIGITAL ARRAY™ IFC microfluidic devices are described in copending U.S. Applications owned by Fluidigm Corp. (South San Francisco, Calif.), such as U.S. application Ser. No. 12/170,414, entitled "Method and Apparatus for Determining Copy Number Variation Using Digital PCR." One illustrative embodiment has 12 input ports corresponding to 12 separate sample inputs to the device. The device can have 12 panels, and each of the 12 panels can contain 765 6 mL reaction compartments with a total volume of 4.59 µL per panel. Microfluidic channels can connect the various reaction compartments on the panels to fluid sources. Pressure can be applied to an accumulator in order to open and close valves connecting the reaction compartments to fluid sources. In illustrative embodiments, 12 inlets can be provided for loading of the sample reagent mixture. 48 inlets can be used to provide a source for reagents, which are supplied to the chip when pressure is applied to accumulator. Additionally, two or more inlets can be provided to provide hydration to the chip.

While the DIGITAL ARRAY™ IFC microfluidic devices are well suited for carrying out certain amplification methods described herein, one of ordinary skill in the art would recognize many variations and alternatives to these devices. The geometry of a given DIGITAL ARRAY™ IFC microfluidic device will depend on the particular application. Additional description related to devices suitable for use in the methods described herein is provided in U.S. Patent Publication No. 20050252773, incorporated herein by reference for its disclosure of DIGITAL ARRAY™ IFC microfluidic devices.

In certain embodiments, the methods described herein can be performed using a microfluidic device that provides for recovery of reaction products. Such devices are described in detail in copending U.S. Application No. 61/166,105, filed Apr. 2, 2009, (which is hereby incorporated by reference in its entirety and specifically for its description of microfluidic devices that permit reaction product recovery and related methods) and sold by Fluidigm Corp. as ACCESS ARRAY™ IFC (Integrated Fluidic Circuit).

In an illustrative device of this type, independent sample inputs are combined with primer inputs in an M×N array configuration. Thus, each reaction is a unique combination of a particular sample and a particular reagent mixture. Samples are loaded into sample compartments in the microfluidic device through sample input lines arranged as columns in one implementation. Assay reagents (e.g., primers) are loaded into assay compartments in the microfluidic device through assay input lines arranged as rows crossing the columns. The sample compartments and the assay compartments are in fluidic isolation during loading. After the loading process is completed, an interface valve operable to obstruct a fluid line passing between pairs of sample and assay compartments is opened to enable free interface diffusion of the pairwise combinations of samples and assays. Precise mixture of the samples and assays enables reactions to occur between the various pairwise combinations, producing one or more reaction product(s) in each compartment. The reaction products are harvested and can then be used for subsequent processes. The terms "assay" and "sample" as used herein are descriptive of particular uses of the devices in some embodiments. However, the uses of the devices are not limited to the use of "sample(s)" and "assay(s)" in all embodiments. For example, in other embodiments, "sample(s)" may refer to "a first reagent" or a plurality of "first reagents" and "assay(s)" may refer to "a second reagent" or a plurality of "second reagents." The M×N character of the devices enable the combination of any set of first reagents to be combined with any set of second reagents.

According to particular embodiments, the reaction products from the M×N pairwise combinations can be recovered from the microfluidic device in discrete pools, e.g., one for each of M samples. Typically, the discrete pools are contained in a sample input port provided on the carrier. In some processes, the reaction products may be harvested on a "per amplicon" basis for purposes of normalization. Utilizing embodiments of the present invention, it is possible to achieve results (for replicate experiments assembled from the same input solutions of samples and assays) for which the copy number of amplification products varies by no more than ±25% within a sample and no more than ±25% between samples. Thus, the amplification products recovered from the microfluidic device will be representative of the input samples as measured by the distribution of specific known genotypes. In certain embodiments, output sample concentration will be greater than 2,000 copies/amplicon/microliter, and recovery of reaction products will be performed in less than two hours.

In some embodiments, reaction products are recovered by dilation pumping. Dilation pumping provides benefits not typically available using conventional techniques. For example, dilation pumping enables for a slow removal of the reaction products from the microfluidic device. In an exemplary embodiment, the reaction products are recovered at a fluid flow rate of less than 100 μl per hour. In this example, for 48 reaction products distributed among the reaction compartments in each column, with a volume of each reaction product of about 1.5 μl, removal of the reaction products in a period of about 30 minutes, will result in a fluid flow rate of 72 μl/hour. (i.e., 48×1.5/0.5 hour). In other embodiments, the removal rate of the reaction products is performed at a rate of less than 90 μl/hr, 80 μl/hr, 70 μl/hr, 60 μl/hr, 50 μl/hr, 40 μl/hr, 30 μl/hr, 20 μl/hr, 10 μl/hr, 9 μl/hr, less than 8 μl/hr, less than 7 μl/hr, less than 6 μl/hr, less than 5 μl/hr, less than 4 μl/hr, less than 3 μl/hr, less than 2 μl/hr, less than 1 μl/hr, or less than 0.5 μl/hr.

Dilation pumping results in clearing of substantially a high percentage and potentially all the reaction products present in the microfluidic device. Some embodiments remove more than 75% of the reaction products present in the reaction compartments (e.g., sample compartments) of the microfluidic device. As an example, some embodiments remove more than 80%, 85%, 90%, 92%, 95%, 96%, 97%, 98%, or 99% of the reaction products present in the reaction compartments.

The methods described herein may use microfluidic devices with a plurality of "unit cells" that generally include a sample compartment and an assay compartment. Such unit cells can have dimensions on the order of several hundred microns, for example unit cells with dimension of 500×500 μm, 525×525 μm, 550×550 μm, 575×575 μm, 600×600 μm, 625×625 μm, 650×650 μm, 675×675, μm, 700×700 μm, or the like. The dimensions of the sample compartments and the assay compartments are selected to provide amounts of materials sufficient for desired processes while reducing sample and assay usage. As examples, sample compartments can have dimensions on the order of 100-400 μm in width×200-600 μm in length×100-500 μm in height. For example, the width can be 100 μm, 125 μm, 150 μm, 175 μm, 200 μm, 225 μm, 250 μm, 275 μm, 300 μm, 325 μm, 350 μm, 375 μm, 400 μm, or the like. For example, the length can be 200 μm, 225 μm, 250 μm, 275 μm, 300 μm, 325 μm, 350 μm, 375 μm, 400 μm, 425 μm, 450 μm, 475 μm, 500 μm, 525 μm, 550 μm, 575 μm, 600 μm, or the like. For example, the height can be 100 μm, 125 μm, 150 μm, 175 μm, 200 μm, 225 μm, 250 μm, 275 μm, 300 μm, 325 μm, 350 μm, 375 μm, 400 μm, 425 μm, 450 μm, 475 μm, 500 μm, 525 μm, 550 μm, 575 μm, 600 μm, or the like. Assay compartments can have similar dimensional ranges, typically providing similar steps sizes over smaller ranges than the smaller compartment volumes. In some embodiments, the ratio of the sample compartment volume to the assay compartment volume is about 5:1, 10:1, 15:1, 20:1, 25:1, or 30:1. Smaller compartment volumes than the listed ranges are included within the scope of the invention and are readily fabricated using microfluidic device fabrication techniques.

Higher density microfluidic devices will typically utilize smaller compartment volumes in order to reduce the footprint of the unit cells. In applications for which very small sample sizes are available, reduced compartment volumes will facilitate testing of such small samples.

Figure 9:
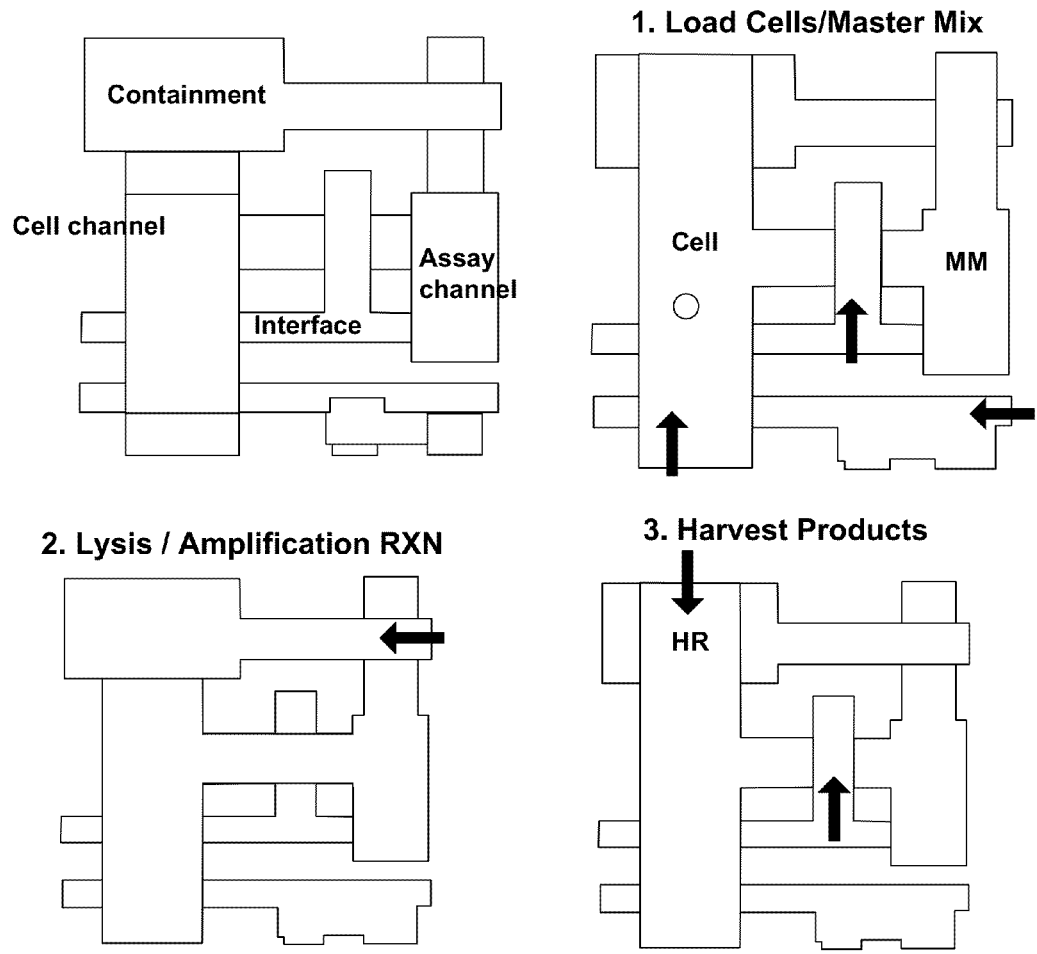
FIG. 9: A schematic diagram of the unit cell architecture for a microfluidic device adapted for Cell handling ("MA006"), showing on-chip processes.

For single-particle analysis, microfluidic devices can be designed to facilitate loading and capture of the particular particles to be analyzed. FIG. 9 shows the unit cell architecture for an illustrative microfluidic device for analyzing mammalian cells. Each unit cell has a "cell channel" (i.e., sample compartment) and an "assay channel" (i.e., assay compartment). The cell channel is rounded for loading mammalian cells, with dimensions on the order of tens microns in diameter to a hundred of several hundred microns in length. Diameters can be about 15 μm, about 20 μm, about 25 μm, about 30 μm, about 35 μm, about 40 μm, or about 45 μm or more, or can fall within a range having any of these values as endpoints, depending on the size of the cells being analyzed. Lengths can be about 60 μm, about 90 μm, about 120 μm, about 150 μm, about 170 μm, about 200 μm, about 230 μm, about 260 μm, about 290 μm or more, or can fall within a range having any of these values as endpoints, depending on the size of the cells being analyzed. In an illustrative microfluidic device based on the ACCESS ARRAY™ IFC platform (the "MA006"), a unit cell for loading mammalian cells can be about 30 μm×170 μm. Such a device can be equipped to provide, or to facilitate providing, heat to cell channels after loading to lyse the cells. As shown in FIG. 9, the device can include assay channels separate from cell channels for conducting reactions such as nucleic acid amplification. 170 μm×170 containment valves can be used to close cell channels.

Co-pending U.S. App. No. 61/605,016, filed Feb. 29, 2012, and entitled "Methods, Systems, And Devices For Multiple Single-Particle or Single-Cell Processing Using Microfluidics," describes methods, systems, and devices for multiple single-particle or single-cell processing utilizing microfluidics. Various embodiments provide for capturing, partitioning, and/or manipulating individual particles or cells from a larger population of particles of cells along with generating genetic information and/or reaction(s) related to each individual particle or cell. Some embodiments may be configured for imaging the individual particles or cells or associated reaction products as part of the processing. This application is incorporated by reference herein it its entirety and, in particular, for its description of microfluidic devices configured for multiple single-particle or single-cell processing and related systems.

In specific embodiments, a microfluidic device is employed that facilitates assays having a dynamic range of at least 3 orders of magnitude, more often at least 4, at least 5, at least 6, at least 7, or at least 8 orders of magnitude.

Fabrication methods using elastomeric materials and methods for design of devices and their components have been described in detail in the scientific and patent literature. See, e.g., Unger et al. (2000) Science 288:113-116; U.S. Pat. No. 6,960,437 (Nucleic acid amplification utilizing microfluidic devices); U.S. Pat. No. 6,899,137 (Microfabricated elastomeric valve and pump systems); U.S. Pat. No. 6,767, 706 (Integrated active flux microfluidic devices and methods); U.S. Pat. No. 6,752,922 (Microfluidic chromatography); U.S. Pat. No. 6,408,878 (Microfabricated elastomeric valve and pump systems); U.S. Pat. No. 6,645,432 (Microfluidic devices including three-dimensionally arrayed channel networks); U.S. Patent Application Publication Nos. 2004/0115838; 2005/0072946; 2005/0000900; 2002/0127736; 2002/0109114; 2004/0115838; 2003/0138829; 2002/0164816; 2002/0127736; and 2002/0109114; PCT Publication Nos. WO 2005/084191; WO 05/030822A2; and WO 01/01025; Quake & Scherer, 2000, "From micro to nanofabrication with soft materials" Science 290: 1536-40; Unger et al., 2000, "Monolithic microfabricated valves and pumps by multilayer soft lithography" Science 288:113-116; Thorsen et al., 2002, "Microfluidic large-scale integration" Science 298:580-584; Chou et al., 2000, "Microfabricated Rotary Pump" Biomedical Microdevices 3:323-330; Liu et al., 2003, "Solving the "world-to-chip" interface problem with a microfluidic matrix" Analytical Chemistry 75, 4718-23, Hong et al, 2004, "A nanoliter-scale nucleic acid processor with parallel architecture" Nature Biotechnology 22:435-39.

Data Output and Analysis

In certain embodiments, when the methods described herein are carried out on a matrix-type microfluidic device, the data can be output as a heat matrix (also termed "heat map"). In the heat matrix, each square, representing a reaction compartment on the DA matrix, has been assigned a color value which can be shown in gray scale, but is more typically shown in color. In gray scale, black squares indicate that no amplification product was detected, whereas white squares indicate the highest level of amplification produce, with shades of gray indicating levels of amplification product in between. In a further aspect, a software program may be used to compile the data generated in the heat matrix into a more reader-friendly format.

Applications

In particular embodiments, the methods described herein are used in the analysis of one or more nucleic acids, e.g. (in some embodiments), in or associated with a particle. Thus, for example, these methods are applicable to identifying the presence of particular polymorphisms (such as SNPs), alleles, or haplotypes, or chromosomal abnormalities, such as amplifications, deletions, rearrangements, or aneuploidy. The methods may be employed in genotyping, which can be carried out in a number of contexts, including diagnosis of genetic diseases or disorders, cancer, pharmacogenomics (personalized medicine), quality control in agriculture (e.g., for seeds or livestock), the study and management of populations of plants or animals (e.g., in aquaculture or fisheries management or in the determination of population diversity), or paternity or forensic identifications. The methods described herein can be applied in the identification of sequences indicative of particular conditions or organisms in biological or environmental samples. For example, the methods can be used in assays to identify pathogens, such as viruses, bacteria, and fungi. The methods can also be used in studies aimed at characterizing environments or microenvironments, e.g., characterizing the microbial species in the human gut.

In certain embodiments, these methods can also be employed in determinations of DNA or RNA copy number. Determinations of aberrant DNA copy number in genomic DNA is useful, for example, in the diagnosis and/or prognosis of genetic defects and diseases, such as cancer. Determination of RNA "copy number," i.e., expression level is useful for expression monitoring of genes of interest, e.g., in different individuals, tissues, or cells under different conditions (e.g., different external stimuli or disease states) and/or at different developmental stages.

In addition, the methods can be employed to prepare nucleic acid samples for further analysis, such as, e.g., DNA sequencing.

Furthermore, nucleic acid samples can be tagged as a first step, prior subsequent analysis, to reduce the risk that mislabeling or cross-contamination of samples will compromise the results. For example, any physician's office, laboratory, or hospital could tag samples immediately after collection, and the tags could be confirmed at the time of analysis. Similarly, samples containing nucleic acids collected at a crime scene could be tagged as soon as practicable, to ensure that the samples could not be mislabeled or tampered with. Detection of the tag upon each transfer of the sample from one party to another could be used to establish chain of custody of the sample.

As discussed above, the methods described herein can be used in the analysis of other parameters of particles besides nucleic acids, such as, for example, the expression level(s) of one or more proteins in or associated with each particle. In some embodiments, one or more nucleic acids are analyzed, together with one or more other parameters, for each particle.

The ability to associate assay results for multiple parameters with each particle in a population of particles can be exploited in a variety of different types of investigations. In various embodiments, the methods described herein can be employed to identify two or more of a variation such as a copy number variation, a mutation, an expression level variation, or a splice variant, wherein the variations are, together, correlated with a phenotype. The phenotype can, for example, be risk, presence, severity, prognosis, and/or responsiveness to a specific therapy of a disease or resistance to a drug. The methods described here can also be used to detect the co-occurrence of particular nucleic acid sequences, which can indicate genomic recombination, co-expression of particular splice variants, co-expression of particular light and heavy chains in B cells. The methods are also applicable to detecting presence of a particular pathogen in a particular host cell, e.g., where both pathogen-specific and host cell-specific nucleic acids (or other parameter) co-occur in the same cell. The methods can also be employed for targeted re-sequencing from circulating tumor cells, e.g., at mutation hot spots in different cancers.

Kits

Kits according to the invention can include one or more reagents useful for practicing one or more assay methods described herein. A kit generally includes a package with one or more containers holding the reagent(s) (e.g., primers and/or probe(s)), as one or more separate compositions or, optionally, as admixture where the compatibility of the reagents will allow. The kit can also include other material(s) that may be desirable from a user standpoint, such as a buffer(s), a diluent(s), a standard(s), and/or any other material useful in sample processing, washing, or conducting any other step of the assay. In specific embodiments, the kit includes one or more matrix-type microfluidic devices discussed above.

In certain embodiments, the invention includes kits for performing the above-described method of adding adaptor molecules to each end of a plurality of target nucleic acids that include sticky ends. These embodiments are useful, for example, in fragment generation for high-throughput DNA sequencing. Such kits can include a plurality of adaptor molecules that are designed to be used in this method (see above) and one or more components selected from the group consisting of a DNAse enzyme, an exonuclease, an endonuclease, a polymerase, and a ligase.

In particular embodiments, the invention includes kits for combinatorial barcoding. A kit for performing a four-primer method, for example, can include a polymerase and:
 (i) inner primers including:
  a forward, inner primer including a first nucleotide tag, a first barcode nucleotide sequence, and a target-specific portion; and
  a reverse, inner primer including a target-specific portion, a first barcode nucleotide sequence, and a second nucleotide tag; and
 (ii) outer primers including:
  a forward, outer primer including a second barcode nucleotide sequence and a first nucleotide tag-specific portion; and
  a reverse, outer primer including a second nucleotide tag-specific portion and a second barcode nucleotide sequence, wherein the outer primers are in excess of the inner primers. A kit for performing a six-primer, combinatorial barcoding method can include a polymerase and:
 (i) inner primers including:
  a forward, inner primer including a first nucleotide tag and a target-specific portion; and
  a reverse, inner primer including a target-specific portion and a second nucleotide tag;
 (ii) stuffer primers including:
  a forward, stuffer primer including a third nucleotide tag, a first barcode nucleotide sequence, and a first nucleotide tag-specific portion; and
  a reverse, stuffer primer including a second nucleotide tag-specific portion, a first barcode nucleotide sequence, a fourth nucleotide tag; and
 (iii) outer primers including:
  a forward, outer primer including a second barcode nucleotide sequence and a third nucleotide tag-specific portion; and
  a reverse, outer primer including a fourth nucleotide tag-specific portion and a second barcode nucleotide sequence, wherein the outer primers are in excess of the stuffer primers, which are in excess of the inner primers.

In other embodiments, the invention includes kits for combinatorial ligation-based tagging. These kits include a plurality of adaptors including:
 a plurality of first adaptors, each comprising the same endonuclease site, N different barcode nucleotide sequences, wherein N is an integer greater than 1, a first primer binding site and a sticky end;
 a second adaptor comprising a second primer binding site and a sticky end; and
 a plurality of third adaptors including a second barcode nucleotide sequence and sticky ends complementary to those produced upon cutting the first adaptors at the endonuclease site, wherein the plurality of third adaptors include M different second barcode nucleotide sequences, wherein M is an integer greater than 1. Such kits can optionally include an endonuclease specific for the endonuclease site in the first adaptors and/or a ligase.

The invention also provides kits for tagging by insertional mutagenesis, which can also be employed for combinatorial tagging, as described above. In certain embodiments, such kits include:
 one or more nucleotide tags(s); and
 a plurality of barcode primers, wherein each barcode primer includes:
  a first portion that is specific for a first portion of the nucleotide tag(s) linked to;
  a barcode nucleotide sequence that does not anneal to the nucleotide tag(s) linked to;
  a second portion that is specific for a second portion of the nucleotide tag(s), wherein the barcode primers in the plurality each include the same first and second tag-specific portions, but M different second barcode nucleotide sequences, wherein M is an integer greater than one. In specific embodiments, the nucleotide tag(s) include transposon ends, and the kit additionally includes a transposase, which can add transposon ends to target nucleic acids. Such kits can also, optionally, include a polymerase.

The invention includes kits useful in bidirectional nucleic acid sequencing. In particular embodiments, such a kit can include:
 a first set of outer primers, wherein the set includes:
  a first outer, forward primer including a portion specific for a first primer binding site; and
  a first outer, reverse primer including a barcode nucleotide sequence and a portion specific for a second primer binding site, wherein the first and second primer binding sites are different;
 a second set of outer primers, wherein the set includes:
  a second outer, forward primer including a barcode nucleotide sequence and a portion specific for the first primer binding site; and
  a second outer, reverse primer including a portion specific for the second primer binding site. The first and second primer binding sites can, in certain embodiments, be binding sites for DNA sequencing primers. In some embodiments, the outer primers can each additionally include an additional nucleotide sequence, wherein:
 the first outer, forward primer includes a first additional nucleotide sequence, and the first outer, reverse primer includes a second additional nucleotide sequence; and
 the second outer, forward primer includes the second additional nucleotide sequence, and the second outer, reverse primer includes the first additional nucleotide sequence; and the first and second additional nucleotide sequences are different. In a specific, illustrative embodiment, the first set of outer primers includes PE1-CS1 and PE2-BC-CS2, and the second set of outer primers includes PE1-CS2 and PE2-BC-CS1 (Table 1, Example 9).

Bidirectional nucleic acid sequencing kits including the two sets of outer primers can also, optionally, include a set of inner primers, wherein the set includes:
 an inner, forward primer including a target-specific portion and the first primer binding site; and
 an inner, reverse primer including a target-specific portion and the second primer binding site. In certain embodiments, the kit can include a plurality of sets of inner primers, each specific for a different target nucleic acid.

Any of these bidirectional nucleic acid sequencing kits can also, optionally, include DNA sequencing primers that:
 bind to the first and second primer binding sites and prime sequencing of the target nucleotide sequence(s); and/or
 bind to the first and second primer binding sites and prime sequencing of the barcode nucleotide sequence(s). In particular embodiments, both types of DNA sequencing primer are included in the kit, and the primers that bind to the first and second primer binding sites and prime sequencing of the barcode nucleotide sequences(s) are reverse complements of the primers that prime sequencing of the target nucleotide sequences. In a specific, illustrative embodiment, the kit includes DNA sequencing primers CS1, CS2, CS1rc, and CS2rc (Table 2, Example 9).

Kits generally include instructions for carrying out one or more of the methods described herein. Instructions included in kits can be affixed to packaging material or can be included as a package insert. While the instructions are typically written or printed materials they are not limited to such. Any medium capable of storing such instructions and communicating them to an end user is contemplated by this invention. Such media include, but are not limited to, electronic storage media (e.g., magnetic discs, tapes, cartridges, chips), optical media (e.g., CD ROM), RF tags, and the like. As used herein, the term "instructions" can include the address of an internet site that provides the instructions.

It is understood that the examples and embodiments described herein are for illustrative purposes only and that various modifications or changes in light thereof will be suggested to persons skilled in the art and are to be included within the spirit and purview of this application and scope of the appended claims.

In addition, all other publications, patents, and patent applications cited herein are hereby incorporated by reference in their entirety for all purposes.

EXAMPLES

Example 1

A General Library Preparation Method for DNA Sequencing

Current methods of preparing libraries for nucleic acid sequencing are cumbersome and require multiple steps. The essence of the methods involves random fragmentation of the DNA (for example), followed by end repair, polishing of fragment ends and ligation of end adaptors. These steps each require specific reaction conditions and purification of products between each step.

This Example and FIGS. 1 and 2 describe an alternative approach to library preparation. This approach uses a degenerate sequencing adaptor, which can be a double stranded DNA molecule that comprises the end adaptors (or portions thereof) for a given sequencer, a restriction enzyme digestion site (or other specific cleavage site), and flanking degenerate sequences at the 3' end of both strands. Alternatively, the adaptors can be hairpin sequences, or double stranded oligonucleotides. It would also be possible for the end adaptors to be single-stranded oligonucleotides with degenerate sequences at the 3' end.

DNA would be fragmented using standard methods (enzymatic digest, nebulization, sonication, for example). Enzymatic digests would be preferred, as they cause less damage to the DNA molecules for downstream steps. For example, DNAse I would be added to the DNA to be sequenced. This reaction could be stopped by heat treatment.

Double stranded DNA would then be digested back to single-stranded DNA at the ends using T4 polymerase in the absence of NTPs, or a strand-specific exonuclease without polymerase activity. An exonuclease would be preferred, as it could work in concert with a ligase (e.g., a thermostable ligase) and polymerase (e.g. PHUSION®) within a single reaction. However, the prep method would still work in multiple steps if T4 polymerase were used.

The nuclease digestion would expose one strand at the ends of the DNA. Adaptor sequences would be added in the presence of a polymerase and a ligase. Adaptor sequences will anneal to the digested DNA, and gaps will be filled and repaired with the polymerase/ligase mixture. In one version of this protocol, the adaptor sequences would be made from hairpin structures, so that during the digestion/ligation/polymerisation, the end product would be circularized DNA. This would be protected from further degradation by the exonuclease, resulting in the accumulation of end product.

Example 2

Combinatorial Ligation-Based Barcoding for Illumina Sequencing

Prepare DNA sequencing libraries, with standard PE2-BC-tag sequence replaced by RE-1-BC-tag.

PE2 tag sequence downstream of barcode sequence replaced with recognition site (RE-1) for restriction enzyme, (e.g. BsrD1) which leaves short overhang:
5'-TGCATAGCAATGNN|CTAGGTGACTGGAGTTCA GACGTGTGCTCTTCCGATCT-Target-3' (SEQ ID NO:2)
3'-ACGTATCGTTAC|NNGATCCACTGACCTCAAGTCT GCACACGAGAAGGCTAGA-Target-5' (SEQ ID NO:3)

Cut library with enzyme.

Ligate adapter molecules containing the appropriate overhang and a second barcode sequence:

```
                                              (SEQ ID NO: 4)
5'-CAAGCAGAAGACGGCATACGAGATAGCTNN + CTAGGTGACTG
GAGTTCAGACGTGTGCTCTTCCGATCT-Target-3'

(SEQ ID NO: 5)
3'-GTTCGTCTTCTGCCGTATGCTCTATCGA NNGATCCACTGACCT
CAAGTCTGCACACGAGAAGGCTAGA-Target-5'
```

Ligation will result in the following construct:

```
                                              (SEQ ID NO: 6)
5'-CAAGCAGAAGACGGCATACGAGATAGCTNNCTAGGTGACTGGAG
TTCAGACGTGTGCTCTTCCGATCT-Target-3'

(SEQ ID NO: 7)
3'-GTTCGTCTTCTGCCGTATGCTCTATCGANNGATCCACTGACCTC
AAGTCTGCACACGAGAAGGCTAGA-Target-5'
```

Remove left-over adaptor molecules before sequencing using standard cleanup methods.

During the index read on the sequencing run, the index sequence reported back will be: CTAGNNAGCT (SEQ ID NO:8).

Example 3

Single-Cell Analysis of Gene Expression

Problem:

To obtain single cell gene expression data for a panel of genes using a DYNAMIC ARRAY™ IFC, the cell is first be isolated in a tube off-chip. The methods to isolate this cell are difficult to perform and/or require a large number of cells. Where cells are limited, such as primary cells from tissue and/or cells from drug screening experiments in mini-well plates, this last obstacle becomes more of a barrier to obtaining gene expression data from single cells using the BioMark.

Figure 7A:
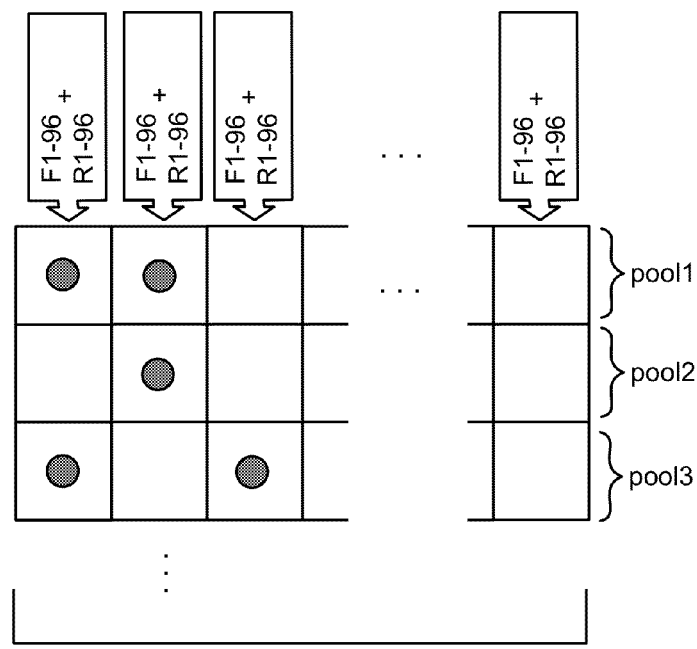
FIG. 7A-C: Barcoding and pooling of reaction mixtures for subsequent analysis: production of barcoded target nucleotide sequences. (A) In an illustrative embodiment, cells are loaded in limiting dilution in an ACCESS ARRAY™ IFC ("Integrated Fluidic Circuit," also referred to herein as a "chip"). Primer sets are loaded as shown, with each chamber in the chip receiving a complete set of 96 forward primers (F1-96) and 96 reverse primers (R1-96) for amplifying 96 targets. The reverse primer is tagged with a tag that can anneal to a barcode primer. Each chamber in a row of the chip receives a different barcode primer. (B) As described in Example 5, reverse transcription and preamplification is carried out in the chip to generate barcoded target nucleotide sequences using a 3-primer method. Any given chamber will have amplified all genes, and all amplicons will have been tagged with a single barcode. The reaction products are exported by pool (90 degrees to different primer sets, i.e. by sample). (C) For detection, a DYNAMIC ARRAY™ IFC can be loaded as shown, with the forward primer (e.g., F1) used to amplify a particular target nucleic acid and the barcode primer (e.g., BC1) used to amplify this sequence in a particular chamber in a particular pool (e.g. pool 1).

Solution:

An ACCESS ARRAY™ IFC ("chip"), or similar chip that allows recovery of reaction mixtures, can be used to load single cells via limiting dilution (MA006 chip, for example.) By using the chip as an apparatus to sort and prepare the cells for downstream gene expression analysis, a limited number of cells can be prepped for the DYNAMIC ARRAY™ IFC with ease, thus providing a solution to the problems outlined above. The steps of the invention are as follows:

1) Load cells in limiting dilution in an ACCESS ARRAY™ IFC. Load primer sets as shown in FIG. 7A. Any given cell will be exposed to all gene-specific primers and a single unique barcode primer.

Figure 7B:
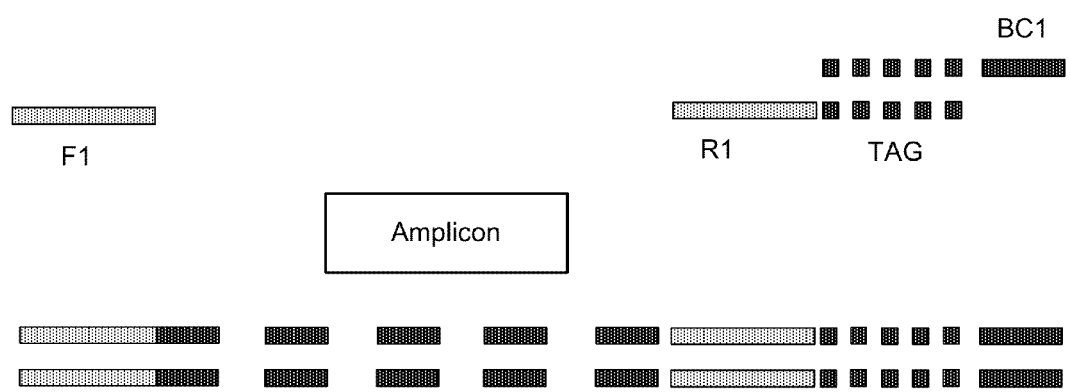

2) Do reverse transcription and preamplification in the chip. An example of an amplicon generated is shown in FIG. 7B. This is a 3 primer approach. The advantage of using this approach is that only one set of 96 primer pairs (or more, for as many genes that are desired) needs to be designed and ordered for a particular experiment. The BC reverse primers are universal and used in all experiments. Any given cell will have amplified all genes and all amplicons will have been tagged with a single barcode. (See possible variations below).

3) Export the reaction products by pool (90 degrees to different primer sets, i.e. by sample). Pool N now contains a preamp of 96 genes (or more or less), with a mixture of barcodes, where one barcode is matched with one cell. The pools are kept separate, such that even though multiple cells are tagged with the same barcode, they are distinguishable because they belong to different pools.

Figure 7C:
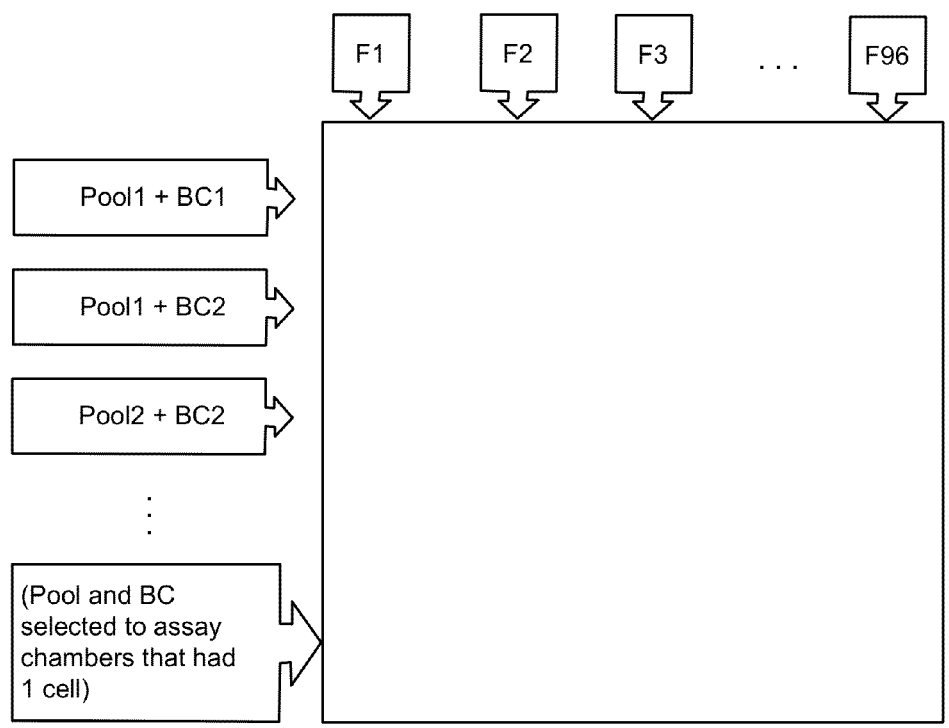

4) Load a DYNAMIC ARRAY™ IFC as shown in FIG. 7C. Note: Single cells can be tracked on the ACCESS ARRAY™ chip via a variety of methods. This provides the information regarding which pool and which barcode pre-amp reaction had a single cell, i.e., which should be loaded on a DYNAMIC ARRAY™ IFC. This selection allows us to read only ACCESS ARRAY™ IFC chambers which contained a cell, resulting in efficient use of the DYNAMIC ARRAY™ IFC. Moreover, if cells of interest are delineated by using cell-specific stains, i.e., antibody for a cell-surface marker, then only this subset of cells could be selected for loading in the DYNAMIC ARRAY™ IFC. This could become important where cells are rare in a heterogeneous population of cells, i.e., stem cells, cancer stem cells, cancer cells.

5) Run qPCR, with EvaGreen for detection. By amplifying a combination of one BC primer and one gene specific primer, gene expression for a single cell (whose amplicons were tagged with a BC primer during preamplification in the ACCESS ARRAY™ IFC) for a given gene (whose amplification will be detected by the gene specific primer in the DYNAMIC ARRAY™ IFC) can be obtained.

Possible Variations:

There are different detection methods, that have the common end result of preamplifying a set of genes and tagging individual cells with a unique barcode. Examples are as follows:

Doing the same as above but use a 2-primer approach.
Use Fen-Ligase Chain Reaction.
Use Melting Temperature strategy.

Example 4

Alternative Methods of Detecting Reaction Products from Example 3

Instead of detecting BC-tagged amplicons from preamplification in the ACCESS ARRAY™ IFC using qPCR with EvaGreen, ligase chain reaction is carried out in a DYNAMIC ARRAY™ IFC (e.g., M96) with real time detection:

An illustrative amplicon has the structure: 5'-forward primer sequence-target nucleotide sequence-reverse primer sequence-barcode nucleotide sequence-3'. In this case, one primer can anneal to the reverse primer sequence, and the other primer can anneal to the adjacent barcode nucleotide sequence, which is followed by ligation and repeated cycles of annealing and ligation. See FIG. 8A. Amplicons in the pool that have either a different reverse primer ("R") are derived from a different target nucleic acids (here, messenger RNA), and amplicons in the pool that have a different barcode primer ("BC") will not be amplified. Therefore, amplification of pool$_N$ with $BC_M$ amplifies barcoded target nucleic acids from the chamber in ACCESS ARRAY™ IFC row N, column M. The use of $R_1$ as the other primer in this amplification amplifies the amplicon derived from the target nucleic acid corresponding to $R_1$.

Figure 8B:
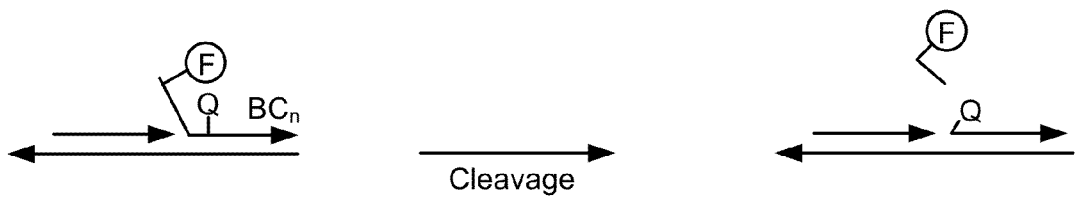
Figure 8C:
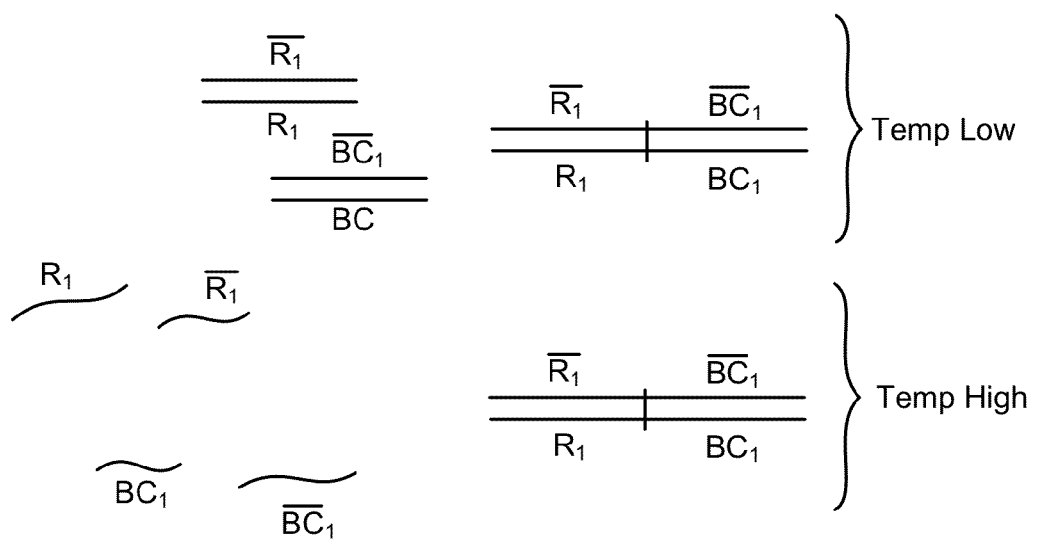

One method of real time detection is flap endonuclease-ligase chain reaction, which uses a 5' flap endonuclease and labeled $BC_n$ primers, as shown in FIG. 8B. This reaction employs a labeled probe and an unlabeled probe, wherein the simultaneous hybridization of the probes to a reaction product results in the formation of a flap at the 5' end of the labeled probe, and cleavage of the flap can cleave a fluorophore from a quencher, producing a signal. Since the BCs are not amplicon-specific, these primers need only be made once. One set of, e.g., 96 BCs would suffice for any number of different sets of $F_n R_n$ amplicons.

Advantages of this Strategy:

Selection of a pool and BC allows analysis of only those ACCESS ARRAY™ IFC chambers that contained a single cell (where single-cell analysis is the goal). Unlabeled cells can be detecting using brightfield or fluorescence imaging of the ACCESS ARRAY™ IFC. In addition, cells can be stained with a dye and/or a labeled antibody, prior to or upon loading into the ACCESS ARRAY™ IFC to identify cells of interest (e.g., stem cells, cancer cells, cancer stem cells, etc.). Selection of a pool and BC allows analysis of only those ACCESS ARRAY™ IFC chambers that contained a cell of interest, improving efficiency.

This strategy requires far fewer cells than FACS, which makes it possible for use in analyses that cannot be carried out using FACS, such as analyses of population of primary cells or cells from screening experiments.

Example 5

Method to Prepare Nucleic Acids for Sequencing from Single Cells Using ACCESS ARRAY™ IFC Adapted for Cell Handling ("MA006")

Summary of General Approach

A "chip," herein referred to as MA006, has been developed using the ACCESS ARRAY™ IFC platform as have methods using MA006 that integrate cell handling and sample preparation for nucleic acid sequencing. See FIG. 9 for a schematic diagram of the MA006 unit cell architecture, showing on-chip processes. This integration simplifies the steps required to execute the experiment. Moreover, only hundreds of cells are required to load the chip.

The MA006 chip has the following features:
Unit cell with 170×30 pm rounded channel to load mammalian cells
48.48 matrix format;
Use heat to lyse cells in cell channels;
Separate reaction chamber for amplification reaction;
170×170 pm containment valves to close cell channels;
Extra resist layer: PourOB—30 gm rounded resist;
Chip fabrication: Use current AA48.48 processes;
65 pm alignment tolerance;
130 pm punch diameter;

65×85 pm valve size; and 3-layer design process.

There are no cell capture features on the MA006 chip. The result is that a limiting dilution strategy is used to obtain the desired number of cells per chamber. However, cell capture features can be designed into the chip. They can be physical (for example, cups, or chalice structures), biological (for example, spotted peptides), or chemical (for example, charged ions).

Cell Handling off of the chip: Cells to be analyzed are prepared to a density such that a desired number of cells per sample chamber ("cell channel" in FIG. 9) is obtained. Since the MA006 chip uses a limiting dilution strategy, the number of cells per chamber follows a Poisson distribution, both theoretical and real. Since, in the first instance, a maximum number of chambers containing a single cell was desired, the optimal cell density was 300-600 cells per microliter. Minimal volumes of one to two microliters can be applied to the inlets. Therefore, experiments can be carried out with only hundreds of cells. Any cell type (i.e., mammalian, bacterial, etc.) from any source can be used (i.e., living organisms, tissue culture, etc.). Any form or extent of preparation, washing, and/or staining can be used, as long as this is compatible with downstream applications.

Cell tracking in the chip: In the absence of any polymerase/amplification dependent chemistry, the cells in the chip can be monitored for position, identity, and/or content using brightfield or fluorescence microscopy. The cells can be stained with any stain (i.e., nucleic acid-specific staining, such as SYTO10; immunodetection, such as Cy5 conjugated anti-CD19; etc.) as long as this is compatible with downstream applications. This can be used, for example, to identify rare cells, i.e. cancer stem cells, in a heterogeneous cell population.

Chemistry: After the cells are loaded into the MA006, the assays are loaded in the assay chamber ("assay channel" in FIG. 9), and the interface valves are released to mix the contents of the sample and assay chambers. The chip is subjected to thermal cycling according to the selected chemistry and imaged in real-time or at the end point if this is required and/or supported by the chemistry. This procedure is not limited to gene-specific amplification, i.e. non-specific degenerate primers can be used, or RNA-specific amplification can be carried out. In the case of gene-specific amplification, more than one gene can be targeted simultaneously using a "multiplex" strategy. The chemistry is flexible, provided that the output is a substrate for sequencing, and should not be restricted to polymerase chain reaction or even amplification.

Cell Handling

Cell Counting: Brightfield Imaging

RAMOS cells were handled as follows:

(1) Harvest cells.

(2) Wash 2-3× in ice-cold Tris Saline BSA buffer.

Figure 10:
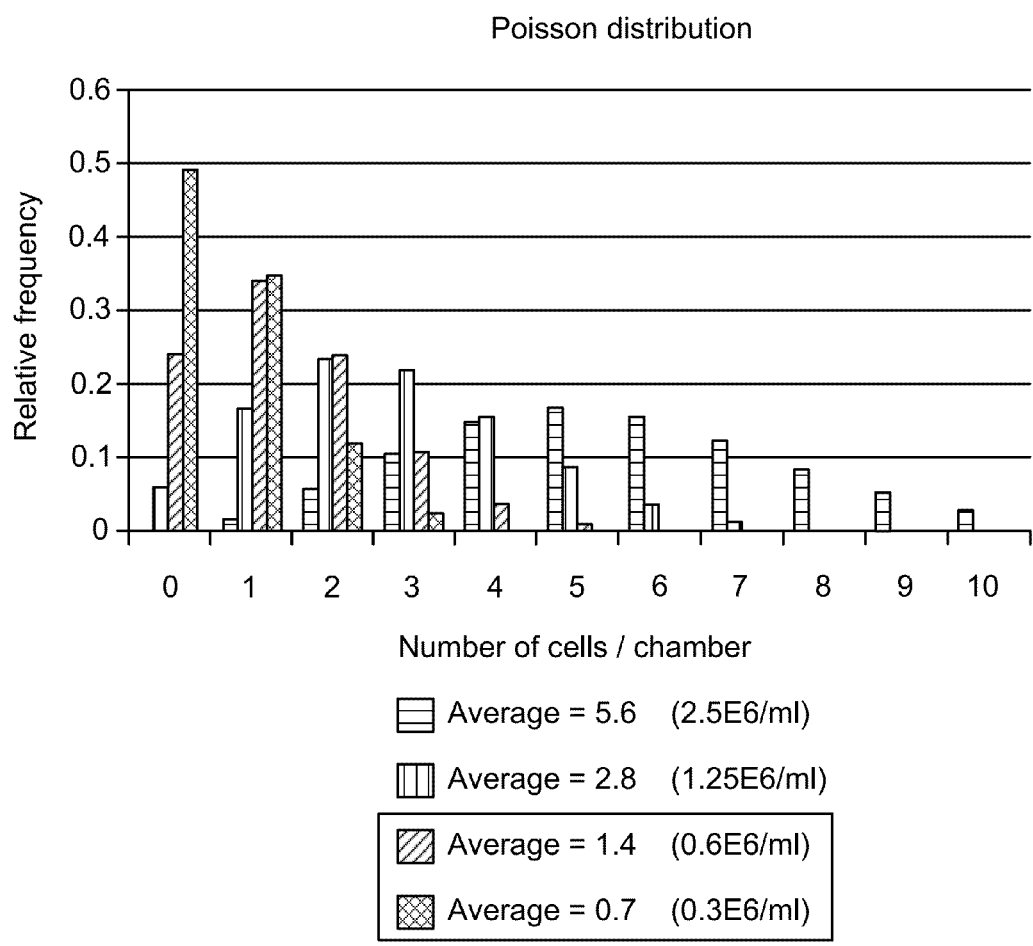
FIG. 10: The use of limiting dilution of a cell suspension to obtain a single cell per separate reaction volume ("chamber" of a microfluidic device or "chip"). The theoretical distribution (Poisson distribution) for various cell densities is shown.

(3) Count and make appropriate dilution. The theoretical distribution (Poisson distribution) for various cell densities is shown in FIG. 10.

(4) Push cells into MA006 chip.

(5) Image by brightfield.

Figure 11A:
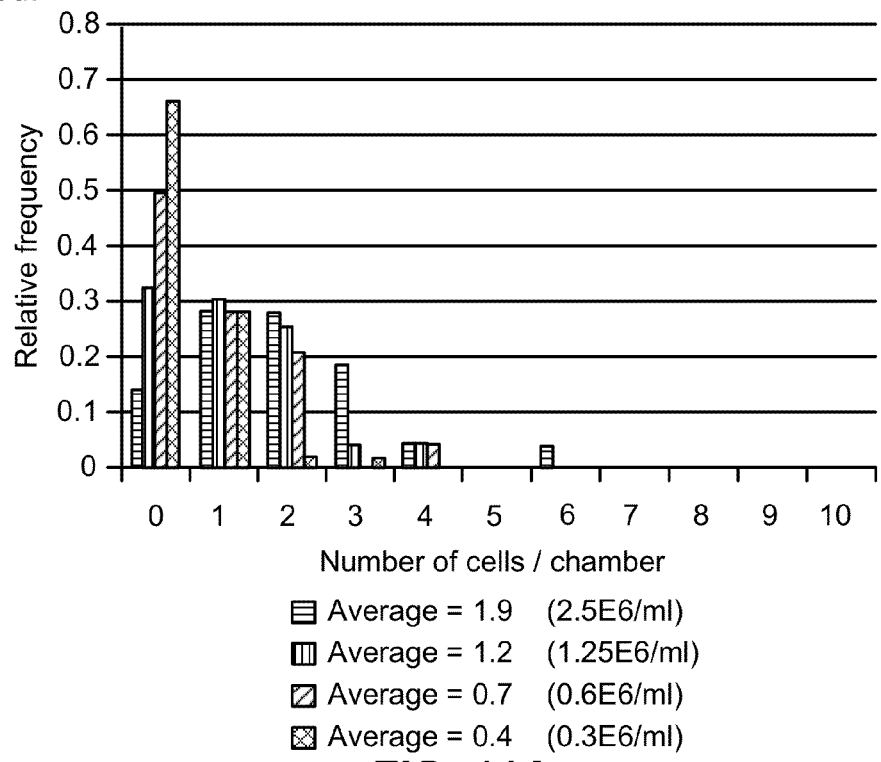
FIG. 11A-B: The results of cell counting in a chip using brightfield (A) to image, as compared to the theoretical distribution (B). Cell density in the chip, based on brightfield imaging, is close to, but lower than, the Poisson distribution, with this tendency exacerbated at higher cell densities.
Figure 11B:
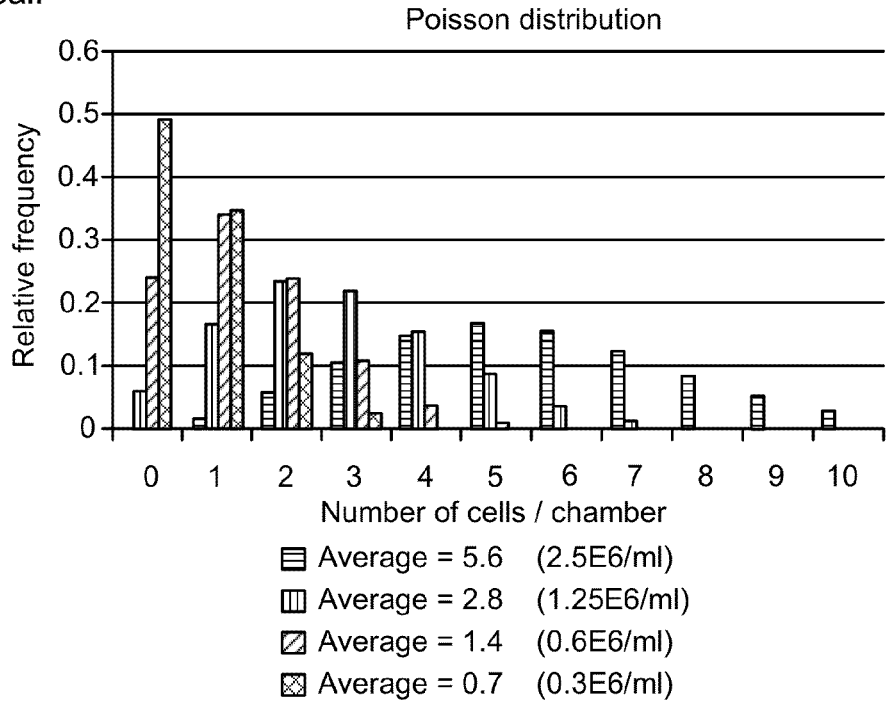

FIG. 11A-B shows the results of cell counting in the chip using brightfield (A) to image, as compared to the theoretical distribution (B). Cell density in the chip, based on brightfield imaging, is close to, but lower than, the Poisson distribution, with this tendency exacerbated at higher cell densities. This may be due, in part, to "shadowing" created by chip features, which can reduce the measurable area within which cells can be detected using brightfield imaging.

Cell Counting: Post-PCR Fluorescence

Figure 12A:
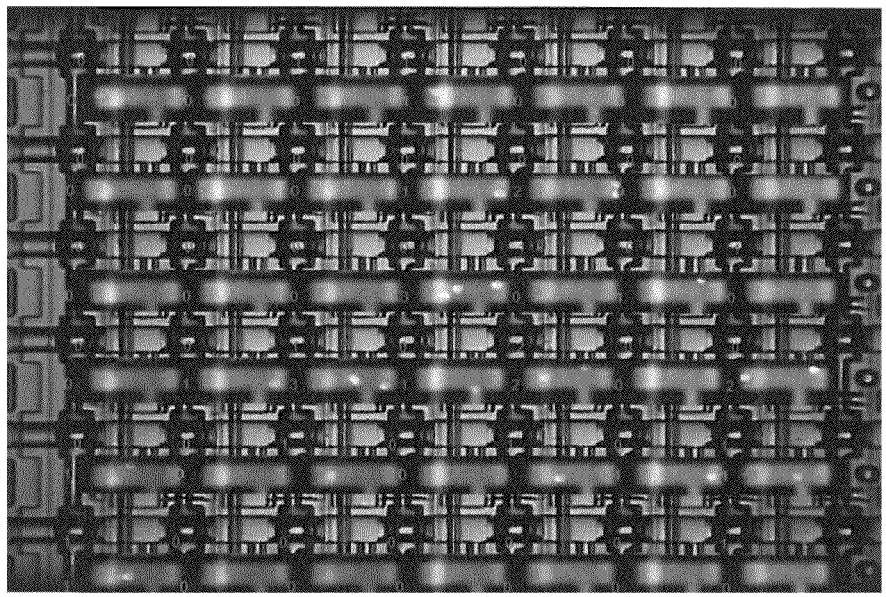
FIG. 12A-B: Fluorescent cell "ghost" images (A) permit detection of more cells than pre-PCR brightfield imaging, so that the cell density more closely approximates the Poisson distribution (B).
Figure 12B:
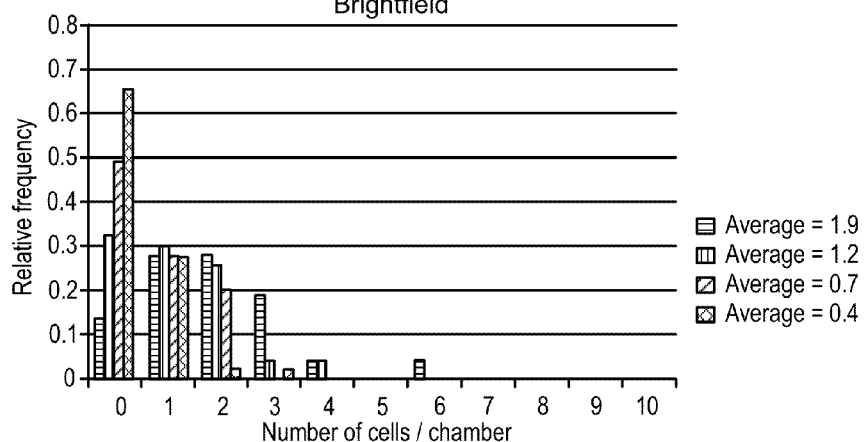
Figure 12B:
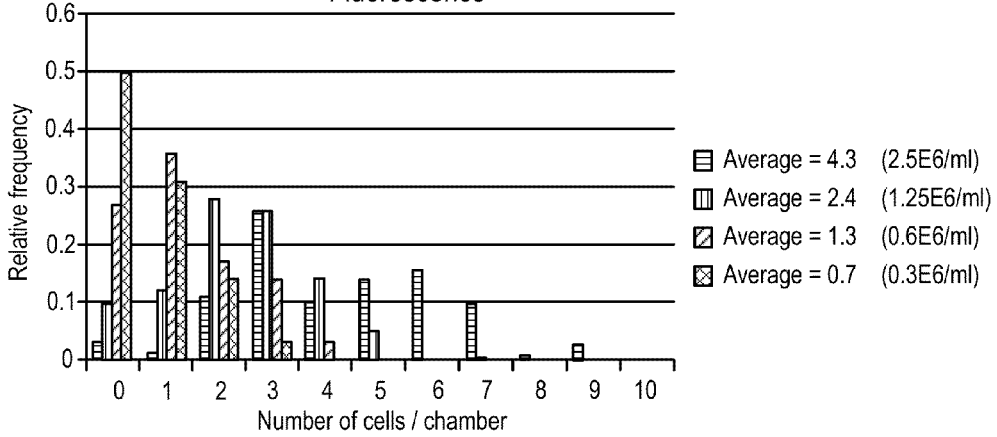
Figure 12B:
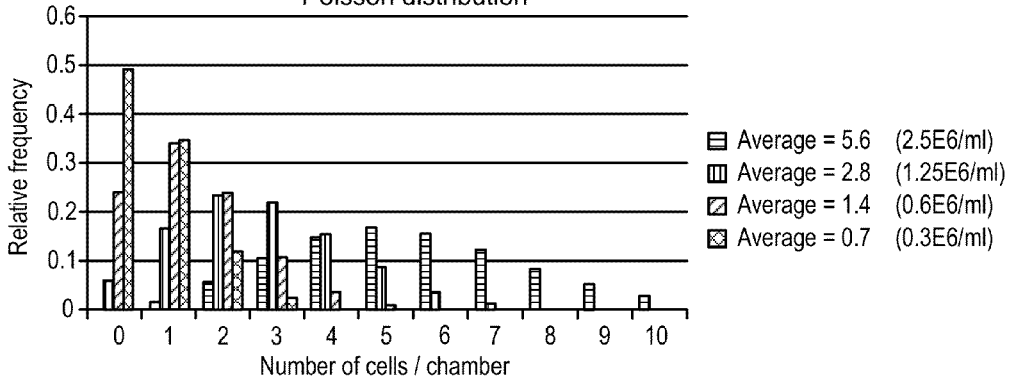

Cells were loaded into the MA006 chip at 0.15E6/ml and subjected to RT-PCR using Cells-Direct™ RT PCR components, Rox, and EVA green. FIGS. 12A-B show that fluorescent cell "ghost" images (A) permit detection of more cells then pre-PCR brightfield, so that the cell density more closely approximates the Poisson distribution (B). Based on these results, if 4000 cells are applied per inlet (e.g., 4 µl of 1000 cell/µl) of the MA006 chip and distributed throughout, approximately ⅓ of 2304 (48×48) or 800 chambers have a single cell.

More Specific Approaches

More specific methods for detecting cells in the chip that can be used include, e.g., the use of a cell membrane-permeant nucleic acid stain and/or cell-specific surface marker detection with an antibody. Thus, for example, RAMOS cells could be handled as follows:

(1) Harvest cells.

(2) Wash 2-3× in ice-cold Tris Saline BSA buffer.

(3) Stain with Syto10 DNA stain and/or Cy5-labeled anti-CD19 antibodies.

(4) Wash 2-3× in ice-cold Tris Saline BSA buffer.

(5) Count and make appropriate dilution.

(6) Push cells into MA006 chip.

(7) Image.

Figure 13:
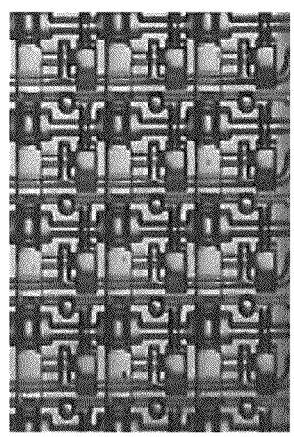
FIG. 13: Specific methods for detecting cells in a chip that can be used include, e.g., the use of a cell membrane-permeant nucleic acid stain and/or cell-specific surface marker detection with an antibody. The results of these more specific approaches are shown for a cell density of 1 E6/ml.
Figure 13:
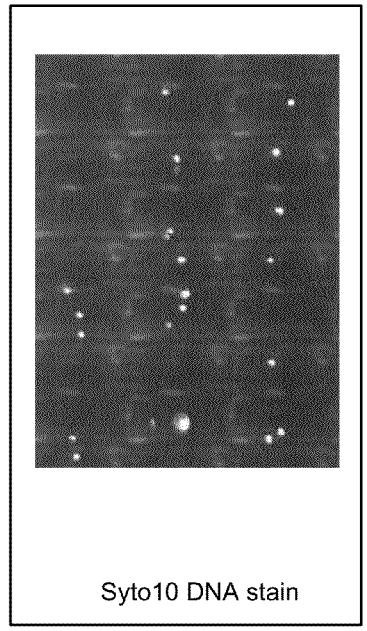
Figure 13:
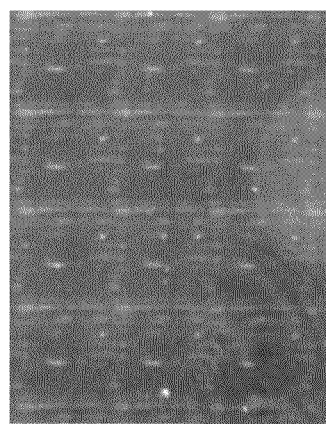
Figure 14A:
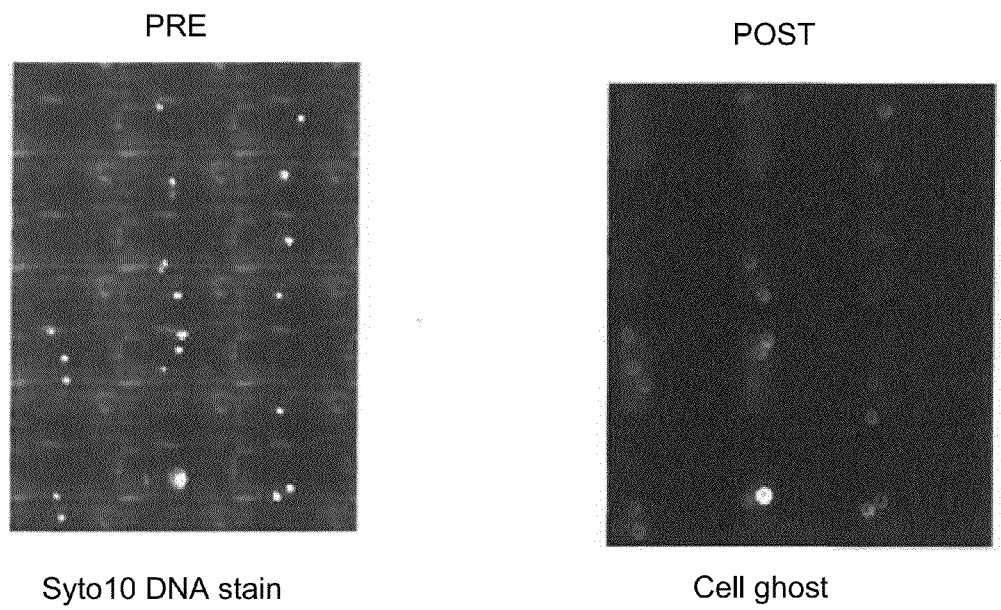
FIG. 14A-B: (A) A comparison the use of pre-RT-PCR nucleic acid stain (Syto10 DNA stain) to detect cells in a chip versus post RT-PCR ghost images (Cell ghost). (B) Syto10 does not inhibit RT-PCR of GAPDH.
Figure 14B:
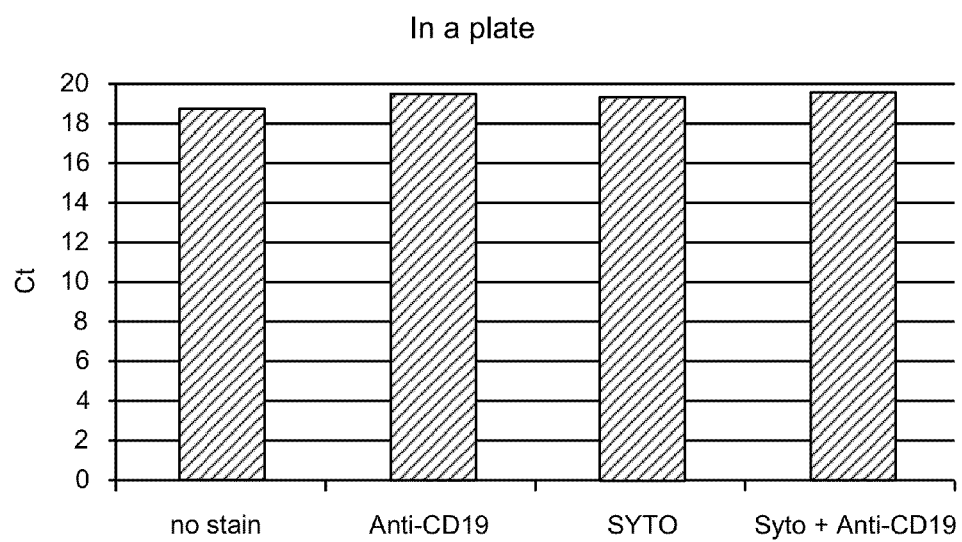

The results of these more specific approaches are shown for a cell density of 1 E6/ml in FIG. 13. FIG. 14A shows a comparison between pre-RT-PCR nucleic acid stain (Syto10 DNA stain) versus post RT-PCR ghost images (Cell ghost), and FIG. 14B shows that Syto10 does not inhibit RT-PCR of GAPDH. A workflow for cell detection in the chip could include staining cells with a DNA stain and/or antibody, followed by counting pre-RT-PCR and then counting cell ghosts as a back-up post-RT-PCR.

Chemistry: One-Step Gene-Specific RT-PCR

Different chemistries were investigated to find an efficient chemistry to convert gene-specific RNA in cells into amplicons in the MA006 chip. Cells are pushed into cell channels in Tris Saline BSA (0.5 µg/ml) buffer. Reagents loaded into assay channels included:

Primers (500 nM final concentration)

CellsDirect™ One-Step qRT-PCR kit components (available from Life Technologies, Foster City, Calif.)

Reaction Mix

Enzyme Mix: Superscripte III+Platinum Taq Polymerase

Buffer

Rox

EVA Green

Loading Reagent—AA or GE (available from Fluidigm Corp., South San Francisco, Calif.) to prevent non-specific absorption by PDMS ("depletion effect") and to lyse cells.

Figure 15:
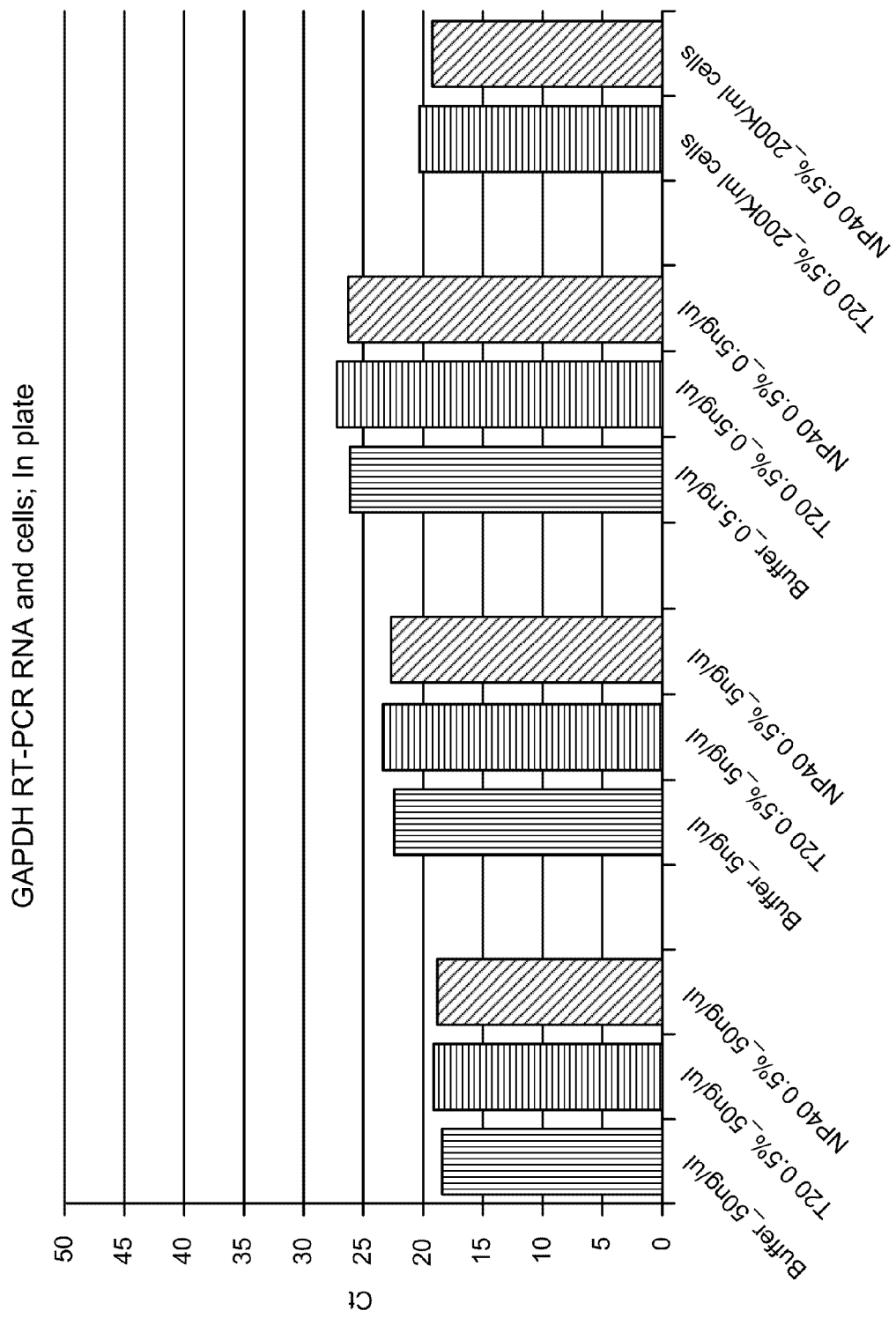
FIG. 15: RT-PCR of GAPDH carried out in the presence of 0.5% Tween 20 or 0.5% NP40 (the latter is a cell lysis reagent). Neither inhibited RT-PCR of GAPDH significantly

RT-PCR of GAPDH was carried out with or without AA or GE loading reagent. The results showed that both loading reagents inhibited RT-PCR. The loading reagents contain: Prionex (AA) or BSA (GE) and 0.5% Tween-20. RT-PCR of GAPDH was carried out in the presence of Prionex or BSA. Prionex, but not BSA, was found to inhibit RT-PCR. RT-PCR of GAPDH was carried out in the presence of 0.5% Tween 20 or 0.5% NP40 (the latter is a cell lysis reagent). The results of this study are shown in FIG. 15. Neither 0.5% Tween 20 or 0.5% NP40 inhibited RT-PCR of GAPDH significantly.

Figure 16:
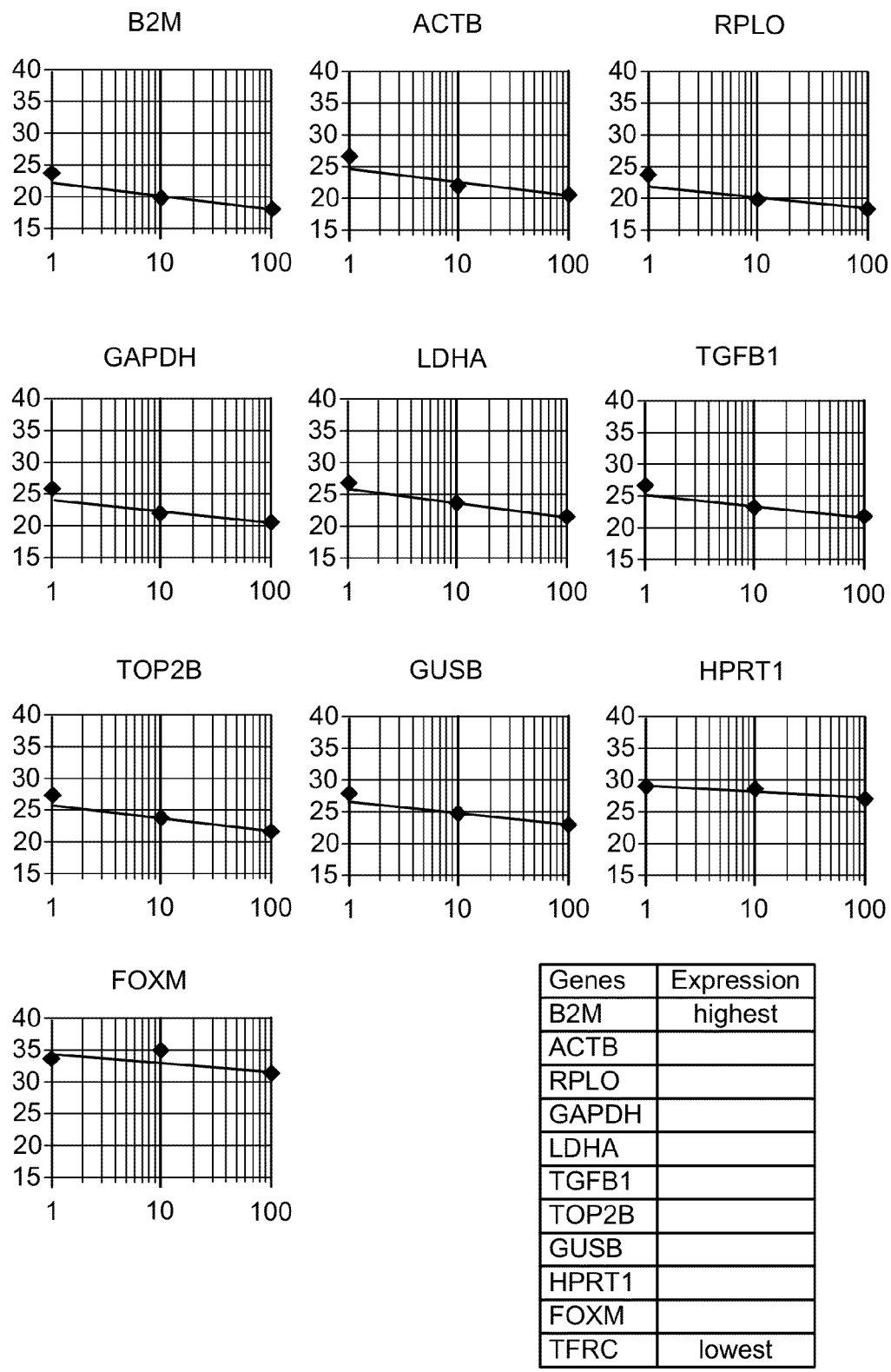
FIG. 16: Standard curve amplification of 11 genes, carried out in the MA006 chip. These results demonstrate that the CellsDirect™ One-Step qRT-PCR kit can be used with 0.5% NP40 (for cell lysis and to prevent the depletion effect in the chip) to convert gene-specific RNA in cells into amplicons in an MA006 chip.

To determine that the reaction conditions developed for RT-PCR of GAPDH from cells would permit RT-PCR of other genes, expressed at different levels, RT-PCR of 11 genes covering a range of expression levels was carried out with 10 ng/µl of RNA and the reagents described above, except that 0.5% NP40 was substituted for AA/GE Loading Reagent. The thermal protocol was 50° C. for 30 minutes; 55° C. for 30 minutes; 95° C. for 2 minutes; and then 45 cycles of: 95° C. for 15 seconds, 60° C. for 30 seconds, and 72° C. for 60 seconds. Standard curve amplification of these 11 genes, carried out in the MA006 chip, is shown in FIG. 16. These results demonstrate that the CellsDirect™ One-Step qRT-PCR kit can be used with 0.5% NP40 (for cell lysis and to prevent the depletion effect in the chip) to convert gene-specific RNA in cells into amplicons in the MA006 chip.

Sequencing

Figure 17:
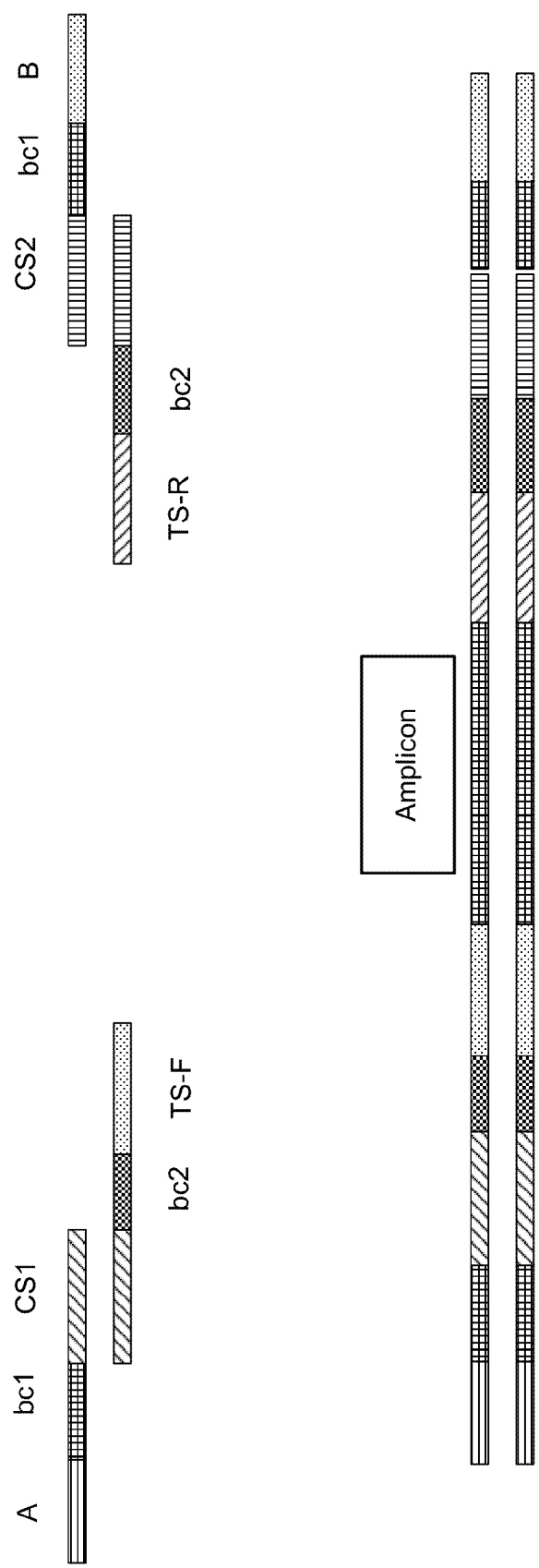
FIG. 17: A four-primer, combinatorial barcoding method was employed to put a combination of two barcodes on either end of each amplicon Inner primers include target-specific portions ("TS-F" in the forward primer and "TS-R" in the reverse primer), a barcode nucleotide sequence ("bc2"), and different nucleotide tags. Outer primers include tag-specific portions ("CS1" and "CS2"), a different barcode nucleotide sequence ("bc1"), primer binding sites for sequencing primers ("A" and "B").
Figure 18A:
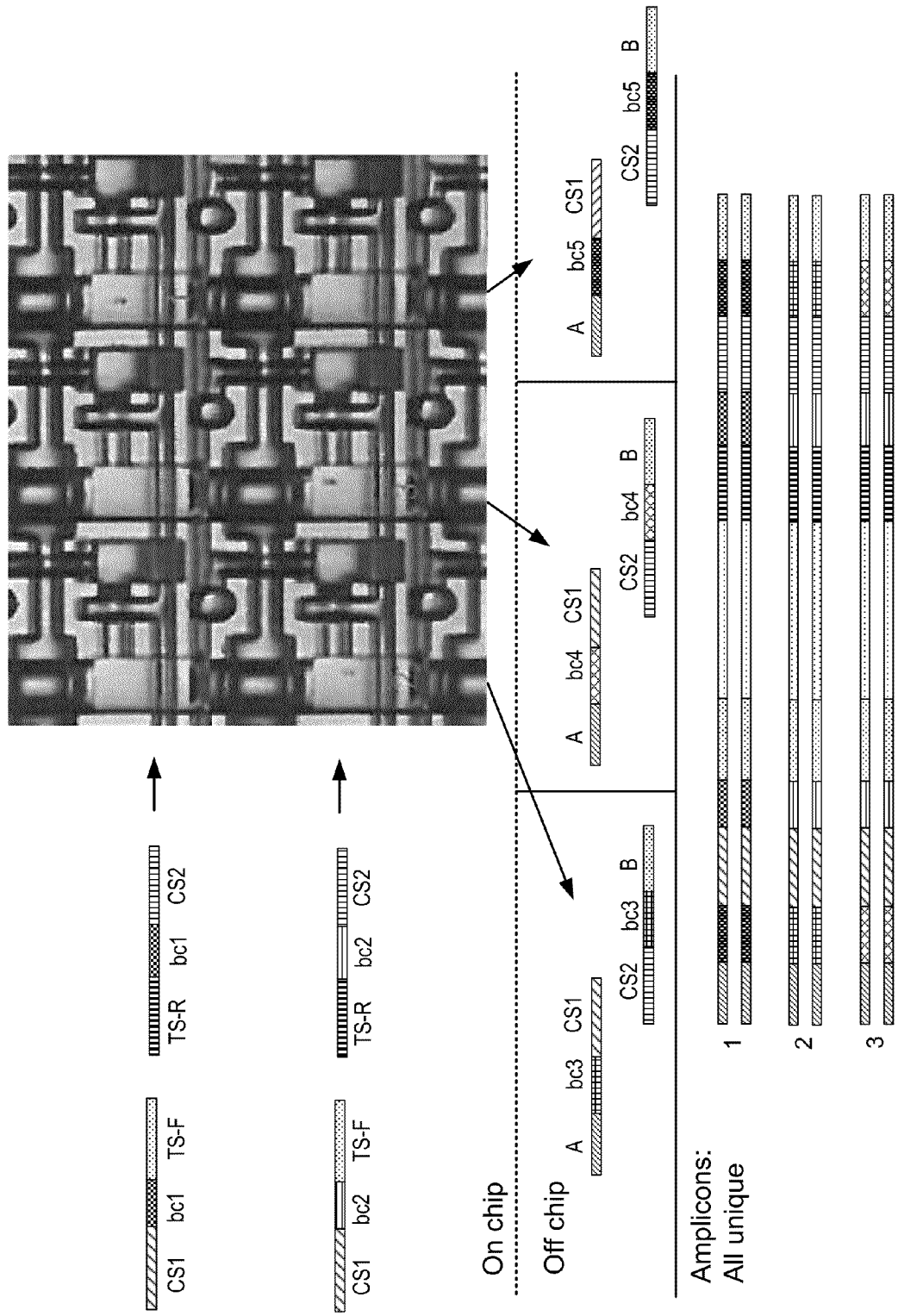
FIG. 18A-B: An illustration of how 4-primer barcoding can be carried out on a chip, such as the MA006. (A) Amplification is carried out on-chip with inner primers, where each row of chambers has the same pair of inner primers with the same barcode. (B) Reaction products from each column of chambers can be harvested as a pool and each pool subjected to amplification using a different pair of outer primers. This amplification produces amplicons having barcode combinations at either end of the amplicon that uniquely identify the chamber (by row and column) in which the initial amplification was carried out.
Figure 18B:
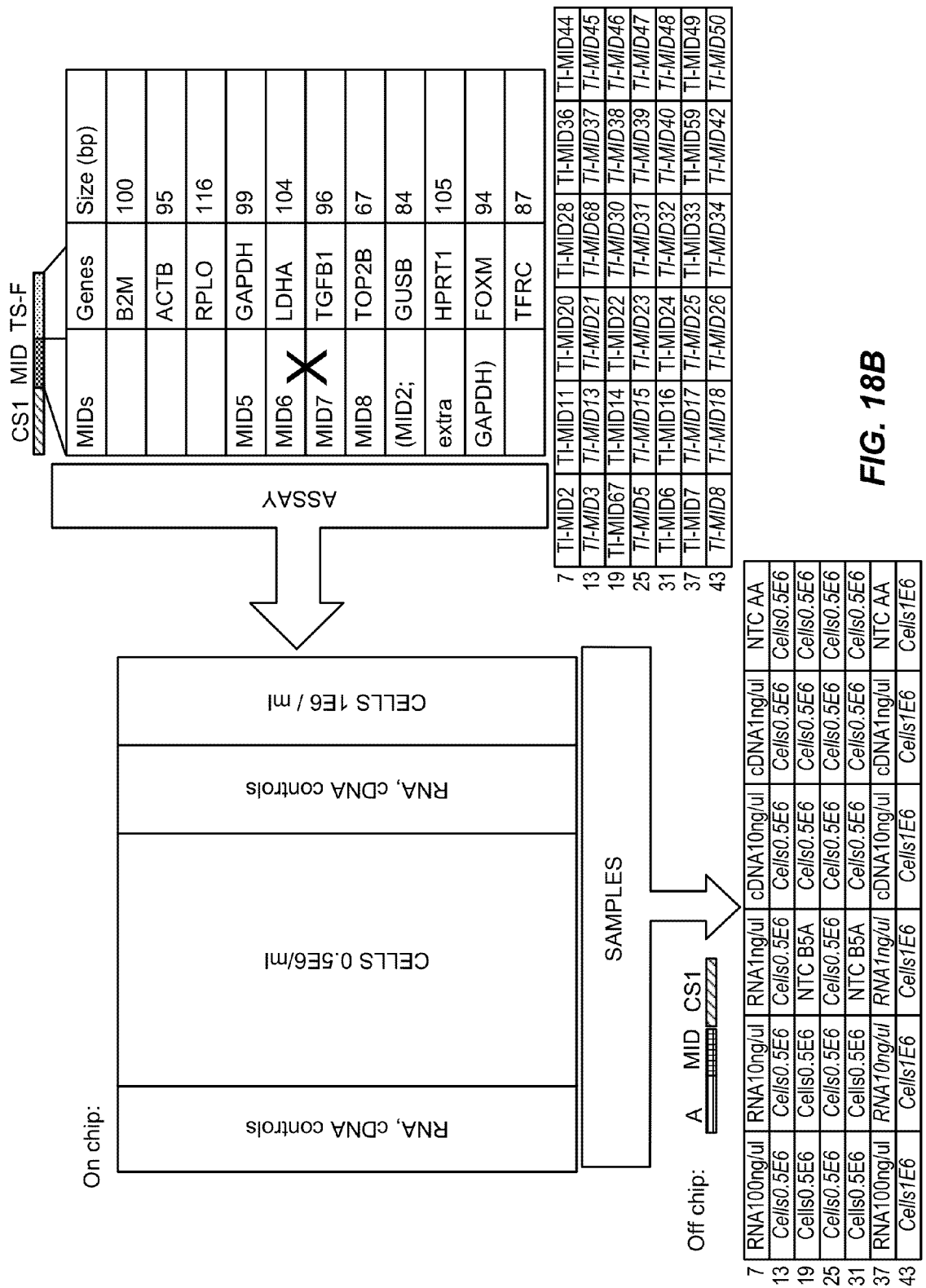
Figure 19:
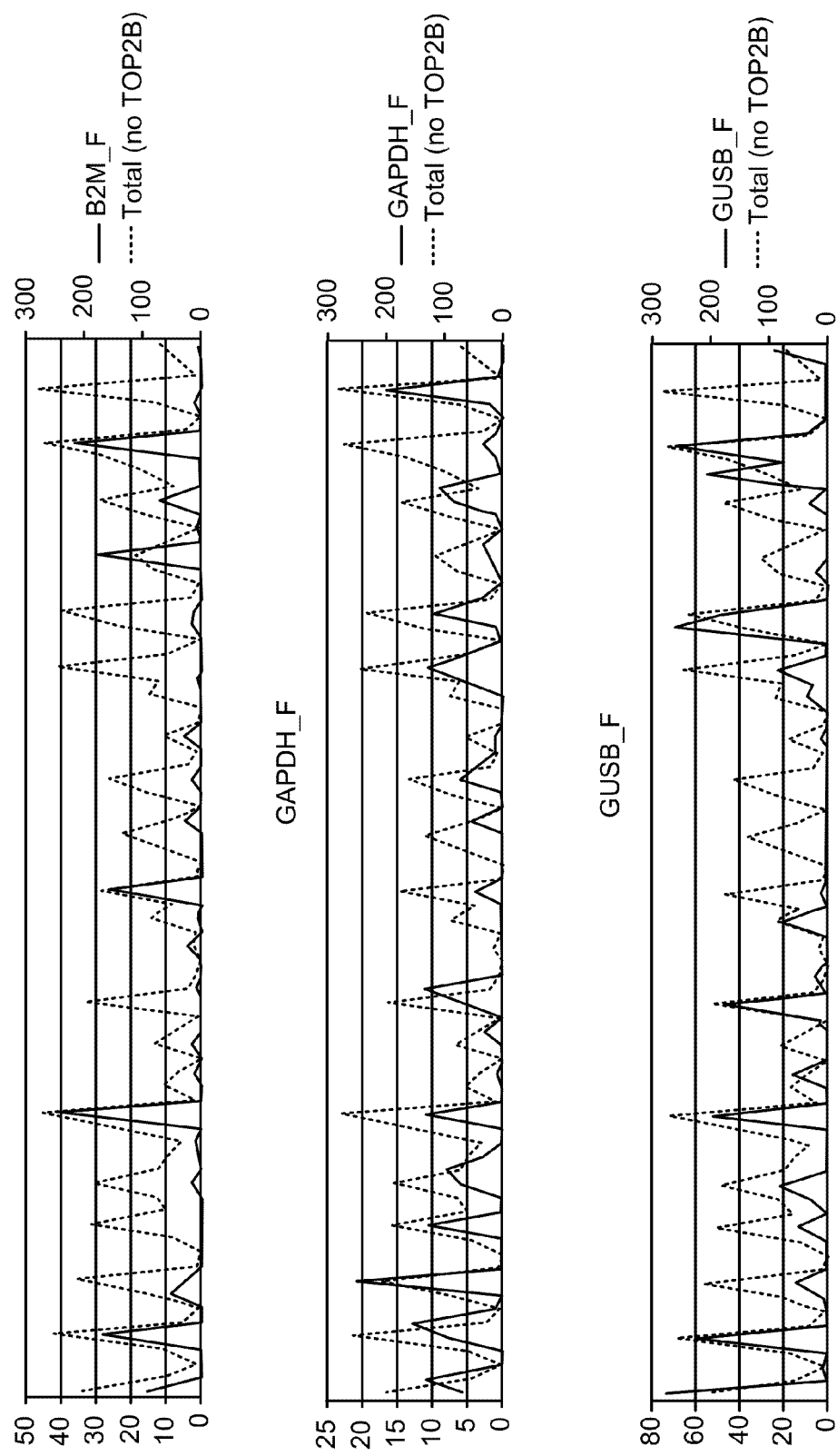
FIG. 19: A comparison of the results obtained upon sequencing gene-specific amplicons from single cells (Example 5), expressed as number of reads for each gene-specific amplicon, as compared to that for total RNA. As is apparent from this figure, the representation of these RNAs is different when measured in individual cells, as compared to that observed in the total RNA.

To facilitate sequencing of gene-specific amplicons generated in the MA006 chip, a barcoding method was employed to distinguish amplicons from different chambers (e.g., cells). More specifically, a four-primer, combinatorial barcoding method was employed to put a combination of two barcodes on either end of each amplicon. This method is shown schematically in FIG. 17. Inner primers include target-specific portions ("TS-F" in the forward primer and "TS-R" in the reverse primer), a barcode nucleotide sequence ("bc2"), and different nucleotide tags. Outer primers include tag-specific portions ("CS1" and "CS2"), a different barcode nucleotide sequence ("bc1"), and primer binding sites for sequencing primers ("A" and "B"). FIG. 18A-B illustrates how 4-primer barcoding can be carried out on a chip, such as the MA006. Amplification is carried out on-chip with inner primers, where each row of chambers has the same pair of inner primers with the same barcode. Reaction products from each column of chambers can be harvested as a pool and each pool subjected to amplification using a different pair of outer primers. This amplification produces amplicons having barcode combinations at either end of the amplicon that uniquely identify the chamber (by row and column) in which the initial amplification was carried out. The reaction products were sequenced and the number of reads of each sequence for each reaction chamber was determined. This determination was carried out for RAMOS cells and for spleen RNA. FIG. 19 shows a comparison of the results obtained, expressed as number of reads for each gene-specific amplicon (red), as compared to that for total RNA. As is apparent from this figure, the representation of these RNAs is different when measured in individual cells, as compared to that observed in the total RNA.

Example 6

Size-Based Microfluidic Single-Particle Capture

Figure 20A:
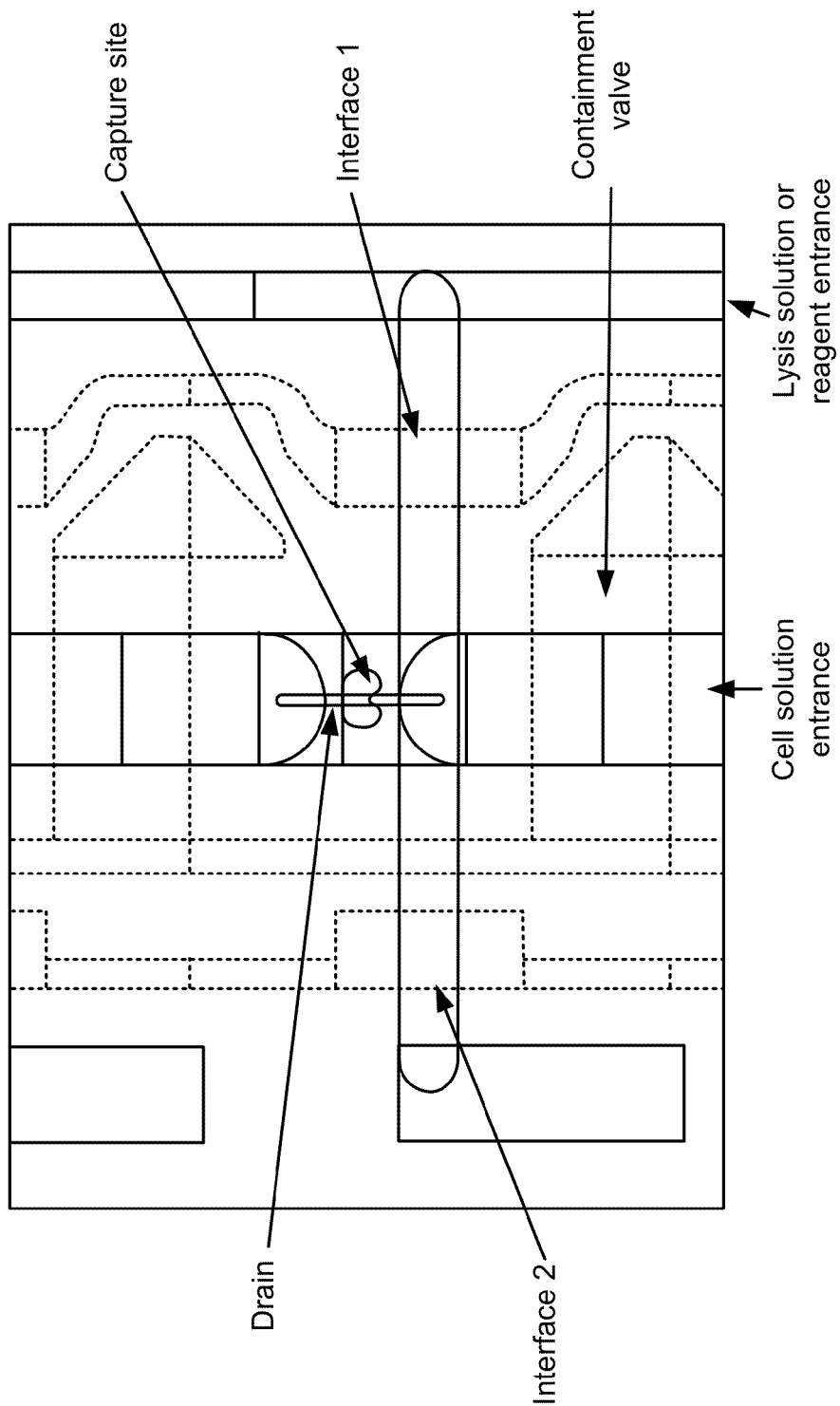
FIG. 20A-B: A capture site with a capture feature and drain. (A) A site without baffles to focus flow. (B) A site with baffles.
Figure 20B:
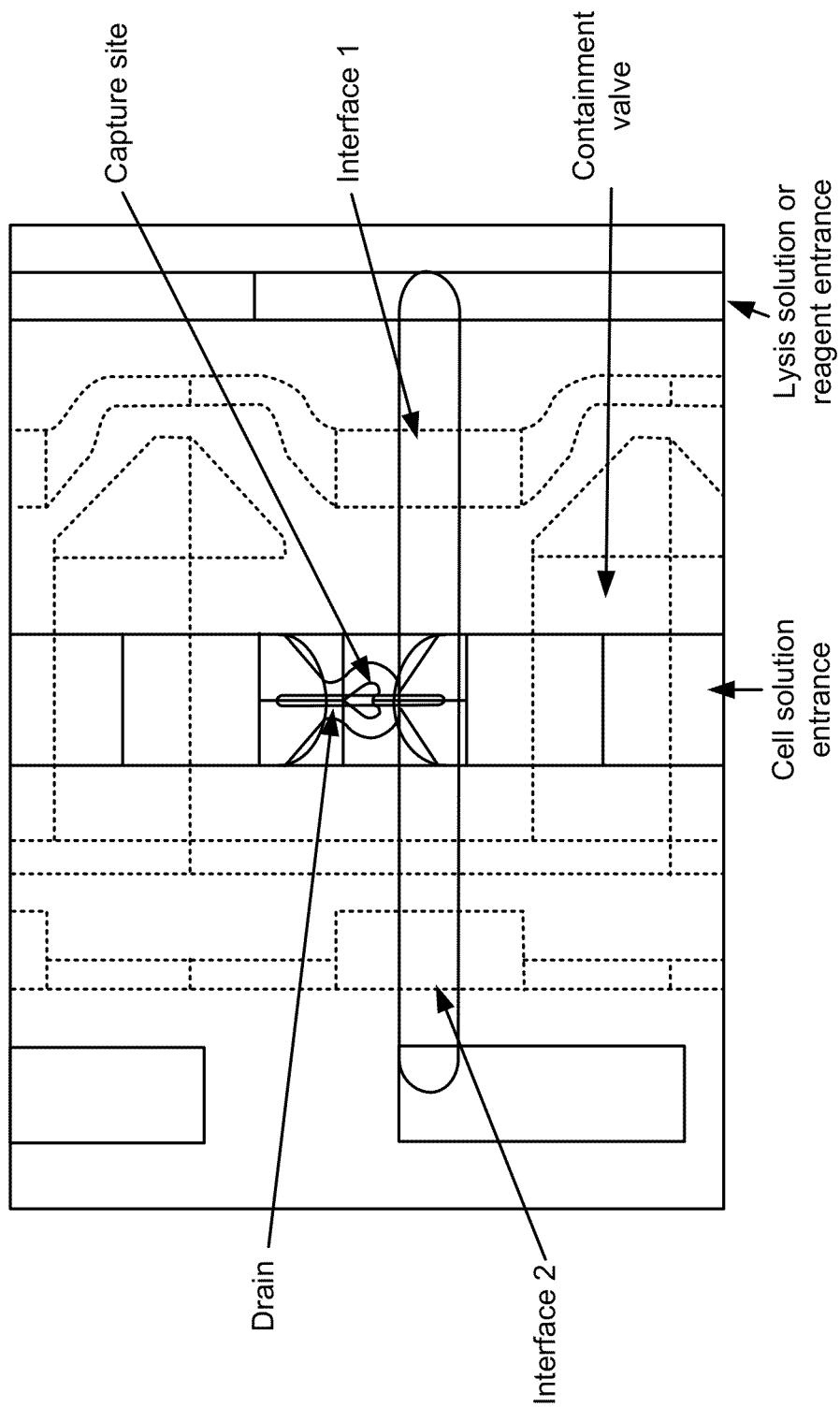
Figure 21:
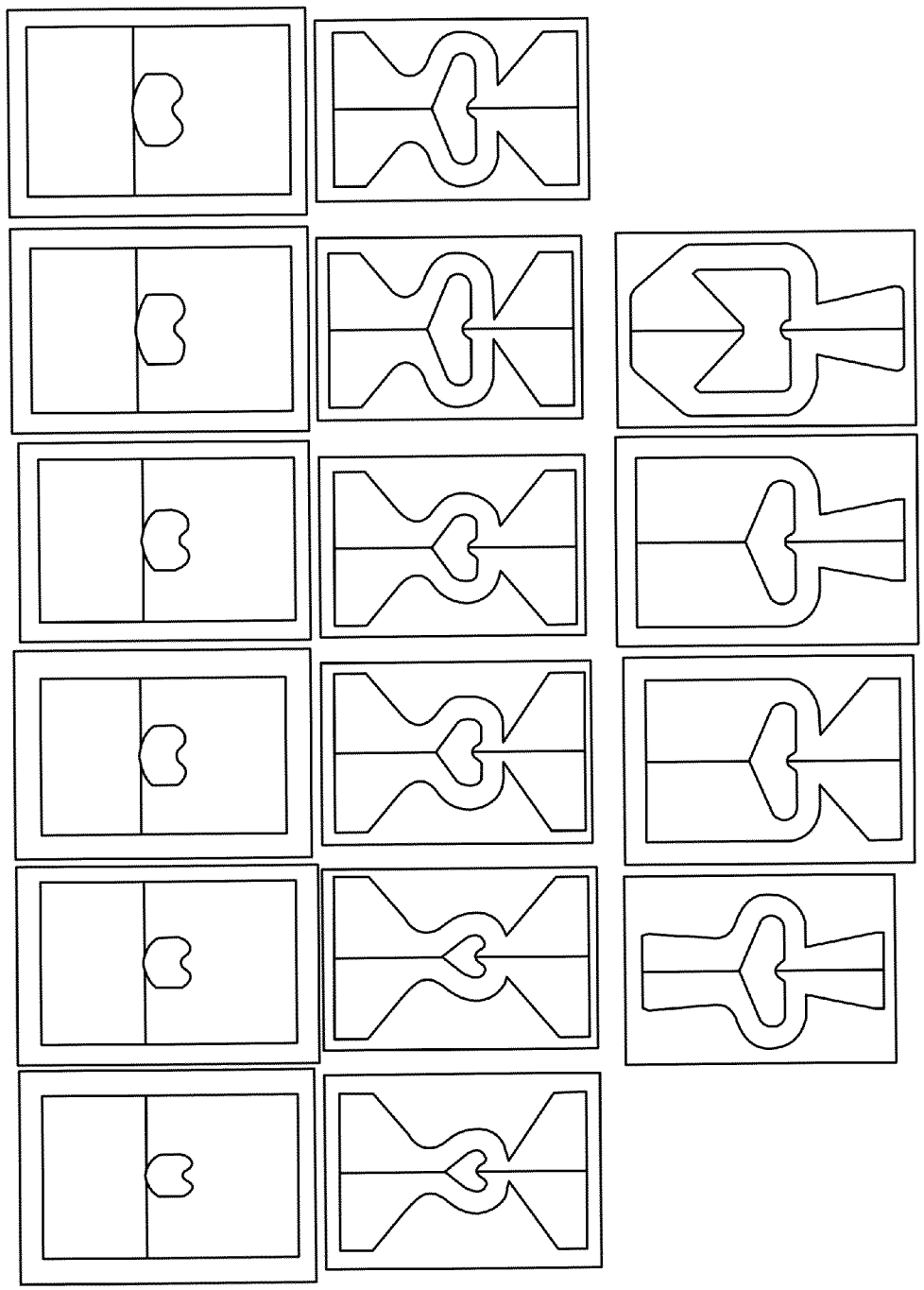
FIG. 21: Additional capture site designs.

One approach to discretely capturing single cells from suspension as they flow through a microfluidic device is to define a microfluidic geometry that guides flow of a suspension of particles (such as cells or beads) over a capture site in a manner that the capture site catches a single particle, efficiently captures single particles (e.g., the probability of the capture of a particle passing near a capture site is high), and/or guides the remaining suspension around the capture site. The geometries can be size-based, i.e., the capture site is just large enough to contain one particle (and no more), but still permit the flow of particle-free suspension through the site at reasonably low fluidic impedance, such that an empty capture site would guide the flow of particles toward it rather than around it. This goal can be accomplished by the use of a drain. Additional geometries can also focus the flow of particles in a manner that increases the likelihood of particles coming in close enough proximity to the capture site for high probability of successful capture. Variations on these geometries have focused on controlling the flow resistance of the fluidics surrounding the capture site and drain, including the drain itself, as well as varying the aperture of focusing geometry in attempts to position the flow of particles close to the capture site. FIG. 20A-B illustrates a capture site with a capture feature and drain. Panel A shows a site without baffles to focus flow, whereas panel B shows a site with baffles. Additional capture site designs are shown in FIG. 21.

Example 7

Surface Marker-Based Capture of Particles

Single-cell studies within microfluidic architectures require the isolation of individual cells into individual reaction partitions (chambers, droplets, particles). Limiting dilution is one method for achieving this isolation. Cells are loaded at concentrations of less than one cell per partition on average, and distribute into those partitions in a pattern described by Poisson statistics. Another approach is to rely on mechanical traps to capture cells. These traps are designed to capture cells of a given size range (see Example 6). This results in a biased selection of cells from the population within that size range.

For some applications, an ideal capture method would use biological markers expressed on the surface of cells. Antibodies can be patterned in specific locations on a microfluidic array, although this approach may not be simple, depending on the structure of the microfluidic array.

This example describes a method for capture of single particles (e.g., cells) based on the initial capture of a single, affinity-reagent-coated bead in a specific location in a microfluidic device. The surface area presented by this bead at the opening of a capture site provides a defined surface of affinity reagent accessible for cell binding. The bead size and capture site can be chosen/designed such that once a single cell is bound to the bead, the rest of the accessible surface area of the bead is sterically blocked by the first-bound cell. Selection of an appropriate sized bead capture site also provides for capture of a broad range of cell sizes. As long as the cell is larger than the exposed capture area, and expresses the appropriate surface marker or binding partner for the affinity reagent, it should be possible to capture that cell.

Figure 22B:
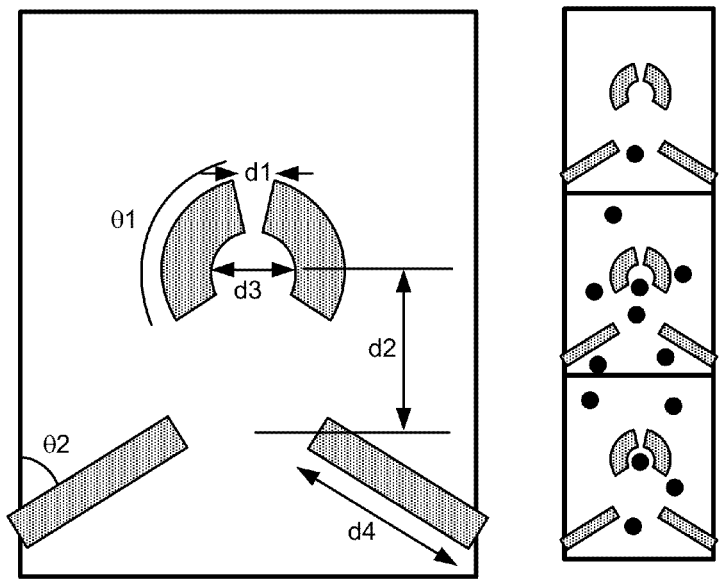
Figure 22C:
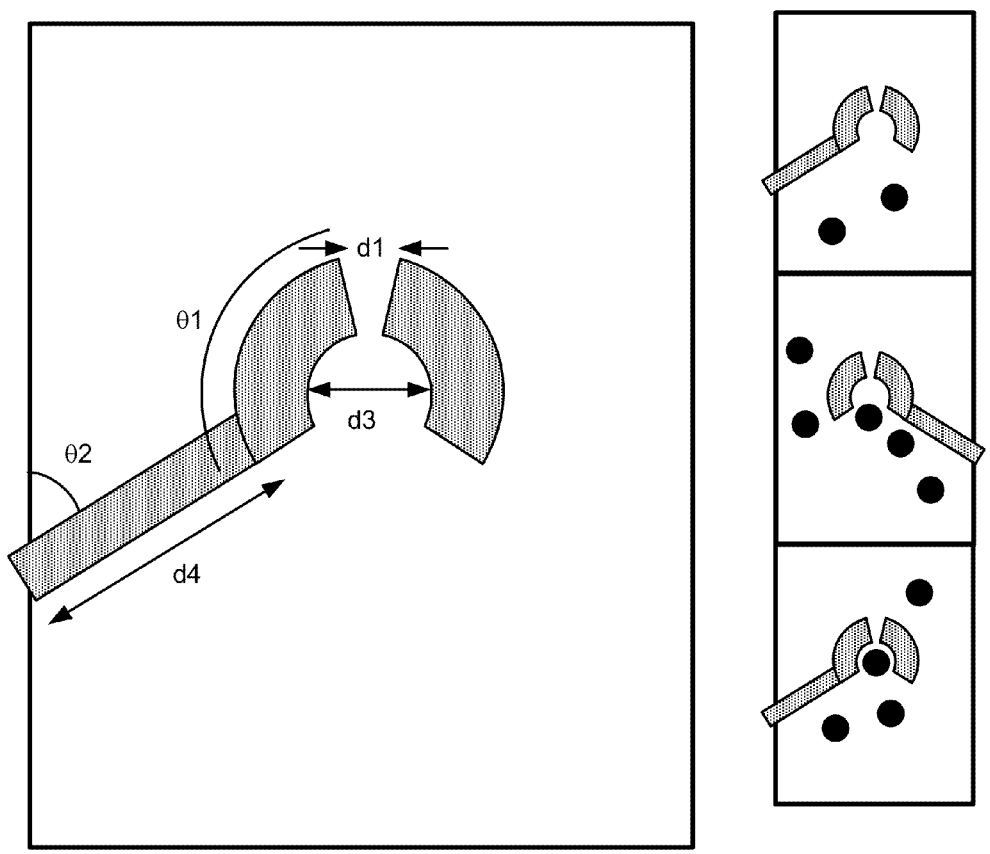

Capture architectures can be designed to maximize the probability that cells will come into contact with the surface markers. For example, baffles on one or more channel walls can be used to direct beads towards capture feature. See FIG. 22A for illustrative capture feature/baffle combinations. Performance of the capture feature can be adjusted by adjusting one or more variables, including angle of baffles, distance of baffles from capture site, length of baffles, size and shape of capture feature, size of drain in capture feature (if present). See FIGS. 22B and C illustrating the variables for, and performance of, capture feature/baffle combinations. In FIG. 22B, baffles on the channel wall are used to direct beads towards a capture feature. In FIG. 22C, the capture feature is coupled to a baffle on a channel wall; individual capture feature/baffle combinations can be located on alternate walls to focus flow towards the adjacent capture feature/baffle combination. These combinations can be located at sites that, in use, are separable (e.g., using valves) to form separate reaction chambers.

Figure 23B:
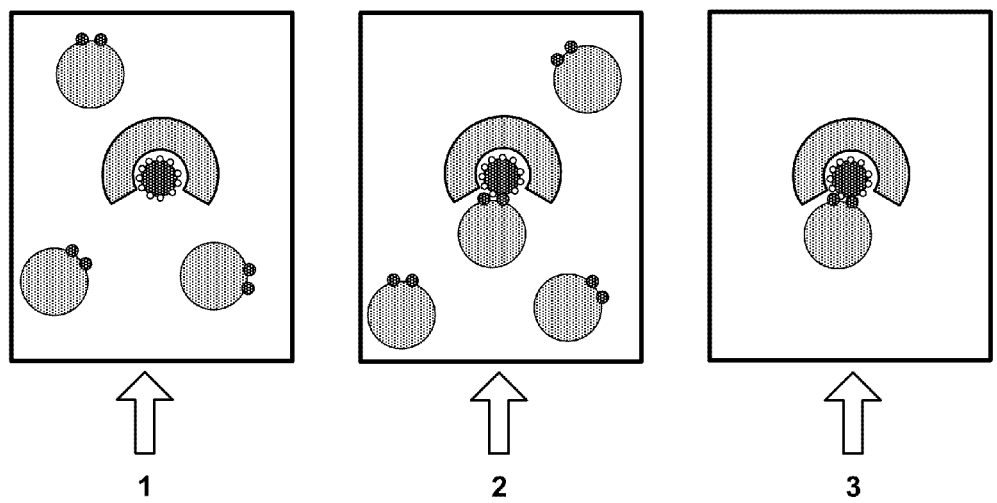

FIGS. 23A and B illustrate (in simplified form, lacking baffles) a strategy for using capture features to catch single, affinity-reagent-coated beads, which then display the affinity reagent (e.g., antibody) so as to capture single particles (e.g., cells). In FIG. 23A-1, flow is initiated in a channel containing capture features. In panel A-2, antibody-bound beads flow toward the capture features until a bead lodges in the capture feature, as shown in panel A-3. The channel is then washed to remove non-captured beads. Subsequently, as shown in FIG. 23B-1, cells bearing a cell-surface marker to which the antibody binds are flowed into the channel containing the captured beads. Panel B-2 illustrates how cells bearing the marker interact with and bind to antibodies displayed by the captured bead. The display area is sized so that a bound cell will inhibit other cells from interacting with the captured bead through steric occlusion, such that only one cell binds to each captured bead. The channel is then washed to remove non-bound cells, as shown in panel B-3, leaving one cell immobilized at each capture site.

Example 8

Microfluidic Device for Cell Capture ("CCap")

Figure 24A:
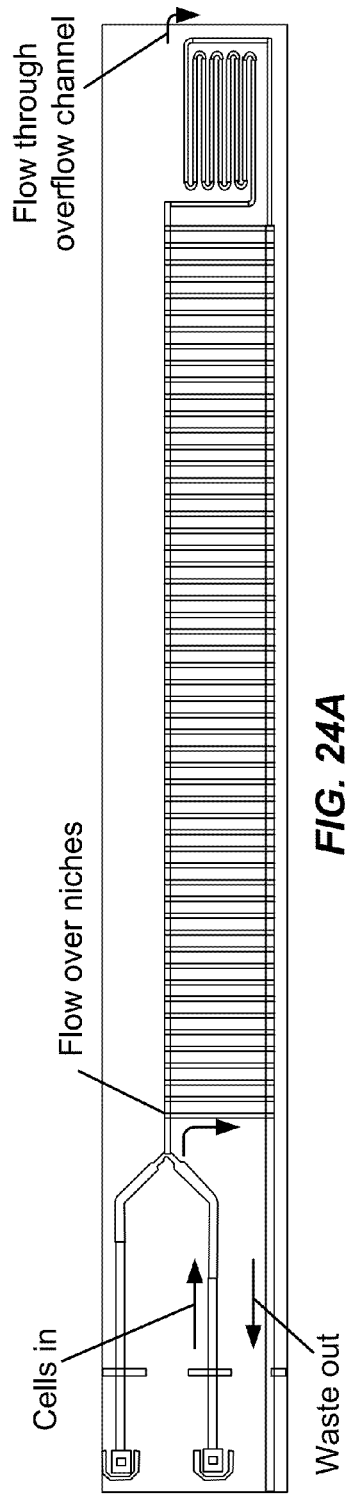
FIG. 24A-G: (A) A schematic of a microfluidic device designed to capture single cells at discrete locations (niches). Single cell capture allows analysis of biological events at the single cell level. (B) Flow is designed to be stronger over niches than through an overflow channel. Niches contain small gaps (~3 μm tall). When a cell enters a niche, it blocks the niche and prevents any more flow into the niche. Flow passes through to the next unoccupied niche, until it too is blocked by a cell. Every niche should capture one cell before cells pass through the overflow channel and out to waste. (C) Schematic of (A) shown with additional detail provided in (D)-(F). (D) A buffer inlet converges with a cell inlet so as to force cells to a side of a feeder channel that is closest to a series of transverse cell capture channels. (E) The resistance of the transverse cell capture channels is lower than that of a cell overflow channel to induce preferential flow of cells into niches versus into the cell overflow channel. (F) Each niche is large enough to capture just one cell. A cell in a niche raises the resistance of that particular circuit, and flow is directed to the circuits without cells. (G) An actual device of (A), with captured human umbilical vein endothelial cells (HUVEC) located in niches.
Figure 24B:
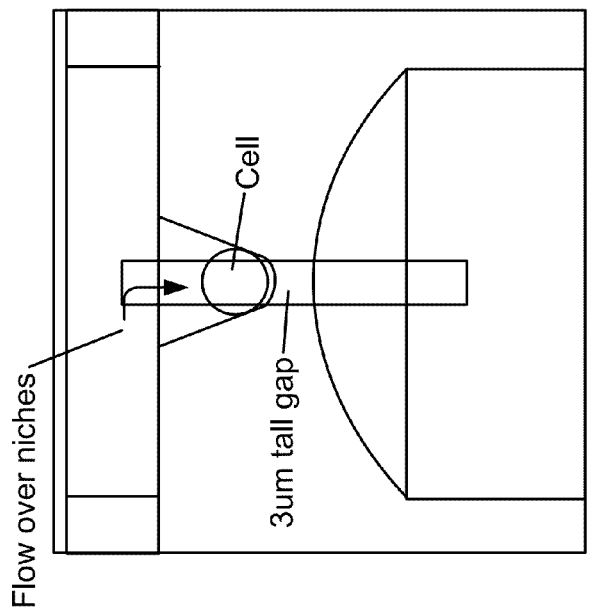
Figure 24C:
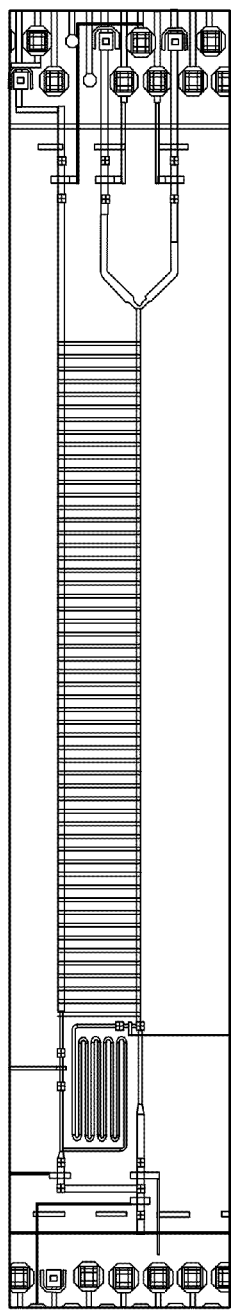
Figure 24D:
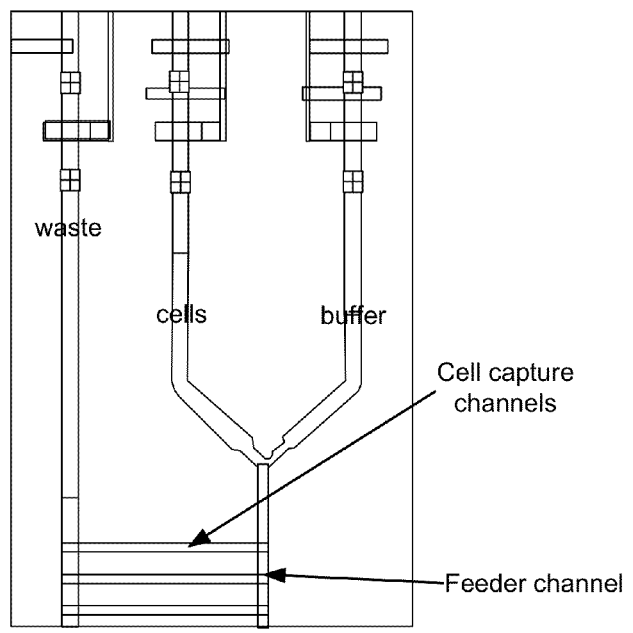
Figure 24E:
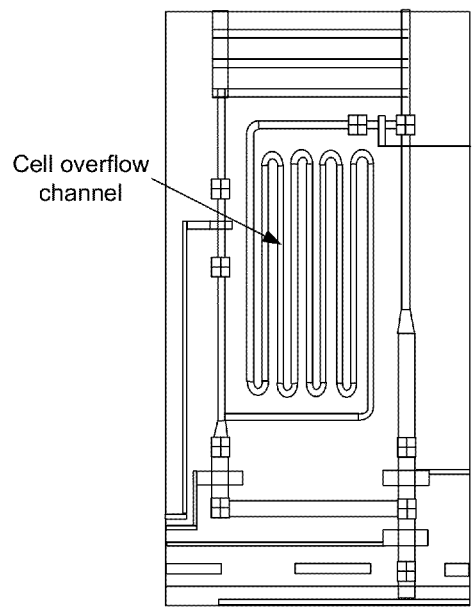
Figure 24F:
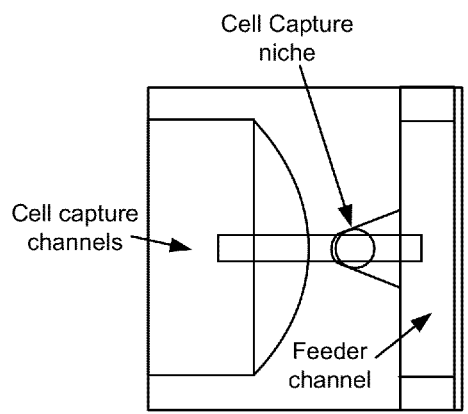
Figure 24G:
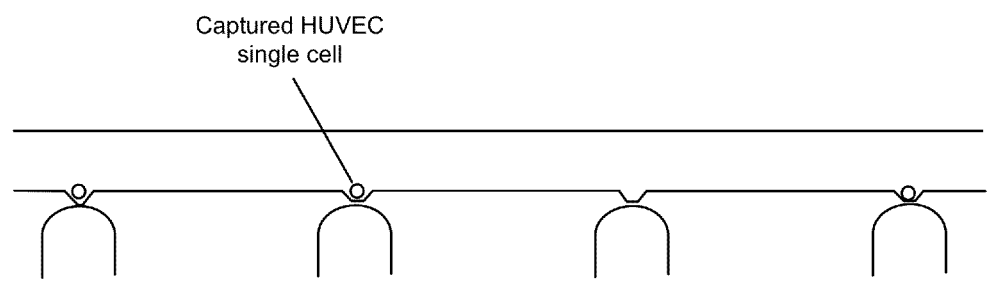

FIG. 24A shows a schematic of a microfluidic device designed to capture single cells at discrete locations (niches). Flow is designed to be stronger over niches than through an overflow channel. Niches contain small gaps (~3 µm tall). See FIG. 24B. When a cell enters niche, it blocks the niche and prevents any more flow into the niche. Flow passes through next unoccupied niche, until it too is blocked by a cell. In theory, every niche should capture one cell before cells pass through the overflow channel and out to waste. Referring to FIG. 24C-F for more detail, a buffer inlet converges with a cell inlet so as to force cells to a side of a feeder channel that is closest to a series of transverse cell capture channels. See FIG. 24D. The resistance of the transverse cell capture channels is lower than that of a cell overflow channel to induce preferential flow of cells into niches versus into the cell overflow channel. See FIG. 24E. As shown in FIG. 24F, each niche is large enough to capture just one cell. The niche gap is sufficiently small that cells are captured at the operational pressure/flow levels. If the latter are too high and/or the niche gaps are too large, cells may deform and be pushed through the niche gaps. The presence of a cell in a niche raises the resistance of that particular circuit, and flow is therefore directed to circuits without cell. FIG. 24G shows an actual device with captured human umbilical vein endothelial cells (HUVEC) located in niches.

Example 9

Bidirectional DNA Sequencing Amplicon Tagging for Illumina Sequencers Using the 48.48 ACCESS ARRAY™ IFC—Protocol 1

Introduction

Figure 25:
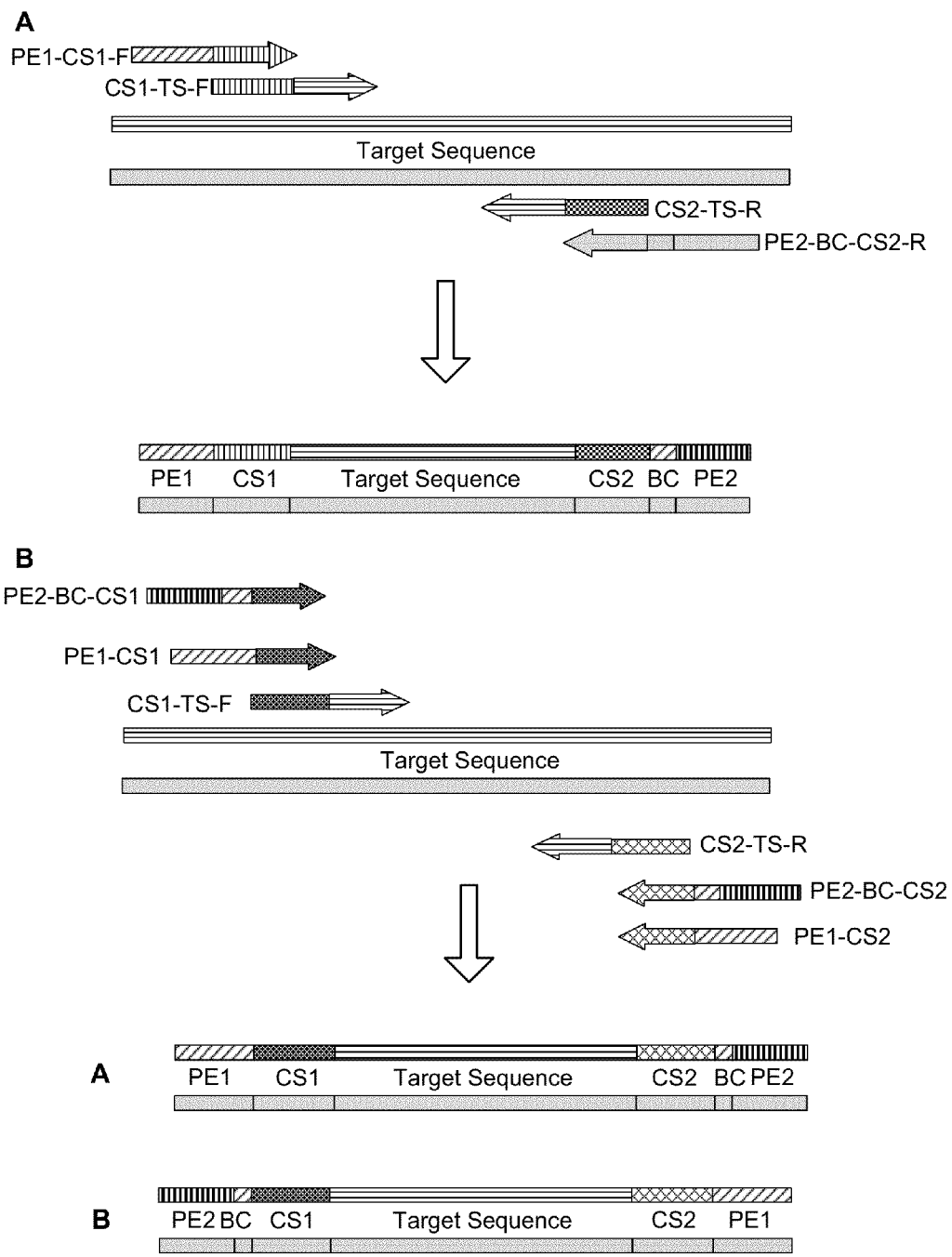
FIG. 25A-B: The amplicon tagging strategy employed in Example 9. (A) Standard 4-primer amplicon tagging versus bidirectional sequencing amplicon tagging. The standard 4-primer amplicon tagging approach incorporated the paired-end Illumina sequencing primer annealing sites in Common Sequence tag 1 (CS1) and Common Sequence tag 2 (CS2). Sequencing of both the 5' end and the 3' end of each PCR product required a paired-end sequencing run. (B) Target-specific primers were appended with Common Sequence tags CS1 and CS2. The sample-specific primer pairs were comprised of common sequence tags CS1 or CS2, appended with the adaptor sequences used by the Genome Analyzer (PE1 and PE2) in both permutations. Two PCR product types were generated from the same target region: Product A allowed for sequencing of the 5' end of the target region whereas product B allowed for sequencing of the 3' end of the target region during the same sequencing read.

The following protocol outlines a bidirectional sequencing strategy on the Illumina Genome GAII, HiSeq, and MiSeq Sequencers for amplicon libraries that have been generated on the ACCESS ARRAY™ System. The goal of this protocol is to sequence both ends of PCR products with a single read sequencing run. In a standard 4-primer amplicon tagging approach, tagged target-specific (TS) primer pairs were combined with sample-specific primer pairs containing a barcode sequence (BC) and the adaptor sequences used by the Illumina sequencers (PE1 and PE2, FIG. 25A). Here, in the bidirectional sequencing amplicon tagging strategy, by contrast, tagged target-specific primer pairs were combined with two sets of sample-specific primer pairs. The sample-specific primer pairs were comprised of common sequence tags CS1 or CS2, appended with the Illumina adaptor sequences in both permutations (PE1 and PE2, FIG. 25B). This approach required only one set of target-specific primer pairs while the sample-specific barcode primers were universal and could be used in multiple experiments.

Bidirectional sequencing amplicon tagging generated two types of PCR products per target region: one PCR product that allowed for sequencing of the 5' end of the target region (product A) and one PCR product that allowed for sequencing of the 3' end of the target region (product B). Because both PCR products were present on the flow cell at the same time, one sequencing read yielded sequence information for both ends of the target region. The main difference between this strategy and paired-end sequencing is that the 5' read and the 3' read were not derived from the same cluster, i.e., from the same template molecule. Instead, an average of the template population was derived.

Amplification of multiple target sequences can be done prior to adding the Bidirectional barcode. In short, the protocol adopts a two-step approach: the PCR on the ACCESS ARRAY IFC was run in the presence of multiplexed, tagged, target-specific primers only. The harvested PCR product pools were then used as template in a second PCR with the sample-specific barcode primers. The two sets of barcode primers were added in independent PCR reactions as described below.

Figure 26:
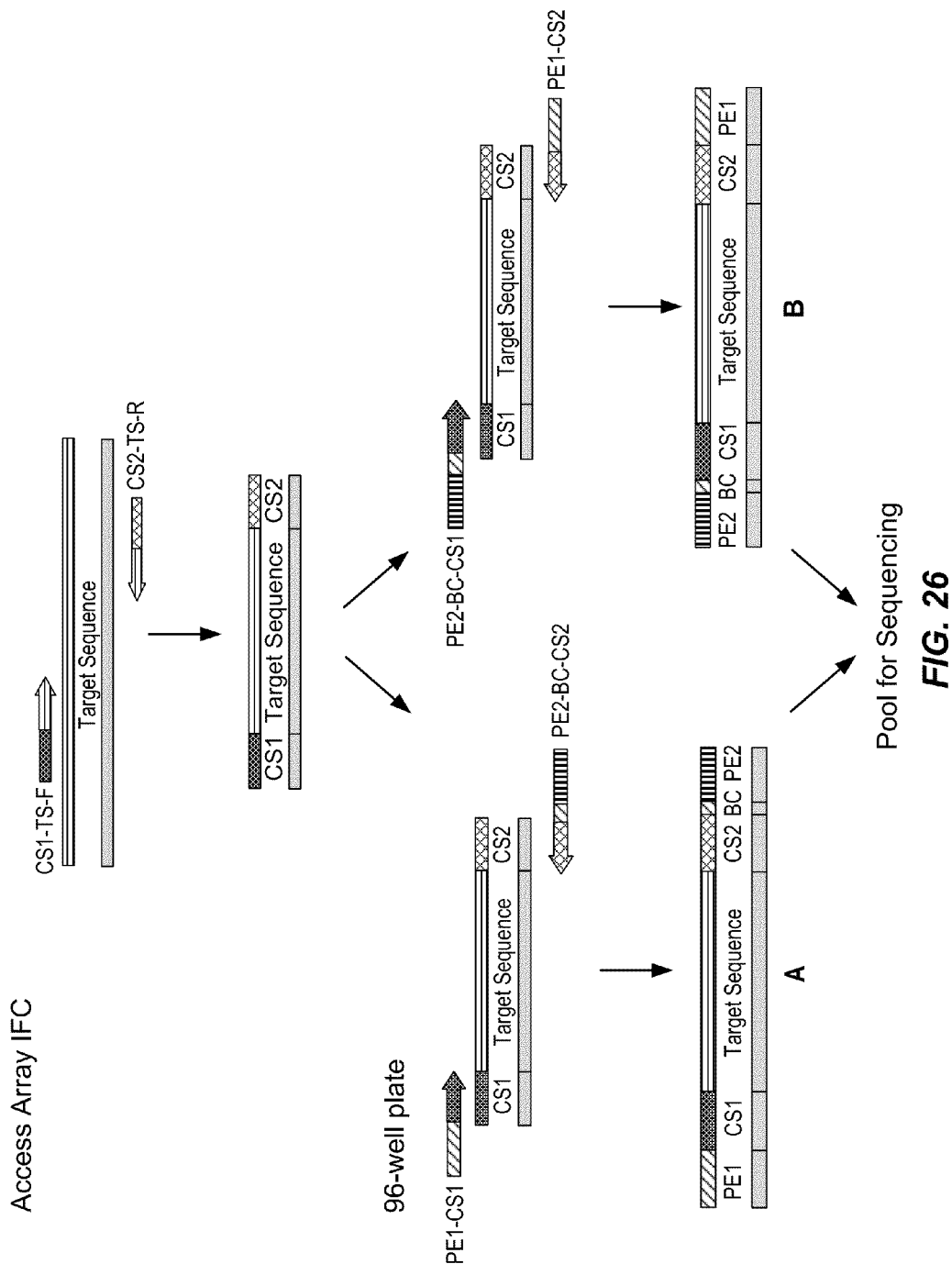
FIG. 26A-B: Overview of the segregated-primer PCR strategy used in Example 9. The first PCR with the target-specific primer pairs was carried out in the ACCESS ARRAY™ IFC. The harvested PCR product pools were split into two subsequent PCR reactions with sample-specific barcode primers. (A) The reaction that generated products that allowed for sequencing of the 5' end of the target region utilized the PE1_CS1 and PE2_BC_CS2 primer combination. (B) The reaction that generated products that allowed for sequencing of the 3' end of the target region utilized the PE1_CS2 and PE2_BC_CS1 primer combination.

Sample-specific barcode primer pairs were segregated out into two separate PCR reactions (FIG. 26; see also Table 1).

TABLE 1

Barcode primers used in the segregated-primer PCR strategy.

| Primer | Sequence |
|---|---|
| PE1-CS1 | 5'-AATGATACGGCGACCACCGAGATCTACACTGACGACAT GGTTCTACA-3' (SEQ ID NO: 1) |
| PE2-BC-CS2 | 5'-CAAGCAGAAGACGGCATACGAGAT-[BC]-TACGGTAG CAGAGACTTGGTCT-3' (SEQ ID NOS 803 and 2) |
| PE1-CS2 | 5'-AATGATACGGCGACCACCGAGATCTTACGGTAGCAGAG ACTTGGTCT-3' (SEQ ID NO: 3) |
| PE2-BC-CS1 | 5'-CAAGCAGAAGACGGCATACGAGAT-[BC]-ACACTGAC GACATGGTTCTACA-3' (SEQ ID NOS 803 and 4) |

Figure 27:
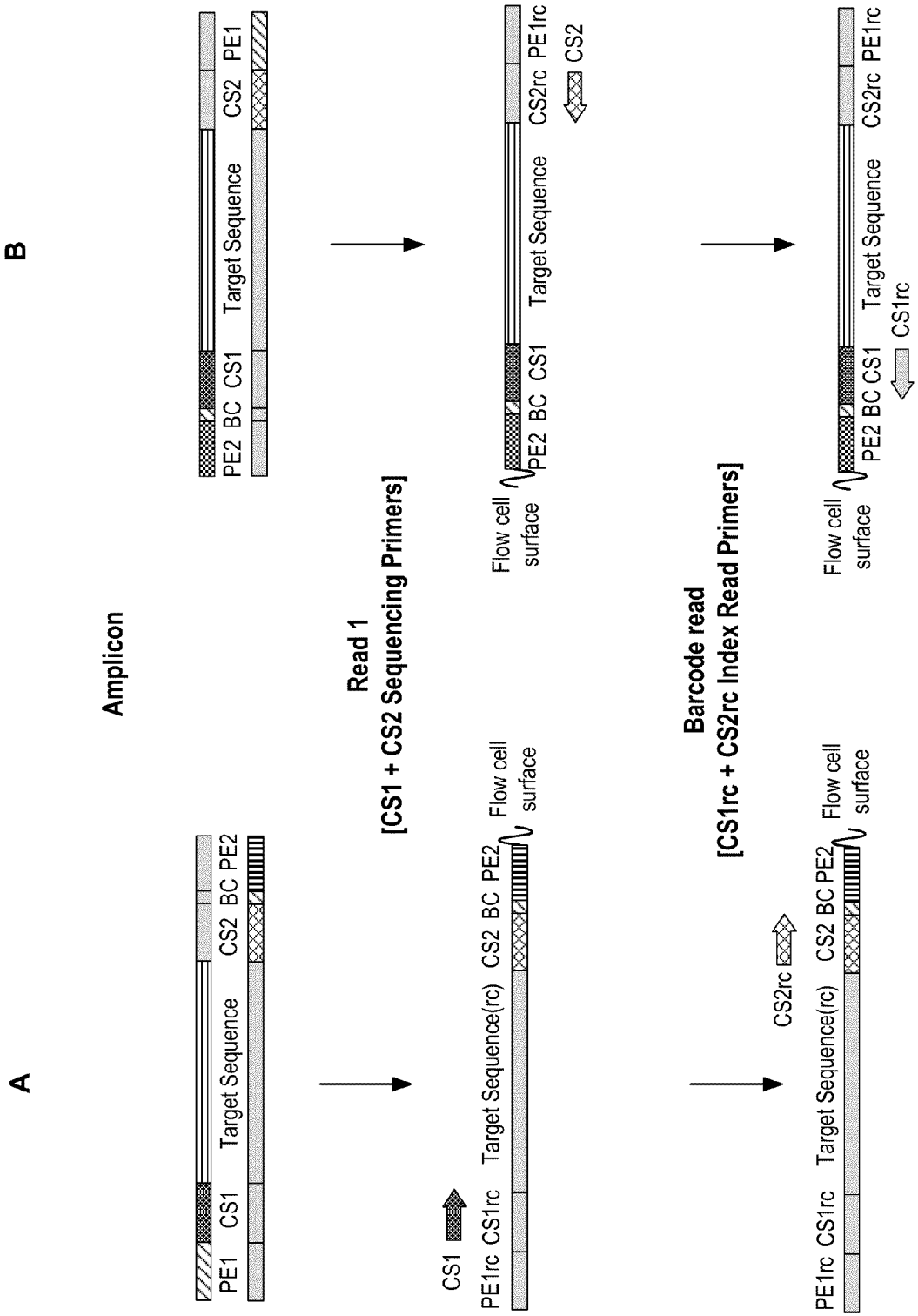
FIG. 27: Overview of the sequencing work flow used in Example 9. Both PCR product types were present on the flow cell. An equimolar mixture of CS1 and CS2 allowed for sequencing of both the 5' end and 3' end of the target regions. After stripping and rehybridization of the clusters with an equimolar mixture of CS1rc and CS2rc the barcodes were sequenced. The sequencing primers CS1 and CS2 were provided in the reagent FL1. The indexing primers CS1rc and CS2rc were provided in the reagent FL2.

After the barcoding PCR, the PCR products of both the 5' reaction and the 3' reaction were combined and used as template for cluster formation on the flow cell. Because both PCR product types were present and formed clusters on the flow cell, an equimolar mixture of the CS1 and CS2 sequencing primers allowed for simultaneous sequencing of both PCR product types (FIG. 27). Similarly, the index read with an equimolar mixture of the CS1rc and CS2rc sequencing primers allowed for simultaneous sequencing of the barcodes of both PCR product types.

The *Fluidigm® IFC Controller for ACCESS ARRAY™ System User Guide* (PN 68000157) may be consulted as a reference for this protocol. The Illumina website may be consulted for up to date protocols, reagent and catalog number information.

Preparing and Sequencing Amplicons

The following reagents were used for this protocol and were stored at −20° C.: FastStart High Fidelity PCR System, dNTPack (Roche, PN 04-738-292-001); 20× ACCESS ARRAY™ Loading Reagent (Fluidigm, PN 100-0883); Target-specific primer pairs with universal tags (CS1 forward tag, CS2 reverse tag), including 50 µM CS1-Tagged TS Forward Primer and 50 µM CS2-Tagged TS Reverse Primer; and Bidirectional 384 Barcode Kit for the Illumina GAII HiSeq and MiSeq Sequencers (Fluidigm, PN 100-3771). Additional reagents were stored at 4° C., including: Agilent DNA 1000 Kit Reagents (Agilent, PN 5067-1504); and 1× ACCESS ARRAY™ Harvest Solution (Fluidigm, PN 100-1031). Other reagents were stored at room temperature, including PCR Certified Water (Teknova, PN W330); DNA Suspension Buffer (10 mM Tris HCl, 0.1 mM EDTA, pH8.0) (Teknova, PN T0221); and Agilent DNA 1000 Chips (included in the Agilent DNA 1000 DNA kit) (Agilent).

The following equipment and consumables were used for this protocol: 1.5 mL or 2 mL microcentrifuge tubes; Microcentrifuge with rotor for 2 mL tubes; Microcentrifuge with rotor for 0.2 mL PCR tube strips; Centrifuge with plate carriers; Agilent 2100 BioAnalyzer (Agilent); 96-Well Reaction Plate; MicroAmp Clear Adhesive Film (Applied Biosystems, PN 4306311); IFC Controller AX (2 quantity, pre- and post-PCR) (Fluidigm); FC1 Cycler (Fluidigm); 48.48 ACCESS ARRAY™ IFC s (Fluidigm); and Control Line Fluid Syringes (Fluidigm, PN 89000020).

Multiplex PCR on the ACCESS ARRAY™ IFC was performed according to the instructions as detailed in Chapter 6—Multiplex PCR on the 48.48 ACCESS ARRAY™ IFC of the *Fluidigm ACCESS ARRAY™ System for Illumina Platform User Guide*.

Barcoding PCR was performed according to the instructions as detailed in Chapter 6—Attaching Sequence Tags and Sample Barcodes of the *Fluidigm ACCESS ARRAY System for Illumina Platform User Guide*. The 100× dilution of the harvested PCR product pool served as template in two rather than one barcoding PCR reactions: one reaction generated PCR product A that allowed for sequencing of the 5' end of the target region, the other reaction generated PCR product B that allowed for sequencing of the 3' end of the target region. The set up of the reaction was identical to "Attaching Sequence Tags and Sample Barcodes" in the *Fluidigm ACCESS ARRAY System for Illumina Platform User Guide*. However, the quantities in the Sample Pre-Mix Master Mix were doubled to compensate for the increase in the number of wells. After the second PCR had finished, PCR Product A and PCR Product B pools were combined prior to sequencing. Chapter 8 of the *Fluidigm ACCESS ARRAY™ System for Illumina Platform User Guide* provides methods describing post-PCR product library purification and quantitation.

The remainder of this Example provides the sequencing workflow used in the protocol.

The following instructions for preparing reagents are intended for use with Illumina TruSeq sequencing reagents. The Fluidigm reagents FL1 and FL2 contain equimolar mixtures of the CS1 and CS2 sequencing and indexing primers respectively. FL1 is the sequencing primer and contains 50 µM each of the CS1 and CS2 primers. FL2 is the indexing primer and contains 50 µM each of the CS1rc and CS2rc primers. Sequences for these primers are shown in Table 2.

TABLE 2

Primers and sequences

| Primer | Sequence |
| --- | --- |
| CS1 | 5'-ACACTGACGACATGGTTCTACA-3' (SEQ ID NO: 13) |
| CS2 | 5'-TACGGTAGCAGAGACTTGGTCT-3' (SEQ ID NO: 14) |
| CS1rc | 5'-TGTAGAACCATGTCGTCAGTGT-3' (SEQ ID NO: 15) |

TABLE 2-continued

Primers and sequences

| Primer | Sequence |
| --- | --- |
| CS2rc | 5'-AGACCAAGTCTCTGCTACCGTA-3' (SEQ ID NO: 16) |

The sequencing primer HP6/FL1 was prepared by diluting Fluidigm reagent FL1 (which contains the custom sequencing primers) to a final concentration of 0.25 µM in TruSeq reagent HP6 in a DNAse, RNAse free 0.5 mL microfuge tube, as shown in Table 3. The primer was vortexed after mixing to ensure complete mixing.

TABLE 3

| Instructions for Preparing HP6/FL 1 (per mL) | |
| --- | --- |
| Reagent | Volume |
| TruSeq reagent HP6 | 995 µL |
| FL1 | 5 µL |
| Total | 1000 µL |

The indexing primer HP8/FL2 was prepared by diluting Fluidigm reagent FL2 (which contains the custom indexing primers) to a final concentration of 0.25 µM in Truseq reagent HP8 in a DNAse, RNAse free 0.5 ml microfuge tube, as shown in Table 4. The primer was vortexed after mixing to ensure complete mixing.

TABLE 4

| Instructions for Preparing HP8/FL2 (per mL) | |
| --- | --- |
| Reagent | Volume |
| TruSeq reagent HP8 | 995 µL |
| FL2 | 5 µL |
| Total | 1000 µL |

Clusters were generated using detailed instructions in the *Illumina cBot™ User Guide, Illumina Cluster Station User Guide*, or *Illumina MiSeq User Guide*. To hybridize the sequencing primer, the sequencing primer reagent HP6/FL1 was used for the first read.

Sequencing reagents were prepared and loaded onto the sequencer according to the manufacturer's instructions. For Read 1, the instructions provided by the manufacturer were followed for conducting a multiplexed single-read sequencing run.

For the index read, the index reagent HP7/FL2 was substituted rather than the HP7 reagent. The barcode sequences used in the Fluidigm Bidirectional Primer Library were designed so that they could be distinguished even when sequencing errors are present. As more samples are run in parallel, the length of the index read required to distinguish the barcode sequences unambiguously increases. Recommendations for index reads are described in Table 5.

TABLE 5

| Index Read Recommendations | | | |
|---|---|---|---|
| | Number of samples per lane | | |
| | 1-96 | 97-384 | 385-1920 |
| Length of index read | 6 bases | 8 bases | 10 bases |

When preparing the sequencing run, the length of the index read was adjusted according to the guidelines in Table 5. The volumes of the sequencing reagents loaded onto the sequencer were ensured to be sufficient for the index cycles. These changes were implemented according to the manufacturer's recommendations.

Example 10

Detailed Procedure for Tagging Target Nucleic Acids for Bidirectional Illumina Sequencing Using a Microfluidic Device that Permits Recovery of Amplification Products 394 primer pairs were designed to PCR amplify exons from the genes BRCA1, BRCA2, PTEN, PI3KCA, APC, EGFR, TP53 (See Table 6 below). Forward primers were appended with the Tag8 sequence, and reverse primers were appended with the Tag5 sequence. The 394 primers were arranged in 48 groups containing, on average, approximately 8 primer pairs per group, at a concentration of 1 µM per primer in 0.05% Tween-20. Sample mixes were prepared from 48 cell-line genomic DNA samples (see Table 7 below) by adding 1 µl of sample (50 ng/ul) to 3 µl pre-sample mix, which contained 1U Roche Faststart HiFi polymerase, 1× buffer, 100 µM dNTPs, 4.5 mM $MgCl_2$, 5% DMSO, and 1× ACCESS ARRAY™ sample loading solution.

The ACCESS ARRAY™ IFC was run according to instructions in the ACCESS ARRAY™ User Guide. Sample mixes were loaded into the sample ports of an ACCESS ARRAY 48.48™ IFC. Groups of primers were loaded into the inlets of the ACCESS ARRAY 48.48™ IFC. PCR was carried out on a Fluidigm stand-alone thermal cycler using the standard PCR protocol supplied with the thermal cycler. After PCR, products were harvested from the ACCESS ARRAY™ IFC using a separate controller. One microliter of each product was then transferred to a PCR plate and diluted 100× with PCR-grade water. Three PCR plates were then prepared containing 4 µl of PCR mastermix (1U Roche Faststart HiFi polymerase, 1× buffer, 100 µM dNTPs, 4.5 mM $MgCl_2$, 5% DMSO and barcode primers as described below in Table 8).

Plate 1 contained a pair of primers bearing barcodes FL001-FL0048 of the form PE2-CS1/PE1-BC-CS2, with each primer having a concentration of 400 nM. Plate 2 contained a pair of primers bearing barcodes FL001-FL0048 of the form PE2-CS2/PE1-BC-CS1, with each primer at a concentration of 400 nM. Plate 3 contained two pairs of primers bearing barcodes FL0049-FL0096 of the form PE2-CS1/PE2-CS2/PE1-BC-CS1/PE1-BC-CS2. All three plates were subjected to 15 cycles of PCR using the following thermal protocol (95° C. 10 min; 15× (95° C. 15 s, 60° C. 30 s, 72° C. 90 s); 72° C. 3 min).

Figure 28:
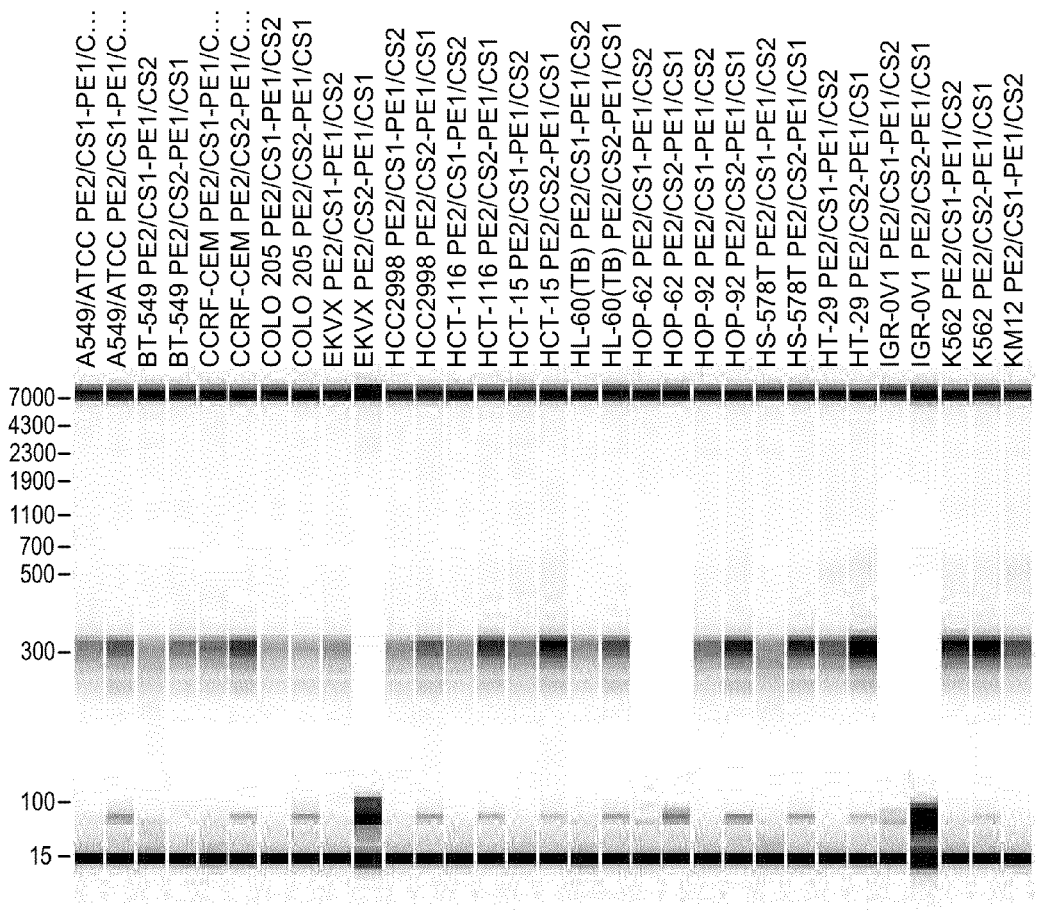
FIG. 28: Bioanalyzer products obtained from barcoding reactions run with barcodes from Plate 1 and Plate 2 in Example 10.
Figure 28:
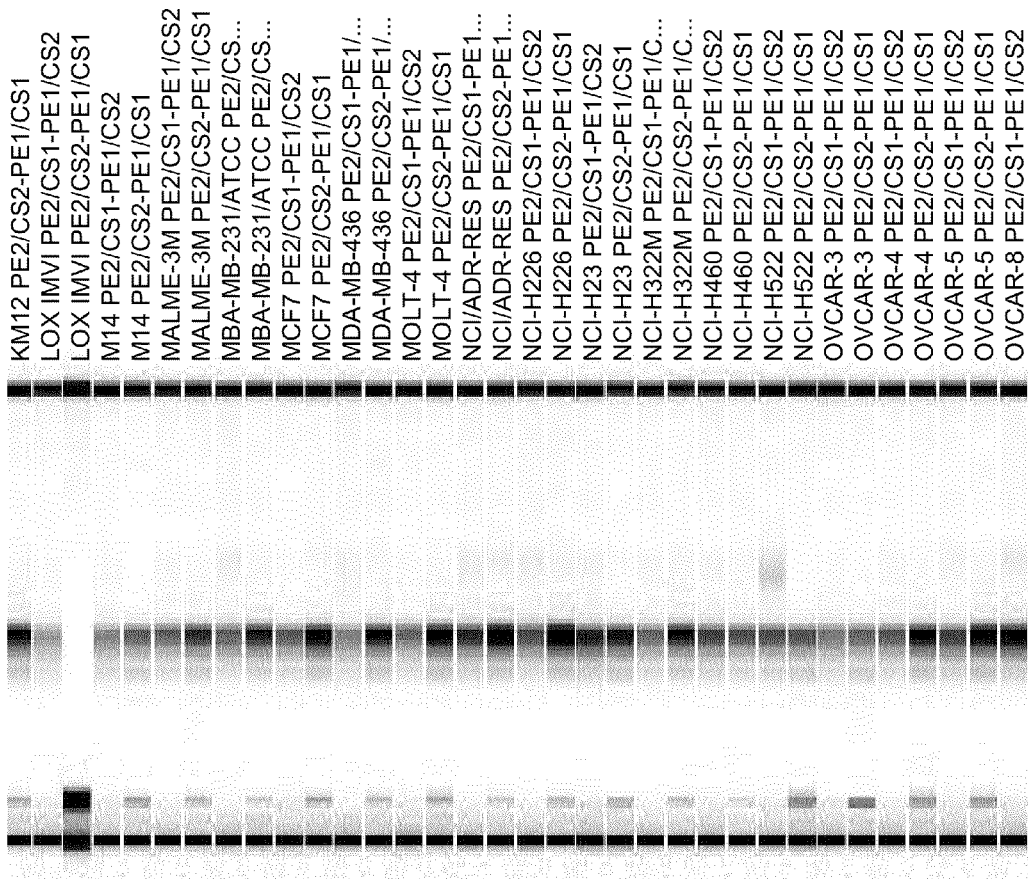
Figure 28:
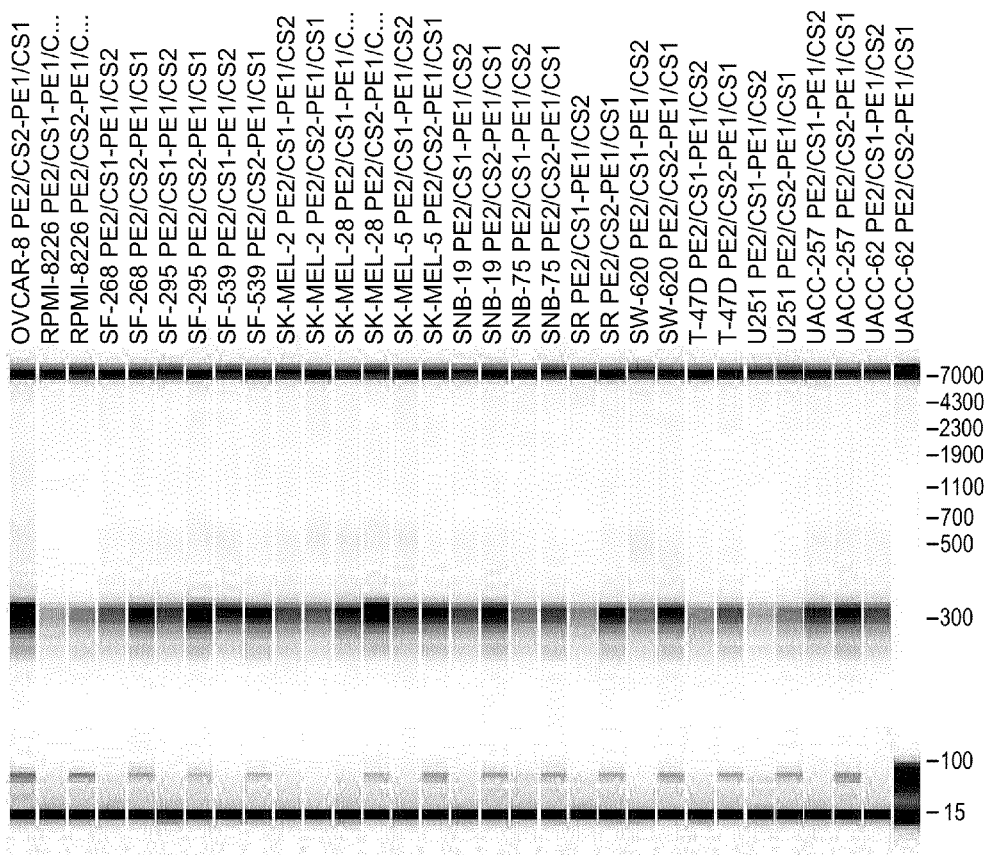

Each of the reaction products from each plate was analyzed on an Agilent 1000 Bioanalyzer chip, and concentrations of the PCR product pool were measured based on electropherograms from the analysis (FIG. 28). PCR products from each plate were pooled to equal concentrations using volumes adjusted according to concentrations obtained from the Agilent Bioanalyzer.

The pooled sample was cleaned up using AMPure beads (Beckman Coulter) with a bead to sample ratio of 1:1.

The amplicon pool was sequenced on two separate lanes of a Genome Analyzer II (Illumina). The first lane used CS1 and CS2 primers for the first read, and the CS1rc and CS2rc primers for the index read. Because the annealing temperatures of CS1 and CS2 are predicted to be 10° C. below those of the standard Illumina Read 1 and Index sequencing primers, LNA (locked-nucleic acid) versions of CS1, CS2, CS1rc and CS2rc were used in order to optimize hybridization to the cluster under the standard conditions described in the Illumina Cluster Station and Genome Analyzer manuals.

Figure 29:
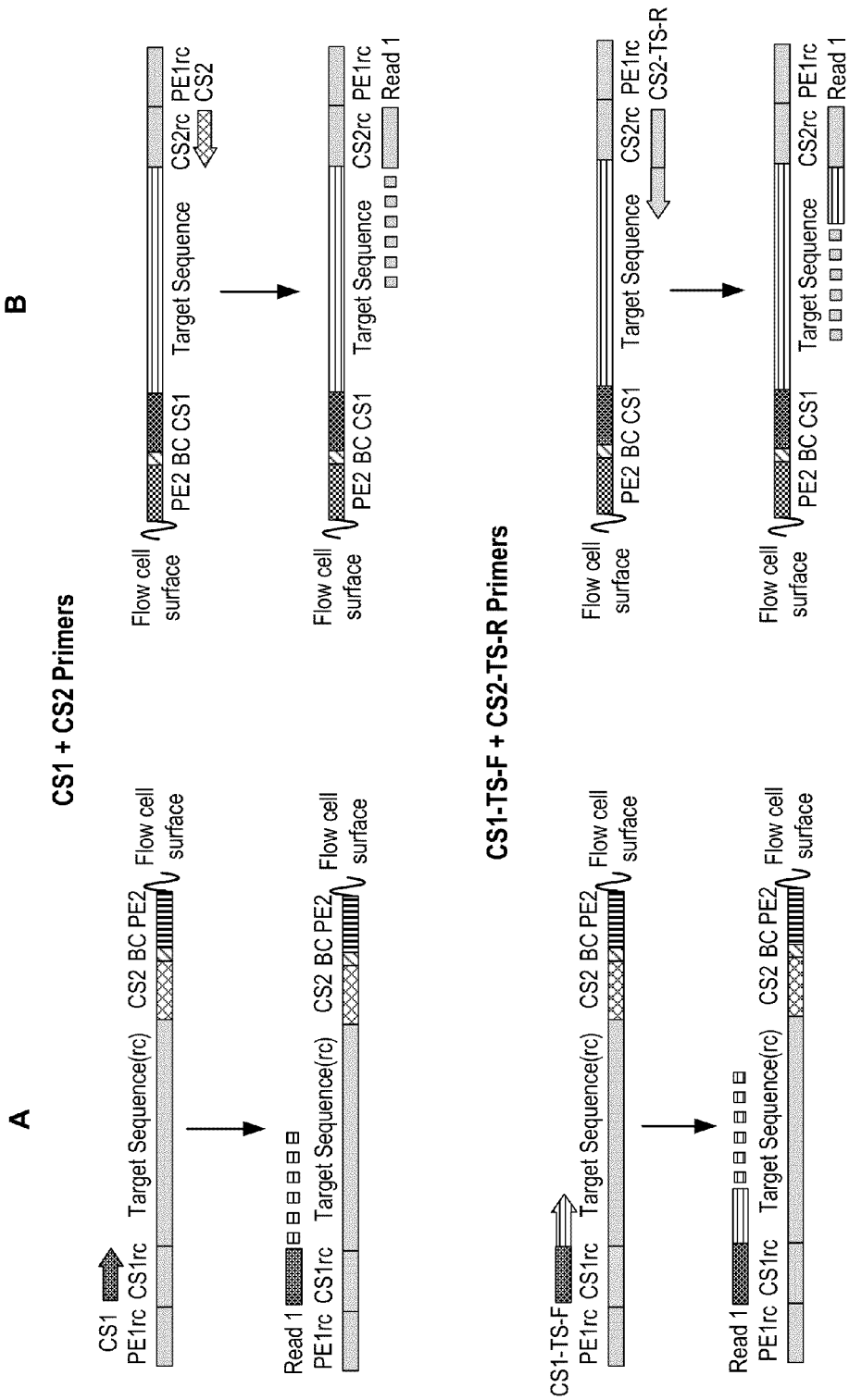
FIG. 29: Alternative sequencing primers used in Example 10. Use of an equimolar mixture of all target-specific PCR primers that were used on the ACCESS ARRAY™ IFC as a sequencing primer pool circumvents sequencing through the uninformative target-specific primer region.

For sequencing, the second lane used a pool of the target-specific forward and reverse primers assembled from primers that were used during amplification on the ACCESS ARRAY™ IFC (FIG. 29). The CS1/CS2rc indexing primer was used for the index read. Due to their increased length, the target-specific primers have annealing temperatures higher than those of CS1 or CS2. This approach circumvented reading through the uninformative target-specific primer portion of the PCR products. Instead, sequencing information with the lowest error rate was obtained from an informative region of the PCR product where there was the least amount of overlap between the 5' and 3' reads. The approach also allowed for greater overlap where the sequencing error rate is the greatest (i.e., the middle of the PCR product), and an increase in PCR product size of 30-40 bp.

Figure 30:
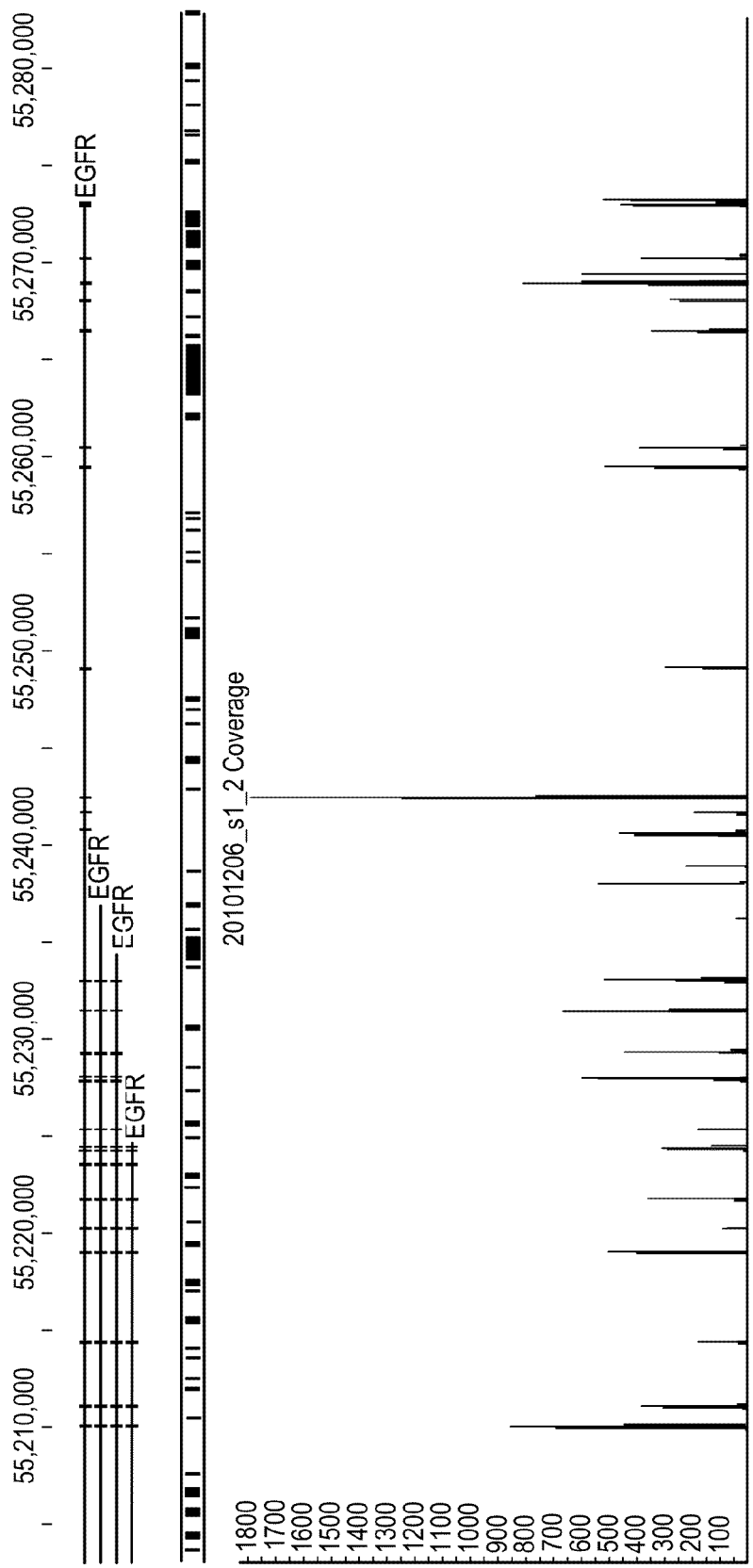
FIG. 30: Per-base coverage of the gene EGFR for one sample in Example 10. Reads from each strand are shown in different shades.

Sequence data were demultiplexed using Illumina software and aligned to the human genome reference sequence build hg19 using the aligner ELAND (Illumina). The per-base coverage of the gene EGFR for an illustrative sample is shown in FIG. 30.

TABLE 6

Primers for Amplifying Exons from the Genes BRCA1, BRCA2, PTEN, PI3KCA, APC, EGFR, TP53

| Primer plate well | Gene/ chr | Name | F-primer | R-primer |
|---|---|---|---|---|
| A1 | APC | APC_SE00000972224_1 | ACACTGACGACATGGTTCTACACCT TATAGGTCCAAGGGTAGC (SEQ ID NO: 5) | TACGGTAGCAGAGACTTGGTCTAAA GTCACAGTCTTGATACCTTCA (SEQ ID NO: 6) |
| B1 | APC | APC_972224_1_1 | ACACTGACGACATGGTTCTACAGTT GAGGCACTGAAGATGG (SEQ ID NO: 7) | TACGGTAGCAGAGACTTGGTCTTTT AAGTAAAGTGTCTTACCTCAAGTTT (SEQ ID NO: 8) |

TABLE 6-continued

Primers for Amplifying Exons from the Genes BRCA1, BRCA2, PTEN, PI3KCA, APC, EGFR, TP53

| Primer plate well | Gene/chr | Name | F-primer | R-primer |
|---|---|---|---|---|
| C1 | APC | APC_SE00000917796_1 | ACACTGACGACATGGTTCTACAGCATACTTAAATGTCAAGAAATACAGAATCA (SEQ ID NO: 9) | TACGGTAGCAGAGACTTGGTCTTAAAATCTACCTTTAAGACGCTCTAATAAAT (SEQ ID NO: 10) |
| D1 | APC | APC_SE00000917796_2 | ACACTGACGACATGGTTCTACAGTACTTAAACAACTACAAGGAAGTATTGA (SEQ ID NO: 1) | TACGGTAGCAGAGACTTGGTCTACCAACACCCAAATCGAGAGA (SEQ ID NO: 12) |
| E1 | APC | APC_972225_2 | ACACTGACGACATGGTTCTACATCAGTCATGTATATTTGTGGTTAAAATGT (SEQ ID NO: 13) | TACGGTAGCAGAGACTTGGTCTCCTTCCCGGCTTCCATAAGA (SEQ ID NO: 14) |
| F1 | APC | APC_SE00000972225_7 | ACACTGACGACATGGTTCTACAGCGGTCAAAAATGTCCCTCC (SEQ ID NO: 15) | TACGGTAGCAGAGACTTGGTCTACTGGAGTACACAAGGCAATGTT (SEQ ID NO: 16) |
| G1 | APC | APC_SE0000_0917798-1 | ACACTGACGACATGGTTCTACATCTTCTGCAGTCTTTATTAGCATTGT (SEQ ID NO: 17) | TACGGTAGCAGAGACTTGGTCTAGTTTCAAATAAGTTGTACTGCCAAG (SEQ ID NO: 18) |
| H1 | APC | APC_SE00000972226_1 | ACACTGACGACATGGTTCTACATGCTTTTTTGCTTTTACTGATTAACG (SEQ ID NO: 19) | TACGGTAGCAGAGACTTGGTCTCCTGTGCTCGTTTTTCCATATCC (SEQ ID NO: 20) |
| A2 | APC | APC_SE00000972226_2 | ACACTGACGACATGGTTCTACATTACAAACAGATATGACCAGAAGGC (SEQ ID NO: 21) | TACGGTAGCAGAGACTTGGTCTTAACAGAGCTgTAATTCATTTTATTCCT (SEQ ID NO: 22) |
| B2 | APC | APC_SE00000972227_1 | ACACTGACGACATGGTTCTACACCCTGAGCTTTTAAGTGGTAGC (SEQ ID NO: 23) | TACGGTAGCAGAGACTTGGTCTACCCACAAACAAGAAAGGCAA (SEQ ID NO: 24) |
| C2 | APC | APC_SE00000972228_1 | ACACTGACGACATGGTTCTACATGGGCTAAGAAAGCCTACACC (SEQ ID NO: 25) | TACGGTAGCAGAGACTTGGTCaCCTGACCATTACCAGAAGTTGC (SEQ ID NO: 26) |
| E2 | APC | APC_SE00000917801_1 | ACACTGACGACATGGTTCTACACTTCATTTGGAGTACCTTAACA (SEQ ID NO: 27) | TACGGTAGCAGAGACTTGGTCTACCTTGGTTCCCAGATGACT (SEQ ID NO: 28) |
| F2 | APC | APC_SE00000917801_2 | ACACTGACGACATGGTTCTACATCTATAATGTGCTTAATTTTTAGGGTTCA (SEQ ID NO: 29) | TACGGTAGCAGAGACTTGGTCTAGAATGTCTTAGCAAAGTAGTCATGG (SEQ ID NO: 30) |
| G2 | APC | APC_SE00000917803_1 | ACACTGACGACATGGTTCTACATCACTTAATTGGTTTTTGGCTTTTGA (SEQ ID NO: 31) | TACGGTAGCAGAGACTTGGTCTCCAGACTGTCGCATGGAT (SEQ ID NO: 32) |
| H2 | APC | APC_SE00000917803_2 | ACACTGACGACATGGTTCTACATGTTGTCAATGCTTGGTACTCAT (SEQ ID NO: 33) | TACGGTAGCAGAGACTTGGTCTGGCCCGAGCCTCTTTACTG (SEQ ID NO: 34) |
| A3 | APC | APC_SE00000917803_3 | ACACTGACGACATGGTTCTACACCTCATCCAGCTTTTACATGGC (SEQ ID NO: 35) | TACGGTAGCAGAGACTTGGTCTGCCACTCCCAACAGGTTTC (SEQ ID NO: 36) |
| B3 | APC | APC_SE00000917803_4 | ACACTGACGACATGGTTCTACATGCAGCACTCCACAACATCA (SEQ ID NO: 37) | TACGGTAGCAGAGACTTGGTCTGCTTTGAAACATGCACTACGA (SEQ ID NO: 38) |
| C3 | APC | APC_SE00000917804_1 | ACACTGACGACATGGTTCTACATCATTGCTCTTCAAATAACAAAGCAT (SEQ ID NO: 39) | TACGGTAGCAGAGACTTGGTCTAAAAATCCACCAGTAATTGTCTATGTC (SEQ ID NO: 40) |
| D3 | APC | APC_SE00000917807_1 | ACACTGACGACATGGTTCTACAGGTACCAGTTTGTTTTATTTTAGATGATTGT (SEQ ID NO: 41) | TACGGTAGCAGAGACTTGGTCTACATACCTTGTTGGCTACATCTCC (SEQ ID NO: 42) |
| E3 | APC | APC_917807_7 | ACACTGACGACATGGTTCTACACGATATGCTGGAATGGCTT (SEQ ID NO: 43) | TACGGTAGCAGAGACTTGGTCTCAGTCATTGTTTAATGAGGAGAGTG (SEQ ID NO: 44) |

TABLE 6-continued

Primers for Amplifying Exons from the Genes BRCA1, BRCA2, PTEN, PI3KCA, APC, EGFR, TP53

| Primer plate well | Gene/chr | Name | F-primer | R-primer |
|---|---|---|---|---|
| F3 | APC | APC_SE00000760099_1 | ACACTGACGACATGGTTCTACAGCTTGGCTTCAAGTTGTCT (SEQ ID NO: 45) | TACGGTAGCAGAGACTTGGTCTAGGTGAAATTCTAAATAGTACCTGCT (SEQ ID NO: 46) |
| G3 | APC | APC_SE00000917809_1 | ACACTGACGACATGGTTCTACAGCTAGCATTAAAAACAAAAAAGCAACT (SEQ ID NO: 47) | TACGGTAGCAGAGACTTGGTCTAAAGCACATTCCATCAATGC (SEQ ID NO: 48) |
| A4 | APC | APC_SE00000972229_6 | ACACTGACGACATGGTTCTACAATTAGATGACCCATATTCTGTTTCTTAC (SEQ ID NO: 49) | TACGGTAGCAGAGACTTGGTCTCAATAATGGCTAAAGTGTTTGTCTGG (SEQ ID NO: 50) |
| B4 | APC | APC_E00000972229_15 | ACACTGACGACATGGTTCTACAGTGCTGTAGATGGTGCACTTG (SEQ ID NO: 51) | TACGGTAGCAGAGACTTGGTCTATTAGGTCtTTTTGAGAGTATGAATTCTG (SEQ ID NO: 52) |
| C4 | APC | APC_SE00000972230_1 | ACACTGACGACATGGTTCTACACTGCATACACATTGTGACCTT (SEQ ID NO: 53) | TACGGTAGCAGAGACTTGGTCTCCCCCATGTCCCATAATGCTT (SEQ ID NO: 54) |
| D4 | APC | APC_SE00000972230_2 | ACACTGACGACATGGTTCTACATGCATGTGGAACTTTGTGGA (SEQ ID NO: 55) | TACGGTAGCAGAGACTTGGTCTTGGCATCCTTGTACTTCGC (SEQ ID NO: 56) |
| E4 | APC | APC_SE00000972230_5 | ACACTGACGACATGGTTCTACAATGATTGCTATGGGAAGTGCT (SEQ ID NO: 57) | TACGGTAGCAGAGACTTGGTCTCGATGAGATGCCTTGGGACT (SEQ ID NO: 58) |
| G4 | APC | APC_E00000972230_22 | ACACTGACGACATGGTTCTACACAAGCAAAGTCTCTATGGTGAT (SEQ ID NO: 59) | TACGGTAGCAGAGACTTGGTCTACTTCTATCTTTTCAGAACGAGAACTAT (SEQ ID NO: 60) |
| H4 | APC | APC_E00000972230_24 | ACACTGACGACATGGTTCTACAGCAACATGACTGTCCTTTCACC (SEQ ID NO: 61) | TACGGTAGCAGAGACTTGGTCTGCAAACCTCGCTTTGAAGA (SEQ ID NO: 62) |
| A5 | APC | APC_E00000972230_25 | ACACTGACGACATGGTTCTACAGGCAACTACCATCCAGCAA (SEQ ID NO: 63) | TACGGTAGCAGAGACTTGGTCTGCAGAGCTTCTTCTAAGTGCAT (SEQ ID NO: 64) |
| B5 | APC | APC_E00000972230_27 | ACACTGACGACATGGTTCTACAGTCATGGAAGAAGTGTCAGC (SEQ ID NO: 65) | TACGGTAGCAGAGACTTGGTCTTGTATTCTAATTTGGCATAAGGCAT (SEQ ID NO: 66) |
| C5 | APC | APC_E00000972230_28 | ACACTGACGACATGGTTCTACAGCCCATACACATTCAAACACTTAC (SEQ ID NO: 67) | TACGGTAGCAGAGACTTGGTCTCAGAATAGGATTCAATCGAGGGT (SEQ ID NO: 68) |
| D5 | APC | APC_E00000972230_29 | ACACTGACGACATGGTTCTACATCAAATGATAGTTTAAATAGTGTCAGTAGTAG (SEQ ID NO: 69) | TACGGTAGCAGAGACTTGGTCTATAATTTATTGGTGTATCTAGTTCTCCATC (SEQ ID NO: 70) |
| E5 | APC | APC_E00000972230_30 | ACACTGACGACATGGTTCTACAGCcGACCTAGCCCATAAA (SEQ ID NO: 71) | TACGGTAGCAGAGACTTGGTCTCCTTGATTGTCTTTGCTCACTT (SEQ ID NO: 72) |
| F5 | APC | APC_E00000972230_31 | ACACTGACGACATGGTTCTACAACTCTGGAAGGCAAAGTCCT (SEQ ID NO: 73) | TACGGTAGCAGAGACTTGGTCTCCCCGTGACCTGTATGGAGA (SEQ ID NO: 74) |
| G5 | APC | APC_E00000972230_33 | ACACTGACGACATGGTTCTACATGGACAGCAGGAATGTGTTT (SEQ ID NO: 75) | TACGGTAGCAGAGACTTGGTCTGGTCTCTCTTCTTCTTCATGCT (SEQ ID NO: 76) |
| H5 | APC | APC_E00000972230_35 | ACACTGACGACATGGTTCTACATGATAAGCCTACCAATTATAGTGAACG (SEQ ID NO: 77) | TACGGTAGCAGAGACTTGGTCTGCTTTGTCCAGATGAACTCTTT (SEQ ID NO: 78) |
| A6 | APC | APC_E00000972230_36 | ACACTGACGACATGGTTCTACAGTTTAAAATATGCCACAGATATTCCTTCA (SEQ ID NO: 79) | TACGGTAGCAGAGACTTGGTCTGCCTTTTGAGGCTGACCACT (SEQ ID NO: 80) |

TABLE 6-continued

Primers for Amplifying Exons from the Genes BRCA1, BRCA2, PTEN, PI3KCA, APC, EGFR, TP53

| Primer plate well | Gene/chr | Name | F-primer | R-primer |
|---|---|---|---|---|
| B6 | APC | APC_E00000972230_37 | ACACTGACGACATGGTTCTACAGCAGTGAGAATACGTCCACAC (SEQ ID NO: 81) | TACGGTAGCAGAGACTTGGTCTCAGCTGATGACAAAGATGATAATGAA (SEQ ID NO: 82) |
| C6 | APC | APC_E00000972230_38 | ACACTGACGACATGGTTCTACAGCCACTTGCAAAGTTTCTTCT (SEQ ID NO: 83) | TACGGTAGCAGAGACTTGGTCTAGCTGACCTAGTTCCAATCTTTT (SEQ ID NO: 84) |
| D6 | APC | APC_E00000972230_39 | ACACTGACGACATGGTTCTACAGACGACACAGGAAGCAGAT (SEQ ID NO: 85) | TACGGTAGCAGAGACTTGGTCTGGAGATTTCGCTCCTGAAGAA (SEQ ID NO: 86) |
| E6 | APC | APC_E00000972230_40 | ACACTGACGACATGGTTCTACATCCTGTGAGCGAAGTTCCA (SEQ ID NO: 87) | TACGGTAGCAGAGACTTGGTCTACATCTGCTAAACATGAGTGGG (SEQ ID NO: 88) |
| F6 | APC | APC_E00000972230_41 | ACACTGACGACATGGTTCTACACCCaAAAGTCCACCTGA (SEQ ID NO: 89) | TACGGTAGCAGAGACTTGGTCTGCTTGGTGGCATGGTTTG (SEQ ID NO: 90) |
| G6 | APC | APC_E00000972230_43 | ACACTGACGACATGGTTCTACAGCCAGCTCCGTTCAGAGT (SEQ ID NO: 91) | TACGGTAGCAGAGACTTGGTCTGCAGCTTGCTTAGGTCCAC (SEQ ID NO: 92) |
| H6 | APC | APC_E00000972230_45 | ACACTGACGACATGGTTCTACAGCACCTACTGCTGAAAAGAGAG (SEQ ID NO: 93) | TACGGTAGCAGAGACTTGGTCTCCACATCTTTCTGTATAAATGGCTCA (SEQ ID NO: 94) |
| A7 | APC | APC_E00000972230_47 | ACACTGACGACATGGTTCTACACCACgGAAAGTAcTCCAGATG (SEQ ID NO: 95) | TACGGTAGCAGAGACTTGGTCTGCCTCTTTCTCTTGGTTTTCA (SEQ ID NO: 96) |
| B7 | APC | APC_E00000972230_52 | ACACTGACGACATGGTTCTACACCAGTTCAGGAAAATGACAATGGG (SEQ ID NO: 97) | TACGGTAGCAGAGACTTGGTCTGGGCTGGCTTTTTTGCTT (SEQ ID NO: 98) |
| C7 | APC | APC_E00000972230_59 | ACACTGACGACATGGTTCTACATCTGCCATGCCAACAAAGTC (SEQ ID NO: 99) | TACGGTAGCAGAGACTTGGTCTGTCCCTTCAACACAATACACCC (SEQ ID NO: 100) |
| D7 | APC | APC_E00000972230_60 | ACACTGACGACATGGTTCTACATCTACCATCACAAAACAGGTTGC (SEQ ID NO: 101) | TACGGTAGCAGAGACTTGGTCTGACTGTGCcCCTCCTCTA (SEQ ID NO: 102) |
| E7 | APC | APC_E00000972230_61 | ACACTGACGACATGGTTCTACAACTTTTCCACAGCTACATCTCT (SEQ ID NO: 103) | TACGGTAGCAGAGACTTGGTCTTGTCATCCAATTCAGGTATGGT (SEQ ID NO: 104) |
| F7 | APC | APC_E00000972230_62 | ACACTGACGACATGGTTCTACACCATTCCTACAGAAGGCAGAA (SEQ ID NO: 105) | TACGGTAGCAGAGACTTGGTCTAAGAaGAcGCAGATGCTTGC (SEQ ID NO: 106) |
| G7 | APC | APC_E00000972230_63 | ACACTGACGACATGGTTCTACAGCATTAATTCTGCTATGCCCAAA (SEQ ID NO: 107) | TACGGTAGCAGAGACTTGGTCTTTTTGAGTCTGCATTTTTTCTTACAC (SEQ ID NO: 108) |
| H7 | APC | APC_E00000972230_64 | ACACTGACGACATGGTTCTACATGCACCCAACAAAAATCAGTTAG (SEQ ID NO: 109) | TACGGTAGCAGAGACTTGGTCTAGCTTATCATTGAAGaCCTTGGAA (SEQ ID NO: 110) |
| B8 | APC | APC_E00000972230_70 | ACACTGACGACATGGTTCTACAGAGTCAGAGGAAGTTTTGCTTTTG (SEQ ID NO: 111) | TACGGTAGCAGAGACTTGGTCTGgTTAGTTCTGTGTGGCTGGT (SEQ ID NO: 112) |
| C8 | APC | APC_E00000972230_71 | ACACTGACGACATGGTTCTACATTCCAGGGAAAAGGCTGAATTA (SEQ ID NO: 113) | TACGGTAGCAGAGACTTGGTCTGGTATGTCTTTGGATGACTGGG (SEQ ID NO: 114) |
| D8 | APC | APC_E00000972230_85 | ACACTGACGACATGGTTCTACAGGCATACTTCAGAAACAATCCACT (SEQ ID NO: 115) | TACGGTAGCAGAGACTTGGTCTGGGCTCAGTCTCTTTGATAGGT (SEQ ID NO: 116) |

TABLE 6-continued

Primers for Amplifying Exons from the Genes BRCA1, BRCA2, PTEN, PI3KCA, APC, EGFR, TP53

| Primer plate well | Gene/chr | Name | F-primer | R-primer |
|---|---|---|---|---|
| E8 | APC | APC_E00000972230_87 | ACACTGACGACATGGTTCTACATCTCTCAgTGACATTGACCAAGAA (SEQ ID NO: 117) | TACGGTAGCAGAGACTTGGTCTGCAACAGGTCATCTTCAGAGT (SEQ ID NO: 118) |
| F8 | APC | APC_E00000972230_93 | ACACTGACGACATGGTTCTACAtctCAAGAAACAGTTCTCTCAGTT (SEQ ID NO: 119) | TACGGTAGCAGAGACTTGGTCTGTTCTGAATCTGGTCTCTGTATATCT (SEQ ID NO: 120) |
| G8 | APC | APC_E00000972230_95 | ACACTGACGACATGGTTCTACAGGGTGATAATGAAAAACATAGTCCCA (SEQ ID NO: 121) | TACGGTAGCAGAGACTTGGTCTGCAGCAGCAGCTTGATGTAA (SEQ ID NO: 122) |
| H8 | APC | APC_972230_953 | ACACTGACGACATGGTTCTACAGCTATTCAGGAAGGTGCAAA (SEQ ID NO: 123) | TACGGTAGCAGAGACTTGGTCTCCCTGGTTTTAGAATTCGTGGG (SEQ ID NO: 124) |
| A9 | APC | APC_00000972230_116 | ACACTGACGACATGGTTCTACATGATTCAGATTCCATCCTTTCCCT (SEQ ID NO: 125) | TACGGTAGCAGAGACTTGGTCTACTTTCAGATTCTATCTTTTTAGTTTCCAA (SEQ ID NO: 126) |
| B9 | APC | APC_00000972230_126 | ACACTGACGACATGGTTCTACAGGCCCACGAATTCTAAAACCA (SEQ ID NO: 127) | TACGGTAGCAGAGACTTGGTCTGTCCTGCCTCGAGAGATTG (SEQ ID NO: 808) |
| C9 | APC | APC_972230_126_2 | ACACTGACGACATGGTTCTACATGAAAGTAAAGGAATCAAAGGAGGA (SEQ ID NO: 128) | TACGGTAGCAGAGACTTGGTCTACAGGACTTGTACTTGAGGAGC (SEQ ID NO: 129) |
| E9 | APC | APC_00000972230_140 | ACACTGACGACATGGTTCTACAGGAGTTCGAAATAGCTCCTCAAG (SEQ ID NO: 130) | TACGGTAGCAGAGACTTGGTCTAGAAGGTGCTTTACTTGACCCA (SEQ ID NO: 131) |
| F9 | APC | APC_00000972230_141 | ACACTGACGACATGGTTCTACATCCTAGAGGAGcCAAGCCAT (SEQ ID NO: 132) | TACGGTAGCAGAGACTTGGTCTAGGACTTATTCCATTTCTACCAGGG (SEQ ID NO: 133) |
| G9 | APC | APC_00000972230_142 | ACACTGACGACATGGTTCTACATCTAGAGATTCgACCCCTTCA (SEQ ID NO: 134) | TACGGTAGCAGAGACTTGGTCTCATCTGTCTACCTGGAGATGTATATG (SEQ ID NO: 135) |
| H9 | APC | APC_00000972230_143 | ACACTGACGACATGGTTCTACATGAACTTCCAAGGACATCATCCC (SEQ ID NO: 136) | TACGGTAGCAGAGACTTGGTCTGGCTCCATTACCATTATTCATCTG (SEQ ID NO: 137) |
| A10 | APC | APC_00000972230_144 | ACACTGACGACATGGTTCTACAGGCAACAGAACCTTACCAAACA (SEQ ID NO: 138) | TACGGTAGCAGAGACTTGGTCTGACTGGCGTACTAATACAGGT (SEQ ID NO: 139) |
| B10 | APC | APC_00000972230_145 | ACACTGACGACATGGTTCTACATCAACTAAATCAAGTGGAAGTGAATCTG (SEQ ID NO: 140) | TACGGTAGCAGAGACTTGGTCTAACTGGAGTTTGTGCCTGGG (SEQ ID NO: 141) |
| C10 | APC | APC_00000972230_147 | ACACTGACGACATGGTTCTACAAGAAGAAAATTGGAGGAATCTGC (SEQ ID NO: 142) | TACGGTAGCAGAGACTTGGTCTCCATCATTATACTCTATAGTGGGACTG (SEQ ID NO: 143) |
| D10 | APC | APC_00000972230_148 | ACACTGACGACATGGTTCTACAGTCCTTCCCTTCCTGATATGTCTC (SEQ ID NO: 144) | TACGGTAGCAGAGACTTGGTCTGTGCTCACGTTTCCAGGTT (SEQ ID NO: 145) |
| E10 | APC | APC_00000972230_149 | ACACTGACGACATGGTTCTACACCAgCAAAGCGCCATGATA (SEQ ID NO: 146) | TACGGTAGCAGAGACTTGGTCTCACTTTTTGCTTTTTCACTGGATT (SEQ ID NO: 147) |
| F10 | APC | APC_00000972230_150 | ACACTGACGACATGGTTCTACATTCATCATCCCTTCCTCG (SEQ ID NO: 148) | TACGGTAGCAGAGACTTGGTCTCCATGTTCCTTTTGCGGAT (SEQ ID NO: 149) |
| G10 | APC | APC_00000972230_152 | ACACTGACGACATGGTTCTACAGGAACCAAACAAAGTAAAGAAAACCA (SEQ ID NO: 150) | TACGGTAGCAGAGACTTGGTCTGGACAGTCCTCAATTCTCACCC (SEQ ID NO: 151) |

TABLE 6-continued

Primers for Amplifying Exons from the Genes BRCA1, BRCA2, PTEN, PI3KCA, APC, EGFR, TP53

| Primer plate well | Gene/chr | Name | F-primer | R-primer |
|---|---|---|---|---|
| H10 | APC | APC_00000972230_153 | ACACTGACGACATGGTTCTACACCG TTTCCTCAGGTGCTACAA (SEQ ID NO: 152) | TACGGTAGCAGAGACTTGGTCTGAA TCTTTAATGTTTGGATTTGCCTT (SEQ ID NO: 153) |
| A11 | APC | APC_00000972230_155 | ACACTGACGACATGGTTCTACACGG TGATTGACAGTGTTTCAG (SEQ ID NO: 154) | TACGGTAGCAGAGACTTGGTCTCTG ATACAGGGACAGGATTA (SEQ ID NO: 155) |
| B11 | APC | APC_00000972230_157 | ACACTGACGACATGGTTCTACATGG ATGCCCCTGACCAAAAA (SEQ ID NO: 156) | TACGGTAGCAGAGACTTGGTCTGCT TTTCCTAGGGCTTGGGT (SEQ ID NO: 157) |
| C11 | APC | APC_00000972230_159 | ACACTGACGACATGGTTCTACATCT AGCAGCTCAAGCAAACAC (SEQ ID NO: 158) | TACGGTAGCAGAGACTTGGTCTCCA CTGGATTCTGTGCTGTC (SEQ ID NO: 159) |
| D11 | APC | APC_00000972230_160 | ACACTGACGACATGGTTCTACACGC AGATAGCACTTCAGCTC (SEQ ID NO: 160) | TACGGTAGCAGAGACTTGGTCTAGA ATTTCTTAGTTTCATTCTTCCTCTC (SEQ ID NO: 161) |
| A1 | PTEN | PTEN_E00001456562_1 | ACACTGACGACATGGTTCTACAGCA GCTTCTGCCATCTCTCT (SEQ ID NO: 162) | TACGGTAGCAGAGACTTGGTCTCCG TCTACTCCCACGTTCT (SEQ ID NO: 163) |
| B1 | PTEN | PTEN_E00001156351_1 | ACACTGACGACATGGTTCTACATGCT GCATATTTCAGATATTTCTTTCCTTA (SEQ ID NO: 164) | TACGGTAGCAGAGACTTGGTCTATGA AAACACAACATGAATATAAACATCAAT (SEQ ID NO: 165) |
| C1 | PTEN | PTEN_E00001156344_1 | ACACTGACGACATGGTTCTACAATC TGTCTTTTGGTTTTTCTTGATAGT (SEQ ID NO: 166) | TACGGTAGCAGAGACTTGGTCTAAT AGTTGTTTTAGAAGATATTTGCAAGC (SEQ ID NO: 167) |
| D1 | PTEN | PTEN_E00001156337_4 | ACACTGACGACATGGTTCTACATATAT CACTTTTAAACTTTTCTTTTAGTTGTGC (SEQ ID NO: 168) | TACGGTAGCAGAGACTTGGTCTCGA TAATCTGGATGACTCATTATTGTT (SEQ ID NO: 169) |
| E1 | PTEN | PTEN_E00001156330_1 | ACACTGACGACATGGTTCTACAttCT TATTCTGAGGTTATCTTTTTACCAC (SEQ ID NO: 170) | TACGGTAGCAGAGACTTGGTCTCAT TACACCAGTTCGTCCCT (SEQ ID NO: 171) |
| F1 | PTEN | PTEN_E00001156330_3 | ACACTGACGACATGGTTCTACATGA CCAATGGCTAAGTGAAGATGA (SEQ ID NO: 172) | TACGGTAGCAGAGACTTGGTCTCCA GGAAGAGGAAAGGAAAAACA (SEQ ID NO: 173) |
| G1 | PTEN | PTEN_E00001156327_1 | ACACTGACGACATGGTTCTACATCT TAAATGGCTACGACCCAG (SEQ ID NO: 174) | TACGGTAGCAGAGACTTGGTCTCCA GATGATTCTTTAACAGGTAGC (SEQ ID NO: 175) |
| H1 | PTEN | PTEN_E00001156327_4 | ACACTGACGACATGGTTCTACAGTC AGAGGCGCTATGTGT (SEQ ID NO: 176) | TACGGTAGCAGAGACTTGGTCTAGA TATGGTTAAGAAAACTGTTCCA (SEQ ID NO: 177) |
| A2 | PTEN | PTEN_E00001156321_1 | ACACTGACGACATGGTTCTACATGA CAGTTTGACAGTTAAAGGCAT (SEQ ID NO: 178) | TACGGTAGCAGAGACTTGGTCTCAC ACACAGGTAACGGCTGA (SEQ ID NO: 179) |
| B2 | PTEN | PTEN_E00001156321_2 | ACACTGACGACATGGTTCTACATGT GGTCTGCCAGCTAAAGG (SEQ ID NO: 180) | TACGGTAGCAGAGACTTGGTCTCCC AATGAAAGTAAAGTACAAACC (SEQ ID NO: 181) |
| C2 | PTEN | PTEN_E00001156321_4 | ACACTGACGACATGGTTCTACATCC ACAAACAGAACAAGATGCT (SEQ ID NO: 182) | TACGGTAGCAGAGACTTGGTCTGG CCTTTTCCTTCAAACAGGATT (SEQ ID NO: 183) |
| D2 | PTEN | PTEN_E00001156315_1 | ACACTGACGACATGGTTCTACAGCA ACAGATAACTCAGATTGCCTT (SEQ ID NO: 184) | TACGGTAGCAGAGACTTGGTCTGTT TCCTCTGGTCCTGGTATGA (SEQ ID NO: 185) |
| E2 | PTEN | PTEN_E00001156315_5 | ACACTGACGACATGGTTCTACAGGA CAAAATGTTTCACTTTTGGGTAA (SEQ ID NO: 186) | TACGGTAGCAGAGACTTGGTCTACT AGATATTCCTTGTCATTATCTGCAC (SEQ ID NO: 187) |

TABLE 6-continued

Primers for Amplifying Exons from the Genes BRCA1, BRCA2, PTEN, PI3KCA, APC, EGFR, TP53

| Primer plate well | Gene/chr | Name | F-primer | R-primer |
|---|---|---|---|---|
| F2 | PTEN | PTEN_E00001156315_7 | ACACTGACGACATGGTTCTACACCT CAGAAAAAgTAGAAAATGGAAGTC (SEQ ID NO: 188) | TACGGTAGCAGAGACTTGGTCTACA AGTCAaCAACCCCCACA (SEQ ID NO: 189) |
| G2 | PTEN | PTEN_E00001456541_1 | ACACTGACGACATGGTTCTACAGAT GAGTcATATTTGTGGGTTTTCA (SEQ ID NO: 190) | TACGGTAGCAGAGACTTGGTCTGGA TCAGAGTCAGTGGT (SEQ ID NO: 191) |
| H2 | PTEN | PTEN_E00001456541_2 | ACACTGACGACATGGTTCTACAGTA GAGGAGCCGTCAAATCCA (SEQ ID NO: 192) | TACGGTAGCAGAGACTTGGTCTTCA TGGTGTTTTATCCCTCTTGA (SEQ ID NO: 193) |
| A3 | PIK3CA | PIK3CA_0001825398_1 | ACACTGACGACATGGTTCTACAGGT TTCTGCTTTGGGACAACC (SEQ ID NO: 194) | TACGGTAGCAGAGACTTGGTCTCCT CACGGAGGCATTCTAAAG (SEQ ID NO: 195) |
| B3 | PIK3CA | PIK3CA_0001825398_3 | ACACTGACGACATGGTTCTACAGTa GAATGTTTACTACCAAATGGAATG (SEQ ID NO: 196) | TACGGTAGCAGAGACTTGGTCTCAC AAAGTCGTCTTGTTTCATCA (SEQ ID NO: 197) |
| C3 | PIK3CA | PIK3CA_0001825398_4 | ACACTGACGACATGGTTCTACAGCA AGAAAATACCCCCTCCA (SEQ ID NO: 198) | TACGGTAGCAGAGACTTGGTCTGAT CTTTTCTTCACGGTTGCC (SEQ ID NO: 199) |
| D3 | PIK3CA | PIK3CA_1825398_3 | ACACTGACGACATGGTTCTACAGAC GACTTTGTGACCTTCGG (SEQ ID NO: 200) | TACGGTAGCAGAGACTTGGTCTTTT AGAAAGGGACAACAGTTAAGC (SEQ ID NO: 201) |
| E3 | PIK3CA | PIK3CA_0000997375_1 | ACACTGACGACATGGTTCTACATGT TCATGCTGTGTATGTAATAGAA (SEQ ID NO: 202) | TACGGTAGCAGAGACTTGGTCTACA TACATTGCTCTACTATGAGGTGA (SEQ ID NO: 203) |
| F3 | PIK3CA | PIK3CA_0000997375_3 | ACACTGACGACATGGTTCTACATTC TgAAcGTTTGTAAAGAAGCTGT (SEQ ID NO: 204) | TACGGTAGCAGAGACTTGGTCTGATT AGAGTAGATTAGTCATTTTCTTACCTT (SEQ ID NO: 205) |
| G3 | PIK3CA | PIK3CA_997375_3 | ACACTGACGACATGGTTCTACACCA GAATTGCCAAAGCACA (SEQ ID NO: 206) | TACGGTAGCAGAGACTTGGTCTATT TAGCACTCAACTATATCTTGTCAG (SEQ ID NO: 207) |
| H3 | PIK3CA | PIK3CA_0001077693_1 | ACACTGACGACATGGTTCTACACCC TTGAAAAATGAAAGAGAGATGGT (SEQ ID NO: 208) | TACGGTAGCAGAGACTTGGTCTCAG AGGATAGCAACATACTTCGAG (SEQ ID NO: 209) |
| A4 | PIK3CA | PIK3CA_1077693_2 | ACACTGACGACATGGTTCTACACCA TGACTGTGTACCAGAAC (SEQ ID NO: 210) | TACGGTAGCAGAGACTTGGTCTAAC TTGTTACTCACCTTATACTGACT (SEQ ID NO: 211) |
| B4 | PIK3CA | PIK3CA_0001077692_1 | ACACTGACGACATGGTTCTACATGA AAAACCTTACAGGAAATGGC (SEQ ID NO: 212) | TACGGTAGCAGAGACTTGGTCTGTG GAAATGCGTCTGGAATAAGA (SEQ ID NO: 213) |
| C4 | PIK3CA | PIK3CA_0001077692_3 | ACACTGACGACATGGTTCTACAGCC TTTATTCTCAACTGCCAA (SEQ ID NO: 214) | TACGGTAGCAGAGACTTGGTCTAGC ATCAGCATTTGACTTTACCT (SEQ ID NO: 215) |
| D4 | PIK3CA | PIK3CA_0001077692_4 | ACACTGACGACATGGTTCTACATCT ACAAAATCCCTTTGGGT (SEQ ID NO: 216) | TACGGTAGCAGAGACTTGGTCTGAA AACATACTACAGGTCAACAGA (SEQ ID NO: 217) |
| E4 | PIK3CA | PIK3CA_0001077694_1 | ACACTGACGACATGGTTCTACATCG AGTGTGTGCATATGTGT (SEQ ID NO: 218) | TACGGTAGCAGAGACTTGGTCTACT GCTAAACACTAATATAACCTTTGGA (SEQ ID NO: 219) |
| F4 | PIK3CA | PIK3CA_0001077691_5 | ACACTGACGACATGGTTCTACAATT TTACATAGGTGGAATGAATGGCTGA (SEQ ID NO: 220) | TACGGTAGCAGAGACTTGGTCTATC AGCGGTATAATCAGGAGTTTTAAAGG (SEQ ID NO: 221) |
| G4 | PIK3CA | PIK3CA_0001128465_1 | ACACTGACGACATGGTTCTACAGG GAAGAAAAGTGTTTTGAAATGTGT (SEQ ID NO: 222) | TACGGTAGCAGAGACTTGGTCTACA CCAATAGGGTTCAGCAAA (SEQ ID NO: 223) |

TABLE 6-continued

Primers for Amplifying Exons from the Genes BRCA1, BRCA2, PTEN, PI3KCA, APC, EGFR, TP53

| Primer plate well | Gene/ chr | Name | F-primer | R-primer |
|---|---|---|---|---|
| H4 | PIK3CA | PIK3CA_0001128465_3 | ACACTGACGACATGGTTCTACATCT TTGGCCAGTACCTCATGG (SEQ ID NO: 224) | TACGGTAGCAGAGACTTGGTCTCAC ACTGCTGAACCAGTCAA (SEQ ID NO: 225) |
| A5 | PIK3CA | PIK3CA_0001128465_5 | ACACTGACGACATGGTTCTACATGG CAGTCAAACCTTCTCTCTT (SEQ ID NO: 226) | TACGGTAGCAGAGACTTGGTCTACC AGTCCTGCGTGGGAA (SEQ ID NO: 227) |
| B5 | PIK3CA | PIK3CA_1128465_2 | ACACTGACGACATGGTTCTACAGAC TGGTTCAGCAGTGTGGT (SEQ ID NO: 228) | TACGGTAGCAGAGACTTGGTCTGCC AGTAAAATATAtGGATCCTTTTCCA (SEQ ID NO: 229) |
| C5 | PIK3CA | PIK3CA_0001077674_1 | ACACTGACGACATGGTTCTACATGC TTTTTCTGTAAATCATCTGTGAA (SEQ ID NO: 230) | TACGGTAGCAGAGACTTGGTCTGTA GAAATTGCTTTGAGCTGTTCTT (SEQ ID NO: 231) |
| D5 | PIK3CA | PIK3CA_0000826291_1 | ACACTGACGACATGGTTCTACATCA ACCTTTTGAACAGCATGCAA (SEQ ID NO: 232) | TACGGTAGCAGAGACTTGGTCTGAG AGAAAACAATTTAAGTGACATACCA (SEQ ID NO: 233) |
| E5 | PIK3CA | PIK3CA_0000826292_1 | ACACTGACGACATGGTTCTACAGGC AGTGTTTTAGATGGCTCA (SEQ ID NO: 234) | TACGGTAGCAGAGACTTGGTCTCCA AGCACcGAACAGCAAAA (SEQ ID NO: 235) |
| F5 | PIK3CA | PIK3CA_0000826292_2 | ACACTGACGACATGGTTCTACAtTCT CATACACAGATGTATTGCTTGG (SEQ ID NO: 236) | TACGGTAGCAGAGACTTGGTCTaCcA TGTACTAGCTGAATTAAATACTGAGAA (SEQ ID NO: 237) |
| G5 | PIK3CA | PIK3CA_0000826293_1 | ACACTGACGACATGGTTCTACATCG GCCATGCAGAAACTGA (SEQ ID NO: 238) | TACGGTAGCAGAGACTTGGTCTACC TTAAGAATTTAATGGGAAAATAATTA GACTT (SEQ ID NO: 239) |
| H5 | PIK3CA | PIK3CA_0000826294_1 | ACACTGACGACATGGTTCTACAATGA GTGTTTAAATTGTTTAGCAAAGATTA (SEQ ID NO: 240) | TACGGTAGCAGAGACTTGGTCTGCC TcGACTTGCCTATTCA (SEQ ID NO: 241) |
| A6 | PIK3CA | PIK3CA_0000826294_2 | ACACTGACGACATGGTTCTACACCA GAGGTTTGGCCTGCTT (SEQ ID NO: 242) | TACGGTAGCAGAGACTTGGTCTGAAA AGAGTCTCAAACACAaACTAGAGTCA (SEQ ID NO: 243) |
| B6 | PIK3CA | PIK3CA_0000826295_1 | ACACTGACGACATGGTTCTACATGT GAGAAAGAGATTAGCAGTTAGTT (SEQ ID NO: 244) | TACGGTAGCAGAGACTTGGTCTCAA TGAAACCCCCAAGAAAGT (SEQ ID NO: 245) |
| C6 | PIK3CA | PIK3CA_0000826296_1 | ACACTGACGACATGGTTCTACAtcAG GGTAAAATAATAATAAAGCAAAGGT (SEQ ID NO: 246) | TACGGTAGCAGAGACTTGGTCTACT CTTCCTTACCATCCCCAT (SEQ ID NO: 247) |
| D6 | PIK3CA | PIK3CA_0000826296_2 | ACACTGACGACATGGTTCTACAGGC CACTGTGGTTGAATTGG (SEQ ID NO: 248) | TACGGTAGCAGAGACTTGGTCTGG CTTTCAGTAGTTTTcATGGTTCA (SEQ ID NO: 249) |
| E6 | PIK3CA | PIK3CA_0000826297_1 | ACACTGACGACATGGTTCTACATGA TGGCGTGATCCCCAAAT (SEQ ID NO: 250) | TACGGTAGCAGAGACTTGGTCTACT TTCAACATACAGGTTGCCTT (SEQ ID NO: 251) |
| F6 | PIK3CA | PIK3CA_0000826298_1 | ACACTGACGACATGGTTCTACACTA ATAAAATACTCATGTTTTAGCCTGTT (SEQ ID NO: 252) | TACGGTAGCAGAGACTTGGTCTTTC AAGCCGCCTTTGC (SEQ ID NO: 253) |
| G6 | PIK3CA | PIK3CA_0000826298_2 | ACACTGACGACATGGTTCTACATGT GGGACTTATTGAGGTGGTG (SEQ ID NO: 254) | TACGGTAGCAGAGACTTGGTCTACA CAAACACCgACAGACTCA (SEQ ID NO: 255) |
| H6 | PIK3CA | PIK3CA_0000826299_1 | ACACTGACGACATGGTTCTACATCT CAAGTTGGCCTGAATCACT (SEQ ID NO: 256) | TACGGTAGCAGAGACTTGGTCTCCA AAACATTTTAAACAGAGAAAACCA (SEQ ID NO: 257) |
| C7 | PIK3CA | PIK3CA_0001139987_1 | ACACTGACGACATGGTTCTACATGC TCCAAACTGACCAAACTG (SEQ ID NO: 258) | TACGGTAGCAGAGACTTGGTCTGCT AGgGTCTTTCGAATGTATGC (SEQ ID NO: 259) |

TABLE 6-continued

Primers for Amplifying Exons from the Genes BRCA1, BRCA2, PTEN, PI3KCA, APC, EGFR, TP53

| Primer plate well | Gene/chr | Name | F-primer | R-primer |
|---|---|---|---|---|
| A1 | EGFR | EGFR_E00001633131-1 | ACACTGACGACATGGTTCTACAGCCAACGCCACAACCAC (SEQ ID NO: 260) | TACGGTAGCAGAGACTTGGTCTggcgAGACACGCCCTTAC (SEQ ID NO: 261) |
| B1 | EGFR | EGFR_E00001882478-1 | ACACTGACGACATGGTTCTACACCTGGACCTTGAGGGATTG (SEQ ID NO: 262) | TACGGTAGCAGAGACTTGGTCTTCCCAAGGACCACCTCACA (SEQ ID NO: 263) |
| C1 | EGFR | EGFR_E00001882478_2 | ACACTGACGACATGGTTCTACACGCAGTTGGGCACTTTTG (SEQ ID NO: 264) | TACGGTAGCAGAGACTTGGTCTCCCAGGCctTTCTCCACTTA (SEQ ID NO: 265) |
| D1 | EGFR | EGFR_E00001704157_1 | ACACTGACGACATGGTTCTACAGGCTCCCTGGACCCATTTTA (SEQ ID NO: 266) | TACGGTAGCAGAGACTTGGTCTACTGCTAAGGCATAGGAATTTTCG (SEQ ID NO: 267) |
| E1 | EGFR | EGFR_E00001704157_2 | ACACTGACGACATGGTTCTACACAGTGGAGCgAATTCCTTT (SEQ ID NO: 268) | TACGGTAGCAGAGACTTGGTCTGGGAGCCATCGGAACTG (SEQ ID NO: 269) |
| F1 | EGFR | EGFR_E00001688856_1 | ACACTGACGACATGGTTCTACATGCTCACCGCAGTTCCATTC (SEQ ID NO: 270) | TACGGTAGCAGAGACTTGGTCTCCCCCATAGGAGCTGGAG (SEQ ID NO: 271) |
| G1 | EGFR | EGFR_E00001683983_1 | ACACTGACGACATGGTTCTACAGGGAAAGGGCGTCATCAGTT (SEQ ID NO: 272) | TACGGTAGCAGAGACTTGGTCTAGCAAGTGAAGGAAGAGAGGG (SEQ ID NO: 273) |
| H1 | EGFR | EGFR_E00001652975_1 | ACACTGACGACATGGTTCTACATGATCCTACCCTCACTCTTCA (SEQ ID NO: 274) | TACGGTAGCAGAGACTTGGTCTCCAGGGAGGCTGCT (SEQ ID NO: 275) |
| A2 | EGFR | EGFR_E00001623732_1 | ACACTGACGACATGGTTCTACAGTGTGGCgCTGAGTGTACTT (SEQ ID NO: 276) | TACGGTAGCAGAGACTTGGTCTAGGTGGCACCAAAGCTGTAT (SEQ ID NO: 277) |
| B2 | EGFR | EGFR_E00001623732_2 | ACACTGACGACATGGTTCTACACCATAGGTCTGCCGCAAATTC (SEQ ID NO: 278) | TACGGTAGCAGAGACTTGGTCTGACAGAGCGGGACAAGGATG (SEQ ID NO: 279) |
| C2 | EGFR | EGFR_E00001694314_1 | ACACTGACGACATGGTTCTACACCTGGTGCCACCGTCATC (SEQ ID NO: 280) | TACGGTAGCAGAGACTTGGTCTCAGCAGCcGAGAACAAG (SEQ ID NO: 281) |
| D2 | EGFR | EGFR_E00001639282_1 | ACACTGACGACATGGTTCTACAGTGGATCCCTAGCTATTCTTAATCCA (SEQ ID NO: 282) | TACGGTAGCAGAGACTTGGTCTAACCTGTGACTCACCCCCTA (SEQ ID NO: 283) |
| E2 | EGFR | EGFR_E00001639282_2 | ACACTGACGACATGGTTCTACACTCACTCTCCATAAATGCTACGA (SEQ ID NO: 284) | TACGGTAGCAGAGACTTGGTCTGTGTGAAGGAGTCACTGAAACA (SEQ ID NO: 285) |
| F2 | EGFR | EGFR_E00001639282_3 | ACACTGACGACATGGTTCTACATGCTTGTATAAAGAAAAACAAAATCTGC (SEQ ID NO: 286) | TACGGTAGCAGAGACTTGGTCTCTCTAAAACACTGATTTCCCA (SEQ ID NO: 287) |
| G2 | EGFR | EGFR_E00001084926_1 | ACACTGACGACATGGTTCTACAGTCCCTGAGAGTCTAGAGTAATGT (SEQ ID NO: 288) | TACGGTAGCAGAGACTTGGTCTACCAGGCTTTGGCTGTG (SEQ ID NO: 289) |
| H2 | EGFR | EGFR_E00001084941_1 | ACACTGACGACATGGTTCTACAAAGTTTTCAGGGATACATTGTTTTAT (SEQ ID NO: 290) | TACGGTAGCAGAGACTTGGTCTACAGTTTTTTCCAGTTTATTGTATTTGC (SEQ ID NO: 291) |
| A3 | EGFR | EGFR_E00001084941_2 | ACACTGACGACATGGTTCTACATCCTTGGGATTACGCTCCCT (SEQ ID NO: 292) | TACGGTAGCAGAGACTTGGTCTGGACCCATTAGAACCAACTCCA (SEQ ID NO: 293) |
| B3 | EGFR | EGFR_E00001084939_1 | ACACTGACGACATGGTTCTACATCTCCTCCGGCCCCTC (SEQ ID NO: 294) | TACGGTAGCAGAGACTTGGTCTAACCTCCTACCCCTCCAGAA (SEQ ID NO: 295) |

TABLE 6-continued

Primers for Amplifying Exons from the Genes BRCA1, BRCA2, PTEN, PI3KCA, APC, EGFR, TP53

| Primer plate well | Gene/chr | Name | F-primer | R-primer |
|---|---|---|---|---|
| C3 | EGFR | EGFR_E00001084939_2 | ACACTGACGACATGGTTCTACATCTCTTGCCGGAATGTCAGC (SEQ ID NO: 296) | TACGGTAGCAGAGACTTGGTCTCCCCACAGAAAACCCA (SEQ ID NO: 297) |
| D3 | EGFR | EGFR_E00001084927_1 | ACACTGACGACATGGTTCTACATTGAAGAGGTGATTTGTGTTCCTG (SEQ ID NO: 298) | TACGGTAGCAGAGACTTGGTCTGAcGTGGATAGCAGCAAGGG (SEQ ID NO: 299) |
| E3 | EGFR | EGFR_E00001627115_1 | ACACTGACGACATGGTTCTACACTTCCATTTTGAAAGAGAAAAGAAAGAG (SEQ ID NO: 300) | TACGGTAGCAGAGACTTGGTCTgGCGTCTGCGTACTTCCA (SEQ ID NO: 301) |
| F3 | EGFR | EGFR_E00001627115_2 | ACACTGACGACATGGTTCTACATTGACGGCCCCCAC (SEQ ID NO: 302) | TACGGTAGCAGAGACTTGGTCTTGCCgGAAAACTTGGGAGA (SEQ ID NO: 303) |
| G3 | EGFR | EGFR_E00001802824_3 | ACACTGACGACATGGTTCTACAAAAATGTTAGTGGTCATTTTTCTAATGTCT (SEQ ID NO: 304) | TACGGTAGCAGAGACTTGGTCTAGTGTCAGGACTTTATTTGAAGCA (SEQ ID NO: 305) |
| H3 | EGFR | EGFR_E0000137151_1 | ACACTGACGACATGGTTCTACAtGTACTTGTCCATCTTTCTCCAG (SEQ ID NO: 306) | TACGGTAGCAGAGACTTGGTCTCCCAACCCAGCTGAAACTCT (SEQ ID NO: 307) |
| A4 | EGFR | EGFR_E00001371541_3 | ACACTGACGACATGGTTCTACATAATGATGGCAGCGTGTCCC (SEQ ID NO: 308) | TACGGTAGCAGAGACTTGGTCTGGGAACAGACAcGTGAAGGC (SEQ ID NO: 309) |
| B4 | EGFR | EGFR_E00001768076_1 | ACACTGACGACATGGTTCTACATGCCAAAGAAGTAGAATGAGAAAAATG (SEQ ID NO: 310) | TACGGTAGCAGAGACTTGGTCTAGGACAGTCAGAAATGCAGGA (SEQ ID NO: 311) |
| C4 | EGFR | EGFR_E00001699330_1 | ACACTGACGACATGGTTCTACAGGAAAAgTGTGCCTGGTAGGG (SEQ ID NO: 312) | TACGGTAGCAGAGACTTGGTCTGGAGGAACAAGGAAGGGTG (SEQ ID NO: 313) |
| D4 | EGFR | EGFR_E00001699330_2 | ACACTGACGACATGGTTCTACAGCTACATAGTGTCTCACTTTCCAA (SEQ ID NO: 314) | TACGGTAGCAGAGACTTGGTCTGATCCCCAGGGCCACCA (SEQ ID NO: 315) |
| E4 | EGFR | EGFR_E00001699330_4 | ACACTGACGACATGGTTCTACAGCCCTCCTCTTGCTGCT (SEQ ID NO: 316) | TACGGTAGCAGAGACTTGGTCTGTATcTAACATACACAACTGCTAATGG (SEQ ID NO: 317) |
| F4 | EGFR | EGFR_E00001778519_1 | ACACTGACGACATGGTTCTACATGGTGAGGGCTGAGGTG (SEQ ID NO: 318) | TACGGTAGCAGAGACTTGGTCTcCTGTGCCAGGGACCTTAC (SEQ ID NO: 319) |
| G4 | EGFR | EGFR_Exon19 | ACACTGACGACATGGTTCTACATCACAATTGCCAGTTAACGTCT (SEQ ID NO: 320) | TACGGTAGCAGAGACTTGGTCTCCACACAGCAAAGCAGAAAC (SEQ ID NO: 321) |
| H4 | EGFR | EGFR_E00001601336_1 | ACACTGACGACATGGTTCTACAGCGTCTTCACCTGGAAGGG (SEQ ID NO: 322) | TACGGTAGCAGAGACTTGGTCTCCGGACATAGTCCAGGAGG (SEQ ID NO: 323) |
| A5 | EGFR | EGFR_E00001601336_2 | ACACTGACGACATGGTTCTACAGCGTGGACAACCCCCAC (SEQ ID NO: 324) | TACGGTAGCAGAGACTTGGTCTGGCTCCTTATCTCCCCTCC (SEQ ID NO: 325) |
| B5 | EGFR | EGFR_E00001681524_1 | ACACTGACGACATGGTTCTACAGGATGCAGAGCTTCTTCCCA (SEQ ID NO: 326) | TACGGTAGCAGAGACTTGGTCTTTCTCTTCCGCACCCAG (SEQ ID NO: 327) |
| C5 | EGFR | EGFR_E00001681524_2 | ACACTGACGACATGGTTCTACAGGTCTTCTCTGTTTCAGGGCAT (SEQ ID NO: 328) | TACGGTAGCAGAGACTTGGTCTGCTGACCTAAAGCCACCTCC (SEQ ID NO: 329) |
| D5 | EGFR | EGFR_E00001631695_1 | ACACTGACGACATGGTTCTACAGTGTCACTCGTAATTAGGTCCA (SEQ ID NO: 330) | TACGGTAGCAGAGACTTGGTCTGGCCTCAGTACAAACTCATTAGC (SEQ ID NO: 331) |

TABLE 6-continued

Primers for Amplifying Exons from the Genes BRCA1, BRCA2, PTEN, PI3KCA, APC, EGFR, TP53

| Primer plate well | Gene/chr | Name | F-primer | R-primer |
|---|---|---|---|---|
| E5 | EGFR | EGFR_E00001779947_1 | ACACTGACGACATGGTTCTACATGT TCATTCATGATCCCACTGC (SEQ ID NO: 332) | TACGGTAGCAGAGACTTGGTCTCCA CCAGTCACTCACACTTG (SEQ ID NO: 333) |
| F5 | EGFR | EGFR_E00001779947_2 | ACACTGACGACATGGTTCTACATCC CTGCCAGCGAGAT (SEQ ID NO: 334) | TACGGTAGCAGAGACTTGGTCTAGG GATGCAAAGGCCTCA (SEQ ID NO: 335) |
| G5 | EGFR | EGFR_E00001790701_1 | ACACTGACGACATGGTTCTACAGCC TTCTTTAAGCAATGCCATCTTTAT (SEQ ID NO: 336) | TACGGTAGCAGAGACTTGGTCTCAA TGGAAGCaCAGACTGCAA (SEQ ID NO: 337) |
| H5 | EGFR | EGFR_E00001801208_1 | ACACTGACGACATGGTTCTACACCC CTGCTCCTATAGCCAA (SEQ ID NO: 338) | TACGGTAGCAGAGACTTGGTCTATG AGGTACTCGTCGGCATC (SEQ ID NO: 339) |
| A6 | EGFR | EGFR_E00001801208_2 | ACACTGACGACATGGTTCTACAACT TCTACCGTGCCCTGA (SEQ ID NO: 340) | TACGGTAGCAGAGACTTGGTCTGTT CAAATGAGTAGACACAGCTT (SEQ ID NO: 341) |
| B6 | EGFR | EGFR_E00001773562_1 | ACACTGACGACATGGTTCTACATAC CCTCCATGAGGCACAC (SEQ ID NO: 342) | TACGGTAGCAGAGACTTGGTCTGGA GAgCTGTAAATTCTGGCTT (SEQ ID NO: 343) |
| C6 | EGFR | EGFR_E00001610532_1 | ACACTGACGACATGGTTCTACAccct gACCGGAGTAACCTTC (SEQ ID NO: 344) | TACGGTAGCAGAGACTTGGTCTAGG AGCAGGACTGTTTCCAG (SEQ ID NO: 345) |
| D6 | EGFR | EGFR_E00001610532_4 | ACACTGACGACATGGTTCTACAGAC GACACCTTCCTCCCAGT (SEQ ID NO: 346) | TACGGTAGCAGAGACTTGGTCTGCA GGCTCGGTCATGTGTTTA (SEQ ID NO: 347) |
| E6 | EGFR | EGFR_E00001245887_1 | ACACTGACGACATGGTTCTACATGT TGAGGACATTCACAGGGT (SEQ ID NO: 348) | TACGGTAGCAGAGACTTGGTCTGGT CCTGGTAGTGTGGGTCT (SEQ ID NO: 349) |
| F6 | EGFR | EGFR_E00001245887_2 | ACACTGACGACATGGTTCTACAGCT CTGTGCAGAATCCTGTCT (SEQ ID NO: 350) | TACGGTAGCAGAGACTTGGTCTTTG GTGGcTGCCTTTCTGG (SEQ ID NO: 351) |
| G6 | EGFR | EGFR_E00001245887_3 | ACACTGACGACATGGTTCTACAGCA ACCCCGAGTATCTCAACA (SEQ ID NO: 352) | TACGGTAGCAGAGACTTGGTCTGC GCGACCCTTAGGTATTCT (SEQ ID NO: 353) |
| H6 | EGFR | EGFR_Exon28-2 | ACACTGACGACATGGTTCTACATGT CAACAGCACATTCGACAG (SEQ ID NO: 354) | TACGGTAGCAGAGACTTGGTCTGGT CCTGGGTATCGAAAGAGT (SEQ ID NO: 355) |
| A1 | TP53 | TP53_E00001757276_1 | ACACTGACGACATGGTTCTACAGAC CCAAAACCCAAAATGGC (SEQ ID NO: 356) | TACGGTAGCAGAGACTTGGTCTCCC TGCTTCTGTCTCCTAC (SEQ ID NO: 357) |
| B1 | TP53 | TP53_E00001728015_1 | ACACTGACGACATGGTTCTACAGGA ATCCTATGGCTTTCCAACC (SEQ ID NO: 358) | TACGGTAGCAGAGACTTGGTCTCCC CCTCCTCTGTTGCTG (SEQ ID NO: 359) |
| C1 | TP53 | TP53_00001404886_13 | ACACTGACGACATGGTTCTACAtctgT ATCAGGCAAAGTCATAGAA (SEQ ID NO: 360) | TACGGTAGCAGAGACTTGGTCTGCC TCAAAGACAATGGCTCC (SEQ ID NO: 361) |
| D1 | TP53 | TP53_E00001789298_1 | ACACTGACGACATGGTTCTACAGAA AACGGCATTTTGAGTGT (SEQ ID NO: 362) | TACGGTAGCAGAGACTTGGTCTAAG GGTGCAGTTATGCCTCA (SEQ ID NO: 363) |
| E1 | TP53 | TP53_E00001789298_2 | ACACTGACGACATGGTTCTACACTG GTGtTGTTGGGCAGT (SEQ ID NO: 364) | TACGGTAGCAGAGACTTGGTCTATC TCCgCAAGAAAGGGGAG (SEQ ID NO: 365) |
| F1 | TP53 | TP53_E00001789298_3 | ACACTGACGACATGGTTCTACATGT CCTGCTTGCTTACCTCG (SEQ ID NO: 366) | TACGGTAGCAGAGACTTGGTCTGCC TCTTGCTTCTCTTTTCCT (SEQ ID NO: 367) |

TABLE 6-continued

Primers for Amplifying Exons from the Genes BRCA1, BRCA2, PTEN, PI3KCA, APC, EGFR, TP53

| Primer plate well | Gene/chr | Name | F-primer | R-primer |
|---|---|---|---|---|
| G1 | TP53 | TP53_E00001665758_1 | ACACTGACGACATGGTTCTACAGGGGTCAGaGGCAAGCAG (SEQ ID NO: 368) | TACGGTAGCAGAGACTTGGTCTTGGGCCTGTGTTATCTCC (SEQ ID NO: 369) |
| H1 | TP53 | TP53_E00001255919_1 | ACACTGACGACATGGTTCTACAGAGAAAGCCCCCCTACTGC (SEQ ID NO: 370) | TACGGTAGCAGAGACTTGGTCTAGCATCTTATCCGAGTGGAAGG (SEQ ID NO: 371) |
| A2 | TP53 | TP53_E00001255919_3 | ACACTGACGACATGGTTCTACATCCAAATACTCCACACGCAAA (SEQ ID NO: 372) | TACGGTAGCAGAGACTTGGTCTgCTGCCCCCACCATGAG (SEQ ID NO: 373) |
| B2 | TP53 | TP53_E00001255919_5 | ACACTGACGACATGGTTCTACAGCTGCTCACCATCGCTA (SEQ ID NO: 374) | TACGGTAGCAGAGACTTGGTCTCCAACTGgCCAAGACCT (SEQ ID NO: 375) |
| C2 | TP53 | TP53_E00001255919_6 | ACACTGACGACATGGTTCTACATGTGCTGTGACTGCTTGTAG (SEQ ID NO: 376) | TACGGTAGCAGAGACTTGGTCTGCCCTGACTTTCAACTCTGT (SEQ ID NO: 377) |
| D2 | TP53 | TP53_E00001612188_1 | ACACTGACGACATGGTTCTACATACGGCCAGGCATTGAAGT (SEQ ID NO: 378) | TACGGTAGCAGAGACTTGGTCTCCTCCTGGCCCCTGTC (SEQ ID NO: 379) |
| E2 | TP53 | TP53_E00001612188_2 | ACACTGACGACATGGTTCTACAGGAAACCGTAGCTGCCCTG (SEQ ID NO: 380) | TACGGTAGCAGAGACTTGGTCTAAGACCCAGGTCCAGATGAA (SEQ ID NO: 381) |
| G2 | TP53 | TP53_E00001596491_1 | ACACTGACGACATGGTTCTACATTTCGCTTCCCACAGGTCTC (SEQ ID NO: 382) | TACGGTAGCAGAGACTTGGTCTCAGCCAGACTGCCTTCCG (SEQ ID NO: 383) |
| A1 | BRCA1 | BRCA1_210_28486_164 | ACACTGACGACATGGTTCTACAATATTTAGTAGCCAGGACAGTAGAAG (SEQ ID NO: 384) | TACGGTAGCAGAGACTTGGTCTCtcTAccAgTGCCAGGAGC (SEQ ID NO: 385) |
| B1 | BRCA1 | BRCA1_210_28486_165 | ACACTGACGACATGGTTCTACAATCTGGGGTATCAGGTAGGTGTC (SEQ ID NO: 386) | TACGGTAGCAGAGACTTGGTCTCCTGGAGTCGATTGATTAGAGCC (SEQ ID NO: 387) |
| C1 | BRCA1 | BRCA1_210_41199761 | ACACTGACGACATGGTTCTACAaagGACCCCATATAGCACAGGTA (SEQ ID NO: 388) | TACGGTAGCAGAGACTTGGTCTACACTTTGAATGCTCTTTCCTTCC (SEQ ID NO: 389) |
| D1 | BRCA1 | BRCA1_210_44080_1 | ACACTGACGACATGGTTCTACAGGTGCCAGTCTTGCTCACAG (SEQ ID NO: 390) | TACGGTAGCAGAGACTTGGTCTGTAGAGGGCCTGGGTTAAGTATG (SEQ ID NO: 391) |
| E1 | BRCA1 | BRCA1_210_30488_1 | ACACTGACGACATGGTTCTACATCAACTTGAGGGAGGGAGCTTTA (SEQ ID NO: 392) | TACGGTAGCAGAGACTTGGTCTATATGACGTGTCTGCTCCACTTC (SEQ ID NO: 393) |
| F1 | BRCA1 | BRCA1_210_95889_1 | ACACTGACGACATGGTTCTACAGAAAGTGGTGCATTGATGGAAGG (SEQ ID NO: 394) | TACGGTAGCAGAGACTTGGTCTAAGAGCACGTTCTTCTGCTGTAT (SEQ ID NO: 395) |
| G1 | BRCA1 | BRCA1_210_140341 | ACACTGACGACATGGTTCTACATGCAATTCTGAGGTGTTAAAGGGA (SEQ ID NO: 396) | TACGGTAGCAGAGACTTGGTCTGGACAGCAcTTCCTGATTTTGTT (SEQ ID NO: 397) |
| H1 | BRCA1 | BRCA1_210_78044_1 | ACACTGACGACATGGTTCTACAcgccTCATGTGGTTTTATGCAG (SEQ ID NO: 398) | TACGGTAGCAGAGACTTGGTCTACTAGTATTCTGAGCTGTGTGC (SEQ ID NO: 399) |
| A2 | BRCA1 | BRCA1_210_97215_1 | ACACTGACGACATGGTTCTACATACCtACATAAAACTCTTTCCAGAATGT (SEQ ID NO: 400) | TACGGTAGCAGAGACTTGGTCTGCAatgGAAGAAagtGTGAGCAG (SEQ ID NO: 401) |
| B2 | BRCA1 | BRCA1_210_97215_2 | ACACTGACGACATGGTTCTACATGTTAAGTCTTAGTCATTAGGGAGATACA (SEQ ID NO: 402) | TACGGTAGCAGAGACTTGGTCTAGaGTcCAgctGCTGCTCATA (SEQ ID NO: 403) |

TABLE 6-continued

Primers for Amplifying Exons from the Genes BRCA1, BRCA2, PTEN, PI3KCA, APC, EGFR, TP53

| Primer plate well | Gene/chr | Name | F-primer | R-primer |
|---|---|---|---|---|
| C2 | BRCA1 | BRCA1_210_23203_1 | ACACTGACGACATGGTTCTACAAAG cTGTCAATTCTgGCTTCTCC (SEQ ID NO: 404) | TACGGTAGCAGAGACTTGGTCTcAa CCTCTGCATTGaAAGTTCCC (SEQ ID NO: 405) |
| D2 | BRCA1 | BRCA1_210_23203_2 | ACACTGACGACATGGTTCTACATGC ATTATAcCCAgCAGTATCAG (SEQ ID NO: 406) | TACGGTAGCAGAGACTTGGTCTAAc cCcTTAcCtGGAATCTGGA (SEQ ID NO: 407) |
| E2 | BRCA1 | BRCA1_210_97215_16 | ACACTGACGACATGGTTCTACAtCA ATGCAGAGGtTgAAGATGGT (SEQ ID NO: 408) | TACGGTAGCAGAGACTTGGTCTACT TTGTAATTCAACATTCATCGTTGTG (SEQ ID NO: 409) |
| F2 | BRCA1 | BRCA1_210_21142_01 | ACACTGACGACATGGTTCTACATGT AGGATTCAGAGTAAAATCAAAGTGT (SEQ ID NO: 410) | TACGGTAGCAGAGACTTGGTCTTGC TCTGGGAGTCTTcAGAATAGA (SEQ ID NO: 411) |
| G2 | BRCA1 | BRCA1_210_26566_1 | ACACTGACGACATGGTTCTACAGTG TTTGTTCCAATACAGCAGATGA (SEQ ID NO: 412) | TACGGTAGCAGAGACTTGGTCTTAC ATGCAcagTTGCTCTGGG (SEQ ID NO: 413) |
| H2 | BRCA1 | BRCA1_210_26566_2 | ACACTGACGACATGGTTCTACATcC TcttGAGATGGGtAGTTTCTAT (SEQ ID NO: 414) | TACGGTAGCAGAGACTTGGTCTCTG CCCAGcAAGTATGATTTGTC (SEQ ID NO: 415) |
| A3 | BRCA1 | BRCA1_210_21142_12 | ACACTGACGACATGGTTCTACAtgTG CATGTAcCACcTaTCATCTAA (SEQ ID NO: 416) | TACGGTAGCAGAGACTTGGTCTGG GCTCTTTTTTGCCAGTCATTT (SEQ ID NO: 417) |
| B3 | BRCA1 | BRCA1_210_16775_1 | ACACTGACGACATGGTTCTACAGAT GTCAGATACCACAGCATCTT (SEQ ID NO: 418) | TACGGTAGCAGAGACTTGGTCTTGT TTTCTCATTcCATTTAAAGCAGTA (SEQ ID NO: 419) |
| C3 | BRCA1 | BRCA1_210_1516237_1m | ACACTGACGACATGGTTCTACAGCC AGAACCACCATCTTTCAGTA (SEQ ID NO: 420) | TACGGTAGCAGAGACTTGGTCTTTT TTGAACAGTACCCGTTCCCT (SEQ ID NO: 421) |
| D3 | BRCA1 | BRCA1_210_18525_1 | ACACTGACGACATGGTTCTACAGG GAAGGAAAGAATTTTGCTTAAGAT (SEQ ID NO: 422) | TACGGTAGCAGAGACTTGGTCTGaT AAAgCtCcAGCAGGAAATGG (SEQ ID NO: 423) |
| E3 | BRCA1 | BRCA1_210_18525_10 | ACACTGACGACATGGTTCTACAGTT AGAAGGCTGGCTCCC (SEQ ID NO: 424) | TACGGTAGCAGAGACTTGGTCTTGG AAAGCTTCTCAAAGTATTTCATTTT (SEQ ID NO: 425) |
| F3 | BRCA1 | BRCA1_210_58415_1 | ACACTGACGACATGGTTCTACATAC TGAATGCAAAGGACACCACA (SEQ ID NO: 426) | TACGGTAGCAGAGACTTGGTCTCAG CAAGTTGCAGCGTTTATAGT (SEQ ID NO: 427) |
| G3 | BRCA1 | BRCA1_210_36588_2 | ACACTGACGACATGGTTCTACAGTA AAATGTGCTCCCCAAAAGCA (SEQ ID NO: 428) | TACGGTAGCAGAGACTTGGTCTGTC TGAAAGCCAgGGAGTTGG (SEQ ID NO: 429) |
| H3 | BRCA1 | BRCA1_210_36588_3 | ACACTGACGACATGGTTCTACAAGT TTGAATCCATGCTTTGCTCT (SEQ ID NO: 430) | TACGGTAGCAGAGACTTGGTCTCAC AGTGCAGTGAATTGGAAGAC (SEQ ID NO: 431) |
| A4 | BRCA1 | BRCA1_210_36588_4 | ACACTGACGACATGGTTCTACAGGA TCCTGGGTGTTTGTATTTGC (SEQ ID NO: 432) | TACGGTAGCAGAGACTTGGTCTTGT CTAAGAACACAGAGGAGAATTTA (SEQ ID NO: 433) |
| B4 | BRCA1 | BRCA1_210_36588_5 | ACACTGACGACATGGTTCTACAGCA GAACATTTTGTTTCCTCACT (SEQ ID NO: 434) | TACGGTAGCAGAGACTTGGTCTTCC CTGCTTCCAACACTTGTTAT (SEQ ID NO: 435) |
| C4 | BRCA1 | BRCA1_210_1_1 | ACACTGACGACATGGTTCTACATCAA TGATAATAAATTCTCCTCTGTGTTCT (SEQ ID NO: 436) | TACGGTAGCAGAGACTTGGTCTCTA GTGAGGATGAAGAGCTTCCC (SEQ ID NO: 437) |
| D4 | BRCA1 | BRCA1_210_1_2 | ACACTGACGACATGGTTCTACAACC AAATAACAAGTGTTGGAAGCA (SEQ ID NO: 438) | TACGGTAGCAGAGACTTGGTCTAGT CCTAGCCCTTTCACCCATA (SEQ ID NO: 439) |

TABLE 6-continued

Primers for Amplifying Exons from the Genes BRCA1, BRCA2, PTEN, PI3KCA, APC, EGFR, TP53

| Primer plate well | Gene/chr | Name | F-primer | R-primer |
|---|---|---|---|---|
| E4 | BRCA1 | BRCA1_210_36588_6 | ACACTGACGACATGGTTCTACAACAAGTGTTGGAAGCAGGG (SEQ ID NO: 440) | TACGGTAGCAGAGACTTGGTCTCAGGAGTCCTAGCCCTTTCA (SEQ ID NO: 441) |
| F4 | BRCA1 | BRCA1_210_36588_7 | ACACTGACGACATGGTTCTACAAGGGAAGCTCTTCATCCTCACTA (SEQ ID NO: 442) | TACGGTAGCAGAGACTTGGTCTTGGTGAAATAAAGGAAGATACTAGTTTTG (SEQ ID NO: 443) |
| G4 | BRCA1 | BRCA1_210_36588_8 | ACACTGACGACATGGTTCTACACTCCTTTCTGGACGCTTTTGCTA (SEQ ID NO: 444) | TACGGTAGCAGAGACTTGGTCTTCAGACTGTTAATACAGATTTCTCTCCA (SEQ ID NO: 445) |
| H4 | BRCA1 | BRCA1_210_36588_9 | ACACTGACGACATGGTTCTACAGTCTCAGAACAAACCTGAGATGC (SEQ ID NO: 446) | TACGGTAGCAGAGACTTGGTCTAGATTAGGGGTTTTGCAACCTGA (SEQ ID NO: 447) |
| A5 | BRCA1 | BRCA1_210_36588_10 | ACACTGACGACATGGTTCTACATCTTGCTTTTTTATTTCAGGATGCTT (SEQ ID NO: 448) | TACGGTAGCAGAGACTTGGTCTCCAGTACTAATGAAGTGGGCTCC (SEQ ID NO: 449) |
| B5 | BRCA1 | BRCA1_210_36588_126 | ACACTGACGACATGGTTCTACAtctAAGCATAGCATTCaATTTTGGC (SEQ ID NO: 450) | TACGGTAGCAGAGACTTGGTCTGTGAGCACAATTAgCcgTAATAACA (SEQ ID NO: 451) |
| C5 | BRCA1 | BRCA1_210_36588_127 | ACACTGACGACATGGTTCTACAGCATTCAATTTTGGCCCTCTGTT (SEQ ID NO: 452) | TACGGTAGCAGAGACTTGGTCTTGGGAAATGAGAACATTCCAAGTACA (SEQ ID NO: 453) |
| D5 | BRCA1 | BRCA1_210_36588_128 | ACACTGACGACATGGTTCTACAGTTTTCATCACTGGAACCTATTTCA (SEQ ID NO: 454) | TACGGTAGCAGAGACTTGGTCTTGCTAGAGGAAAACTTTGAGGAACA (SEQ ID NO: 455) |
| E5 | BRCA1 | BRCA1_210_36588_129 | ACACTGACGACATGGTTCTACAATATTGCTTGAGCTGGCTTCTTT (SEQ ID NO: 456) | TACGGTAGCAGAGACTTGGTCTTCGTATACCACCACTTTTTCCCA (SEQ ID NO: 457) |
| F5 | BRCA1 | BRCA1_210_36588_130 | ACACTGACGACATGGTTCTACATGTGCTCACTGTACTTGGAATGT (SEQ ID NO: 458) | TACGGTAGCAGAGACTTGGTCTTCTCAGTTCAGAGGCAACGAAAC (SEQ ID NO: 459) |
| G5 | BRCA1 | BRCA1_210_36588_131 | ACACTGACGACATGGTTCTACAAGTGGTGGTATACGATATGGGTT (SEQ ID NO: 460) | TACGGTAGCAGAGACTTGGTCTAGACAGTTAATATCACTGCAGGCTT (SEQ ID NO: 461) |
| H5 | BRCA1 | BRCA1_210_36588_132 | ACACTGACGACATGGTTCTACAACAAAACCTAGAGCCTCCTTTGA (SEQ ID NO: 462) | TACGGTAGCAGAGACTTGGTCTCTGCCCACTCTGGGTCCTTA (SEQ ID NO: 463) |
| A6 | BRCA1 | BRCA1_210_36588_133 | ACACTGACGACATGGTTCTACAACTCATTCTTTCCTTGATTTTCTTCCT (SEQ ID NO: 464) | TACGGTAGCAGAGACTTGGTCTAGTGAACTTGATGCTCAGTATTTGC (SEQ ID NO: 465) |
| B6 | BRCA1 | BRCA1_210_36588_216 | ACACTGACGACATGGTTCTACATCCTCTTcTGcATTTCCTGGATT (SEQ ID NO: 466) | TACGGTAGCAGAGACTTGGTCTaAGTATCCATTGGGACATGAAGTTA (SEQ ID NO: 467) |
| C6 | BRCA1 | BRCA1_210_36588_217 | ACACTGACGACATGGTTCTACACCTGGATTTGAAAACGGAGCAAA (SEQ ID NO: 468) | TACGGTAGCAGAGACTTGGTCTAACCCCAAGGGACTAATTCATGG (SEQ ID NO: 469) |
| D6 | BRCA1 | BRCA1_210_36588_218 | ACACTGACGACATGGTTCTACATCTATGCTTGTTTCCCGACTGTG (SEQ ID NO: 470) | TACGGTAGCAGAGACTTGGTCTGGCACTCAGGAAAGTATCTCGTT (SEQ ID NO: 471) |
| E6 | BRCA1 | BRCA1_210_36588_219 | ACACTGACGACATGGTTCTACACTGCACACTGACTCACACATTTA (SEQ ID NO: 472) | TACGGTAGCAGAGACTTGGTCTGCTGAAGACCCCAAAGATCTCAT (SEQ ID NO: 473) |
| F6 | BRCA1 | BRCA1_210_36588_267 | ACACTGACGACATGGTTCTACACCtgaGTGCCataATCAGTACCA (SEQ ID NO: 474) | TACGGTAGCAGAGACTTGGTCTcAAATACCAGTGAACTTaaagAATTTGTC (SEQ ID NO: 475) |

TABLE 6-continued

Primers for Amplifying Exons from the Genes BRCA1, BRCA2, PTEN, PI3KCA, APC, EGFR, TP53

| Primer plate well | Gene/chr | Name | F-primer | R-primer |
|---|---|---|---|---|
| G6 | BRCA1 | BRCA1_210_36588_274 | ACACTGACGACATGGTTCTACAttcTT CTcTTgGAagGCTAGGAT (SEQ ID NO: 476) | TACGGTAGCAGAGACTTGGTCTtGg AAGGTAAAgaacCTGCAACT (SEQ ID NO: 477) |
| H6 | BRCA1 | BRCA1_21036588_282 | ACACTGACGACATGGTTCTACAAGG TGCatttGttaACTTCAGCTC (SEQ ID NO: 478) | TACGGTAGCAGAGACTTGGTCTCAA ATTgATaGTTGTTcTAGCAGTGA (SEQ ID NO: 479) |
| A7 | BRCA1 | BRCA1_210_46602_1 | ACACTGACGACATGGTTCTACATAC TCttcTtGGCTCCAGTTGC (SEQ ID NO: 480) | TACGGTAGCAGAGACTTGGTCTGGa gGaAGTCTtctaCCAGGCAT (SEQ ID NO: 481) |
| B7 | BRCA1 | BRCA1_210_46602_104 | ACACTGACGACATGGTTCTACAcCa TGagtTgTaggTTTCTGCTG (SEQ ID NO: 482) | TACGGTAGCAGAGACTTGGTCTGGa gGaAGTCTtctaCCAGGCAT (SEQ ID NO: 483) |
| C7 | BRCA1 | BRCA1_210_46602_2 | ACACTGACGACATGGTTCTACAACA CtATcAATTTGCaATtcaGTACAATTA (SEQ ID NO: 484) | TACGGTAGCAGAGACTTGGTCTAGC AGCaGTAtaAGCAATATGGA (SEQ ID NO: 485) |
| D7 | BRCA | BRCA1_210_46602_3 | ACACTGACGACATGGTTCTACATGC AATTCAGTACAATTAGGTGGG (SEQ ID NO: 486) | TACGGTAGCAGAGACTTGGTCTGCT TTCAAAACGAAAGCTGAACC (SEQ ID NO: 487) |
| E7 | BRCA1 | BRCA1_210_46602_4 | ACACTGACGACATGGTTCTACATTT TAGGTGCTTTTGAATTGTGGA (SEQ ID NO: 488) | TACGGTAGCAGAGACTTGGTCTCG GAGCAGAATGGTCAAGTGAT (SEQ ID NO: 489) |
| F7 | BRCA1 | BRCA1_210_46602_105 | ACACTGACGACATGGTTCTACATCC ATATTGCTtaTACtGCTGCTTA (SEQ ID NO: 490) | TACGGTAGCAGAGACTTGGTCTAGc AGAATGGTcAAGTGATGAAT (SEQ ID NO: 491) |
| G7 | BRCA1 | BRCA1_210_46602_106 | ACACTGACGACATGGTTCTACACGA GTGATTCTATTGGGTTAGGATT (SEQ ID NO: 492) | TACGGTAGCAGAGACTTGGTCTGAG ACCTACATCAGGCCTTCATC (SEQ ID NO: 493) |
| H7 | BRCA1 | BRCA1_210_46602_48 | ACACTGACGACATGGTTCTACACCA AATcTGcTTTctTGAtaAAATCCTC (SEQ ID NO: 494) | TACGGTAGCAGAGACTTGGTCTCCC CAaCTtAAGCCaTGTAACTGA (SEQ ID NO: 495) |
| A8 | BRCA1 | BRCA1_210_46602_49 | ACACTGACGACATGGTTCTACAGG GGACGCTCTTGTATTATCTGT (SEQ ID NO: 496) | TACGGTAGCAGAGACTTGGTCTGTG AAAGAGTTCACTCCAAATCAGT (SEQ ID NO: 497) |
| B8 | BRCA1 | BRCA1_210_46602_50 | ACACTGACGACATGGTTCTACACCT TCTTCCGATAGGTTTTCCCA (SEQ ID NO: 498) | TACGGTAGCAGAGACTTGGTCTTGA TGGGGAGTCTGAATCAAATG (SEQ ID NO: 499) |
| C8 | BRCA1 | BRCA1_210_46602_51 | ACACTGACGACATGGTTCTACATGG CCAGTAAGTCTATTTTCTCTGAAG (SEQ ID NO: 500) | TACGGTAGCAGAGACTTGGTCTAGA GATACTGAAGATGTTCCTTGGAT (SEQ ID NO: 501) |
| D8 | BRCA1 | BRCA1_210_46602_107 | ACACTGACGACATGGTTCTACACCA TCATGTgAGTCATCAGAACCT (SEQ ID NO: 502) | TACGGTAGCAGAGACTTGGTCTCTg ATcCCCTGTGTgAGAGAAAA (SEQ ID NO: 503) |
| E8 | BRCA1 | BRCA1_210_46602_103 | ACACTGACGACATGGTTCTACATgA GTCATCAGAACCTAACAGTTCAT (SEQ ID NO: 504) | TACGGTAGCAGAGACTTGGTCTCTg ATcCCCTGTGTgAGAGAAAA (SEQ ID NO: 505) |
| F8 | BRCA1 | BRCA1_210_46602_108 | ACACTGACGACATGGTTCTACAcCA AGGAacatcTtcaGTATCTCTAGG (SEQ ID NO: 506) | TACGGTAGCAGAGACTTGGTCTCAG ATgGgCTGGaAGTAAGGAAA (SEQ ID NO: 507) |
| G8 | BRCA1 | BRCA1_210_36588_437 | ACACTGACGACATGGTTCTACAccAT TcTTTTCTCtCACACAGGG (SEQ ID NO: 508) | TACGGTAGCAGAGACTTGGTCTcagc ATGAGAACAGCAGTTTATT (SEQ ID NO: 509) |
| H8 | BRCA1 | BRCA1_210_36588_454 | ACACTGACGACATGGTTCTACAAGC CAGgctGTtGctTTTATTAC (SEQ ID NO: 510) | TACGGTAGCAGAGACTTGGTCTtGaT tTGAACAcCACTGAGAAGC (SEQ ID NO: 511) |

TABLE 6-continued

Primers for Amplifying Exons from the Genes BRCA1, BRCA2, PTEN, PI3KCA, APC, EGFR, TP53

| Primer plate well | Gene/chr | Name | F-primer | R-primer |
|---|---|---|---|---|
| A9 | BRCA1 | BRCA1_210_36588_467 | ACACTGACGACATGGTTCTACAcaC ATGGCTCCAcatGCAAGTTT (SEQ ID NO: 512) | TACGGTAGCAGAGACTTGGTCTTGA CAATTCAGTTTTTGAGTACCTTGTT (SEQ ID NO: 513) |
| B9 | BRCA1 | BRCA1_210_83677_1 | ACACTGACGACATGGTTCTACATCT ACCCACTCTCTTTTCAGTGC (SEQ ID NO: 514) | TACGGTAGCAGAGACTTGGTCTTCT TGGTCATTTGACAGTTCTGC (SEQ ID NO: 515) |
| C9 | BRCA1 | BRCA1_210_83677_2 | ACACTGACGACATGGTTCTACAAATAT TAACTAAATAGGAAAATACCAGCTTCA (SEQ ID NO: 516) | TACGGTAGCAGAGACTTGGTCTTTTAT TTTTTGGGGGGAAATTTTTTAGGATCT (SEQ ID NO: 517) |
| D9 | BRCA1 | BRCA1_210_83677_3 | ACACTGACGACATGGTTCTACAAGT TGCCTTATTAACGGTATCTTCA (SEQ ID NO: 518) | TACGGTAGCAGAGACTTGGTCTACC ACTTCTCTGTATTACATACTAGCTTA (SEQ ID NO: 519) |
| E9 | BRCA1 | BRCA1_210_86573_1 | ACACTGACGACATGGTTCTACACAA AACTATAAGATAAGGAATCCAGCAA (SEQ ID NO: 520) | TACGGTAGCAGAGACTTGGTCTTCT TTACCATACTGTTtaGCAGGAAA (SEQ ID NO: 521) |
| F9 | BRCA1 | BRCA1_210_86573_2 | ACACTGACGACATGGTTCTACAGTtg TATCcgCTgCTTTGTCC (SEQ ID NO: 522) | TACGGTAGCAGAGACTTGGTCTACA TGTTAGCTGACTGATGATGGT (SEQ ID NO: 523) |
| G9 | BRCA1 | BRCA1_210_17948_3 | ACACTGACGACATGGTTCTACAACA AATGGTTTtACCAAGGAAGGAT (SEQ ID NO: 524) | TACGGTAGCAGAGACTTGGTCTTCA TACATTTTtCTCTAAcTGCAAACA (SEQ ID NO: 525) |
| H9 | BRCA1 | BRCA1_210_17948_10 | ACACTGACGACATGGTTCTACAGca cggTTTCtgtAGCCCATA (SEQ ID NO: 526) | TACGGTAGCAGAGACTTGGTCTACA CAACAAAGAGCATACATAGGGT (SEQ ID NO: 527) |
| A10 | BRCA1 | BRCA1_210_13831_1 | ACACTGACGACATGGTTCTACATTC CTGAGTTTTCATGGACAGCA (SEQ ID NO: 528) | TACGGTAGCAGAGACTTGGTCTTCA CTTGCTGAGTGTGTTTCTCA (SEQ ID NO: 529) |
| B10 | BRCA1 | BRCA1_210_45886_1 | ACACTGACGACATGGTTCTACATTT CCTACTGTGGTTGCTTCCAA (SEQ ID NO: 530) | TACGGTAGCAGAGACTTGGTCTTTC ATGGCTATTTGCCTTTTGAG (SEQ ID NO: 531) |
| C10 | BRCA1 | BRCA1_210_1751963_1 | ACACTGACGACATGGTTCTACATGG AGCCACATAACACATTCAAA (SEQ ID NO: 532) | TACGGTAGCAGAGACTTGGTCTACT CAGTCATAACAGCTCAAAGT (SEQ ID NO: 533) |
| D10 | BRCA1 | BRCA1_210_1751963_2 | ACACTGACGACATGGTTCTACAACA TGTCTTTTCTTCCCTAGTATGT (SEQ ID NO: 534) | TACGGTAGCAGAGACTTGGTCTATG TGTTAAAGTTCATTGGAACAGAA (SEQ ID NO: 535) |
| A1 | BRCA2 | BRCA2_210_1484009_1 | ACACTGACGACATGGTTCTACATTT CCAGCGCTTCTGAGTTTTAC (SEQ ID NO: 536) | TACGGTAGCAGAGACTTGGTCTTGT CAATACCTGCttTGTTGCAG (SEQ ID NO: 537) |
| B1 | BRCA2 | BRCA2_210_1484009_2 | ACACTGACGACATGGTTCTACAAgC ATTGGAGGAATATcGTAGGTAA (SEQ ID NO: 538) | TACGGTAGCAGAGACTTGGTCTACA CTGTGACGTACTGGGTTTTT (SEQ ID NO: 539) |
| C1 | BRCA2 | BRCA2_210_890597_2 | ACACTGACGACATGGTTCTACAgCA TTGGAGGAATATCGTAGGT (SEQ ID NO: 540) | TACGGTAGCAGAGACTTGGTCTTTT TTAGAAAACACTTTCTCGGTGT (SEQ ID NO: 541) |
| D1 | BRCA2 | BRCA2_210_0939160_1 | ACACTGACGACATGGTTCTACAGTC ACTGGTTAAAACTAAGGTGGG (SEQ ID NO: 542) | TACGGTAGCAGAGACTTGGTCTtTG GAGtTgAAGcCAGCTGATTA (SEQ ID NO: 543) |
| E1 | BRCA2 | BRCA2_210_1_1 | ACACTGACGACATGGTTCTACACTT TCTTCAGAAGCTCCACCCTA (SEQ ID NO: 544) | TACGGTAGCAGAGACTTGGTCTGAG ATTGGTACAGCGGCAGAG (SEQ ID NO: 545) |
| F1 | BRCA2 | BRCA2_210_893213_24 | ACACTGACGACATGGTTCTACAAACC TATTTAAAACTCCACAaAGGAAACC (SEQ ID NO: 546) | TACGGTAGCAGAGACTTGGTCTATC TAATTCTTTTACAGGAGATTGGTACA (SEQ ID NO: 547) |

TABLE 6-continued

Primers for Amplifying Exons from the Genes BRCA1, BRCA2, PTEN, PI3KCA, APC, EGFR, TP53

| Primer plate well | Gene/chr | Name | F-primer | R-primer |
|---|---|---|---|---|
| G1 | BRCA2 | BRCA2_210_1_2 | ACACTGACGACATGGTTCTACATGT TTCAGGAAGGAATGTTCCCA (SEQ ID NO: 548) | TACGGTAGCAGAGACTTGGTCTaGC TTCATCATACCTTTCACTAAGA (SEQ ID NO: 549) |
| H1 | BRCA2 | BRCA2_210_0939163_1 | ACACTGACGACATGGTTCTACAAAA ATAACCTAAGGGATTTGCTTTGT (SEQ ID NO: 550) | TACGGTAGCAGAGACTTGGTCTTgA AACaAACTCCCACATACCACT (SEQ ID NO: 550) |
| B2 | BRCA2 | BRCA2_210_900378_1 | ACACTGACGACATGGTTCTACATGTT AATAAAAATAAAACTTAACAATTTTC CCCTT (SEQ ID NO: 552) | TACGGTAGCAGAGACTTGGTCTATT ACTAAGTCATAAAAAtAAACCAGGTA GAATA (SEQ ID NO: 553) |
| C2 | BRCA2 | BRCA2_210_0939164_1 | ACACTGACGACATGGTTCTACATCC TTAATGATCAGGGCATTTCT (SEQ ID NO: 554) | TACGGTAGCAGAGACTTGGTCTTGC TCTTTCTTGTAAATACACATTTGCT (SEQ ID NO: 555) |
| D2 | BRCA2 | BRCA2_210_900635_1 | ACACTGACGACATGGTTCTACATCC TTAATGATCAGGGCATTTCT (SEQ ID NO: 556) | TACGGTAGCAGAGACTTGGTCTACC AAGACATATCAGGATCCACC (SEQ ID NO: 557) |
| E2 | BRCA2 | BRCA2_210_900635_3 | ACACTGACGACATGGTTCTACAaCA TATTTCTGAAAGTCTAGGAGCTGA (SEQ ID NO: 558) | TACGGTAGCAGAGACTTGGTCTTGC TCTTTCTTGTAAATACACATTTGCT (SEQ ID NO: 559) |
| F2 | BRCA2 | BRCA2_210_0939165_1 | ACACTGACGACATGGTTCTACATGT GTCaTGTAATCAAATAGTAGATGTG (SEQ ID NO: 560) | TACGGTAGCAGAGACTTGGTCTAGC AATTTCAACAGTCTAATCAATGTC (SEQ ID NO: 561) |
| G2 | BRCA2 | BRCA2_210_0939166_1 | ACACTGACGACATGGTTCTACActact ACTATATGTGCATTGAGAGTTTTT (SEQ ID NO: 562) | TACGGTAGCAGAGACTTGGTCTACA GAGGACTTACCATGACTTGC (SEQ ID NO: 563) |
| H2 | BRCA2 | BRCA2_210_905055_1 | ACACTGACGACATGGTTCTACATGTG CATTGAGAGTTTTTATaCTAGTGATTT (SEQ ID NO: 564) | TACGGTAGCAGAGACTTGGTCTTGA TTTGTGTTTTCACTGTCTGTC (SEQ ID NO: 565) |
| A3 | BRCA2 | BRCA2_210_905055_5 | ACACTGACGACATGGTTCTACATCA TGATgAAAGTCTGAAGAAAAATGA (SEQ ID NO: 566) | TACGGTAGCAGAGACTTGGTCTCAG AGGACTTACCATGACTTGC (SEQ ID NO: 567) |
| B3 | BRCA2 | BRCA2_210_0939167_1 | ACACTGACGACATGGTTCTACATGG CTTATAAAATATTAATGTGCTTCTGT (SEQ ID NO: 568) | TACGGTAGCAGAGACTTGGTCTacaa CTGTTTCAtATACTTCATCTTCTAGG (SEQ ID NO: 569) |
| C3 | BRCA2 | BRCA2_210_2_1 | ACACTGACGACATGGTTCTACATGG CTTATAAAATATTAATGTGCTTCTGT (SEQ ID NO: 570) | TACGGTAGCAGAGACTTGGTCTTCT TCAGAGGTATCTACAACTGTTTC (SEQ ID NO: 571) |
| D3 | BRCA2 | BRCA2_210_2_3 | ACACTGACGACATGGTTCTACAACA GGATTTGGAAAAACATCAGGG (SEQ ID NO: 572) | TACGGTAGCAGAGACTTGGTCTTTC CTAGTCTTGCTAGTTCTTACTTT (SEQ ID NO: 573) |
| E3 | BRCA2 | BRCA2_210_2_4 | ACACTGACGACATGGTTCTACATGG AAAGTCAATGCCAAATGTCC (SEQ ID NO: 574) | TACGGTAGCAGAGACTTGGTCTTCA CATTCATCAGCGTTTGCTTC (SEQ ID NO: 575) |
| F3 | BRCA2 | BRCA2_210_3_3 | ACACTGACGACATGGTTCTACAtgtag ATAcCTCTGAAgAAGATAGTTTTT (SEQ ID NO: 576) | TACGGTAGCAGAGACTTGGTCTTGG ATCAGTATCATTTGGTTCCACT (SEQ ID NO: 577) |
| H3 | BRCA2 | BRCA2_210_39167_43 | ACACTGACGACATGGTTCTACAAaa TcTcCaAGGAAGTTGTACCG (SEQ ID NO: 578) | TACGGTAGCAGAGACTTGGTCTgGC TAGAAaTAcgTGGCAAAGAA (SEQ ID NO: 579) |
| A4 | BRCA2 | BRCA2_210_4_1 | ACACTGACGACATGGTTCTACAACC CCTATTGCATATTTCTTCATGTG (SEQ ID NO: 580) | TACGGTAGCAGAGACTTGGTCTTCT GTATGAGATTCAAGATGCTGCT (SEQ ID NO: 581) |
| B4 | BRCA2 | BRCA2_210_4_2 | ACACTGACGACATGGTTCTACAGCC TACCAAAATCAGAGAAGCCAT (SEQ ID NO: 582) | TACGGTAGCAGAGACTTGGTCTTGC ATTGAAAGTCTCTTTAGGTGAT (SEQ ID NO: 583) |

TABLE 6-continued

Primers for Amplifying Exons from the Genes BRCA1, BRCA2, PTEN, PI3KCA, APC, EGFR, TP53

| Primer plate well | Gene/chr | Name | F-primer | R-primer |
|---|---|---|---|---|
| C4 | BRCA2 | BRCA2_210_4_3 | ACACTGACGACATGGTTCTACAGCAGTAAAGCAGGCAATATCTGG (SEQ ID NO: 584) | TACGGTAGCAGAGACTTGGTCTGAGTCCTCCTTCTGTGAGCAAAC (SEQ ID NO: 585) |
| D4 | BRCA2 | BRCA2_210_4_5 | ACACTGACGACATGGTTCTACACCTCTGAAAGTGGACTGGAAA (SEQ ID NO: 586) | TACGGTAGCAGAGACTTGGTCTAACTTATTTGTTTTCTTTTTCAAAGTGGAT (SEQ ID NO: 587) |
| E4 | BRCA2 | BRCA2_210_39167_124 | ACACTGACGACATGGTTCTACATCTGTAGCTTTGAAGAATGCAGGT (SEQ ID NO: 588) | TACGGTAGCAGAGACTTGGTCTTTGCAAATgtaAGTGGTGCTTC (SEQ ID NO: 589) |
| F4 | BRCA2 | BRCA2_210_5_2 | ACACTGACGACATGGTTCTACAGTTCAGCCCAGTTTGAAGCA (SEQ ID NO: 590) | TACGGTAGCAGAGACTTGGTCTAAACACAGAAGGAATCGTCATCT (SEQ ID NO: 591) |
| G4 | BRCA2 | BRCA2_210_0939168_1 | ACACTGACGACATGGTTCTACAAATATTTAGTgAATGTGATTGATGGTACTTTA (SEQ ID NO: 592) | TACGGTAGCAGAGACTTGGTCTAGAACATTTCcTCAGAATTGTCCCAAA (SEQ ID NO: 593) |
| H4 | BRCA2 | BRCA2_210_0939168_3 | ACACTGACGACATGGTTCTACAACcAACTTTGTCCTTAACTAGCTCT (SEQ ID NO: 594) | TACGGTAGCAGAGACTTGGTCTGGATCATTTTCACACTGTCCTTCC (SEQ ID NO: 595) |
| A5 | BRCA2 | BRCA2_210_39168_22 | ACACTGACGACATGGTTCTACAactaCAgTTATttattACCCCAGAAGC (SEQ ID NO: 596) | TACGGTAGCAGAGACTTGGTCTagtcaGTATCACtGTATTCCACTTT (SEQ ID NO: 597) |
| B5 | BRCA2 | BRCA2_210_39168_32 | ACACTGACGACATGGTTCTACATCAGATATAAAAGAAGAGGTCTTGGC (SEQ ID NO: 598) | TACGGTAGCAGAGACTTGGTCTTGCCTCTAgAAAATCAtGACTAGGTTTG (SEQ ID NO: 599) |
| C5 | BRCA2 | BRCA2_210_39168_49 | ACACTGACGACATGGTTCTACATGCCAGCAcTCTTATTTTAACTCCT (SEQ ID NO: 600) | TACGGTAGCAGAGACTTGGTCTACAGCTCAACgTTTTTatAATTTTCATTT (SEQ ID NO: 601) |
| D5 | BRCA2 | BRCA2_210_6_1 | ACACTGACGACATGGTTCTACACTGATGTTGAATTAACCAAAAATATTCCC (SEQ ID NO: 602) | TACGGTAGCAGAGACTTGGTCTTGGATTACTCTTAGATTTGTGTTTTGG (SEQ ID NO: 603) |
| E5 | BRCA2 | BRCA2_210_6_2 | ACACTGACGACATGGTTCTACAGTTGAGCTGTTGCCACCTGAAAA (SEQ ID NO: 604) | TACGGTAGCAGAGACTTGGTCTTCTTCAGAGTCTGGATTGACAGTTAT (SEQ ID NO: 605) |
| F5 | BRCA2 | BRCA2_210_39168_85m | ACACTGACGACATGGTTCTACATTCAaCCaAAaCacaAATCTAAGAGTAA (SEQ ID NO: 606) | TACGGTAGCAGAGACTTGGTCTTCGTTTACACAAGTCAAGTCTGTT (SEQ ID NO: 607) |
| G5 | BRCA2 | BRCA2_210_7_1m | ACACTGACGACATGGTTCTACAAATAATTTTGTCTTCCAAGTAGCTAATGA (SEQ ID NO: 608) | TACGGTAGCAGAGACTTGGTCTATTGACACTTGGGTTGCTTGTTT (SEQ ID NO: 609) |
| H5 | BRCA2 | BRCA2_210_7_2 | ACACTGACGACATGGTTCTACATCTTGCTTTAGGAAATACTAAGGAACT (SEQ ID NO: 610) | TACGGTAGCAGAGACTTGGTCTACCTAGAGTCATTTTTATATGCTGCTTT (SEQ ID NO: 611) |
| A6 | BRCA2 | BRCA2_210_7_3m | ACACTGACGACATGGTTCTACATAAACAAGCAACCCAAGTGTCAA (SEQ ID NO: 612) | TACGGTAGCAGAGACTTGGTCTCCTGCCCATTTGTTCATGTAATC (SEQ ID NO: 613) |
| B6 | BRCA2 | BRCA2_210_39168_132 | ACACTGACGACATGGTTCTACAAAATaGTGTAAAgcAgCATATAAAAATGAC (SEQ ID NO: 614) | TACGGTAGCAGAGACTTGGTCTTGTTCAGAGAgCTTgaTTTCCTTA (SEQ ID NO: 615) |
| C6 | BRCA2 | BRCA2_210_8_1 | ACACTGACGACATGGTTCTACAAACAAATGGGCAGGACTCTTAGG (SEQ ID NO: 616) | TACGGTAGCAGAGACTTGGTCTTTCAACACAAGCTAAACTAGTAGGA (SEQ ID NO: 617) |
| D6 | BRCA2 | BRCA2_210_8_3m | ACACTGACGACATGGTTCTACAAAGGAAATCAAGCTCTCTGAACA (SEQ ID NO: 618) | TACGGTAGCAGAGACTTGGTCTACAATCAGAAACAACTACACTACTCT (SEQ ID NO: 619) |

TABLE 6-continued

Primers for Amplifying Exons from the Genes BRCA1, BRCA2, PTEN, PI3KCA, APC, EGFR, TP53

| Primer plate well | Gene/chr | Name | F-primer | R-primer |
|---|---|---|---|---|
| E6 | BRCA2 | BRCA2_210_39168_171 | ACACTGACGACATGGTTCTACACTT GtGTTGaAATTgTAaaTACCTTGG (SEQ ID NO: 620) | TACGGTAGCAGAGACTTGGTCTTCT gCCTTTTgGCTAGGTG (SEQ ID NO: 621) |
| F6 | BRCA2 | BRCA2_210_39168_188 | ACACTGACGACATGGTTCTACAccctc AGatgTtattTCCAAGCA (SEQ ID NO: 622) | TACGGTAGCAGAGACTTGGTCTGCa CTTCAAATGTAcTCTTCtGCAATATG (SEQ ID NO: 623) |
| A7 | BRCA2 | BRCA2_210_9_3 | ACACTGACGACATGGTTCTACAACA GTTGAAATTAAACGGAAGTTTGCT (SEQ ID NO: 624) | TACGGTAGCAGAGACTTGGTCTGCA GAAGTTTCCTCACTAATATTCTCA (SEQ ID NO: 625) |
| B7 | BRCA2 | BRCA2_210_9_4m | ACACTGACGACATGGTTCTACATAC TGAAGCTCTGCAAAAAGCTG (SEQ ID NO: 626) | TACGGTAGCAGAGACTTGGTCTTGA AACAACAGAATCATGACATTTACTT (SEQ ID NO: 627) |
| C7 | BRCA2 | BRCA2_210_9_5 | ACACTGACGACATGGTTCTACATGT CATGATTCTGTTGTTTCAATGT (SEQ ID NO: 628) | TACGGTAGCAGAGACTTGGTCTTCT ACTGGCAGCAGTATATTTGTT (SEQ ID NO: 629) |
| D7 | BRCA2 | BRCA2_210_9_6 | ACACTGACGACATGGTTCTACAGAAA TTACAAGAGAAATACTGAAATGAAGAT (SEQ ID NO: 630) | TACGGTAGCAGAGACTTGGTCTTCA GTAAATAGCAAGTCCGTTTCA (SEQ ID NO: 631) |
| F7 | BRCA2 | BRCA2_210_10_1m | ACACTGACGACATGGTTCTACAGCA GCAAGCAATTTGAAGGTACA (SEQ ID NO: 632) | TACGGTAGCAGAGACTTGGTCTCAG CTTTTTGCAGAGCTTCAGTA (SEQ ID NO: 633) |
| H7 | BRCA2 | BRCA2_210_10_4 | ACACTGACGACATGGTTCTACACTG CAGAGGTACATCCAATAAGT (SEQ ID NO: 634) | TACGGTAGCAGAGACTTGGTCTAGT ATTTCTCTTGTAATTTTCAGTAATTT CTTC (SEQ ID NO: 635) |
| A8 | BRCA2 | BRCA2_210_39168_291 | ACACTGACGACATGGTTCTACAttgaT GGCAGTGATTCAAGTAAAAA (SEQ ID NO: 636) | TACGGTAGCAGAGACTTGGTCTATG ACATGCTTcttGAGCTTTCG (SEQ ID NO: 637) |
| B8 | BRCA2 | BRCA2_210_39168_305m | ACACTGACGACATGGTTCTACATGG CcAGTTTATGAAGGAGGG (SEQ ID NO: 638) | TACGGTAGCAGAGACTTGGTCTgcga CACTAATATTTTTCCCACTTG (SEQ ID NO: 639) |
| E8 | BRCA2 | BRCA2_210_39168_339 | ACACTGACGACATGGTTCTACAtgTA AATTTCTTTGaTCaGAAACCAGAAG (SEQ ID NO: 640) | TACGGTAGCAGAGACTTGGTCTCCC TGGAAggtCACTAGTTGATT (SEQ ID NO: 641) |
| G8 | BRCA2 | BRCA2_210_12_1 | ACACTGACGACATGGTTCTACACCC AGTTGGTACTGGAAATCAAC (SEQ ID NO: 642) | TACGGTAGCAGAGACTTGGTCTTCA CTAGTACCTTGCTCTTTTTCAT (SEQ ID NO: 643) |
| A9 | BRCA2 | BRCA2_210_39168_381 | ACACTGACGACATGGTTCTACATGA AAAAgAGCAAGgtAcTAGTGAAAT (SEQ ID NO: 644) | TACGGTAGCAGAGACTTGGTCTTtA GGTGGCACcacAGTCTCAAT (SEQ ID NO: 645) |
| B9 | BRCA2 | BRCA2_210_13_1 | ACACTGACGACATGGTTCTACAAGC TGCCCCAAAGTGTAAAGAA (SEQ ID NO: 645) | TACGGTAGCAGAGACTTGGTCTTGA TGTTTTGAGATTTTCAGTTTGTCT (SEQ ID NO: 647) |
| C9 | BRCA2 | BRCA2_210_13_3 | ACACTGACGACATGGTTCTACACTG TGGTGCCACCTAAGCTCT (SEQ ID NO: 648) | TACGGTAGCAGAGACTTGGTCTACA AGTTGCAGGACTTTTTGCTG (SEQ ID NO: 649) |
| D9 | BRCA2 | BRCA2_210_13_17 | ACACTGACGACATGGTTCTACATGAAA GTTAAAGTACATGAAAATGTAGAAAAA (SEQ ID NO: 650) | TACGGTAGCAGAGACTTGGTCTTGG TTGACCATCAAATATTCCTTCTC (SEQ ID NO: 651) |
| E9 | BRCA2 | BRCA2_210_13_25 | ACACTGACGACATGGTTCTACAAAT CAGTCCCCTTATTCAGTCATT (SEQ ID NO: 652) | TACGGTAGCAGAGACTTGGTCTTCAG CTATAGTACTGTTTGAATTATTTTCAT (SEQ ID NO: 653) |
| F9 | BRCA2 | BRCA2_210_13_26 | ACACTGACGACATGGTTCTACATGA GCCTTAGCTTTTTACACAAGT (SEQ ID NO: 654) | TACGGTAGCAGAGACTTGGTCTTCAG CTATAGTACTGTTTGAATTATTTTCAT (SEQ ID NO: 655) |

TABLE 6-continued

Primers for Amplifying Exons from the Genes BRCA1, BRCA2, PTEN, PI3KCA, APC, EGFR, TP53

| Primer plate well | Gene/chr | Name | F-primer | R-primer |
|---|---|---|---|---|
| G9 | BRCA2 | BRCA2_210_13_27 | ACACTGACGACATGGTTCTACAATTTGATGGTCAACCAGAAAGAATAAA (SEQ ID NO: 656) | TACGGTAGCAGAGACTTGGTCTACCTCATCAGAATGGTAGGAATAGC (SEQ ID NO: 657) |
| H9 | BRCA2 | BRCA2_210_39168_458 | ACACTGACGACATGGTTCTACAgACAAAAATcATCTCTccGAAAAACAAG (SEQ ID NO: 658) | TACGGTAGCAGAGACTTGGTCTtgCATCTTTTACAtTGGATATTACTTTGGAA (SEQ ID NO: 659) |
| A10 | BRCA2 | BRCA2_210_39168_471m | ACACTGACGACATGGTTCTACAtgatTCTGgTATTGAGCCAGTATTGA (SEQ ID NO: 660) | TACGGTAGCAGAGACTTGGTCTTtatTTTTGCAGGgtgAAGAGCTA (SEQ ID NO: 661) |
| B10 | BRCA2 | BRCA2_210_14_1 | ACACTGACGACATGGTTCTACATCCAAAGTAATATCCAATGTAAAAGATGC (SEQ ID NO: 662) | TACGGTAGCAGAGACTTGGTCTCAGGTGGCCCTACCTCAAAATTA (SEQ ID NO: 663) |
| C10 | BRCA2 | BRCA2_210_14_2m | ACACTGACGACATGGTTCTACAACTAGCTCTTCACCCTGCAAAAA (SEQ ID NO: 664) | TACGGTAGCAGAGACTTGGTCTTGAAACTGTCTGTAAATATGTCTTTCACT (SEQ ID NO: 665) |
| D10 | BRCA2 | BRCA2_210_39168_501 | ACACTGACGACATGGTTCTACAGGTAGGGCCACctGCATTTAG (SEQ ID NO: 666) | TACGGTAGCAGAGACTTGGTCTgAAgAATATcctcTGAATCATCCAAT (SEQ ID NO: 667) |
| E10 | BRCA2 | BRCA2_210_15_3 | ACACTGACGACATGGTTCTACAGCCAAACGAAAATTATGGCAGGT (SEQ ID NO: 668) | TACGGTAGCAGAGACTTGGTCTTGTTGTAAAATTTCTTCACTCTGAATGTC (SEQ ID NO: 669) |
| F10 | BRCA2 | BRCA2_210_3_1 | ACACTGACGACATGGTTCTACATGAATGTAGCACGCATTCACATAA (SEQ ID NO: 670) | TACGGTAGCAGAGACTTGGTCTTGCAGATGAGACTGACTTATGAAGC (SEQ ID NO: 671) |
| G10 | BRCA2 | BRCA2_210_15_12 | ACACTGACGACATGGTTCTACAACCAAAATATGTCTGGATTGGAGAA (SEQ ID NO: 672) | TACGGTAGCAGAGACTTGGTCTACAGATTTTCCACTTGCTGTGCT (SEQ ID NO: 673) |
| H10 | BRCA2 | BRCA2 210_0401_1237 | ACACTGACGACATGGTTCTACATCACCTTGTGATGTTAGTTTGGA (SEQ ID NO: 674) | TACGGTAGCAGAGACTTGGTCTGCATCTGATAcCTGGACAGATTTT (SEQ ID NO: 675) |
| A11 | BRCA2 | BRCA2_210_0401_1280 | ACACTGACGACATGGTTCTACAAGTGTTTTCTGAAATAGAAGATAGTACCAA (SEQ ID NO: 676) | TACGGTAGCAGAGACTTGGTCTAGcCTTTTTGGGATATTAAATGTTCTGG (SEQ ID NO: 677) |
| B11 | BRCA2 | BRCA2_210_15_26 | ACACTGACGACATGGTTCTACATCAGTCTCATCTGCAAATACTTGTG (SEQ ID NO: 678) | TACGGTAGCAGAGACTTGGTCTTCTTGTGAGCTGGTCTGAATGTT (SEQ ID NO: 679) |
| C11 | BRCA2 | BRCA2_210_15_36 | ACACTGACGACATGGTTCTACAAGGTATCAGATGCTTCATTACAAAACG (SEQ ID NO: 680) | TACGGTAGCAGAGACTTGGTCTGTTCTGGAGTACGTATAGCAGTATTT (SEQ ID NO: 681) |
| D11 | BRCA2 | BRCA2_210_0401_1299 | ACACTGACGACATGGTTCTACAACCAG CTCACAAGAGAAGAAAA (SEQ ID NO: 682) | TACGGTAGCAGAGACTTGGTCTACTTGCTTTCCACTTGCTGT (SEQ ID NO: 683) |
| F11 | BRCA2 | BRCA2_210_16_1 | ACACTGACGACATGGTTCTACATGGTAAATTCATCTGCTTTCTCTGGA (SEQ ID NO: 684) | TACGGTAGCAGAGACTTGGTCTCACAGTGCTCTGGGTTTCTCTTA (SEQ ID NO: 685) |
| H11 | BRCA2 | BRCA2_210_39168_614m | ACACTGACGACATGGTTCTACACCCAGAGCaCTGtgtAAACTCAGAA (SEQ ID NO: 686) | TACGGTAGCAGAGACTTGGTCTAGTGAcACtttGGTTCCTAATACCA (SEQ ID NO: 687) |
| A12 | BRCA2 | BRCA2_210_39168_631 | ACACTGACGACATGGTTCTACATCtCCATatcTCTctcAATTTCAACA (SEQ ID NO: 688) | TACGGTAGCAGAGACTTGGTCTagaaaAAGTTTcagTTTTACCAATTTCCA (SEQ ID NO: 689) |
| B12 | BRCA2 | BRCA2_210_17_2 | ACACTGACGACATGGTTCTACAGGGAAAAGAACAGGCTTCACCTA (SEQ ID NO: 690) | TACGGTAGCAGAGACTTGGTCTTGGCATGACTTGGCAGTTTAGAA (SEQ ID NO: 691) |

TABLE 6-continued

Primers for Amplifying Exons from the Genes BRCA1, BRCA2, PTEN, PI3KCA, APC, EGFR, TP53

| Primer plate well | Gene/chr | Name | F-primer | R-primer |
|---|---|---|---|---|
| C12 | BRCA2 | BRCA2_210_39168_659 | ACACTGACGACATGGTTCTACAACTTTGAAACagaaGCagtAGAAATTG (SEQ ID NO: 692) | TACGGTAGCAGAGACTTGGTCTGGCAACACGAAAGGTAAAAATGAAC (SEQ ID NO: 693) |
| D12 | BRCA2 | BRCA2_210_39168_673 | ACACTGACGACATGGTTCTACAttACATgtCcCGAAAATGAGGAA (SEQ ID NO: 694) | TACGGTAGCAGAGACTTGGTCTACTGACTACACAAAAATGGCTGA (SEQ ID NO: 695) |
| E11 | BRCA2 | BRCA2_210_0939169_1 | ACACTGACGACATGGTTCTACAAGGTCACTATTTGTTGTAAGTATTTTTGTT (SEQ ID NO: 696) | TACGGTAGCAGAGACTTGGTCTAGGATTTTTcTTGATTTTcTATTATCCTGTC (SEQ ID NO: 697) |
| F12 | BRCA2 | BRCA2_210_0939169_2 | ACACTGACGACATGGTTCTACACTTTTTAGgAGAAccCTCAaTCAAAAGAA (SEQ ID NO: 698) | TACGGTAGCAGAGACTTGGTCTcagaaTATTATATACCATACCTATAGAGGGAGA (SEQ ID NO: 699) |
| G12 | BRCA2 | BRCA2_210_0939171_1 | ACACTGACGACATGGTTCTACAAGCATCtgTTACATTCACTGAAAATTG (SEQ ID NO: 700) | TACGGTAGCAGAGACTTGGTCTggtaaTCgGCTCTAAAGAAACATGA (SEQ ID NO: 701) |
| H12 | BRCA2 | BRCA2_210_18_1 | ACACTGACGACATGGTTCTACAGTATTTACAGTAACATGGATATTCTCTTAGATTT (SEQ ID NO: 702) | TACGGTAGCAGAGACTTGGTCTACATGTCTTACCGAAAGGGTACA (SEQ ID NO: 703) |
| A1 | BRCA2 | BRCA2_210_0939173_1 | ACACTGACGACATGGTTCTACAATGTAGCAAATGAGGGTCTGCAA (SEQ ID NO: 704) | TACGGTAGCAGAGACTTGGTCTCCAAAGTCAgATGTTcAtACAAATGAGA (SEQ ID NO: 705) |
| B1 | BRCA2 | BRCA2_210_19_2 | ACACTGACGACATGGTTCTACAAGGGTCTGCAACAAAGGCATA (SEQ ID NO: 706) | TACGGTAGCAGAGACTTGGTCTTCCTGAAACTGCTAAATTGCTTG (SEQ ID NO: 707) |
| C1 | BRCA2 | BRCA2_210_19_1 | ACACTGACGACATGGTTCTACACCATTGCAGCACAACTAAGGAAC (SEQ ID NO: 708) | TACGGTAGCAGAGACTTGGTCTAAAATGGATGTCCTGAAACTGCT (SEQ ID NO: 709) |
| D1 | BRCA2 | BRCA2_210_19_3 | ACACTGACGACATGGTTCTACATTGTATGAACATCTGACTTTGGAAAAA (SEQ ID NO: 710) | TACGGTAGCAGAGACTTGGTCTCTGTTCAACTCTGTGAAAATGTGA (SEQ ID NO: 711) |
| E1 | BRCA2 | BRCA2_210_0939173_ | ACACTGACGACATGGTTCTACATcAAgCAATTTAGCAGTTTCAGG (SEQ ID NO: 712) | TACGGTAGCAGAGACTTGGTCTTTGCtTTTGTCTGTTTTCCTCCA (SEQ ID NO: 713) |
| F1 | BRCA2 | RCA2_210_39173_40 | ACACTGACGACATGGTTCTACAACagagTTGAACAGTGTGTTAGGA (SEQ ID NO: 714) | TACGGTAGCAGAGACTTGGTCTAGTTACAGCTaCTgCTTGATTGGA (SEQ ID NO: 715) |
| G1 | BRCA2 | BRCA2_210_391734_7 | ACACTGACGACATGGTTCTACATGACAATGAgaTTCATCAGTTTAACAA (SEQ ID NO: 716) | TACGGTAGCAGAGACTTGGTCTAGGGCTTTAAAATTACCACCACCA (SEQ ID NO: 717) |
| H1 | BRCA2 | BRCA2_210_20_2 | ACACTGACGACATGGTTCTACAggccAGGGGTTGTGCTTTTT (SEQ ID NO: 718) | TACGGTAGCAGAGACTTGGTCTCGCGTTGCCTTTGTTTCTTCTTA (SEQ ID NO: 719) |
| A2 | BRCA2 | BRCA2_210_20_12 | ACACTGACGACATGGTTCTACAACAAGTCTTCAGAATGCCAGAGAT (SEQ ID NO: 720) | TACGGTAGCAGAGACTTGGTCTTTATGAGAACACGCAGAGGGAAC (SEQ ID NO: 721) |
| B2 | BRCA2 | BRCA2_210_39174_21 | ACACTGACGACATGGTTCTACAAcTTGCAAAaacATCCACTCTG (SEQ ID NO: 722) | TACGGTAGCAGAGACTTGGTCTTTTCATTCATCCATTCCTGCACT (SEQ ID NO: 723) |
| C2 | BRCA2 | BRCA2_210_0939175_1 | ACACTGACGACATGGTTCTACATTGTTTTTATTGTGTGATACATGTTTACTTT (SEQ ID NO: 724) | TACGGTAGCAGAGACTTGGTCTAGCCaACTgTATTCCTTTTCCAGT (SEQ ID NO: 725) |
| D2 | BRCA2 | BRCA2_210_0939175_2 | ACACTGACGACATGGTTCTACAaTTGcaTAAAAattaaCAGCAAAAATGC (SEQ ID NO: 726) | TACGGTAGCAGAGACTTGGTCTTGAGGGAATACATAAAAGTTAACACACA (SEQ ID NO: 727) |

TABLE 6-continued

Primers for Amplifying Exons from the Genes BRCA1, BRCA2, PTEN, PI3KCA, APC, EGFR, TP53

| Primer plate well | Gene/chr | Name | F-primer | R-primer |
|---|---|---|---|---|
| E2 | BRCA2 | BRCA2_210_1394102_1 | ACACTGACGACATGGTTCTACAAGT TTTTGTACAGAGAATAGTTGTAGTTG (SEQ ID NO: 728) | TACGGTAGCAGAGACTTGGTCTcaC ATTCCATAGCTGCCAGTTTC (SEQ ID NO: 729) |
| F2 | BRCA2 | BRCA2_210_21_1 | ACACTGACGACATGGTTCTACATAT TTGTTCAGGGCTCTGTGTGA (SEQ ID NO: 730) | TACGGTAGCAGAGACTTGGTCTAGT TGAAGAAGCACCCTTTCTGG (SEQ ID NO: 731) |
| H2 | BRCA2 | BRCA2_210_0939177_1 | ACACTGACGACATGGTTCTACAGATAA ATTCAGTTTTTATTCTCAGTTATTCAGT (SEQ ID NO: 732) | TACGGTAGCAGAGACTTGGTCTGAA caaGTGTTtTTGCAGCTGTG (SEQ ID NO: 733) |
| A3 | BRCA2 | BRCA2_210_22_3 | ACACTGACGACATGGTTCTACATCG GCTATAAAAAGATAATGGAAAGG (SEQ ID NO: 734) | TACGGTAGCAGAGACTTGGTCTACC CATCTGTAAGTTCAATAATGGC (SEQ ID NO: 735) |
| B3 | BRCA2 | BRCA2_210_22_4 | ACACTGACGACATGGTTCTACAAGC AATAAAACTAGTAGTGCAGATACCC (SEQ ID NO: 736) | TACGGTAGCAGAGACTTGGTCTCAA CTGTCAGTCTGCCATTCTTT (SEQ ID NO: 737) |
| C3 | BRCA2 | BRCA2_210_22_10 | ACACTGACGACATGGTTCTACAATC CTCCCCTCTTAGCTGTCTTA (SEQ ID NO: 738) | TACGGTAGCAGAGACTTGGTCTTTA ACATAAGAGATTCTGGGGCTT (SEQ ID NO: 739) |
| D3 | BRCA2 | BRCA2_210_39177_37 | ACACTGACGACATGGTTCTACATTC TTCATGGAGCAGAACTGGTG (SEQ ID NO: 740) | TACGGTAGCAGAGACTTGGTCTTCA GTAcATCTAAGAAATTGAGCATCC (SEQ ID NO: 741) |
| E3 | BRCA2 | BRCA2_210_39177_41 | ACACTGACGACATGGTTCTACATGA TGCCTGTacACCTCTTGA (SEQ ID NO: 742) | TACGGTAGCAGAGACTTGGTCTGCA CAAAAACTTTAACTGTCTGAAGAATA (SEQ ID NO: 743) |
| F3 | BRCA2 | BRCA2_210_0939178_1 | ACACTGACGACATGGTTCTACACTTTT TAAAGTGAATATTTTTAAGGCAGTTCTA (SEQ ID NO: 744) | TACGGTAGCAGAGACTTGGTCTAGG AAAAGgTCtaGGGTCAGGAA (SEQ ID NO: 745) |
| G3 | BRCA2 | BRCA2_210_23_1 | ACACTGACGACATGGTTCTACACTA ACAGTACTCGGCCTGCTC (SEQ ID NO: 746) | TACGGTAGCAGAGACTTGGTCTACC TGTATAGGGTATGCTCTTTGA (SEQ ID NO: 747) |
| H3 | BRCA2 | BRCA2_210_23_2 | ACACTGACGACATGGTTCTACAGAC CTTTTCCTCTGCCCTTATCA (SEQ ID NO: 748) | ACGGTAGCAGAGACTTGGTCTAGAAAG AAATATATGGTAAGTTTCAAGAATACA (SEQ ID NO: 749) |
| A4 | BRCA2 | BRCA2_210_0939180_1 | ACACTGACGACATGGTTCTACAATG TGACTTTTTTGGTGTGTGTAA (SEQ ID NO: 750) | TACGGTAGCAGAGACTTGGTCTACC TTcATGTTCTTCAaATTCCTCCT (SEQ ID NO: 809) |
| B4 | BRCA2 | BRCA2_210_24_2 | ACACTGACGACATGGTTCTACAAGA GGAAGAAAAGGAAGCAGCAA (SEQ ID NO: 751) | TACGGTAGCAGAGACTTGGTCTTCA TATTAGAAATAACAATGTGTACCATA TAACT (SEQ ID NO: 752) |
| C4 | BRCA2 | BRCA2_210_0939181_1 | ACACTGACGACATGGTTCTACATTA GTTGCTTTTGAATTTAcAGTTTAGTG (SEQ ID NO: 753) | TACGGTAGCAGAGACTTGGTCTAGC CTCATTATATGTCCTCTTACTCTCT (SEQ ID NO: 754) |
| D4 | BRCA2 | BRCA2_210_0939183_1 | ACACTGACGACATGGTTCTACATGG AACTTTTTTGTTCTGATTGCT (SEQ ID NO: 755) | TACGGTAGCAGAGACTTGGTCTCAc ggTTGTGACATcCCTTGATA (SEQ ID NO: 756) |
| E4 | BRCA2 | BRCA2_210_0939183_2 | ACACTGACGACATGGTTCTACAATC ACAGGCAAATGtTgAATGATAA (SEQ ID NO: 757) | TACGGTAGCAGAGACTTGGTCTAAG TTAATAAAACTGATAAAAACAAAGCA TTTAC (SEQ ID NO: 758) |
| F4 | BRCA2 | BRCA2_210_25_3 | ACACTGACGACATGGTTCTACAACT ACTAATGCCCACAAAGAGATAA (SEQ ID NO: 759) | TACGGTAGCAGAGACTTGGTCTTTT TGAAGTTGCAAGATGATAAATTCTG (SEQ ID NO: 760) |

TABLE 6-continued

Primers for Amplifying Exons from the Genes BRCA1, BRCA2, PTEN, PI3KCA, APC, EGFR, TP53

| Primer plate well | Gene/chr | Name | F-primer | R-primer |
|---|---|---|---|---|
| G4 | BRCA2 | BRCA2_210_0939187_6 | ACACTGACGACATGGTTCTACATgg CgTCCATCatcagATTTATATTC (SEQ ID NO: 761) | TACGGTAGCAGAGACTTGGTCTACT AACAAGCACTTATCAAAACTGAAA (SEQ ID NO: 762) |
| H4 | BRCA2 | BRCA2_210_26_1 | ACACTGACGACATGGTTCTACAACC GGTACAAACCTTTCATTGT (SEQ ID NO: 763) | TACGGTAGCAGAGACTTGGTCTGCT GAAAGTCTGGATCTAAAAATTTGCT (SEQ ID NO: 764) |
| A5 | BRCA2 | BRCA2_210_39187_47 | ACACTGACGACATGGTTCTACAAcgg gAGCcCCTTCACTT (SEQ ID NO: 765) | TACGGTAGCAGAGACTTGGTCTGCC AACTGGTAGCTCCAACTAAT (SEQ ID NO: 766) |
| B5 | BRCA2 | BRCA2_210_27_2 | ACACTGACGACATGGTTCTACAAGG CATATTAGAGTTTCCTTTCTTGC (SEQ ID NO: 767) | TACGGTAGCAGAGACTTGGTCTTGC AGCAATTAACATATGAGGCTT (SEQ ID NO: 768) |
| C5 | BRCA2 | BRCA2_210_27_3 | ACACTGACGACATGGTTCTACAACT TGCCCCTTTCGTCTATTTGT (SEQ ID NO: 769) | TACGGTAGCAGAGACTTGGTCTGCC CTCTTTTGGACTAGCAGAA (SEQ ID NO: 770) |
| D5 | BRCA2 | BRCA2_210_39189_30 | ACACTGACGACATGGTTCTACACcA GTgGcgacCAGAATCC (SEQ ID NO: 771) | TACGGTAGCAGAGACTTGGTCTTTC CTTGATACTGGACTGTCAAAA (SEQ ID NO: 772) |
| E5 | BRCA2 | BRCA2_210_0939192_1 | ACACTGACGACATGGTTCTACAACA TTTAGGGTTTTTCATTCTTTTTTGGT (SEQ ID NO: 773) | TACGGTAGCAGAGACTTGGTCTGGA CCACTTGGGATcATTTGCAT (SEQ ID NO: 774) |
| F5 | BRCA2 | BRCA2_210_0939192_3 | ACACTGACGACATGGTTCTACAAAG CAGCTTTTCCACTTATTTTCTT (SEQ ID NO: 775) | TACGGTAGCAGAGACTTGGTCTATAAT ATTCCTTGAGTTTACATTAACTTACCA (SEQ ID NO: 776) |
| G5 | BRCA2 | BRCA2_210_28_1 | ACACTGACGACATGGTTCTACATGT GAACTGAAATCACCTAACCTAT (SEQ ID NO: 777) | TACGGTAGCAGAGACTTGGTCTTGA TAAAGGACTTTGATAATATATCTCAC AATTAG (SEQ ID NO: 778) |
| H5 | BRCA2 | BRCA2_210_28_2 | ACACTGACGACATGGTTCTACAACT GTGTGTAATATTTGCGTGCTT (SEQ ID NO: 779) | TACGGTAGCAGAGACTTGGTCTGTG GAAACAGACTTCCTTTTGGC (SEQ ID NO: 780) |
| A6 | BRCA2 | BRCA2_210_184789_7 | ACACTGACGACATGGTTCTACACTc CTAATTgtGAGAtatAttaTCAAAGTCC (SEQ ID NO: 781) | TACGGTAGCAGAGACTTGGTCTaGA AaTCCAAGGCTcTTCTCTTTT (SEQ ID NO: 782) |
| B6 | BRCA2 | BRCA2_210_184789_10 | ACACTGACGACATGGTTCTACAAGA GATTGATGACCAAAAGAACTGC (SEQ ID NO: 783) | TACGGTAGCAGAGACTTGGTCTTTtA AATGGAGTCATCTGAGGAGAA (SEQ ID NO: 784) |
| D6 | BRCA2 | BRCA2_210_29_2 | ACACTGACGACATGGTTCTACAAGC TGACGAAGAACTTGCATTGA (SEQ ID NO: 785) | TACGGTAGCAGAGACTTGGTCTCCT GGGAACTCTCCTGTTCTTTG (SEQ ID NO: 786) |
| E6 | BRCA2 | BRCA2_210_184789_35 | ACACTGACGACATGGTTCTACAGaA AAACAATTTaTatctGTCAGTGAATCC (SEQ ID NO: 787) | TACGGTAGCAGAGACTTGGTCTTGT gTCCTGCTtAtTTTTCTCACA (SEQ ID NO: 788) |
| F6 | BRCA2 | BRCA2_210_184789_48m | ACACTGACGACATGGTTCTACATCT GATCAaaGAACAGGAGAGTTC (SEQ ID NO: 789) | TACGGTAGCAGAGACTTGGTCTTAA GTACTAATGTGTGGTTTGAAATTATA TTCCAGT (SEQ ID NO: 790) |

TABLE 7

Cell-line Genomic DNA Samples

| Sample | BC |
|---|---|
| K562 | FLD0001 |
| MOLT-4 | FLD0002 |
| CCRF-CEM | FLD0003 |
| RPMI-8226 | FLD0004 |
| HL-60(TB) | FLD0005 |
| SR | FLD0006 |
| SF-268 | FLD0007 |
| SF-295 | FLD0008 |
| SF-539 | FLD0009 |
| SNB-19 | FLD0010 |
| SNB-75 | FLD0011 |
| U251 | FLD0012 |
| BT-549 | FLD0013 |
| HS-578T | FLD0014 |
| MCF7 | FLD0015 |
| NCI/ADR-RES | FLD0016 |
| MBA-MB-231/ATCC | FLD0017 |
| MDA-MB-435 | FLD0018 |
| T-47D | FLD0019 |
| COLO 205 | FLD0020 |
| HCC-2998 | FLD0021 |
| HCT-116 | FLD0022 |
| HCT-15 | FLD0023 |
| HT-29 | FLD0024 |
| KM12 | FLD0025 |
| SW-620 | FLD0026 |
| A549/ATCC | FLD0027 |
| EKVX | FLD0028 |
| HOP-62 | FLD0029 |
| HOP-92 | FLD0030 |
| NCI-H322M | FLD0031 |
| NCI-H226 | FLD0032 |
| NCI-H23 | FLD0033 |
| NCI-H460 | FLD0034 |
| NCI-H522 | FLD0035 |
| LOX IMVI | FLD0036 |
| M14 | FLD0037 |
| MALME-3M | FLD0038 |
| SK-MEL-2 | FLD0039 |
| SK-MEL-28 | FLD0040 |
| SK-MEL-5 | FLD0041 |
| UACC-257 | FLD0042 |
| UACC-62 | FLD0043 |
| IGR-OV1 | FLD0044 |
| OVCAR-3 | FLD0045 |
| OVCAR-4 | FLD0046 |
| OVCAR-5 | FLD0047 |
| OVCAR-8 | FLD0048 |
| K562 | FLD0049 |
| MOLT-4 | FLD0050 |
| CCRF-CEM | FLD0051 |
| RPMI-8226 | FLD0052 |
| HL-60(TB) | FLD0053 |
| SR | FLD0054 |
| SF-268 | FLD0055 |
| SF-295 | FLD0056 |
| SF-539 | FLD0057 |
| SNB-19 | FLD0058 |
| SNB-75 | FLD0059 |
| U251 | FLD0060 |
| BT-549 | FLD0061 |
| HS-578T | FLD0062 |
| MCF7 | FLD0063 |
| NCI/ADR-RES | FLD0064 |
| MBA-MB-231/ATCC | FLD0065 |
| MDA-MB-435 | FLD0066 |
| T-47D | FLD0067 |
| COLO 205 | FLD0068 |
| HCC-2998 | FLD0069 |
| HCT-116 | FLD0070 |
| HCT-15 | FLD0071 |
| HT-29 | FLD0072 |
| KM12 | FLD0073 |
| SW-620 | FLD0074 |
| A549/ATCC | FLD0075 |
| EKVX | FLD0076 |
| HOP-62 | FLD0077 |
| HOP-92 | FLD0078 |
| NCI-H322M | FLD0079 |
| NCI-H226 | FLD0080 |
| NCI-H23 | FLD0081 |
| NCI-H460 | FLD0082 |
| NCI-H522 | FLD0083 |
| LOX IMVI | FLD0084 |
| M14 | FLD0085 |
| MALME-3M | FLD0086 |
| SK-MEL-2 | FLD0087 |
| SK-MEL-28 | FLD0088 |
| SK-MEL-5 | FLD0089 |
| UACC-257 | FLD0090 |
| UACC-62 | FLD0091 |
| IGR-OV1 | FLD0092 |
| OVCAR-3 | FLD0093 |
| OVCAR-4 | FLD0094 |
| OVCAR-5 | FLD0095 |
| OVCAR-8 | FLD0096 |

TABLE 8

Barcode Primers
(SEQ ID NOS 13-14, 9, 803, 10, 11, 803, 12 and 804-807, respectively, in order of appearance)

| Primer | Sequence |
|---|---|
| CS1-TS-F | 5'-ACACTGACGACATGGTTCTACA-[TS-For]-3' |
| CS2-TS-R | 5'-TACGGTAGCAGAGACTTGGTCT-[TS-Rev]-3' |
| PE1-CS1 | 5'-AATGATACGGCGACCACCGAGATCTACACTGACGA CATGGTTCTACA-3' |
| PE2-BC-CS2 | 5'-CAAGCAGAAGACGGCATACGAGAT-[BC]-TACGGTAGCAGAGACTTGGTCT-3' |
| PE1-CS2 | 5'-AATGATACGGCGACCACCGAGATCTTACGGTAGCA GAGACTTGGTCT-3' |
| PE2-BC-CS1 | 5'-CAAGCAGAAGACGGCATACGAGAT-[BC]-ACACTGACGACATGGTTCTACA-3' |
| CS1 | 5'-A+CA+CTG+ACGACATGGTTCTACA-3' |
| CS2 | 5'-T+AC+GGT+AGCAGAGACTTGGTCT-3' |
| CS1rc | 5'-T+GT+AG+AACCATGTCGTCAGTTGT-3' |
| CS2rc | 5'-A+GAC+CA+AGTCTCTGCTACCGTA-3' |

LNA nucleotides preceded by a "+"

Example 11

Bidirectional DNA Sequencing Amplicon Tagging for Illumina Sequencers Using the 48.48 ACCESS ARRAY™ IFC—Protocol 2

This Example provides a modified version of the protocol in Example 9. The Introduction to Example 9 also applies to this Example.
Preparing Amplicons
The following documents may be consulted as references for this protocol: Fluidigm® IFC Controller for ACCESS ARRAY™ System User Guide (PN 68000157); Fluidigm® Control Line Fluid Loading Procedure Quick Reference (PN68000132); and Agilent DNA 1000 Kit Guide.

The following Reagents were used for this protocol and were stored at −20° C.: FastStart High Fidelity PCR System, dNTPack (Roche, PN 04-738-292-001); 20× ACCESS ARRAY™ Loading Reagent (Fluidigm, PN 100-0883); 1× ACCESS ARRAY™ Harvest Solution (Fluidigm, PN 100-1031); ACCESS ARRAY™ Barcode Library for Illumina Sequencers—384 (Bidirectional) (Fluidigm, PN 100-3771); target-specific primer pairs tagged with universal tags (CS1 forward tag, CS2 reverse tag), including 50 µM CS1-Tagged TS Forward Primer and 50 µM CS2-Tagged TS Reverse Primer; and template DNA at 50 ng/µL. (The 1× ACCESS ARRAY™ Harvest Solution (Fluidigm, PN 100-1031) is not packaged for individual sale. It can be purchased in units of 10, under the name ACCESS ARRAY™ Harvest Pack, PN 100-3155, or as a component in the 48.48 ACCESS ARRAY™ Loading Reagent Kit, PN 100-1032.) Also used were the Agilent DNA 1000 Kit Reagents (Agilent, PN 5067-1504), which are Stored at 4° C. Additionally, PCR Certified Water (Teknova, PN W330) was used; this was stored at room temperature.

Multiplex PCR on the 48.48 ACCESS ARRAY™ IFC was performed according to the instructions as detailed in Chapter 6—Multiplex Amplicon Tagging on the 48.48 ACCESS ARRAY™ IFC of the *ACCESS ARRAY™ System for Illumina Platform User Guide*. Alternatively, 2-Primer Target-Specific PCR on the 48.48 ACCESS ARRAY™ IFC was performed to achieve bidirectional amplicon tagging without multiplexing, according to the instructions as detailed in Appendix C of the *ACCESS ARRAY™ System for Illumina Platform User Guide*. The harvested PCR products were then barcoded following the instructions below.

PCR products were barcoded in two 96-well plates for bidirectional amplicon tagging following the instructions as detailed in Chapter 6—Attaching Sequence Tags and Sample Barcodes of the Fluidigm *ACCESS ARRAY™ System for Illumina Platform User Guide*. The 100-fold dilution of the harvested PCR product pool served as template in two (rather than one) barcoding PCR reactions: one reaction generated PCR product A that allowed for sequencing of the 5' end of the target region in one 96-well plate, and the other reaction generated PCR product B that allowed for sequencing of the 3' end of the target region in a second 96-well plate. The setup of the reaction is identical to "Attaching Sequence Tags and Sample Barcodes" in the Fluidigm *ACCESS ARRAY™ System for Illumina Platform User Guide*. However, the quantities in the Sample Pre-Mix Solution were doubled to compensate for the increase in the number of reactions, and ACCESS ARRAY™ Barcode Library for Illumina Sequencers—384 (Bidirectional) (Fluidigm, PN 100-3771) was used in the preparation of the Sample Mix Solution (Tables 9 and 10).

TABLE 9

Sample Mix Solutions—PCR Product A

| Component | Volume (µL) |
| --- | --- |
| Sample Pre-Mix | 15.0 |
| ACCESS ARRAY ™ Barcode Library for Illumina Sequencers - 384 (Bidirectional) A | 4.0 |
| Diluted Harvested PCR Product Pool | 1.0 |
| Total | 20.0 |

TABLE 10

Sample Mix Solutions—PCR Product B

| Component | Volume (µL) |
| --- | --- |
| Sample Pre-Mix | 15.0 |
| ACCESS ARRAY ™ Barcode Library for Illumina Sequencer - 384 (Bidirectional) B | 4.0 |
| Diluted Harvested PCR Product Pool | 1.0 |
| Total | 20.0 |

After the second PCR had finished, PCR Product A and PCR Product B pools were combined prior to sequencing. Chapter 8 of the Fluidigm *ACCESS ARRAY™ System for Illumina Platform User Guide* provides for methods describing post-PCR product library purification and quantitation. It was essential to use ACCESS ARRAY™ Barcode Library for Illumina Sequencers—384 (Bidirectional) (Fluidigm, PN 100-3771) to generate bidirectional amplicons for sequencing.

Sequencing Workflow Using Fluidigm FL1 and FL2 Sequencing Primers

The following instructions are intended for use with Illumina TruSeq sequencing reagents on the Illumina GAII and HiSeq systems. The Fluidigm sequencing reagents FL1 and FL2, contain equimolar mixtures of the CS1 and CS2 sequencing and indexing primers, respectively. FL1 is the custom sequencing primer and contains 50 µM each of the CS1 and CS2 primers. FL2 is the custom indexing primer and contains 50 µM each of the CS1rc and CS2rc primers. For single-read sequencing, reagents were prepared for Read 1 and the Indexing primers. For paired-end sequencing, reagents were prepared for Read 1, the Indexing, and Read 2 primers.

Figure 32:
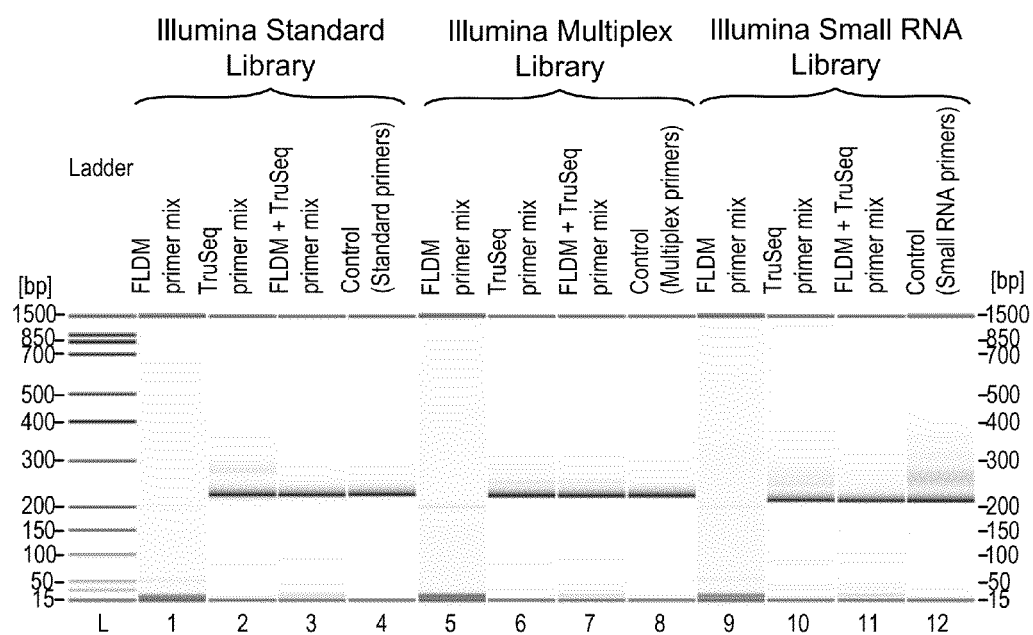
FIG. 32: Agilent Bioanalyzer results from a cross talk experiment between Fluidigm and Illumina TruSeq sequencing primers on Illumina generated libraries. The PCR reactions for each lane are as follows:
1. Illumina standard library+Fluidigm FL1 sequencing primers
2. Illumina standard library+Illumina TruSeq sequencing primers
3. Illumina standard library+Fluidigm FL1 and Illumina TruSeq sequencing primers
4. Illumina standard library+Illumina standard sequencing primers (control)
5. Illumina Multiplex library+Fluidigm FL1 sequencing primers
6. Illumina Multiplex library+Illumina TruSeq sequencing primers
7. Illumina Multiplex library+Fluidigm FL1 and Illumina TruSeq sequencing primers
8. Illumina Multiplex library+Illumina Multiplex sequencing primers (control)
9. Illumina Small RNA library+Fluidigm FL1 sequencing primers
10. Illumina Small RNA library+Illumina TruSeq sequencing primers
11. Illumina Small RNA library+Fluidigm FL1 and Illumina TruSeq sequencing primers
12. Illumina Small RNA library+Illumina Small RNA sequencing primers (control)
Figure 33:
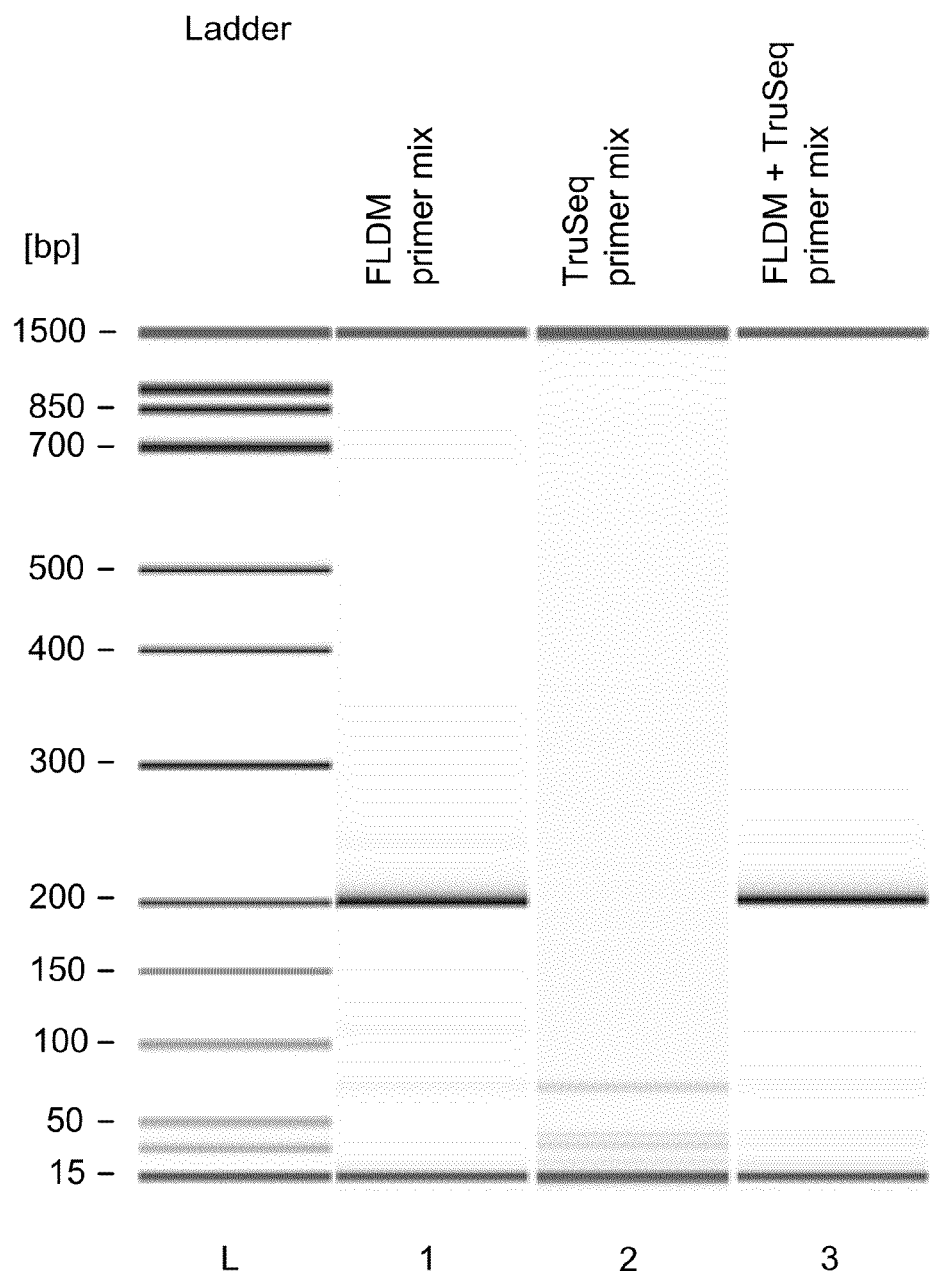
FIG. 33: Agilent Bioanalyzer results from a cross talk experiment between Fluidigm and Illumina TruSeq sequencing primers on an ACCESS ARRAY™ IFC generated library. The PCR reactions for each lane are as follows:
1. Fluidigm ACCESS ARRAY™ IFC library+Fluidigm FL1 sequencing primers
2. Fluidigm ACCESS ARRAY™ IFC library+Illumina TruSeq sequencing primers
3. Fluidigm ACCESS ARRAY™ IFC library+Fluidigm FL1 and Illumina TruSeq sequencing primers

Results from PCR experiments to test for cross talk between Fluidigm Sequencing Primers and TruSeq Sequencing Primers are shown in FIGS. 32 and 33.

The following documents may be consulted as references for sequencing: Illumina cBot™ User Guide; Illumina Genome Analyzer II™ User Guide; and Illumina HiSeq™ User Guide. The Illumina Genome Analyzer II User Guide or the Illumina HiSeq User Guide should be referred to for instructions on how to perform a sequencing run. Technical Support at Illumina may also be contacted.

Preparing Reagents for Sequencing on the Illumina GAII and HiSeq Sequencing Systems The Read 1 Sequencing Primer HT1/FL1 was prepared by first diluting the FL1 stock to a final concentration of 500 nM with Hybridization Buffer (HT1) in a DNase-, RNase-free 1.5 mL microcentrifuge tube (Table 11). The tube was vortexed for a minimum of 20 seconds, and centrifuged for 30 seconds to spin down all components. The following instructions outline preparation of the HT1/FL1 sequencing primer mix for Read 1 (per mL). Approximately 300 µL was used per lane, using the cBot Custom Primers Reagent Stage. The custom primer orientation in the tube strip was aligned with the lanes of the GAII or HiSeq flow cell.

TABLE 11

Instructions for Preparing HT1/FL1 (per mL)

| Reagent | Volume (µL) |
|---|---|
| HT1 Buffer | 990 µL |
| FL1 Stock (from Appendix E) | 10 µL |
| Total | 1.0 mL |

The Indexing Primer HT1/FL2 was prepared by first diluting the FL2 stock to a final concentration of 500 nM with Hybridization Buffer (HT1) in a DNase-, RNase-free 1.5 mL microcentrifuge tube (Table 12). The tube was vortexed for a minimum of 20 seconds, and centrifuged for 30 seconds to spin down all components. The following instructions outline preparation of the HT1/FL2 indexing primer mix for the Index Read. Approximately 3 mL of Index Sequencing Primer Mix (HP8) was used for the Index Read. 1.5 mL of TruSeq Reagent HP8 was substituted for 1.5 mL of HT1/FL2.

TABLE 12

Instructions for Preparing HT1/FL2

| Reagent | Volume |
|---|---|
| HT1 Buffer | 1,485 µL |
| FL1 Stock (from Appendix E) | 15 µL |
| Total | 1.5 mL |

The Read 2 Sequencing Primer HT1/FL1 (for Paired-End Sequencing) was prepared by first diluting the FL1 stock to a final concentration of 500 nM with Hybridization Buffer (HT1) in a DNase-, RNase-free 1.5 mL microcentrifuge tube (Table 13). The tube was vortexed for a minimum of 20 seconds, and centrifuged for 30 seconds to spin down all components. The following instructions outline preparation of the HT1/FL1 sequencing primer mix for Read 2. Approximately 3.2 mL of Read 2 Sequencing Primer (HP7) was used for Read 2. 1.6 mL of TruSeq Reagent HP7 was substituted for 1.6 mL of HT1/FL1.

TABLE 13

Instructions for preparing Read 2 Sequencing Primer HT1/FL1

| Reagent | Volume |
|---|---|
| HT1 Buffer | 1,584 µL |
| FL1 Stock (from Appendix E) | 16 µL |
| Total | 1.6 mL |

Performing a Sequencing Run

The Illumina Genome Analyzer II or HiSeq user guides provide instructions on how to perform a sequencing run. Alternatively, Technical Support at Illumina may be contacted.

For the Index Read, 1.5 mL of TruSeq Reagent HP8 was substituted for 1.5 mL of the Indexing Primer HT1/FL2 for GAII and HiSeq sequencing runs. The barcode sequences used in the ACCESS ARRAY™ Barcode Library for Illumina have been designed so that they can be distinguished even when sequencing errors are present. As more samples are run in parallel, the length of the index read required to distinguish the barcode sequences unambiguously increases. Recommendations for index reads are described in Table 14.

TABLE 14

Index Read Recommendations

| Number of samples per lane | 1-384 | 385-1920 |
|---|---|---|
| Length of index read | 8 bases | 10 bases |

When preparing the sequencing run, the length of the index read was adjusted according to the guidelines in Table 14. The volumes of the sequencing reagents loaded onto the sequencer were ensured to be sufficient for the index cycles. *The Illumina Sequencer User Guide* was consulted, or Technical Support at Illumina was contacted, for detailed instructions on how to implement these changes.

What is claimed is:

1. A method for amplifying a target nucleic acid, the method comprising:

amplifying a target nucleic acid using:

a set of inner primers, wherein the set comprises:

an inner, forward primer comprising a target-specific portion and a first primer binding site;

an inner, reverse primer comprising a target-specific portion and a second primer binding site, wherein the first and second primer binding sites are different;

a first set of outer primers, wherein the set comprises:

a first outer, forward primer comprising a portion specific for the first primer binding site; and a first outer, reverse primer comprising a barcode nucleotide sequence and a portion specific for the second primer binding site;

a second set of outer primers, wherein the set comprises:
a second outer, forward primer comprising a barcode nucleotide sequence and a portion specific for the first primer binding site; and
a second outer, reverse primer comprising a portion specific for the second primer binding site;

to produce two target amplicons, wherein:
a first target amplicon comprises 5'-first primer binding site-target nucleotide sequence-second primer binding site-barcode nucleotide sequence-3'; and
a second target amplicon comprises 5'-barcode nucleotide sequence-first primer binding site-target nucleotide sequence-second primer binding site-3';

wherein the method comprises amplifying a plurality of target nucleic acids and produces target amplicons having common first and common second primer binding sites, wherein at least some target amplicons have different barcode nucleotide sequences.

2. The method of claim 1, wherein the barcode nucleotide sequence in each target amplicon produced from a given target nucleic acid is the same, and wherein each target amplicon comprises only one barcode nucleotide sequence.

3. The method of claim 1, wherein the first and second primer binding sites are binding sites for DNA sequencing primers.

4. The method of claim 1, wherein the outer primers each additionally comprise an additional nucleotide sequence, wherein:
the first outer, forward primer comprises a first additional nucleotide sequence, and the first outer, reverse primer comprises a second additional nucleotide sequence; and
the second outer, forward primer comprises the second additional nucleotide sequence, and the second outer, reverse primer comprises the first additional nucleotide sequence; and
the first and second additional nucleotide sequences are different; and
said amplifying produces two target amplicons, wherein:
a first target amplicon comprises 5'-first additional nucleotide sequence-first primer binding site-target nucleotide sequence-second primer binding site-barcode nucleotide sequence-second additional nucleotide sequence-3'; and
a second target amplicon comprises 5'-second additional nucleotide sequence-barcode nucleotide sequence-first primer binding site-target nucleotide sequence-second primer binding site-first additional nucleotide sequence 3'.

5. The method of claim 4, wherein the first or second additional nucleotide sequence comprises a primer binding site.

6. The method of claim 5, wherein the first and second additional nucleotide sequences each comprise a primer binding site.

7. The method of claim 4, wherein the first set of outer primers comprises PE1-CS1 (SEQ ID NO:9) and PE2-BC-CS2 (SEQ ID NO:10), and the second set of outer primers comprises PE1-CS2 (SEQ ID NO:11) and PE2-BC-CS1 (SEQ ID NO:12).

8. The method of claim 1, wherein said amplifying is carried out in a single amplification reaction.

9. The method of claim 1, wherein said amplifying comprises employing the inner primers in a first amplification reaction and employing the outer primers in a second amplification reaction, wherein said second amplification reaction is separate from the first.

10. The method of claim 9, wherein the second amplification reaction comprises two separate amplification reactions, wherein one employs the first set of outer primers and the other employs the second set of outer primers.

11. The method of claim 10, wherein the target amplicons produced in the two separate second amplification reactions are pooled.

12. The method of claim 1, wherein the plurality of target nucleic acids is selected from the group consisting of genomic DNA, cDNA, fragmented DNA, DNA reverse-transcribed from RNA, a DNA library, and nucleic acids extracted or amplified from a cell, a bodily fluid or a tissue sample.

13. The method of claim 12, wherein the plurality of target nucleic acids is amplified from a formalin-fixed, paraffin-embedded tissue sample.

14. The method of claim 1, wherein the method additionally comprises sequencing the target amplicons.

15. The method of claim 1, wherein the method comprises amplifying the target amplicons using primers that bind to the first and second additional nucleotide sequences to produce templates for DNA sequencing.

16. The method of claim 15, wherein one or both primers that bind to the first and second additional nucleotide sequences are immobilized on a substrate.

17. The method of claim 1, wherein the amplification is carried out by isothermal nucleic acid amplification.

18. The method of claim 15, wherein the method comprises performing DNA sequencing using the templates and target sequencing primers that bind to the first and second primer binding sites, wherein said target sequencing primers prime sequencing of the target nucleotide sequence(s).

19. The method of claim 18, wherein the target sequencing primers are present in substantially equal amounts so as to produce both 5' and 3' DNA sequence information from each target nucleotide sequence.

20. The method of claim 15, wherein the method comprises performing DNA sequencing using the templates and barcode sequencing primers that bind to the first and second primer binding sites, wherein said barcode sequencing primers prime sequencing of the barcode nucleotide sequences(s).

21. The method of claim 20, wherein the barcode sequencing primers are present in substantially equal amounts so as to produce barcode sequences from each of the first and second target amplicons.

22. The method of claim 18, wherein the method comprises performing DNA sequencing using the templates and barcode sequencing primers that are reverse complements of the target sequencing primers.

23. The method of claim 22, wherein the target sequencing primers and the barcode sequencing primers comprise CS1 (SEQ ID NO:13), CS2 (SEQ ID NO:14), CS1rc (SEQ ID NO:15), and CS2rc (SEQ ID NO:16).

24. The method of claim 1, wherein the barcode nucleotide sequence is selected so as to avoid substantial annealing to the target nucleic acids.

25. The method claim 1, wherein the barcode nucleotide sequence identifies a particular sample.

26. The method of claim 15, wherein for at least 50 percent of the sequences determined from DNA sequencing, each determined sequence is present at greater than 50 percent of the average number of copies of that sequence and less than 2-fold said average number of copies.

27. The method of claim 15, wherein for at least 70 percent of the sequences determined from DNA sequencing, each determined sequence is present at greater than 50 percent of the average number of copies of that sequence and less than 2-fold said average number of copies.

28. The method of claim 15, wherein for at least 90 percent of the sequences determined from DNA sequencing, each determined sequence is present at greater than 50 percent of the average number of copies of that sequence and less than 2-fold said average number of copies of sequences.

29. The method of claim 1, wherein the average length of the target amplicons is less than 200 bases.

30. The method of claim 1, wherein the first amplification reaction is carried out in a volume in the range of about 1 picoliter to about 50 nanoliters.

31. The method of claim 1, wherein the first amplification reaction is carried out in a volume in the range of about 5 picoliters to about 25 nanoliters.

32. The method of claim 1, wherein the first amplification reaction(s) is/are formed in, or distributed into, separate compartments of a microfluidic device prior to amplification.

33. The method of claim 32, wherein the microfluidic device is fabricated, at least in part, from an elastomeric material.

34. The method of claim 1, wherein the first amplification reaction(s) is/are carried out in (a) fluid droplet(s).

35. The method of claim 34, wherein a plurality of first amplification reactions are carried out in fluid droplets in an emulsion.

* * * * *